(12) United States Patent
Atkinson et al.

(10) Patent No.: US 8,871,767 B2
(45) Date of Patent: Oct. 28, 2014

(54) 2-ARYLIMIDAZO[1,2-B]PYRIDAZINE, 2-PHENYLIMIDAZO[1,2-A]PYRIDINE, AND 2-PHENYLIMIDAZO[1,2-A]PYRAZINE DERIVATIVES

(75) Inventors: Robert N. Atkinson, Raleigh, NC (US); Andy J. Ommen, Laramie, WY (US); James M. Veal, Apex, NC (US); Kenneth H. Huang, Chapel Hill, NC (US); Emilie D. Smith, Apex, NC (US)

(73) Assignee: Hengrui (USA) Ltd., Cranbury, NJ (US)

( * ) Notice: Subject to any disclaimer, the term of this patent is extended or adjusted under 35 U.S.C. 154(b) by 65 days.

(21) Appl. No.: 13/335,072

(22) Filed: Dec. 22, 2011

(65) Prior Publication Data

US 2012/0178751 A1 Jul. 12, 2012

Related U.S. Application Data

(60) Provisional application No. 61/426,216, filed on Dec. 22, 2010, provisional application No. 61/514,833, filed on Aug. 3, 2011, provisional application No. 61/523,688, filed on Aug. 15, 2011.

(51) Int. Cl.
*A61K 31/50* (2006.01)
*C07D 487/00* (2006.01)

(52) U.S. Cl.
USPC ................... 514/252.05; 544/236

(58) Field of Classification Search
USPC ................... 544/236; 514/252.05
See application file for complete search history.

(56) References Cited

U.S. PATENT DOCUMENTS

| 2011/0133133 A1* | 6/2011 | Fischer et al. | 252/510 |
|---|---|---|---|
| 2013/0224114 A1* | 8/2013 | Kassiou et al. | 424/1.85 |

FOREIGN PATENT DOCUMENTS

| EP | 1 845 098 A1 | 10/2007 |
|---|---|---|
| EP | 1 964 841 A1 | 9/2008 |
| EP | 2 103 614 A1 | 9/2009 |
| FR | 2 918 061 A1 | 1/2009 |
| WO | 2005/066177 A1 | 7/2005 |
| WO | 2006/050506 A1 | 5/2006 |
| WO | 2008/022396 A1 | 2/2008 |
| WO | 2009/027733 A1 | 3/2009 |
| WO | 2009/041552 A1 | 4/2009 |
| WO | 2009/060197 A1 | 5/2009 |
| WO | 2009/077956 A2 | 6/2009 |
| WO | 2010/112874 A1 | 10/2010 |
| WO | 2010/119264 A1 | 10/2010 |
| WO | 2010/129620 A1 | 11/2010 |
| WO | 2011/036461 A1 | 3/2011 |
| WO | 2011/080510 A1 | 7/2011 |
| WO | 2011/089400 A1 | 7/2011 |
| WO | 2011/101644 A1 | 8/2011 |
| WO | 2011/141713 A1 | 11/2011 |
| WO | 2012/052730 A1 | 4/2012 |

OTHER PUBLICATIONS

Enguehard et al., Reactivity of a 6-chloroimidazo[1,2-b]pyridazine derivative towards Suzuki cross-coupling reaction Synthesis (2001), (4), 595-600 CODEN: SYNTBF; ISSN: 0039-7881; English.*
Cai, Lisheng et al., "Synthesis and Structure-Affinity Relationships of 4-(6-Iodo-H-imidazol[1,2-α]pyridine-2-yl)-N-dimethylbenzeneamine Derivatives as Ligands for Human β-Amyloid Plaques", Journal of Medicinal Chemistry (2007), vol. 50, pp. 4746-4758.
Barlin, Gordon B. et al., "Imidazo[1,2-b]pyridazines. XI. Syntheses and CentralNervous System Activities of some 6-(N-Benzyl-N-methylamino)-3-methoxy-2-phenyl(and substituted phenyl)imidazo[1,2-b]pyridazines", Australian Journal of Chemistry (1992), vol. 45, pates 751-757.
Barlin, Gordon B. et al., "Imidazo[1,2-b]pyridazines. XV. synthesis and Anxiolytic Activity of Some 3-(Benzamidomethyl and fluorobenzamidomethyl)-6-(fluro, chloro and methylthio)-2-(4-tolyl and 3,4-methylendixoyphenyl)imidazo[1,2-b]pyridazines", Australian Journal of Chemistry (1994), vol. 47, pp. 609-621.
Harrison, PW et al., "Syntheses, pharmacological evaluation and molecular modelling of substituted 6-alkozyimidazol[1,2-b]pyridazines as new ligands for the benzodiazepine receptor", European Journal of Medicinal Chemistry (1996), vol. 31, pp. 651-662.
Akkaoui, A. El et al., "Efficient and regioselective functionalization of imidazo[1,2-b]pyridazines via palladium-catalyzed cross-coupling reaction and SnAr", Tetrahedron Letters (2008), vol. 49, pp. 2472-2475.
The International Search Report (ISR) of PCT/US2011/066837 dated May 8, 2012.

* cited by examiner

*Primary Examiner* — Paul V. Ward
(74) *Attorney, Agent, or Firm* — McDonnell Boehmen Hulbert & Berghoff LLP

(57) ABSTRACT

Disclosed are compounds of formula (I):

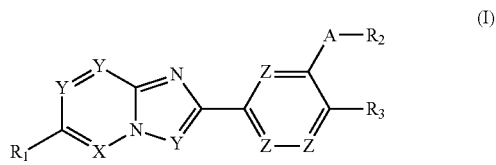

where X, Y, X, A, $R_1$, $R_2$, and $R_3$ are defined herein. Also disclosed are pharmaceutically acceptable salts of the compounds, compositions containing the compounds, and methods of using the compounds to treat, e.g., cancer.

23 Claims, 2 Drawing Sheets

2-ARYLIMIDAZO[1,2-B]PYRIDAZINE, 2-PHENYLIMIDAZO[1,2-A]PYRIDINE, AND 2-PHENYLIMIDAZO[1,2-A]PYRAZINE DERIVATIVES

CROSS-REFERENCE TO RELATED APPLICATIONS

This application claims benefit of U.S. Provisional Application Ser. Nos. 61/426,216, filed Dec. 22, 2010, 61/514,833, filed Aug. 3, 2011, and 61/523,688, filed Aug. 15, 2011, each of which is incorporated by reference herein in its entirety.

BACKGROUND OF THE INVENTION

1. Field of the Invention

This disclosure relates to compounds, compositions and methods for the treatment of various disorders. In particular, the disclosure relates to compounds which antagonize the activity of the protein Smoothened and thereby inhibit the Hedgehog signaling pathway.

2. Description of Related Art

The Hedgehog (Hh) signaling pathway is an important regulator of cellular processes. Hedgehog protein family members mediate events in both vertebrates and invertebrates critical to developmental patterning processes, cellular differentiation, and proliferation. Three vertebrate Hedgehog genes, Sonic Hedgehog (Shh), India Hedgehog (Ihh) and Desert Hedgehog (Dhh), are known. The translated gene products are secreted proteins which are post-translationally modified via autoproteolytic cleavage, palmitoylation, and cholesterol attachment. Post-translational modification acts in part to control Hh proteins spatial and temporal distributions, allowing the proteins to function as morphogens. The inductive actions of Hh proteins occur in both embryos and adult cells, acting to modulate morphogenetic patterns and causing differentiation.

The Hedgehog signaling pathway involves the three Hh ligands (Dhh, Shh or Ihh), the twelve transmembrane protein Patched (PTCH1), the seven transmembrane protein Smoothened (SMO), and the Gli family of transcription factors as well as other regulatory proteins. The Hh signaling pathway normally resides in an inactive state in the absence of Hh ligand, due to Patched protein interacting with Smoothened and thereby inhibiting the activity of Smoothened. Binding of Hh ligands to Patched disrupts the interaction of Patched with Smoothened thereby causing its activation and migration to the plasma membrane. In mammalian systems, Smoothened and other downstream pathway components are localized to non-motile cilia as part of the signaling activation process. Smoothened activation in turn leads to a series of events that result in Gli transcription factors (particularly Gli1 and Gli2) translocating into the nucleus whereby they activate transcription of their target genes. Target genes of the Gli transcription factors include Wnts, TGFβ, c-Myc, cyclins, as well as Patched and Gli themselves.

Under normal conditions, the Hh signaling pathway is tightly controlled given the importance of proper cell proliferation, cell differentiation, and embryonic pattern formation. However, under aberrant conditions, deregulation of the Hedgehog pathway may occur and lead to disease. For example, individuals with Gorlin's disease, a hereditary syndrome which carries a high risk of brain and skin cancer, are observed to have loss of function mutations in Patched. Gain of function mutations in Smoothened or Gli proteins are linked to glioblastoma and basal cell carcinoma (the most common form of skin cancer in the United States). Inappropriate activation of Hh signaling is implicated in the metastasis of prostate cancer. In human pancreatic tumors, abnormal expression of Patched, Smoothened, and sonic Hedgehog also has been observed. Importantly, even when components of the Hh signaling pathway are not directly mutated in a cancer, pathway activation can still be central to the cancer proliferation; the tumor cells establish an active autocrine loop through in which they both make and respond to Hh ligand thereby facilitating proliferation.

Further supporting the role of aberrant Hh pathway signaling in cancer are the effects of cyclopamine in xenograft mouse models of cancer. Cyclopamine is a naturally occurring alkaloid which was discovered to be a Hedgehog pathway antagonist. In a range of xenograft models of different cancer types, treatment with cyclopamine has been found to slow progression of tumor growth or suppress metastasis.

Thus, inappropriate Hedgehog signaling may cause or contribute to a range of diseases including a broad range of cancers. The role of Hh signaling in the disease may be due to loss or gain of function mutations of members of the pathway or inappropriate activation of the pathway. Moreover, small molecule antagonists can suppress or reverse the effects of inappropriate Hedgehog signaling. Accordingly, molecules which antagonize the Hedgehog signaling pathway, such as modulators of Smoothened activity, are needed and are therapeutically useful.

SUMMARY OF THE INVENTION

The disclosure provides compounds of formula (I), shown below, pharmaceutical compositions containing those compounds and methods employing such compounds or compositions in the treatment of diseases and/or disorders, such as hyperproliferative diseases and angiogenesis mediated diseases, or the like.

In a broad embodiment (Embodiment 1), the disclosure provides compounds of formula (I):

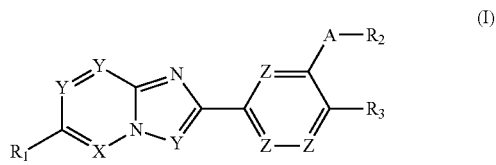

and the pharmaceutically acceptable salts thereof, wherein $R_1$ is $R_{1-A}$ where $R_{1-A}$ is hydrogen, halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, —$CO_2$H, —$CO_2$($C_1$-$C_6$ alkyl), —S($C_1$-$C_6$ alkyl), —SO($C_1$-$C_6$ alkyl), —$SO_2$($C_1$-$C_6$ alkyl), —$CONH_2$, —CONH($C_1$-$C_6$ alkyl), —CON($C_1$-$C_6$ alkyl)$_2$, —NHCO($C_1$-$C_6$ alkyl), —$NHCO_2$($C_1$-$C_6$ alkyl), $C_3$-$C_8$ cycloalkyl, aryl, heteroaryl, heterocyclyl, ($C_3$-$C_8$ cycloalkyl)$C_1$-$C_6$ alkyl, (aryl)$C_1$-$C_6$ alkyl, (heteroaryl)$C_1$-$C_6$ alkyl, (heterocyclyl)$C_1$-$C_6$ alkyl, $C_3$-$C_8$ cycloalkoxy, aryloxy, heteroaryloxy, (aryloxy)$C_1$-$C_6$ alkyl, (heteroaryloxy)$C_1$-$C_6$ alkyl, —$OR_9$, —$SR_9$, or —$NR_9R_{11}$ where $R_{11}$ is hydrogen or unsubstituted $C_1$-$C_6$ alkyl, wherein each alkyl except unsubstituted alkyl, alkenyl, alkynyl, cycloalkyl, aryl, heteroaryl, or heterocyclyl group is optionally substituted at a substitutable position with one or more of $R_8$;

wherein $R_8$ is halogen, —CN, —OH, —SH, —$NO_2$, —$NH_2$, —NH($C_1$-$C_6$ alkyl), —N($C_1$-$C_6$ alkyl)$_2$, —NH($C_1$-$C_6$ alkyl)-OH, —NH($C_1$-$C_6$ alkyl)-($C_1$-$C_6$ alkoxy), —$C_1$-$C_6$ alkoxy-OH, —$C_1$-$C_6$ alkoxy-($C_1$-$C_6$ alkoxy), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), —S($C_1$-$C_6$ alkyl), —$CO_2H$, —$CO_2$($C_1$-$C_6$ alkyl), —C(O)($C_1$-$C_6$ alkyl), —$SO_2$($C_1$-$C_6$ alkyl), —$SO_2NH_2$, —$SO_2$NH($C_1$-$C_6$ alkyl), —$SO_2$N($C_1$-$C_6$ alkyl), —CON(H)O$R_{80}$ where $R_{80}$ is hydrogen or a hydroxy protecting group, —$CONH_2$, —CONH($C_1$-$C_6$ alkyl), —CON($C_1$-$C_6$ alkyl)$_2$, —NHCO($C_1$-$C_6$ alkyl), —C(=NH)$NH_2$, —C(=NH)NH—$NH_2$, —C(=NOH)$NH_2$, or —$NHCO_2$($C_1$-$C_6$ alkyl) wherein each alkyl, alkenyl, alkynyl, alkoxy is optionally substituted at a substitutable carbon with —$CO_2$($C_1$-$C_6$)alkyl or —CON(H)O$R_{80}$;

wherein $R_9$ is $C_3$-$C_8$ cycloalkyl, $C_3$-$C_8$ cycloalkyl-C(O)—, aryl, aryl-C(O)—, heteroaryl, heteroaryl-C(O)—, heterocyclyl, heterocyclyl-C(O)—, aryl-$SO_2$—, heteroaryl-$SO_2$—, ($C_3$-$C_8$ cycloalkyl)$C_1$-$C_6$ alkyl, (aryl)$C_1$-$C_6$ alkyl, (heteroaryl)$C_1$-$C_6$ alkyl, or (heterocyclyl)$C_1$-$C_6$ alkyl, wherein each cyclic portion is optionally substituted at a substitutable position with one or more of halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, hydroxy $C_1$-$C_6$ alkyl, $H_2$N($C_1$-$C_6$ alkyl)-, $C_1$-$C_6$ alkyl-NH—($C_1$-$C_6$ alkyl)-, di-($C_1$-$C_6$ alkyl)-N($C_1$-$C_6$ alkyl)-, $C_1$-$C_6$ haloalkyl, $C_1$-$C_6$ alkoxy, $C_1$-$C_6$ haloalkoxy, —$CO_2$($C_1$-$C_6$)alkyl or —CON(H)O$R_{80}$ wherein each alkyl, alkenyl, alkynyl, alkoxy is optionally substituted at a substitutable carbon with one $R_{92}$, where $R_{92}$ is —CO$R_{94}$ where $R_{94}$ is ($C_1$-$C_6$)alkoxy, NHO$R_{80}$ or —N$R_7R_{96}$ where $R_{96}$ is aryl or heteroaryl, each of which is optionally substituted with up to three of halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), or —S($C_1$-$C_6$ alkyl); or $R_1$ is $R_{1-B}$ where $R_{1-B}$ is $R_W$—$R_Z$—$R_Y$—$R_X$—, wherein $R_X$ is a bond, —O—, —N($R_7$)—, —($C_1$-$C_3$ alkyl)N($R_7$)—, or —C(O)—;

where $R_7$ is hydrogen or $C_1$-$C_8$ alkyl optionally substituted with $C_1$-$C_4$ alkoxycarbonyl;

$R_Y$ is $C_3$-$C_8$ cycloalkyl, aryl, heteroaryl, or heterocyclyl, each optionally substituted with $R_8$;

$R_Z$ is a bond, $C_1$-$C_6$ alkylene, —O—, —O($C_1$-$C_4$ alkylene)-, —($C_1$-$C_4$ alkylene)O—, —N($R_7$)—, —($C_1$-$C_4$ alkylene)N($R_7$)—, —N($R^7$)($C_{1-4}$ alkylene)-, —C(O)—, —C(O)($C_1$-$C_4$ alkylene)-, —($C_1$-$C_4$ alkylene)C(O)—, —N($R_7$)C(O)—, —N($R_7$)C(O)O—, —C(O)N($R_7$)—, —C(O)N($R_7$)($C_1$-$C_4$ alkylene)-, —N($R_7$)C(O)N($R_7$)—, —OC(O)—, —C(O)O—, —C(O)O($C_1$-$C_4$ alkylene)-, —OC(O)O—, —OC(O)N($R_7$)—, —S(O)$_2$—, —S(O)$_2$($C_1$-$C_4$ alkylene)-, —S(O)$_2$N($R_7$)—, —OS(O)$_2$N($R_7$)—, —N($R_7$)S(O)$_2$—, or —OS(O)$_2$O—;

$R_W$ is $C_3$-$C_8$ cycloalkyl, aryl, heteroaryl, or heterocyclyl, each optionally substituted with $R_8$;

$R_2$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkyl, aryl, heteroaryl, heterocyclyl, ($C_3$-$C_8$ cycloalkyl)$C_1$-$C_6$ alkyl, (aryl)$C_1$-$C_6$ alkyl, (heteroaryl)$C_1$-$C_6$ alkyl, (heterocyclyl)$C_1$-$C_6$ alkyl, (aryloxy)$C_1$-$C_6$ alkyl, or (heteroaryloxy)$C_1$-$C_6$ alkyl, wherein each alkyl, alkenyl, alkynyl, cycloalkyl, aryl, heteroaryl, or heterocyclyl group is optionally substituted at a substitutable position with one or more of $R_{10}$;

wherein $R_{10}$ is halogen, —CN, —OH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), —$CO_2$H, —$CO_2$($C_1$-$C_6$ alkyl), —$SO_2$($C_1$-$C_6$ alkyl), —$CONH_2$, —CONH($C_1$-$C_6$ alkyl), —CON($C_1$-$C_6$ alkyl)$_2$, —CON(H)O$R_{80}$, —NHCO($C_1$-$C_6$ alkyl), or —$NHCO_2$($C_1$-$C_6$ alkyl) wherein each alkyl, alkenyl, alkynyl, alkoxy is optionally substituted at a substitutable carbon with one $R_{102}$, where $R_{102}$ is —CO$R_{104}$ where $R_{104}$ is —($C_1$-$C_6$) alkoxy, —NHO$R_{80}$, or —N$R_7R_{110}$, where $R_{110}$ is aryl or heteroaryl, each of which is optionally substituted with up to three of halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), or —S($C_1$-$C_6$ alkyl);

$R_3$ is hydrogen, halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkyl, aryl, heteroaryl, heterocyclyl, (aryl)$C_1$-$C_6$ alkyl, or (heteroaryl)$C_1$-$C_6$ alkyl;

A is a bond, —O—, —N($R_7$)—, —C(O)—, —N($R_7$)C(O)—, —N($R_7$)C(O)O—, —C(O)N($R_7$)—, —N($R_7$)C(O)N($R_7$)—, —OC(O)—, —C(O)O—, —OC(O)O—, —OC(O)N($R_7$)—, —S(O)$_2$—, —S(O)$_2$N($R_7$)—, —OS(O)$_2$N($R_7$)—, —N($R_7$)S(O)$_2$—, or —OS(O)$_2$O—;

X is N or C$R_4$;

$R_4$ is hydrogen, halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), $C_3$-$C_8$ cycloalkyl, aryl, heteroaryl, heterocyclyl, (aryl)$C_1$-$C_6$ alkyl, or (heteroaryl)$C_1$-$C_6$ alkyl;

each Y is independently N or C$R_5$, provided only one Y is N;

each $R_5$ is independently hydrogen, halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), $C_3$-$C_8$ cycloalkyl, aryl, heteroaryl, heterocyclyl, (aryl)$C_1$-$C_6$ alkyl, or (heteroaryl)$C_1$-$C_6$ alkyl wherein each alkyl, alkenyl, alkynyl, cycloalkyl, aryl, heteroaryl, or heterocyclyl group is optionally substituted at a substitutable position with one or more of $R_{10}$;

each Z is independently N or C$R_6$, provided only one Z is N; and each $R_6$ is independently hydrogen, halogen, —CN, —OH, —SH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), $C_3$-$C_8$ cycloalkyl, aryl, heteroaryl, heterocyclyl, (aryl)$C_1$-$C_6$ alkyl, or (heteroaryl)$C_1$-$C_6$ alkyl wherein each alkyl, alkenyl, alkynyl, cycloalkyl, aryl, heteroaryl, or heterocyclyl group is optionally substituted at a substitutable position with one or more of $R_{10}$.

The disclosure also provides intermediate compounds that are useful in making the compounds of formula (I). Some of these intermediate compounds are encompassed within formula (I).

The disclosure also provides methods of preparing compounds of the disclosure and the intermediates used in those methods.

The disclosure also provides pharmaceutical compositions comprising a compound of formula (I) or a pharmaceutically acceptable salt thereof and at least one pharmaceutically acceptable carrier, solvent, adjuvant or diluent.

The disclosure also provides methods for inhibiting hedgehog signaling in vitro and in vivo comprising administering compounds of formula (I).

The disclosure also provides a method of treating a disease or disorder comprising administering compounds of formula (I). Examples of diseases or disorders include hyperproliferative diseases and angiogenesis mediated diseases, such as cancer.

The disclosure further provides a compound or pharmaceutical composition thereof in a kit with instructions for using the compound or composition.

The disclosure further provides compounds that may be administered alone or in combination with other drugs or therapies known to be effective to treat the disease to enhance overall effectiveness of therapy.

DETAILED DESCRIPTION

Figure 1:
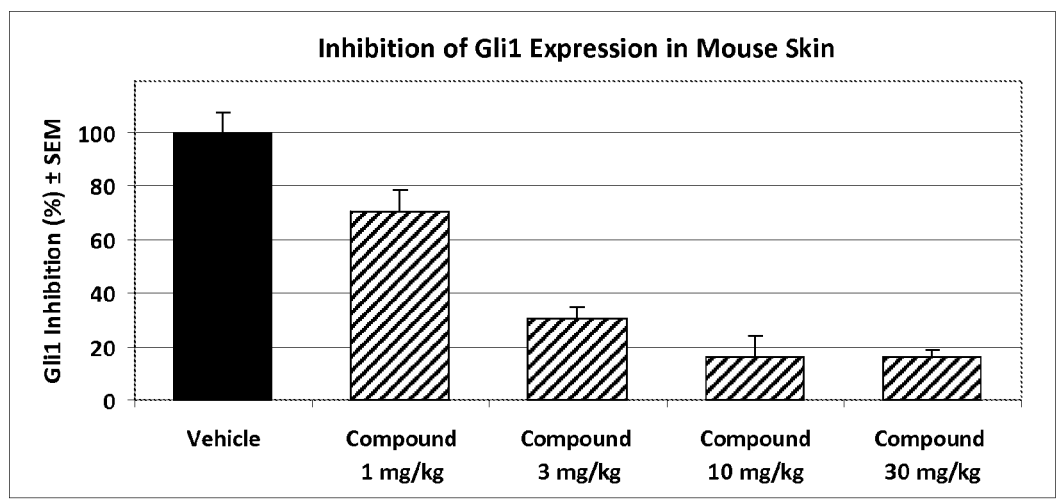
FIG. 1 is a graph showing the results of testing the compound of Example 633 as an inhibitor of expression of Gli1 as described in Example 705.

In another embodiment, Embodiment 2, the disclosure provides compounds of Formula IA

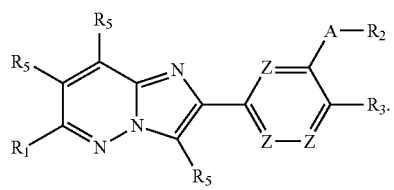

I-A

Compounds of Embodiment 3 are those of embodiment 2 wherein:
each $R_5$ is independently hydrogen, halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkyl, aryl, heteroaryl, or heterocyclyl, wherein each alkyl, alkenyl, alkynyl, cycloalkyl, aryl, heteroaryl, or heterocyclyl group is optionally substituted at a substitutable position with one or more of $R_{10}$;
wherein $R_{10}$ is halogen, —CN, —OH, —NO$_2$, —NH$_2$, —NH($C_1$-$C_6$ alkyl), —N($C_1$-$C_6$ alkyl)$_2$, $C_1$-$C_6$ alkoxy, $C_1$-$C_6$ haloalkyl, $C_1$-$C_6$ alkoxy, $C_1$-$C_6$ haloalkoxy, —CO$_2$H, —CO$_2$($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, —CON(H)OH, —NHCO($C_1$-$C_6$ alkyl), or —NHCO$_2$($C_1$-$C_6$ alkyl);

Compounds of Embodiment 4 are those of embodiment 3 wherein:
each $R_5$ is independently hydrogen, halogen, —CN, —OH, —NH$_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, or aryl, wherein each alkyl, cycloalkyl, or aryl, group is optionally substituted at a substitutable position with one or more of $R_{10}$.

Compounds of Embodiment 5 are those of embodiment 4 wherein:
each $R_5$ is independently hydrogen, $C_1$-$C_6$ alkyl, $C_3$-$C_8$ cycloalkyl, or aryl optionally substituted at a substitutable position with one or more of $R_{10}$.

Compounds of Embodiment 6 are those of embodiments 2-5 where the compounds have the formula I-B:

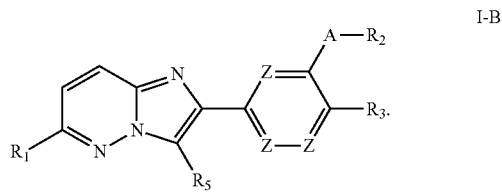

I-B

Compounds of Embodiment 7 are those of embodiment 6 wherein $R_5$ is hydrogen, $C_1$-$C_6$ alkyl, $C_3$-$C_8$ cycloalkyl, or aryl optionally substituted at a substitutable position with one or more of halogen.

Compounds of Embodiment 8 are those of embodiment 7 wherein $R_5$ is hydrogen.

Compounds of Embodiment 9 are those of embodiment 7 wherein $R_5$ is $C_1$-$C_6$ alkyl.

Compounds of Embodiment 10 are those of embodiment 9 wherein $R_5$ is methyl.

Compounds of Embodiment 11 are those of embodiments 2-10 wherein each Z is $CR_6$.

Compounds of Embodiment 12 are those of embodiment 11 wherein each $R_6$ is independently hydrogen, halogen, —CN, —OH, —NH$_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, or $C_1$-$C_6$ haloalkoxy.

Compounds of Embodiment 13 are those of embodiment 12 wherein each $R_6$ is independently hydrogen, halogen, or $C_1$-$C_6$ alkyl.

Compounds of Embodiment 14 are those of embodiment 13 each $R_6$ is independently hydrogen.

Compounds of Embodiment 15 are those of embodiments 2-14 wherein $R_3$ is hydrogen, halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or $C_3$-$C_8$ cycloalkyl.

Compounds of Embodiment 16 are those of embodiment 15 wherein $R_3$ is hydrogen, halogen, —CN, $C_1$-$C_6$ alkyl, $C_1$-$C_6$ haloalkyl, $C_1$-$C_6$ alkoxy, $C_1$-$C_6$ haloalkoxy, or $C_3$-$C_8$ cycloalkyl.

Compounds of Embodiment 17 are those of embodiment 16 wherein $R_3$ is $C_1$-$C_6$ alkyl, $C_1$-$C_6$ haloalkyl, or $C_1$-$C_6$ haloalkoxy.

Compounds of Embodiment 18 are those of embodiments 1-17 wherein $R_3$ is $C_1$-$C_6$ alkyl or $C_1$-$C_6$ haloalkyl.

Compounds of Embodiment 19 are those of embodiment 18 wherein $R_3$ is methyl or trifluoromethyl.

Compounds of Embodiment 19-A include those of embodiments 2-26 wherein -A-$R_2$ is —$C_1$-$C_6$ alkoxy, —$C_1$-$C_6$ alkylamido, or mono- or di-($C_1$-$C_6$)alkylamino, and where the alkyl portion(s) of each is optionally substituted with $C_1$-$C_6$ alkoxycarbonyl, hydroxycarbonyl, aminocarbonyl, or N-hydroxyaminocarbonyl.

Compounds of Embodiment 20 are those of embodiments 2-19 wherein A is a bond, —N($R_7$)—, —N($R_7$)C(O)—, —C(O)N($R_7$)—, or —S(O)$_2$N($R_7$)—.

Compounds of Embodiment 21 are those of embodiment 20 wherein A is —N($R_7$)C(O)—.

Compounds of Embodiment 22 are those of embodiments 2-21 wherein $R_2$ is hydrogen, $C_1$-$C_6$ alkyl, $C_1$-$C_6$ haloalkyl, $C_3$-$C_8$ cycloalkyl, aryl, heteroaryl, ($C_3$-$C_8$ cycloalkyl)$C_1$-$C_6$ alkyl, (aryl)$C_1$-$C_6$ alkyl, (heteroaryl)$C_1$-$C_6$ alkyl, (aryloxy)$C_1$-$C_6$ alkyl, or (heteroaryloxy)$C_1$-$C_6$ alkyl, wherein each alkyl, cycloalkyl, aryl, or heteroaryl group is optionally substituted at a substitutable position with one or more of $R_{10}$.

Compounds of Embodiment 23 are those of embodiment 22 wherein $R_2$ is $C_1$-$C_6$ alkyl, $C_1$-$C_6$ haloalkyl, $C_3$-$C_8$ cycloalkyl, aryl, heteroaryl, ($C_3$-$C_8$ cycloalkyl)$C_1$-$C_6$ alkyl, (aryl)$C_1$-$C_6$ alkyl, or (aryloxy)$C_1$-$C_6$ alkyl, wherein each alkyl, cycloalkyl, or aryl group is optionally substituted at a substitutable position with one or more of $R_{10}$.

Compounds of Embodiment 24 are those of embodiment 23 wherein $R_2$ is $C_1$-$C_6$ alkyl or $C_1$-$C_6$ haloalkyl.

Compounds of Embodiment 25 are those of embodiment 24 wherein $R_2$ is $C_1$-$C_6$ alkyl.

Compounds of Embodiment 26 are those of embodiment 25 wherein $R_2$ is t-butyl.

Compounds of Embodiment 27 are those of embodiments 2-26 wherein -A-$R_2$ is —N($R_7$)C(O)($C_1$-$C_6$ alkyl).

Compounds of Embodiment 28 are those of embodiments 2-26 wherein -A-$R_2$ is —NHC(O)(t-butyl).

Compounds of Embodiment 29 are those of embodiments 2-28 wherein $R_1$ is $R_{1-A}$.

Compounds of Embodiment 30 are those of embodiment 29 wherein $R_{1-8}$, is hydrogen, halogen, —CN, —OH, —SH, —NH$_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, —CO$_2$H, —CO$_2$($C_1$-$C_6$ alkyl), —S($C_1$-$C_6$ alkyl), —SO($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, $C_3$-$C_8$ cycloalkyl, aryl, heteroaryl, heterocyclyl, ($C_3$-$C_8$ cycloalkyl)$C_1$-$C_6$ alkyl, (aryl)$C_1$-$C_6$ alkyl, (heteroaryl)$C_1$-$C_6$ alkyl, (heterocyclyl)$C_1$-$C_6$ alkyl, —OR$_9$, —SR$_9$, or —NHR$_9$, wherein each alkyl, cycloalkyl, aryl, heteroaryl, or heterocyclyl group is optionally substituted at a substitutable position with one or more of $R_8$.

Compounds of Embodiment 31 are those of embodiment 30 wherein $R_{1-8}$, is hydrogen, halogen, —CN, —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), —SO($C_1$-$C_6$ alkyl), —SO$_2$($C_1$-$C_6$ alkyl), —CONH$_2$, $C_3$-$C_8$ cycloalkyl, aryl, heteroaryl, heterocyclyl, —OR$_9$, or —NHR$_9$, wherein each alkyl, cycloalkyl, aryl, heteroaryl, or heterocyclyl group is optionally substituted at a substitutable position with one or more of $R_8$;

where $R_8$ is halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), —S($C_1$-$C_6$ alkyl), —CO$_2$H, —CO$_2$($C_1$-$C_6$ alkyl), —C(O)($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, —NHCO($C_1$-$C_6$ alkyl), —C(=NH)NH$_2$, —C(=NOH)NH$_2$, or —NHCO$_2$($C_1$-$C_6$ alkyl) wherein each alkyl, alkenyl, alkynyl, alkoxy is optionally substituted at a substitutable carbon with —CO$_2$($C_1$-$C_6$)alkyl or —CON(H)OH.

Compounds of Embodiment 32 are those of embodiment 31 wherein $R_{1-8}$, is hydrogen, halogen, —CN, —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), —SO($C_1$-$C_6$ alkyl), —SO$_2$($C_1$-$C_6$ alkyl), —CONH$_2$, $C_3$-$C_8$ cycloalkyl, aryl, heteroaryl, or heterocyclyl, wherein each alkyl, cycloalkyl, aryl, heteroaryl, or heterocyclyl group is optionally substituted at a substitutable position with one or more of $R_8$.

Compounds of Embodiment 33 are those of embodiment 32 wherein $R_{1-8}$, is hydrogen, halogen, —CN, —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), —SO($C_1$-$C_6$ alkyl), —SO$_2$($C_1$-$C_6$ alkyl), or —CONH$_2$, wherein each alkyl group is optionally substituted at a substitutable position with one or more of $R_8$.

Compounds of Embodiment 34 are those of embodiment 33 wherein $R_{1-8}$, is hydrogen, halogen, —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), —SO($C_1$-$C_6$ alkyl), or —SO$_2$($C_1$-$C_6$ alkyl), wherein each alkyl group is optionally substituted at a substitutable position with one or more of $R_8$.

Compounds of Embodiment 35 are those of embodiment 34 wherein $R_{1-A}$ is —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), or —SO$_2$($C_1$-$C_6$ alkyl), wherein each alkyl group is optionally substituted at a substitutable position with one or more of $R_8$.

Compounds of Embodiment 36 are those of embodiment 34 wherein $R_{1-A}$ is hydrogen, halogen, $C_1$-$C_6$ alkyl, or $C_1$-$C_6$ alkoxy, wherein each alkyl group is optionally substituted at a substitutable position with one or more of $R_8$;

wherein $R_8$ is halogen, —CN, —OH, —NH$_2$, —NH($C_1$-$C_6$ alkyl), —N($C_1$-$C_6$ alkyl)$_2$, $C_1$-$C_6$ alkoxy, $C_1$-$C_6$ haloalkyl, $C_1$-$C_6$ alkoxy, —C(=NH)NH$_2$, —C(=NOH)NH$_2$, or $C_1$-$C_6$ haloalkoxy.

Compounds of Embodiment 37 are those of embodiment 36 wherein $R_{1-A}$ is $C_1$-$C_6$ alkoxy optionally substituted at a substitutable position with one or more of $R_8$.

Compounds of Embodiment 38 are those of embodiment 36 wherein $R_{1-A}$ is halogen.

Compounds of Embodiment 39 are those of embodiment 32 wherein $R_{1-A}$ is $C_3$-$C_8$ cycloalkyl, aryl, heteroaryl, or heterocyclyl, wherein each cycloalkyl, aryl, heteroaryl, or heterocyclyl group is optionally substituted at a substitutable position with one or more of $R_8$.

Compounds of Embodiment 39-A include those of embodiment 39 wherein $R_{1-A}$ is piperidinyl substituted by one or two of $R_8$, where one $R_8$ is cyano, halogen, —SO$_2$NH$_2$, —CONH$_2$, —C(=NOH)NH$_2$, —C(=NH)NH$_2$, $C_2$-$C_4$ alkenyl substituted with $C_1$-$C_3$ alkoxycarbonyl, or $C_1$-$C_6$ haloalkyl.

Compounds of Embodiment 39-B include those of embodiment 39 wherein $R_{1-A}$ is piperidinyl substituted by one or two of $R_8$, where one $R_8$ is cyano, halogen, —SO$_2$NH$_2$, —CONH$_2$, —C(=NOH)NH$_2$, —C(=NH)NH$_2$, $C_2$-$C_4$ alkenyl substituted with $C_1$-$C_3$ alkoxycarbonyl or N-hydroxyaminocarbonyl, or trifluoromethyl.

Compounds of Embodiment 40 are those of embodiment 39 wherein $R_{1-A}$ is aryl or heteroaryl, wherein each aryl or heteroaryl group is optionally substituted at a substitutable position with one or more of $R_8$.

Compounds of Embodiment 41 are those of embodiment 40 wherein $R_{1-A}$ is aryl optionally substituted at a substitutable position with one or more of $R_8$;
wherein $R_8$ is halogen, —CN, —OH, —SO$_2$NH$_2$, —CO$_2$H, —CONH$_2$, —NH$_2$, —NH($C_1$-$C_6$ alkyl), —N($C_1$-$C_6$ alkyl)$_2$, —C(=NOH)NH$_2$, —C(=NH)NH$_2$, $C_1$-$C_6$ alkoxy, $C_1$-$C_6$ haloalkyl, $C_2$-$C_4$ alkenyl substituted with $C_1$-$C_3$ alkoxycarbonyl, or $C_1$-$C_6$ haloalkoxy.

Compounds of Embodiment 42 are those of embodiment 40 wherein is heteroaryl optionally substituted at a substitutable position with one or more of $R_8$;
wherein $R_8$ is halogen, —CN, —OH, —SO$_2$NH$_2$, —CO$_2$H, —NH$_2$, —CONH$_2$, —NH($C_1$-$C_6$ alkyl), —N($C_1$-$C_6$ alkyl)$_2$, —C(=NOH)NH$_2$, —C(=NH)NH$_2$, $C_1$-$C_6$ alkoxy, $C_1$-$C_6$ haloalkyl, $C_2$-$C_4$ alkenyl substituted with $C_1$-$C_3$ alkoxycarbonyl or N-hydroxyaminocarbonyl, or $C_1$-$C_6$ haloalkoxy.

Compounds of Embodiment 42-A include those of embodiment 40 wherein is phenyl or pyridyl, where each phenyl and pyridyl is substituted by one or two of $R_8$, where one $R_8$ is $C_1$-$C_6$ alkoxy, $C_1$-$C_6$ alkylamido, or mono- or di-($C_1$-$C_6$)alkylamino, and where the alkyl portion(s) of each is optionally substituted with $C_1$-$C_6$ alkoxy carbonyl, hydroxycarbonyl, aminocarbonyl, or N-hydroxyaminocarbonyl.

Compounds of Embodiment 42-B include those of embodiment 40 wherein is phenyl substituted by one or two of $R_8$, where one $R_8$ is cyano, halogen, —SO$_2$NH$_2$, —CONH$_2$, —C(=NOH)NH$_2$, —C(=NH)NH$_2$, $C_2$-$C_4$ alkenyl substituted with $C_1$-$C_3$ alkoxycarbonyl or N-hydroxyaminocarbonyl, or $C_1$-$C_2$ haloalkyl.

Compounds of Embodiment 42-C include those of embodiment 40 wherein is pyridyl substituted by one or two of $R_8$, where one $R_8$ is cyano, halogen, —SO$_2$NH$_2$, —CONH$_2$, —C(=NOH)NH$_2$, —C(=NH)NH$_2$, $C_2$-$C_4$ alkenyl substituted with $C_1$-$C_3$ alkoxycarbonyl or N-hydroxyaminocarbonyl, or $C_1$-$C_2$ haloalkyl. Compounds of Embodiment 42-D include those of embodiment 40 wherein is phenyl or pyridyl, where each phenyl and pyridyl is substituted by one or two of $R_8$, where one $R_8$ is $C_1$-$C_3$ alkoxy, $C_1$-$C_3$ alkylamido, or mono- or di-($C_1$-$C_3$)alkylamino, and where the alkyl portion(s) of each is optionally substituted with $C_1$-$C_3$ alkoxy carbonyl, hydroxycarbonyl, aminocarbonyl, or N-hydroxyaminocarbonyl.

Compounds of Embodiment 43 are those of embodiments 2-26 wherein is –OR$_9$ or —NHR$_9$;
wherein $R_9$ is $C_3$-$C_8$ cycloalkyl, aryl, heteroaryl, heterocyclyl, ($C_3$-$C_8$ cycloalkyl)$C_1$-$C_6$ alkyl, (aryl)$C_1$-$C_6$ alkyl, (heteroaryl)$C_1$-$C_6$ alkyl, or (heterocyclyl)$C_1$-$C_6$ alkyl, wherein each is optionally substituted at a substitutable position with one or more of halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, —CO$_2$($C_1$-$C_6$)alkyl or —CON(H)OH.

Compounds of Embodiment 44 are those of embodiments 2-28 wherein $R_1$ is $R_{1-B}$.

Compounds of Embodiment 45 are those of embodiment 44 wherein $R_1$ is —$R_X$—$R_Y$—$R_Z$—$R_W$, where
$R_X$ is a bond, —O—, —N($R_7$)—, or —C(O)—;
where $R_7$ is hydrogen or $C_1$-$C_6$ alkyl;
$R_Y$ is $C_3$-$C_8$ cycloalkyl, aryl, heteroaryl, or heterocyclyl, where each is optionally substituted with $R_8$;
$R_Z$ is a bond, $C_1$-$C_6$ alkylene, —O—, —O($C_1$-$C_4$ alkylene)-, —($C_1$-$C_4$ alkylene)O—, —N($R_7$)—, —($C_1$-$C_4$ alkylene)N($R_7$)—, —N($R_7$)($C_1$-$C_4$ alkylene)-, —C(O)—, —C(O)($C_1$-$C_4$ alkylene)-, —($C_1$-$C_4$ alkylene)C(O)—, —N($R_7$)C(O)—, —N($R_7$)C(O)O—, —C(O)N($R_7$)—, or —C(O)N($R_7$)($C_1$-$C_4$ alkylene)-; and
$R_W$ is $C_3$-$C_8$ cycloalkyl, aryl, heteroaryl, or heterocyclyl, each optionally substituted with $R_8$.

Compounds of Embodiment 46 are those of embodiment 45 wherein $R_1$ is —$R_X$—$R_Y$—$R_Z$—$R_W$, where
$R_X$ is a bond, —O—, —N($R_7$)—, or —C(O)—;
where $R_7$ is hydrogen or $C_1$-$C_6$ alkyl;
$R_Y$ is $C_3$-$C_8$ cycloalkyl, aryl, heteroaryl, or heterocyclyl, each optionally substituted with $R_8$;
$R_Z$ is a bond, $C_1$-$C_6$ alkylene, —C(O)—, —C(O)($C_1$-$C_4$ alkylene)-, or —C(O)N($R_7$)—; and
$R_W$ is $C_3$-$C_8$ cycloalkyl, aryl, heteroaryl, or heterocyclyl, each optionally substituted with $R_8$.

Compounds of Embodiment 47 are those of embodiment 45 wherein $R_1$ is —$R_X$—$R_Y$—$R_Z$—$R_W$, wherein
$R_X$ is a bond, —O—, —N($R_7$)—, or —C(O)—;
where $R_7$ is hydrogen or $C_1$-$C_6$ alkyl;
$R_Y$ is aryl, heteroaryl, or heterocyclyl, each optionally substituted with $R_8$;
$R_Z$ is a bond, $C_1$-$C_6$ alkylene, —O—, —O($C_1$-$C_4$ alkylene)-, —($C_1$-$C_4$ alkylene)O—, —N($R_7$)—, —($C_1$-$C_4$ alkylene)N($R_7$)—, —N($R_7$)($C_1$-$C_4$ alkylene)-, —C(O)—, —C(O)($C_1$-$C_4$ alkylene)-, —($C_1$-$C_4$ alkylene)C(O)—, —N($R_7$)C(O)—, —N($R_7$)C(O)O—, —C(O)N($R_7$)—, or —C(O)N($R_7$)($C_1$-$C_4$ alkylene)-; and
$R_W$ is $C_3$-$C_8$ cycloalkyl, aryl, heteroaryl, or heterocyclyl, each optionally substituted with $R_8$.

Compounds of Embodiment 48 are those of embodiment 47 wherein $R_1$ is —$R_X$—$R_Y$—$R_Z$—$R_W$, wherein
$R_X$ is a bond, —O—, —N($R_7$)—, or —C(O)—;
where $R_7$ is hydrogen or $C_1$-$C_6$ alkyl;
$R_Y$ is heteroaryl or heterocyclyl, each optionally substituted with $R_8$;
$R_Z$ is a bond, $C_1$-$C_6$ alkylene, —O—, —O($C_1$-$C_4$ alkylene)-, —($C_1$-$C_4$ alkylene)O—, —N($R_7$)—, —($C_1$-$C_4$ alkylene)N($R_7$)—, —N($R_7$)($C_1$-$C_4$ alkylene)-, —C(O)—, —C(O)($C_1$-$C_4$ alkylene)-, —($C_1$-$C_4$ alkylene)C(O)—, —N($R_7$)C(O)—, or —C(O)N($R_7$)—; and
$R_W$ is $C_3$-$C_8$ cycloalkyl, aryl, heteroaryl, or heterocyclyl, each optionally substituted with $R_8$.

Compounds of Embodiment 49 are those of embodiments 44-48 wherein $R_Y$ is piperidinyl, piperazinyl, or pyridinyl, each optionally substituted with $R_8$.

Compounds of Embodiment 50 are those of any of embodiments 44-49 wherein $R_W$ is phenyl, piperidinyl, piperazinyl, morpholinyl, or pyridinyl, each optionally substituted with $R_8$.

Compounds of Embodiment 51 are those of any of embodiments 44-50 wherein -A-$R_2$ is hydrogen.

Compounds of Embodiment 52 are those of any of embodiments 44-51 wherein $R_3$ is hydrogen or halogen.

Compounds of Embodiment 53 are those of embodiment 52 wherein $R_3$ is hydrogen.

Compounds of Embodiment 54 are those of embodiment 1 where the compounds have any one of formulae I-C, I-D, or I-E:

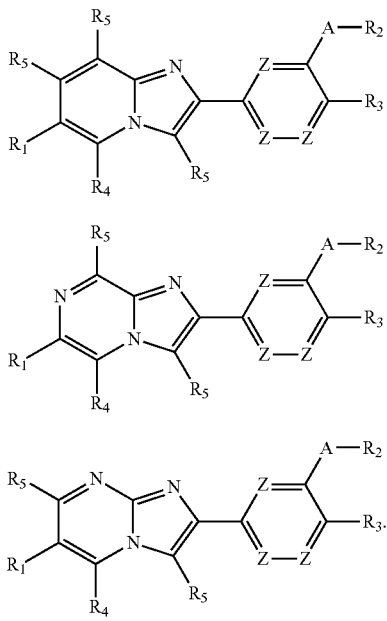

I-C

I-D

I-E

Compounds of Embodiment 55 are those of embodiment 54 wherein each $R_5$ is independently hydrogen, halogen, $C_1$-$C_6$ alkyl, $C_3$-00 cycloalkyl, or aryl optionally substituted at a substitutable position with one or more of $R_{10}$;
wherein $R_{10}$ is halogen, —CN, —OH, —NO$_2$, —NH$_2$, —NH($C_1$-$C_6$ alkyl), —N($C_1$-$C_6$ alkyl)$_2$, $C_1$-$C_6$ alkoxy, $C_1$-$C_6$ haloalkyl, $C_1$-$C_6$ alkoxy, $C_1$-$C_6$ haloalkoxy, —CO$_2$H, —CO$_2$($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, —CON(H)OH, —NHCO($C_1$-$C_6$ alkyl), or —NHCO$_2$($C_1$-$C_6$ alkyl).

Compounds of Embodiment 56 are those of embodiment 55 wherein each $R_5$ is independently hydrogen, halogen, or $C_1$-$C_6$ alkyl.

Compounds of Embodiment 57 are those of embodiment 56 wherein each $R_5$ is independently hydrogen.

Compounds of Embodiment 58 are those of any of embodiments 54-57 wherein $R_4$ is hydrogen, halogen, or $C_1$-$C_6$ alkyl.

Compounds of Embodiment 59 are those of embodiment 58 wherein $R_4$ is hydrogen.

Compounds of Embodiment 60 are those of any of embodiments 54-59 wherein each Z is $CR_6$.

Compounds of Embodiment 61 are those of embodiment 60 wherein each $R_6$ is independently hydrogen, halogen, —CN, —OH, —NH$_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, or $C_1$-$C_6$ haloalkoxy.

Compounds of Embodiment 62 are those of embodiment 61 wherein each $R_6$ is independently hydrogen, halogen, or $C_1$-$C_6$ alkyl.

Compounds of Embodiment 63 are those of embodiment 62 wherein each $R_6$ is independently hydrogen.

Compounds of Embodiment 64 are those of any of embodiments 54-63 wherein $R_3$ is hydrogen, halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or $C_3$-$C_8$ cycloalkyl.

Compounds of Embodiment 65 are those of embodiment 64 wherein $R_3$ is hydrogen, halogen, —CN, $C_1$-$C_6$ alkyl, $C_1$-$C_6$ haloalkyl, $C_1$-$C_6$ alkoxy, $C_1$-$C_6$ haloalkoxy, or $C_3$-$C_8$ cycloalkyl.

Compounds of Embodiment 66 are those of embodiment 65 wherein $R_3$ is $C_1$-$C_6$ alkyl, $C_1$-$C_6$ haloalkyl, or $C_1$-$C_6$ haloalkoxy.

Compounds of Embodiment 67 are those of embodiment 66 wherein $R_3$ is $C_1$-$C_6$ alkyl or $C_1$-$C_6$ haloalkyl.

Compounds of Embodiment 68 are those of embodiment 67 wherein $R_3$ is methyl or trifluoromethyl.

Compounds of Embodiment 69 are those of any of embodiments 54-68 wherein A is a bond, —N($R_7$)—, —N($R_7$)C(O)—, —C(O)N($R_7$)—, or —S(O)$_2$N($R_7$)—.

Compounds of Embodiment 70 are those of embodiment 69 wherein A is —N($R_7$)C(O)—.

Compounds of Embodiment 71 are those of any of embodiments 54-70 wherein $R_2$ is $C_1$-$C_6$ alkyl, $C_1$-$C_6$ haloalkyl, $C_3$-$C_8$ cycloalkyl, aryl, heteroaryl, ($C_3$-$C_8$ cycloalkyl)$C_1$-$C_6$ alkyl, (aryl)$C_1$-$C_6$ alkyl, or (aryloxy)$C_1$-$C_6$ alkyl, wherein each alkyl, cycloalkyl, or aryl group is optionally substituted at a substitutable position with one or more of $R_{10}$.

Compounds of Embodiment 71 are those of embodiment 72 wherein $R_2$ is $C_1$-$C_6$ alkyl or $C_1$-$C_6$ haloalkyl.

Compounds of Embodiment 73 are those of embodiment 72 wherein $R_2$ is $C_1$-$C_6$ alkyl. Compounds of Embodiment 74 are those of embodiment 73 wherein $R_2$ is t-butyl. Compounds of Embodiment 75 are those of any of embodiments 54-74, wherein -A-$R_2$ is —N($R_7$)C(O)($C_1$-$C_6$ alkyl).

Compounds of Embodiment 76 are those of any of embodiments 54-74 wherein -A-$R_2$ is —NHC(O)(t-butyl).

Compounds of Embodiment 77 are those of any of embodiments 54-76 wherein $R_1$ is hydrogen, halogen, —NH($C_1$-$C_6$ alkyl), —N($C_1$-$C_6$ alkyl)$_2$, $C_1$-$C_6$ alkyl, $C_1$-$C_6$ alkoxy, —S($C_1$-$C_6$ alkyl), or —SO$_2$($C_1$-$C_6$ alkyl), wherein each alkyl group is optionally substituted at a substitutable position with one or more of $R_8$;
wherein $R_8$ is halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), —S($C_1$-$C_6$ alkyl), —CO$_2$H, —CO$_2$ ($C_1$-$C_6$ alkyl), —C(O)($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, —CON(H)OH, —NHCO($C_1$-$C_6$ alkyl), —C(=NOH)NH$_2$, —C(=NH)NH$_2$, or —NHCO$_2$($C_1$-$C_6$ alkyl) wherein each alkyl, alkenyl, alkynyl, alkoxy is optionally substituted at a substitutable carbon with —CO$_2$($C_1$-$C_6$)alkyl or —CONH(OH).

Compounds of Embodiment 78 are those of any of embodiments 54-76 wherein $R_1$ is $C_3$-$C_8$ cycloalkyl, aryl, heteroaryl, or heterocyclyl, wherein each cycloalkyl, aryl, heteroaryl, or heterocyclyl group is optionally substituted at a substitutable position with one or more of $R_8$.
wherein $R_8$ is halogen, —CN, —OH, —SH, —NO$_2$, —NH$_2$, —NH($C_1$-$C_6$ alkyl), —N($C_1$-$C_6$ alkyl)$_2$, —NH ($C_1$-$C_6$ alkyl)-OH, —NH($C_1$-$C_6$ alkyl)-($C_1$-$C_6$ alkoxy), —$C_1$-$C_6$ alkoxy-OH, —$C_1$-$C_6$ alkoxy-($C_1$-$C_6$ alkoxy), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, hydroxy($C_1$-$C_6$ alkyl), ($C_1$-$C_6$ alkoxy)$C_1$-$C_6$ alkyl, amino($C_1$-$C_6$ alkyl), —S($C_1$-$C_6$ alkyl), —CO$_2$H, —CO$_2$($C_1$-$C_6$ alkyl), —C(O)($C_1$-$C_6$ alkyl), —SO$_2$($C_1$-$C_6$ alkyl), —CONH$_2$, —CONH($C_1$-$C_6$ alkyl), —CON($C_1$-$C_6$ alkyl)$_2$, —CON(H)OH, —NHCO($C_1$-$C_6$ alkyl), —C(=NOH)NH$_2$, —C(=NH) NH$_2$, or —NHCO$_2$($C_1$-$C_6$ alkyl) wherein each alkyl, alkenyl, alkynyl, alkoxy is optionally substituted at a substitutable carbon with —CO$_2$($C_1$-$C_6$)alkyl or —CONH(OH).

Compounds of Embodiment 79 are those of embodiment 78 wherein $R_1$ is aryl or heteroaryl, wherein each aryl or heteroaryl group is optionally substituted at a substitutable position with one or more of $R_8$.

Compounds of Embodiment 80 are those of embodiment 79 wherein $R_1$ is aryl optionally substituted at a substitutable position with one or more of $R_8$;
  wherein $R_8$ is halogen, —CN, —OH, —NH$_2$, —NH($C_1$-$C_6$ alkyl), —N($C_1$-$C_6$ alkyl)$_2$, $C_1$-$C_6$ alkoxy, $C_1$-$C_6$ haloalkyl, $C_1$-$C_6$ alkoxy, —C(=NOH)NH$_2$, —C(=NH)NH$_2$, or $C_1$-$C_6$ haloalkoxy.

Compounds of Embodiment 81 are those of any of embodiments 54-76 wherein $R_1$ is –OR$_9$ or —NHR$_9$;
  wherein $R_9$ is $C_3$-$C_8$ cycloalkyl, aryl, heteroaryl, heterocyclyl, ($C_3$-$C_8$ cycloalkyl)$C_1$-$C_6$ alkyl, (aryl)$C_1$-$C_6$ alkyl, (heteroaryl)$C_1$-$C_6$ alkyl, or (heterocyclyl)$C_1$-$C_6$ alkyl, wherein each is optionally substituted at a substitutable position with one or more of halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, —CO$_2$($C_1$-$C_6$)alkyl or —CONH(OH).

Compounds of Embodiment 82 are those of any of embodiments 54-76 wherein $R_1$ is —R$_X$—R$_Y$—R$_Z$—R$_W$, wherein
  $R_X$ is a bond, —O—, —N(R$_7$)—, or —C(O)—;
    where $R_7$ is hydrogen or $C_1$-$C_6$ alkyl;
  $R_Y$ is $C_3$-$C_8$ cycloalkyl, aryl, heteroaryl, or heterocyclyl, each optionally substituted with $R_8$;
  $R_Z$ is a bond, $C_1$-$C_6$ alkylene, —O—, —O($C_1$-$C_4$ alkylene)-, —($C_1$-$C_4$ alkylene)O—, —N(R$_7$)—, —($C_1$-$C_4$ alkylene)N(R$_7$)—, —N(R$_7$)($C_1$-$C_4$ alkylene)-, —C(O)—, —C(O)($C_1$-$C_4$ alkylene)-, —($C_1$-$C_4$ alkylene)C(O)—, —N(R$_7$)C(O)—, —N(R$_7$)C(O)O—, —C(O)N(R$_7$)—, or —C(O)N(R$_7$)($C_1$-$C_4$ alkylene)-; and
  $R_W$ is $C_3$-$C_8$ cycloalkyl, aryl, heteroaryl, or heterocyclyl, each optionally substituted with $R_8$.

Compounds of Embodiment 83 are those of embodiments 2-26 wherein $R_{1-A}$ is NR$_9$R$_{11}$ wherein
  $R_9$ is $C_3$-$C_8$ cycloalkyl-C(O)—, aryl-C(O)—, heteroaryl-C(O)—, heterocyclyl-C(O)—, aryl-SO$_2$—, or heteroaryl-SO$_2$—, wherein each is optionally substituted at a substitutable position with one or more of halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkynyl, $C_1$-$C_6$ alkoxy, $C_1$-$C_6$ haloalkyl, $C_1$-$C_6$ haloalkoxy, —CO$_2$($C_1$-$C_6$)alkyl, —SO$_2$NH$_2$, —CONH$_2$, —C(=NOH)NH$_2$, —C(=NH)NH$_2$, $C_2$-$C_6$ alkenyl optionally substituted with $C_1$-$C_3$ alkoxycarbonyl, or —CON(H)OH.

Compounds of Embodiment 84 are those of embodiments 2-26 wherein $R_{1-A}$ is NHR$_9$ wherein
  $R_9$ is $C_5$-$C_6$ heterocyclyl-C(O)—, pyridylcarbonyl, benzoyl, benzenesulfonyl, wherein each is optionally substituted at a substitutable position with one or more of halogen, —CN, —OH, —SH, —NO$_2$, —NH$_2$, —NH ($C_1$-$C_6$ alkyl), —N($C_1$-$C_6$ alkyl)$_2$, $C_1$-$C_6$ alkyl, $C_2$-$C_6$ alkynyl, $C_1$-$C_6$ alkoxy, $C_1$-$C_6$ haloalkyl, $C_1$-$C_6$ haloalkoxy, —CO$_2$($C_1$-$C_6$)alkyl, —SO$_2$NH$_2$, —CONH$_2$, —C(=NOH)NH$_2$, —C(=NH)NH$_2$, $C_2$-$C_6$ alkenyl optionally substituted with $C_1$-$C_3$ alkoxycarbonyl, or —CON(H)OH.

Compounds of Embodiment 85 are those of embodiments 2-26 wherein $R_{1-A}$ is NHR$_9$ wherein
  $R_9$ is benzoyl optionally substituted at a substitutable position with one or more of halogen, —CN, —OH, —SH, —NO$_2$, —NH$_2$, —NH($C_1$-$C_6$ alkyl), —N($C_1$-$C_6$ alkyl)$_2$, $C_1$-$C_6$ alkyl, $C_2$-$C_6$ alkynyl, $C_1$-$C_6$ alkoxy, $C_1$-$C_6$ haloalkyl, $C_1$-$C_6$ haloalkoxy, —CO$_2$($C_1$-$C_6$) alkyl, —SO$_2$NH$_2$, —CONH$_2$, —C(=NOH)NH$_2$, —C(=NH)NH$_2$, $C_2$-$C_6$ alkenyl optionally substituted with $C_1$-$C_3$ alkoxycarbonyl, or —CON(H)OH.

Compounds of Embodiment 86 are those of embodiments 2-26 wherein $R_{1-A}$ is NHR$_9$ and
  $R_9$ is benzoyl optionally substituted at a substitutable position with one or more of halogen, —CN, —NH$_2$, —NH ($C_1$-$C_6$ alkyl), —N($C_1$-$C_6$ alkyl)$_2$, $C_1$-$C_6$ alkyl, $C_2$-$C_6$ alkynyl, $C_1$-$C_6$ alkoxy, $C_1$-$C_6$ haloalkyl, $C_1$-$C_6$ haloalkoxy, —CO$_2$($C_1$-$C_6$)alkyl, —SO$_2$NH$_2$, —CONH$_2$, —C(=NOH)NH$_2$, —C(=NH)NH$_2$, $C_2$-$C_6$ alkenyl optionally substituted with $C_1$-$C_3$ alkoxycarbonyl, or —CON(H)OH.

Compounds of Embodiment 87 are those of any of embodiments 39-43 or 83-86 wherein A is —CONH— and $R_2$ is
  $C_1$-$C_6$ alkyl or
  $C_1$-$C_6$ alkyl optionally substituted with 1 or 2 of $R_{10}$;
    wherein $R_{10}$ is halogen, —CN, —OH, —NO$_2$, —NH$_2$, —NH($C_1$-$C_3$ alkyl), —N($C_1$-$C_3$ alkyl)$_2$, $C_1$-$C_3$ alkyl, $C_2$-$C_4$ alkenyl, $C_2$-$C_3$ alkynyl, $C_1$-$C_3$ alkoxy, $C_1$-$C_2$ haloalkyl, $C_1$-$C_3$ alkoxy, hydroxy($C_1$-$C_3$ alkyl), ($C_1$-$C_3$ alkoxy)$C_1$-$C_3$ alkyl, amino($C_1$-$C_3$ alkyl), —CO$_2$H, —CO$_2$($C_1$-$C_3$ alkyl), —SO$_2$($C_1$-$C_3$ alkyl), —CONH$_2$, —CONH($C_1$-$C_3$ alkyl), —CON($C_1$-$C_3$ alkyl)$_2$, —CON(H)OH, —NHCO($C_1$-$C_3$ alkyl), or —NHCO$_2$($C_1$-$C_6$ alkyl).

The disclosure also provides pharmaceutical compositions comprising a compound according to any one of embodiments 1-82 1-82 and a pharmaceutically acceptable carrier, solvent, adjuvant or diluent.

Further provided herein are methods for inhibiting hedgehog pathway signaling in a sample, comprising contacting the sample with one or more compounds according to any one of embodiments 1-82. More specifically, the disclosure provides methods of treating cancer, the methods comprising administering to a subject in need of such treatment an effective amount of one or more compounds according to any one of embodiments 1-82. Specific cancers include basal cell carcinoma, lung cancer, breast cancer, pancreatic cancer, and prostate cancer.

Further provided herein are methods of inhibiting angiogenesis. These methods comprise administering to a subject in need of such treatment an effective amount of one or more compounds according to any one of embodiments 1-82.

Therapeutics Applications

The methods, compounds, and pharmaceutical compositions of the present invention relate to inhibiting activation of the Hedgehog signaling pathway. Such Hh signaling pathway activation may be dependent on Hh ligand or occur independently of Hh ligand. The methods, compounds, and pharmaceutical compositions of the present invention may be used to regulate or inhibit proliferation and/or differentiation of cells, either in vitro or in vivo; examples of such application are the prevention of the growth of hyperproliferative cells and formation of tissue from stem cells.

In certain embodiments, compounds and pharmaceutical compositions described in the disclosure are useful in inhibiting aberrant or proliferative growth states due to Patched loss of function phenotypes, Smoothened gain of function phenotypes, Gli gain of function phenotypes, and Hh ligand over expression phenotypes. In certain embodiments, compounds and pharmaceutical compositions described in the disclosure are useful in inhibiting Hedgehog signaling in normal or tumor cells or tissues that do not have mutations that activate the Hedgehog pathway.

One aspect of the disclosure relates to inhibiting or decreasing Hedgehog pathway signaling activity in a sample, either in vitro or in vivo, utilizing a compound or pharmaceutical composition described in this disclosure. The sample may be in one of many forms. Examples of the sample, as used herein, include, without limitation Hedgehog pathway components in a recombinant cellular system, in a purified sample, in a partially purified sample, in cultured cells, in cellular extracts, in biopsied cells and extracts thereof, in bodily fluids (e.g. blood, serum, urine, feces, saliva, semen, tears) and extracts thereof. For example, a method of the invention can involve contacting a cell, in vitro or in vivo, with a Smoothened antagonist.

In certain embodiments, compounds, and pharmaceutical compositions of the present invention are antagonist that inhibit activation of Hedgehog signaling by binding to Smoothened. In certain embodiments, proteins in the Hedgehog signaling pathway that are downstream of Smoothened (e.g., Gli) are also inhibited in a cell, either in vitro or in vivo, in addition to the inhibition of Smoothened. For example, the synthesis, expression, regulatory state, stabilization, cellular location, and/or activity of Gli protein(s) may be inhibited.

Another embodiment of the disclosure provides for treating a patient by administering to the patient a compound or pharmaceutical composition described in the disclosure. The treated patient may have a disorder, show symptoms of a disorder, or be at risk of developing a disorder or recurrence of a disorder. Treatment of the patient can cure, remedy, or heal the patient of the disorder. Alternatively, treatment of the patient can prevent, alleviate, diminish, palliate or improve the disorder. Alternatively, treatment of the patient can affect or alter the symptoms of the disorder or predisposition toward the disorder. The disorders that can be treated are those disorders in which inhibition of the Hedgehog signaling pathway inhibits progression of the disorder. For example, diseased cells or tissues can be directly killed or inhibited as a result of Hedgehog signaling pathway inhibition. Alternatively, Hedgehog signaling pathway inhibition can lead to stabilization of proteins that in turn kill or inhibit diseased cells or tissues. Alternatively, Hedgehog signaling pathway inhibition can inhibit the ability of other proteins to activate diseased cells or tissues.

Relevant, non-limiting, disorders that can be treated by administering to the patient a compound or pharmaceutical composition described in the disclosure include: proliferative diseases, especially cancers; skin disorders, e.g. dermatosis such as atopic dermatitis and psoriasis; bone overgrowth disorders, e.g. acromegaly and macrocephaly; and vascular proliferative disorders. In addition, the methods, compounds and compositions provided herein, have therapeutic and cosmetic applications including regulation of bone and cartilage formation and repair, regulation of neural tissues, and regulation of hematopoietic function. Compounds of the invention are also useful in the treatment of liver fibrosis. Applicable disorders also include any disorders whose activity can be regulated by inhibiting the Hedgehog signaling pathway. Applicable disorders also include those in which the existence, maintenance, or progression of the disorder is mediated by Patched loss of function phenotypes, Smoothened gain of function phenotypes, Gli gain of function phenotypes, and Hh ligand over expression phenotypes.

The compounds and pharmaceutical compositions described in the disclosure are particularly useful for the treatment of cancer. Cancer, as defined herein, describes a disorder characterized by uncontrolled or deregulated cellular proliferation, abnormal cellular differentiation, an abnormal ability to invade surrounding tissue, and an inappropriate ability to establish new growth at ectopic sites. Cancer, as defined herein, refers to both primary and metastatic cancers. Treatable cancers include both solid tumors and hematologic (blood) tumor types, and the tumors may occur anywhere in the body including skin, tissues, organs, bone, cartilage, blood, and vessels. Treatable cancers can be in either adults or children.

In some embodiments, the compound or pharmaceutical composition described in the disclosure is used to treat a patient either experiencing or being at risk of developing a recurrence in a cancer. Non-limiting examples of cancers that can be treated by the compounds and pharmaceutical compositions described in the disclosure include acute lymphoblastic leukemia, acute myeloid leukemia, adrenocortical carcinoma, AIDS-related cancers, anal cancer, appendix cancer, astrocytomas, atypical teratoid/rhabdoid tumor, basal cell carcinoma, bile duct cancer, bladder cancer, breast cancer, bronchial tumors, Burkitt lymphoma, carcinoid tumors, cervical cancer, chordoma, chronic lymphocytic leukemia, chronic myelogenous leukemia, chronic myeloproliferative disorders, colon cancer, colorectal cancer, craniopharyngioma, cutaneous t-cell lymphoma, endometrial cancer, ependymoblastoma, ependymoma, esophageal cancer, esthesioneuroblastoma, Ewing sarcoma family of tumors, extracranial germ cell tumor, extragonadal germ cell tumor, gallbladder cancer, gastric (stomach) cancer, gastrointestinal stromal tumor (GIST), gestational trophoblastic tumor, glioma (adult), glioma (childhood brain stem), hairy cell leukemia, head and neck cancer, heart cancer, hepatocellular (liver) cancer, Hodgkin lymphoma, hypopharyngeal cancer, intraocular melanoma, islet cell tumors, Kaposi sarcoma, kidney (renal cell) cancer, Langerhans cell histiocytosis, laryngeal cancer, lip and oral cavity cancer, liver cancer, medulloblastoma, medulloepithelioma, melanoma, Merkel cell carcinoma, mesothelioma, metastatic squamous neck cancer with occult primary, mouth cancer, multiple endocrine neoplasia syndromes, multiple myeloma, mycosis fungoides, myelodysplastic/myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma and malignant fibrous histiocytoma of bone, ovarian cancer, ovarian epithelial cancer, ovarian germ cell tumor, pancreatic cancer, papillomatosis, parathyroid cancer, penile cancer, pharyngeal cancer, pineal parenchymal tumors, pineoblastoma, pituitary tumor, pleuropulmonary blastoma, primary central nervous system (CNS) lymphoma, prostate cancer, rectal cancer, renal cell (kidney) cancer, retinoblastoma, rhabdomyosarcoma, salivary gland cancer, Sezary syndrome, small cell lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, transitional cell cancer of the renal pelvis and ureter, urethral cancer, uterine sarcoma, vaginal cancer, vulvar cancer, Waldenström macroglobulinemia, and Wilms tumor.

In some embodiments, the compound or pharmaceutical composition described in the disclosure is used to treat a patient either experiencing or being at risk of developing a recurrence in a cancer selected from the group consisting of basal cell carcinoma, breast cancer, colorectal cancer, gastric cancer, glioblastoma, a hematological cancer, liver cancer, lung cancer, medulloblastoma, melanoma, ovarian cancer, pancreatic cancer, and prostate cancer.

In some embodiments and for certain disorders, the Smoothened antagonist described in the disclosure is used to treat the disorder in combination with another therapeutic agent already approved or recognized by appropriate governing authorities as suitable for treatment of the disorder. The Smoothened antagonist of the disclosure may be administered in dosage form either separately or in a single combined dosage with the other therapeutic. When the Smoothened antagonist of the disclosure and other agent are administered separately, they may be administered simultaneously or the Smoothened antagonist may be administered first or the other therapeutic agent may be administered first.

Pharmaceutical Compositions

In another aspect, the present disclosure provides compositions comprising one or more of compounds as described above with respect to formula (I) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

Definitions

The following terms and expressions used herein have the indicated meanings.

Terms used herein may be preceded and/or followed by a single dash, "—", or a double dash, "═", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$ alkoxycarbonyloxy and —OC(O)$C_1$-$C_6$ alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means an aromatic hydrocarbon ring system containing at least one aromatic ring, e.g., phenyl (i.e., monocyclic aryl), or a bicyclic ring system containing at least one aromatic hydrocarbon ring, e.g., phenyl, or an aromatic bicyclic ring containing only carbon atoms in the aromatic portion of the ring system. Preferred aryl groups have from 6-14 ring members, and more preferably from 6-10 ring members. Examples of aryl groups include, for example, phenyl, naphthyl, anthracenyl, azulenyl 1,2,3,4-tetrahydronaphthalenyl, indenyl, 2,3-dihydroindenyl, and biphenyl. Preferably, the bicyclic aryl is an azulenyl, naphthyl, or a phenyl fused to a monocyclic cycloalkyl, a monocyclic cycloalkenyl, or a monocyclic heterocyclyl. More preferred aryl groups are phenyl and naphthyl groups. Even more preferred aryl groups are phenyl. The bicyclic aryl is attached to the parent molecular moiety through any carbon atom contained within the aromatic portion of the ring system, e.g., the phenyl portion of the bicyclic system, or any carbon atom within the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The aryl groups of the invention may be substituted with various groups as provided herein. Thus, any carbon atom present within an aryl ring system and available for substitution may be further bonded to a variety of ring substituents, such as, for example, halogen, OH, $NO_2$, CN, $NH_2$, $C_1$-$C_8$ alkyl, $C_1$-$C_8$ alkoxy, $NH(C_1$-$C_8$ alkyl), $N(C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$)alkoxy, oxo, amino($C_1$-$C_8$)alkyl, mono- and di($C_1$-$C_8$ alkyl)amino($C_1$-$C_8$) alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, $C_1$-$C_8$ aminosulfonyl.

An "aralkyl" or "arylalkyl" group comprises an aryl group as defined herein covalently attached to an alkyl group, either of which independently is optionally substituted. Preferably, the aralkyl group is aryl($C_1$-$C_6$)alkyl, including, without limitation, benzyl, phenethyl, and naphthylmethyl. As used herein, the terms "aralkyl" and "arylalkyl" are interchangeable.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. Preferred heteroaryl groups have from 5-14 ring members where from 1-4 of the ring members are hetero atoms selected from the group consisting of O, N, and S, the remaining ring atoms being C. More preferred heteroaryl groups have from 5-10 ring members where from 1-4 of the ring members are hetero atoms selected from the group consisting of O, N, and S, the remaining ring atoms being C.

Examples of aryl groups include, for example, phenyl, naphthyl, anthracenyl, azulenyl 1,2,3,4-tetrahydronaphthalenyl, indenyl, 2,3-dihydroindenyl, and biphenyl. Even more preferred heteroaryl groups are monocyclic heteroaryl groups having a 5- or 6-membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The heteroaryl groups of the invention may be substituted with various groups as provided herein. Thus, any carbon atom present within an heteroaryl ring system and available for substitution may be further bonded to a variety of ring substituents, such as, for example, halogen, OH, $NO_2$, CN, $NH_2$, $C_1$-$C_8$ alkyl, $C_1$-$C_8$ alkoxy, NH($C_1$-$C_8$ alkyl), N($C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$) alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, $C_1$-$C_8$ aminosulfonyl.

The terms "heterocyclyl" and "heterocycloalkyl" as used herein, are interchangeable and mean a monocyclic heterocycle or a bicyclic heterocycle. Heterocycloalkyl aryl groups of the invention have from 3-14 ring members where from 1-4 of the ring members are hetero atoms selected from the group consisting of O, N, and S, the remaining ring atoms being C. More preferred heterocycloalkyl groups have from 5-10 ring members where from 1-4 of the ring members are hetero atoms selected from the group consisting of O, N, and S, the remaining ring atoms being C. Thus, the monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy protecting group" refers to a group that prevents or blocks the hydroxy from taking part in a subsequent reaction until the protecting group is removed. Examples of hydroxy protecting groups include acetyl, allyl, benzoyl, benzyl, β-methoxyethoxymethyl, methoxymethyl, dimethoxytrityl[bis-(4-methoxyphenyl)phenylmethyl], methoxytrityl[(4-methoxyphenyl)diphenylmethyl), p-methoxybenzyl ether, methylthiomethyl, pivaloyl, tetrahydropyranyl, triphenylmethyl, silyl (e.g., trimethylsilyl, t-butyldimethylsilyl, t-butyldiphenylsilyl, tri-1-propylsilyloxymethyl, and triisopropylsilyl). Other examples include alkyl groups such as methyl and t-butyl, and other ethers, such as ethoxyethyl.

The term "nitro" as used herein, means a —$NO_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R', —C(R')=C(R')$_2$, —C≡C—R', —OR', —SR'", —S(O)R'", —$SO_2$N(R")$_2$, —$SO_2$N(R")$_2$, —N(R")$_2$, —NR"C(O)R', —NR"C(O)N(R")$_2$, —NR"$CO_2$R'", —O—$CO_2$R", —OC(O)N(R")$_2$, —C—C(O)R', —$CO_2$R', —C(O)—C(O)R', —C(O)R', —C(O)N(R")$_2$, —C(=NR")—N(R")$_2$, —C(=NR")—OR', —N(R")—N(R")$_2$, —N(R")C(=NR")—N(R")$_2$, —NR"$SO_2$R", —NR"$SO_2$N(R"), —P(O)(R")$_2$, —P(O)(R')$_2$, —O—P(O)—OR', and —P(O)(NR")—N(R")$_2$, wherein R' is an optionally substituted aliphatic or aryl group, and R' and R" are as defined above, or two adjacent substituents, taken together with their intervening atoms, form a 5- to 6-membered unsaturated or partially unsaturated ring having 0-3 ring atoms selected from the group consisting of N, O, and S.

A non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R')$_2$, =N—N(R")$_2$, =N—OR', =N—NHC(O)R', =N—NHCO$_2$R'", =N—NHSO$_2$R", or =N—R' where each R', R", and R' is as defined above. For the purposes of clarity, the term "substituted aliphatic" refers to an aliphatic group having at least one non-aliphatic substituent.

Suitable substituents on a substitutable nitrogen atom of a heteroaryl or heterocyclic ring include —R', —N(R')$_2$, —C(O)R', —$CO_2$R', —C(O)—C(O)R', —C(O)CH$_2$C(O)R', —$SO_2$R', —$SO_2$N(R')$_2$, —C(=S)N(R')$_2$, —C(=NH)—N(R')$_2$, and —NR'$SO_2$R'; wherein each R' is as defined above.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. By way of example, the compounds of formula (I) wherein $R^{3a}$ is hydroxy can have an R or S configuration at the carbon atom bearing $R^{3a}$. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present disclosure can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Methods of Preparation

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

General Procedure
Representative synthetic procedures for the preparation of compounds of the disclosure are outlined below in following schemes. Unless otherwise indicated, $R_1$, $R_2$, $R_3$, $R_5$-$R_{12}$, X, and Y, and carry the definitions set forth above in connection with formula (I).
Scheme 1
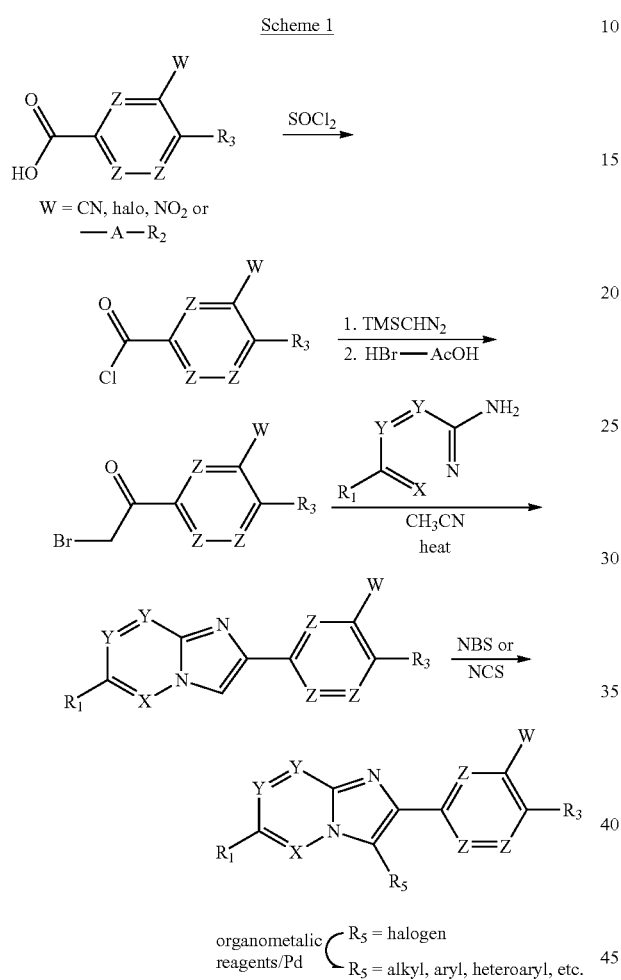
Scheme 2
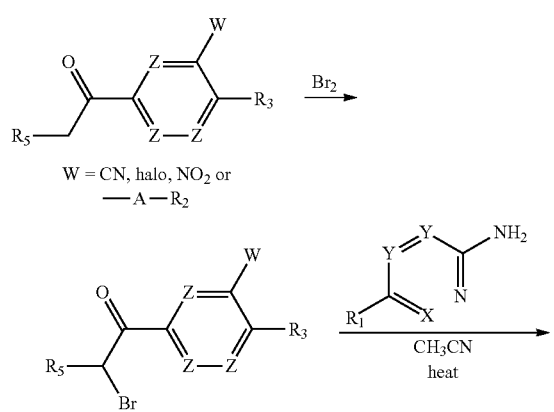
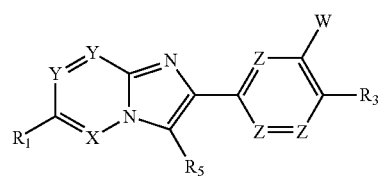
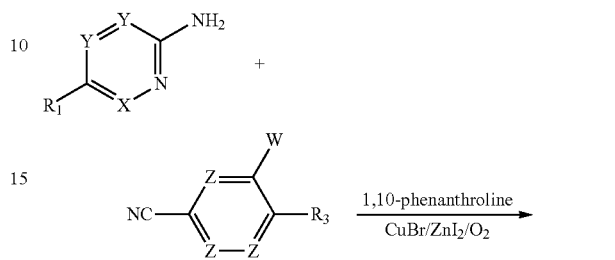
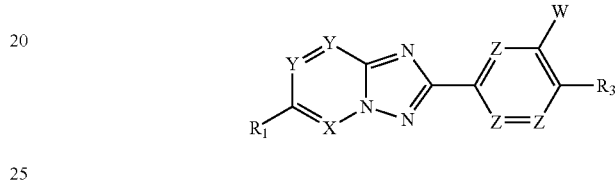
Scheme 3
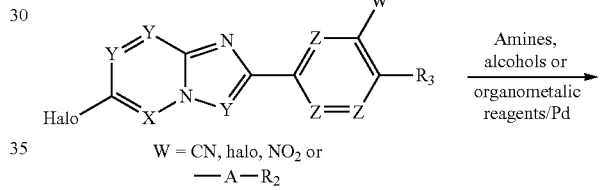
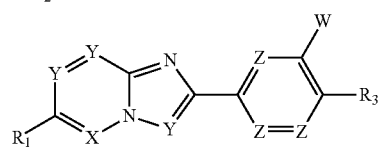
$R^1$ = Amino, CN, alkyl, aryl, alkoxy, heteroaryl, etc.
Scheme 4
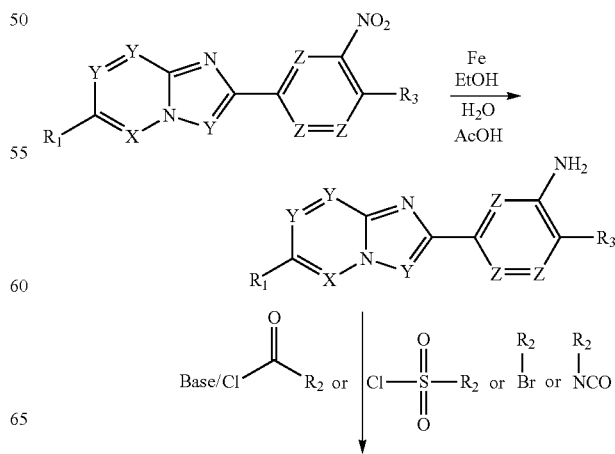

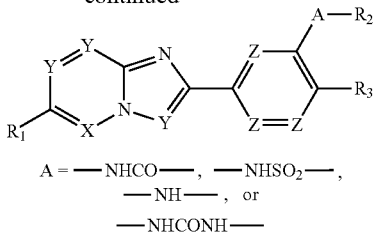

A = —NHCO—, —NHSO₂—,
—NH—, or
—NHCONH—

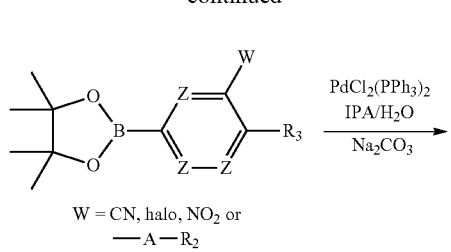

W = CN, halo, NO₂ or
—A—R₂

Scheme 5

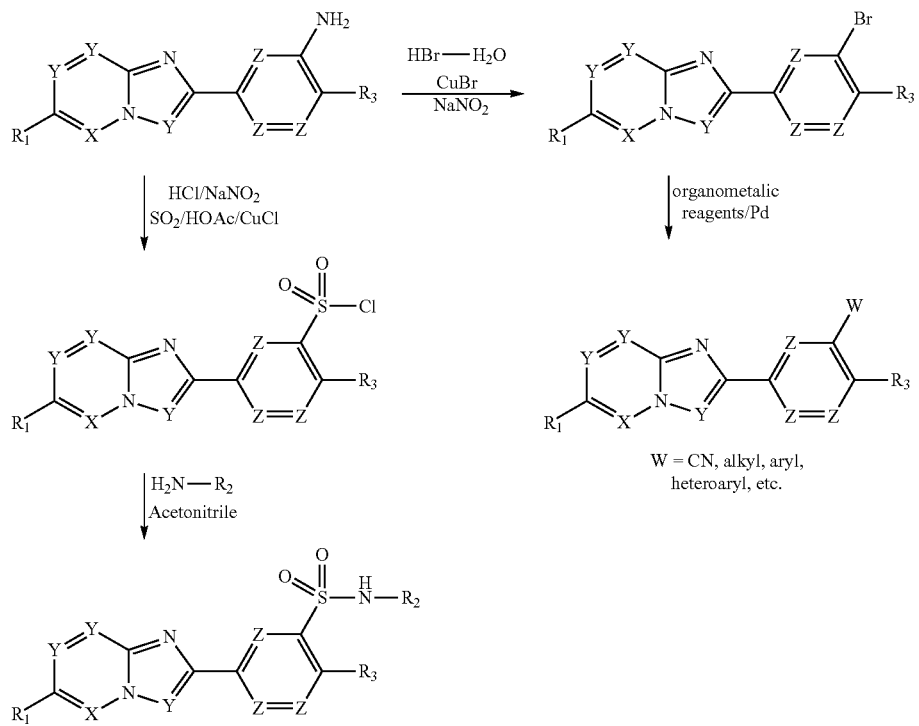

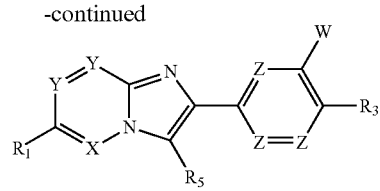

W = CN, alkyl, aryl, heteroaryl, etc.

Scheme 6

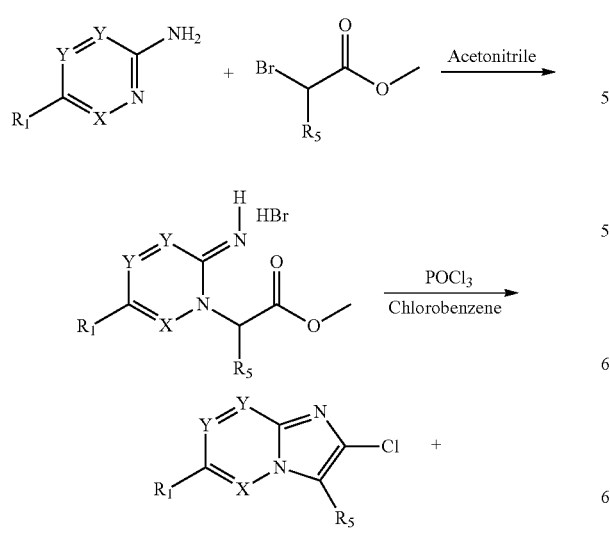

EXAMPLES

The preparation and utility of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Compound identity and purity confirmations are performed by LC/UV/MS using a Waters Micromass ZQ™ Detector and Waters 2695 Separations Module and Waters 2487 Dual I Absorbance Detector (Waters Corporation, Milford, Mass.). The diode array detector wavelength is 254 nm, and the MS is operated in positive electrospray ionization mode. The samples are maintained at room temperature in the autosampler, and an aliquot (5 μL) is injected onto an Ascentis Express C18 column, 30 mm×3 mm, 2.7 μm (Supelco Analytical, Bellefonte, Pa.) maintained at 40° C. The samples are eluted at a flow rate of 1 mL/min with a mobile phase system composed of solvent A (water containing 0.1% formic acid) and B (acetonitrile containing 0.1% formic acid) with an isocratic gradient 90% A for 0.3 min, then with a linear gradient 10% B to 90% B in 3.6 min, and then isocratic for 0.4 min with 90% B. The column was equilibrated back to the initial conditions for 0.4 min before the next run. In a few instances which are indicated in the examples, a long method is used utilizing 10-minute as total run time. Compound polarized mass and retention time ($t_R$), relative UV absorption area are used to assess purity and identity. Further, NMR spectra are utilized to characterize key intermediates and compounds. Optionally, compound $R_f$ values on silica TLC plates are measured.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Chemical names in this document were generated using Chemdraw Ultra Version 10.0 or Version 12.0, commercially available from CambridgeSoft.

Example 1

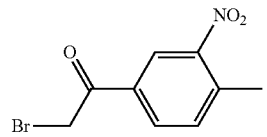

2-bromo-1-(4-methyl-3-nitrophenyl)ethanone

To a stirred solution of 4-methyl-3-nitrobenzoyl chloride (Sigma-Aldrich, 2.0 g, 10 mmol) in $CH_2Cl_2$ (50 mL) is added trimethylsilyldiazomethane (2.0 M in hexanes, 40 mmol). The mixture is stirred for 2 hours at room temp, then cooled to 0° C. and a solution of HBr/HOAc (6.33 mL, 33% of HBr in HOAc, 35 mmol) is added dropwise ($N_2$ evolution). After addition the mixture is stirred at 0° C. for 5 minutes, concentrated and purified by silica gel chromatography ($CH_2Cl_2$) to give the title compound (2.42 g, 93% yield) as a light yellow solid: $R_f$ 0.61 ($CH_2Cl_2$)

Example 2

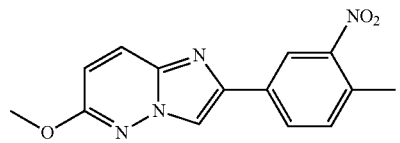

6-methoxy-2-(4-methyl-3-nitrophenyl)imidazo[1,2-b]pyridazine

A stirred solution of 6-methoxypyridazin-3-amine (Apollo Scientific, 0.750 g, 5.99 mmol) and 2-bromo-1-(4-methyl-3-nitrophenyl)ethanone (1.54 g, 5.99 mmol) in acetonitrile (20 mL) is heated at 80° C. for 16 hours. The reaction mixture is concentrated to dryness and purified via chromatography (hexanes to EtOAc) to afford the title compound (1.45 g, 85%) as a light yellow solid: $R_f$ 0.45 (1:1 EtOAc:hexanes); LCMS (m/z)=285.4 [M+H]$^+$, $t_R$=7.47 min. (10 min run)

Example 3

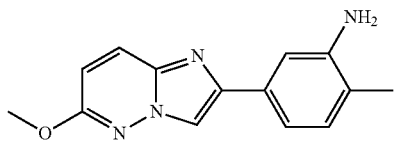

5-(6-methoxyimidazo[1,2-b]pyridazin-2-yl)-2-methylaniline

To a stirred solution of 6-methoxy-2-(4-methyl-3-nitrophenyl)imidazo[1,2-b]pyridazine (0.5 g, 1.75 mmol) in ethanol (20 mL) and water (5 mL) containing AcOH (10.5 mmol) is added iron (0.491 g, 8.79 mmol). The mixture is heated at 80° C. for 4 hours, cooled, concentrated under reduced pressure, and sat. aqueous NaHCO$_3$ (100 mL) is added. The mixture is extracted with EtOAc (3×50 mL), the organic layer is collected, dried over Na$_2$SO$_4$, filtered and concentrated to dryness. The crude product is purified via chromatography (hexanes to EtOAc) to afford the title compound (0.328 g, 73%) as a light yellow solid: R$_f$ 0.21 (EtOAc); LCMS (m/z)= 255.5 [M+H]$^+$, t$_R$=4.89 min. (10 min run).

Example 4

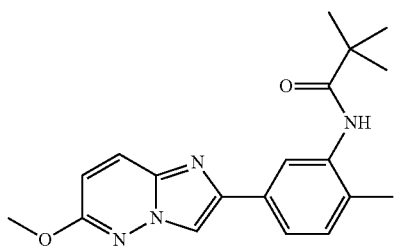

N-(5-(6-methoxyimidazo[1,2-b]pyridazin-2-yl)-2-methylphenyl)pivalamide

To a stirred solution of 5-(6-methoxyimidazo[1,2-b]pyridazin-2-yl)-2-methylaniline (0.050 g, 0.206 mmol) in acetonitrile (5 mL) containing pyridine (0.618 mmol) is added trimethylacetylchloride (0.206 mmol). The mixture is stirred at room temperature for 4 hours, concentrated to dryness, then purified via chromatography (hexanes to EtOAc) to afford the title compound (0.060 g, 86%) as a white solid: R$_f$ 0.57 (EtOAc); LCMS (m/z)=339.4 [M+H]$^+$, t$_R$=6.37 min. (10 min run)

Example 5

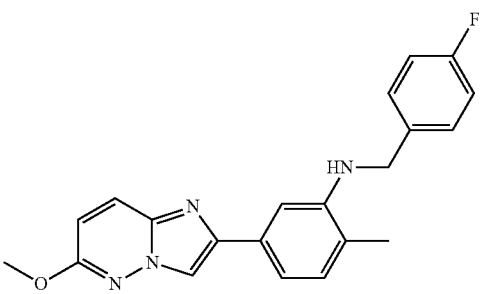 [SMILES: COc1ccc2nc(-c3ccc(C)c(NCc4ccc(F)cc4)c3)cn2n1]

N-(4-fluorobenzyl)-5-(6-methoxyimidazo[1,2-b]pyridazin-2-yl)-2-methylaniline

An 8 mL vial is charged with 5-(6-methoxyimidazo[2,1-f]pyridazin-2-yl)-2-methyl-aniline (20.3 mg, 0.08 mmol) in acetonitrile (0.5 mL), K$_2$CO$_3$ (13 mg) and 4-fluorobenzyl bromide (19 mg, 0.1 mmol). The mixture is stirred for 30 min then filtered, and the filtrate is added into water (10 mL). Solids precipitated and are collected by filtration to give the title compound (10 mg, 34% yield) (compound same as Example 102). LCMS m/z=363.3 [M+H]$^+$, t$_R$=2.57 min.

Example 6

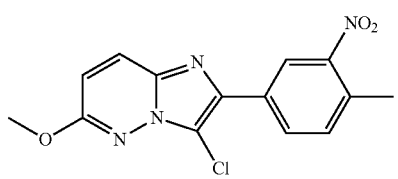

3-chloro-6-methoxy-2-(4-methyl-3-nitrophenyl)imidazo[1,2-b]pyridazine

To a stirred solution of 6-methoxy-2-(4-methyl-3-nitrophenyl)imidazo[1,2-b]pyridazine (0.250 g, 0.879 mmol) in acetonitrile (20 mL) is added N-chlorosuccinimide (0.879 mmol) and the mixture is heated at 60° C. for 8 hours. The reaction mixture is diluted with water (50 mL), and sat. aqueous NaHCO$_3$ (50 mL). The precipitate that forms is collected by filtration, washed with water (3×25 mL) and dried under vacuum to give the title compound (0.277 g, 98% yield) as a yellow solid: R$_f$ 0.60 (1:1 EtOAc:hexanes); LCMS (m/z)= 319.3, 321.2 [M+H]$^+$, t$_R$=3.02 min.

Example 7

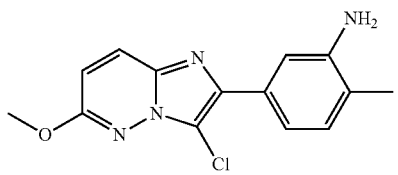

5-(3-chloro-6-methoxyimidazo[1,2-b]pyridazin-2-yl)-2-methylaniline

To a stirred solution of 3-chloro-6-methoxy-2-(4-methyl-3-nitrophenyl)imidazo[1,2-b]pyridazine (0.25 g, 0.784 mmol) in ethanol (50 mL) and water (10 mL) containing AcOH (4.70 mmol) is added iron (0.218 g, 3.92 mmol). The reaction mixture is heated at 80° C. for 2 hours, cooled, concentrated under reduced pressure and sat. aqueous NaHCO$_3$ (100 mL) is added. The mixture is extracted with EtOAc (3×50 mL). Organic layer is collected, dried over Na$_2$SO$_4$, filtered and concentrated to dryness. The crude product is purified via chromatography (hexanes to EtOAc) to afford the title compound (0.201 g, 89%) as a yellow solid: R$_f$ 0.32 (EtOAc); LCMS (m/z)=289.4, 291.2 [M+H]$^+$, t$_R$=2.21 min.

Example 8

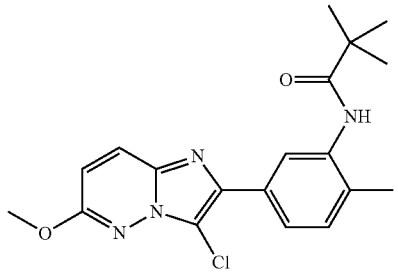

N-(5-(3-chloro-6-methoxyimidazo[1,2-b]pyridazin-2-yl)-2-methylphenyl)pivalamide

A stirred solution of 5-(3-chloro-6-methoxyimidazo[1,2-b]pyridazin-2-yl)-2-methylaniline (0.025 g, 0.0867 mmol) in acetonitrile (1 mL) containing pyridine (0.261 mmol) is added trimethylacetylchloride (0.0867 mmol). The mixture is stirred at room temperature for 4 hours, then concentrated to dryness and purified via chromatography (hexanes to EtOAc) to afford the title compound (0.030 g, 93%) as a white solid: LCMS (m/z)=373.4, 375.3 [M+H]$^+$, t$_R$=2.74 min. (compound same as Example 109)

Example 9

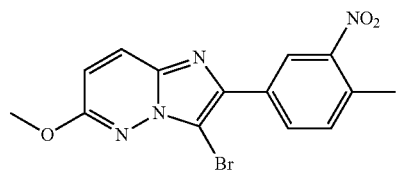

3-bromo-6-methoxy-2-(4-methyl-3-nitrophenyl)imidazo[1,2-b]pyridazine

To a stirred solution of 6-methoxy-2-(4-methyl-3-nitrophenyl)imidazo[1,2-b]pyridazine (0.250 g, 0.879 mmol) in acetonitrile (20 mL) is added N-bromosuccinimide (0.879 mmol) and the mixture is heated at 60° C. for 8 hours. The reaction mixture is diluted with water (50 mL) and sat. aqueous NaHCO$_3$ (50 mL). The precipitate that forms is collected by filtration, washed with water (3×25 mL) and dried under vacuum to give the title product (0.300 g, 94% yield) as a yellow solid: R$_f$ 0.51 (1:1 EtOAc:hexanes); LCMS (m/z)= 363.2, 365.2 [M+H]$^+$, t$_R$=3.02 min.

Example 10

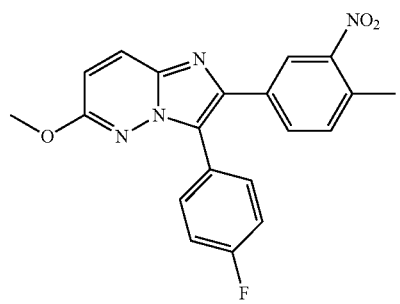

3-(4-fluorophenyl)-6-methoxy-2-(4-methyl-3-nitrophenyl)imidazo[1,2-b]pyridazine

To a stirred mixture of 3-bromo-6-methoxy-2-(4-methyl-3-nitrophenyl)imidazo[1,2-b]pyridazine (0.100 g, 0.275 mmol), 4-fluorophenylboronic acid (0.412 mmol), Na$_2$CO$_3$ (0.825 mmol) in 2-propanol (6 mL) and water (2 mL) that has been degassed with N$_2$ (5 minutes) is added PdCl$_2$(PPh$_3$)$_2$ (0.0275 g). The reaction mixture is heated at 80° C. for 6 hours, cooled, diluted with sat. aqueous NaHCO$_3$ (50 mL) and extracted with EtOAc (3×25 mL). Organic layer is collected, dried over Na$_2$SO$_4$, filtered and concentrated to dryness. The crude product is purified via chromatography (hexanes to EtOAc) to afford 0.092 g (88%) of the title compound as a yellow solid: R$_f$ 0.47 (1:1 EtOAc:hexanes); LCMS (m/z)= 379.4 [M+H]$^+$, t$_R$=3.07 min.

Example 11

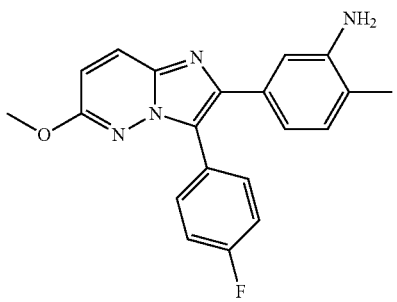

5-(3-(4-fluorophenyl)-6-methoxyimidazo[1,2-b]pyridazin-2-yl)-2-methylaniline

To a stirred solution of 3-(4-fluorophenyl)-6-methoxy-2-(4-methyl-3-nitrophenyl)imidazo[1,2-b]pyridazine (0.075 g, 0.0198 mmol) in ethanol (6 mL) and water (2 mL) containing AcOH (1.18 mmol) is added iron (0.055 g, 0.991 mmol). The reaction mixture is heated at 80° C. for 2 hours, cooled, concentrated under reduced pressure and sat. aqueous NaHCO$_3$ (50 mL) is added. The mixture is extracted with EtOAc (3×20 mL). Organic layer is collected, dried over Na$_2$SO$_4$, filtered and concentrated to dryness. The crude product is purified via chromatography (hexanes to EtOAc) to afford 0.065 g (95%) of the title compound as a yellow solid: R$_f$ 0.36 (95:5 CH$_2$Cl$_2$:MeOH); LCMS (m/z)=349.4 [M+H]$^+$, t$_R$=2.31 min.

Example 12

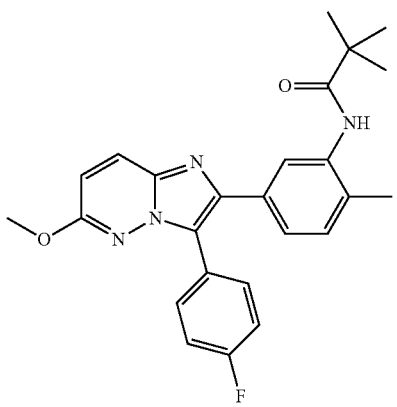

N-(5-(3-(4-fluorophenyl)-6-methoxyimidazo[1,2-b]pyridazin-2-yl)-2-methylphenyl)pivalamide A stirred solution of 5-(3-(4-fluorophenyl)-6-methoxyimidazo[1,2-b]pyridazin-2-yl)-2-methylaniline (0.025 g, 0.072 mmol) in acetonitrile (1 mL) containing pyridine (0.215 mmol) is added trimethylacetylchloride (0.072 mmol). The mixture is stirred at room temperature for 4 hours, then concentrated to dryness and purified via chromatography (hexanes to EtOAc) to afford the title compound (0.028 g, 90%) as a yellow solid: R$_f$ 0.28 (1:1 EtOAc:hexanes); LCMS (m/z)= 433.5 [M+H]$^+$, t$_R$=2.74 min. (compound same as Example 114)

Example 13

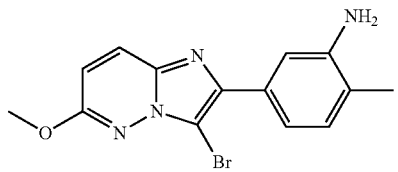

5-(3-bromo-6-methoxyimidazo[1,2-b]pyridazin-2-yl)-2-methylaniline

To a stirred solution of 3-bromo-6-methoxy-2-(4-methyl-3-nitrophenyl)imidazo[1,2-b]pyridazine (0.190 g, 0.523 mmol) in ethanol (15 mL) and water (5 mL) containing AcOH (3.13 mmol) is added iron (0.146 g, 2.61 mmol). The reaction mixture is heated at 80° C. for 2 hours, cooled, concentrated under reduced pressure and sat. aqueous NaHCO$_3$ (50 mL) is added. The mixture is extracted with EtOAc (3×25 mL). Organic layer is collected, dried over Na$_2$SO$_4$, filtered and concentrated to dryness. The crude product is purified via chromatography using a gradient of hexanes to EtOAc to afford the title compound (0.170 g, 89%) as an off-white solid: R$_f$ 0.18 (1:1 EtOAc:hexanes); LCMS (m/z)=333.2, 335.2 [M+H]$^+$, t$_R$=2.22 min.

Example 14

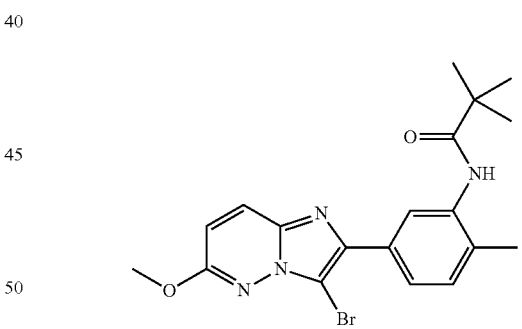

N-(5-(3-bromo-6-methoxyimidazo[1,2-b]pyridazin-2-yl)-2-methylphenyl)pivalamide

A solution of 5-(3-bromo-6-methoxyimidazo[1,2-b]pyridazin-2-yl)-2-methylaniline (0.165 g, 0.495 mmol) in acetonitrile (25 mL) containing pyridine (1.48 mmol) is added trimethylacetylchloride (0.495 mmol). The mixture is stirred at room temperature for 4 hours, then concentrated to dryness and purified via chromatography (hexanes to EtOAc) to afford 0.200 g (97%) of the title compound as a white solid: R$_f$ 0.41 (1:1 EtOAc:hexanes); LCMS (m/z)=417.3, 419.3 [M+H]$^+$, t$_R$=2.76 min.

Example 15

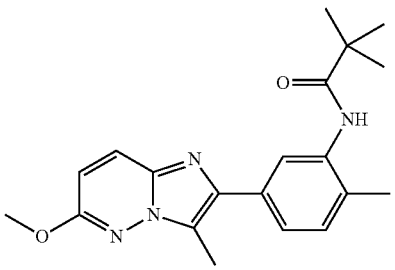

N-(5-(6-methoxy-3-methylimidazo[1,2-b]pyridazin-2-yl)-2-methylphenyl)pivalamide

To a mixture of N-(5-(3-bromo-6-methoxyimidazo[1,2-b]pyridazin-2-yl)-2-methylphenyl)pivalamide (0.050 g, 0.119 mmol), methylboronic acid (0.357 mmol), tripotassium phosphate (0.714 mmol), 2-dicyclohexylphosphino-2',6'-dimethoxybiphenyl (0.0238 mmol) in toluene (4 mL) and water (0.4 mL) that has been degassed with $N_2$ (5 minutes) is added Pd(OAc)$_2$ (0.0119 mmol). The reaction mixture is heated at 100° C. for 14 hours, then cooled and concentrated to dryness. The crude product is purified via chromatography (hexanes to EtOAc) to afford 2.4 mg (6%) of the title compound as a white solid: $R_f$ 0.64 (EtOAc); LCMS (m/z)=353.4 [M+H]$^+$, $t_R$=2.15 min. (compound same as Example 121)

Example 16

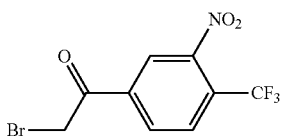 [SMILES: O=C(CBr)c1ccc(C(F)(F)F)c([N+](=O)[O-])c1]

2-bromo-1-[3-nitro-4-(trifluoromethyl)phenyl]ethanone

3-Nitro-4-(trifluoromethyl)benzoic acid (Matrix Scientific, 2.35 g, 10 mmol) is dissolved in thionyl chloride (22 mL, 300 mmol). The stirred solution is heated at 95° C. for 16 hr, then cooled, concentrated and CH$_2$Cl$_2$ (51 mL) and trimethylsilyldiazomethane (20 mL, 2 M in Hexanes, 40 mmol) are added and the reaction is stirred for 2 hr at room temp. The mixture is cooled to 0° C. and HBr/HOAc (6.33 mL, 33% of HBr in HOAc) is added dropwise (N$_2$ evolution). After addition the mixture is stirred at 0° C. for 5 min, then concentrated and purified by silica gel chromatography (CH$_2$Cl$_2$) to give the title compound (2.59 g, 83% yield). LCMS m/z=313.5 [M+H]$^+$, $t_R$=2.65 min.

Example 17

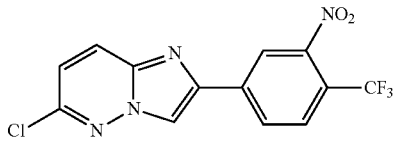 [SMILES: O=[N+]([O-])c1cc(-c2cn3nc(Cl)ccc3n2)ccc1C(F)(F)F]

6-chloro-2-[3-nitro-4-(trifluoromethyl)phenyl]imidazo[2,1-f]pyridazine

A stirred solution of 6-chloropyridazin-3-amine (0.842 g, 0.0065 mol) and 2-bromo-1-[3-nitro-4-(trifluoromethyl)phenyl]ethanone (2.03 g, 0.65 mmol) in acetonitrile (37.34 mL) is heated at 90° C. for 48 hr. The reaction mixture is concentrated and purified by silica gel chromatography (CH$_2$Cl$_2$ to EtOAc) to give the title compound (1.62 g, 73% yield). LCMS m/z=343.3 [M+H]$^+$, $t_R$=3.15 min.

Example 18

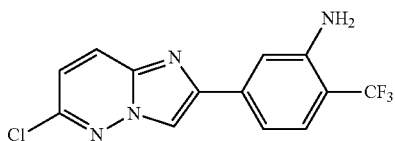

5-(6-chloroimidazo[2,1-f]pyridazin-2-yl)-2-(trifluoromethyl)aniline

Iron (0.489 g) is added to a mixture of 6-chloro-2-[3-nitro-4-(trifluoromethyl)phenyl]imidazo[2,1-f]pyridazine (0.600 g, 1.75 mmol), HOAc (0.802 mL), EtOH-water (10 mL, 4:1). The mixture is heated at 80° C. for 2 hours, then cooled, concentrated, taken into sat. aqueous NaHCO$_3$ (50 mL) and extracted with EtOAc (2×50 mL). Organic is dried and concentrated to give the title compound (530 mg), which is used without further purification. LCMS m/z=313.4 [M+H]$^+$, $t_R$=2.82 min.

Example 19

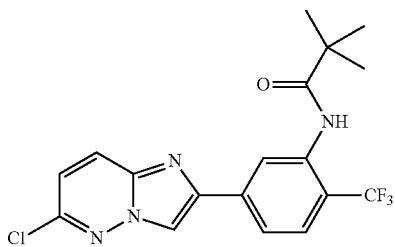 [SMILES: CC(C)(C)C(=O)Nc1cc(-c2cn3nc(Cl)ccc3n2)ccc1C(F)(F)F]

N-(5-(6-chloroimidazo[1,2-b]pyridazin-2-yl)-2-(trifluoromethyl)phenyl)pivalamide A 40 mL vial is charged with 5-(6-chloroimidazo[2,1-f]pyridazin-2-yl)-2-(trifluoromethyl)aniline (0.531 g, 1.7 mmol), acetonitrile (14 mL), and pyridine (0.275 mL). The stirred mixture is added trimethylacetyl chloride (0.419 mL, 3.4 mmol) and heated for 20 min at 80° C. The reaction is concentrated, taken into EtOAc (25 mL), washed once with HCl (15 mL, 1M) then NaOH (15 mL, 1M). Organic is dried, concentrated and purified by silica gel chromatography (0-100% EtOAc in Hexanes) to give the title compound (630 mg, 93% yield). LCMS (m/z)=397.4, 399.3 [M+H]$^+$, $t_R$=2.87 min. (compound same as Example 126)

Example 20

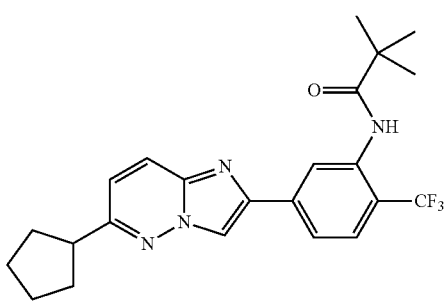 [SMILES: CC(C)(C)C(=O)Nc1cc(-c2cn3nc(C4CCCC4)ccc3n2)ccc1C(F)(F)F]

N-[5-(6-cyclopentylimidazo[2,1-f]pyridazin-2-yl)-2-(trifluoromethyl)phenyl]-dimethyl-propanamide A small vial is charged with N-[5-(6-chloroimidazo[2,1-f]pyridazin-2-yl)-2-(trifluoromethyl)phenyl]-2,2-dimethyl-propanamide (0.032 g, 0.08 mol), cyclopropylzinc bromide (0.12 mL, 2 M in THF, 0.24 mmol), [1,1'-bis(diphenylphosphino)ferrocene]dichloropalladium(II) (6 mg, 0.01 mol), and THF (0.32 mL). The reaction vessel is purged with N$_2$ and heated to 150° C. in the microwave for 2 hr. Sat. aqueous NH$_4$Cl is added to the mixture and it is extracted with EtOAc. The combined organic layers are dried over Na$_2$SO$_4$, filtered, concentrated, and purified by silica gel chromatography (hexanes to ethyl acetate) to give the title compound (3.5 mg, 11% yield). LCMS m/z=431.5 [M+H]$^+$, $t_R$=3.21 min. (compound same as Example 316)

Example 21

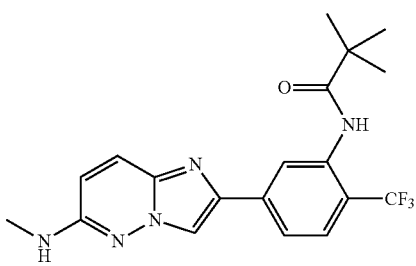 [SMILES: CNc1ccc2nc(-c3ccc(C(F)(F)F)c(NC(=O)C(C)(C)C)c3)cn2n1]

2,2-dimethyl-N-[5-(6-methylaminoimidazo[2,1-f]pyridazin-2-yl)-2-(trifluoromethyl)phenyl]propanamide A 8 mL vial is charged with N-[5-(6-chloroimidazo[2,1-f]pyridazin-2-yl)-2-(trifluoromethyl)phenyl]-2,2-dimethyl-propanamide (0.032 g, 0.08 mmol), THF (0.649 mL), and methylamine (0.08 mL, 2 M in THF, 0.16 mol). The mixture is stirred and heated to 80° C. for 16 hr. The mixture is concentrated onto celite and purified by silica gel chromatography (0-100% EtOAc in CH$_2$Cl$_2$) to give the title compound (11 mg, 35% yield). LCMS m/z=392.5 [M+H]$^+$, $t_R$=2.36 min. (compound same as Example 137)

Example 22

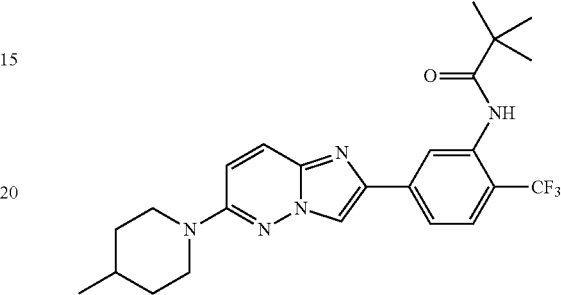

2,2-dimethyl-N-[5-[6-(4-methyl-1-piperidyl)imidazo[2,1-f]pyridazin-2-yl]-2-(trifluoromethyl)phenyl]propanamide An 8 mL vial is charged with DMF (1 mL), 4-methylpiperidine (0.030 g), Cs$_2$CO$_3$ (0.130 g), and N-[5-(6-chloroimidazo[2,1-f]pyridazin-2-yl)-2-(trifluoromethyl)phenyl]-2,2-dimethyl-propanamide (0.0396 g, 0.1 mmol). The mixture is stirred at 120° C. for 16 hr, then diluted with H$_2$O (5 mL) and extracted with Et$_2$O (3 mL×2). Organics are dried and concentrated onto celite, purified by silica gel chromatography (0-100% EtOAc in Hexanes) to give the title compound (0.020 g, 43% yield). LCMS m/z=460.6 [M+H]$^+$, $t_R$=3.14 min. (compound same as Example 233)

Example 23

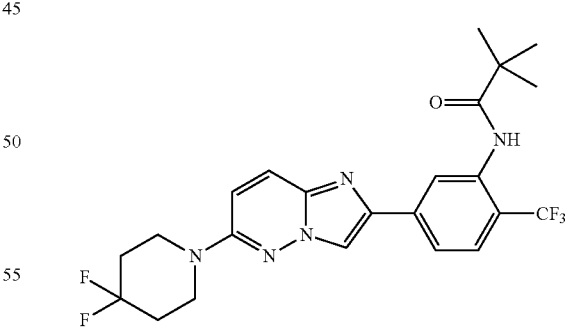

N-[5-[6-(4,4-difluoro-1-piperidyl)imidazo[2,1-f]pyridazin-2-yl]-2-(trifluoromethyl)phenyl]-2,2-dimethyl-propanamide An 8 mL vial is charged with DMF (1 mL), 4,4-difluoropiperidine hydrochloride (0.048 g), Cs$_2$CO$_3$ (0.200 g), and N-[5-(6-chloroimidazo[2,1-f]pyridazin-2-yl)-2-(trifluoromethyl)phenyl]-2,2-dimethyl-propanamide (0.0396 g, 0.1 mmol). The mixture is stirred at 120° C. for 16 hr, then diluted with $H_2O$ (5 mL) and extracted with $Et_2O$ (3 mL×2). Organics are dried and concentrated onto celite, purified by silica gel chromatography (0-100% EtOAc in Hexanes) to give the title compound (0.015 g, 31% yield). LCMS m/z=482.56 [M+H]$^+$, $t_R$=2.89 min. (compound same as Example 235)

Example 24

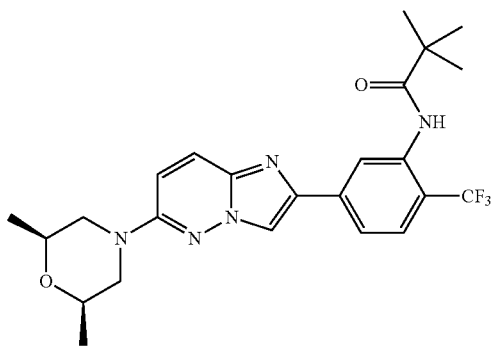 [SMILES: C[C@@H]1CN(c2ccc3nc(-c4ccc(C(F)(F)F)c(NC(=O)C(C)(C)C)c4)cn3n2)C[C@H](C)O1]

N-[5-[6-[(cis)-2,6-dimethylmorpholin-4-yl]imidazo[2,1-f]pyridazin-2-yl]-2-(trifluoromethyl)phenyl]-2,2-dimethyl-propanamide An 8 mL vial is charged with DMF (1 mL), cis-2,6-dimethylmorpholine (0.034 g), $Cs_2CO_3$ (0.130 g), and N-[5-(6-chloroimidazo[2,1-f]pyridazin-2-yl)-2-(trifluoromethyl)phenyl]-2,2-dimethyl-propanamide (0.0396 g, 0.1 mmol). The mixture is stirred at 120° C. for 16 hr, then diluted with $H_2O$ (5 mL) and extracted with $Et_2O$ (3 mL×2). Organics are dried and concentrated onto celite, purified by silica gel chromatography (0-100% EtOAc in Hexanes) to give the title compound (0.027 g, 57% yield). LCMS m/z=476.6 [M+H]$^+$, $t_R$=2.77 min. (compound same as Example 250)

Example 25

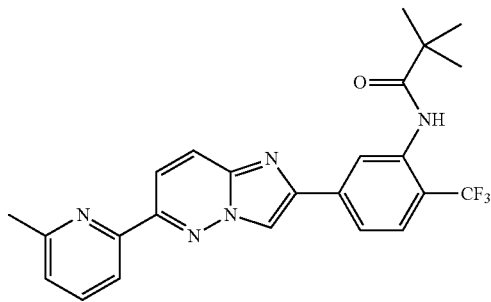 [SMILES: Cc1cccc(-c2ccc3nc(-c4ccc(C(F)(F)F)c(NC(=O)C(C)(C)C)c4)cn3n2)n1]

2,2-dimethyl-N-[5-[6-(6-methyl-2-pyridyl)imidazo[2,1-f]pyridazin-2-yl]-2-(trifluoromethyl)phenyl]propanamide An 8 mL vial is charged with N-tert-butyl-5-(6-chloroimidazo[2,1-f]pyridazin-2-yl)-2-(trifluoromethyl)benzamide (0.025 g, 0.063 mmol), 6-methyl-2-pyridylzinc bromide (Sigma-Aldrich, 0.26 mL, 0.5 M in THF, 0.13 mmol), bis(triphenylphosphine)palladium(II) dichloride (0.0044 g, 0.0063 mmol) and THF (0.26 mL). The reaction vessel is purged with $N_2$ and the mixture stirred at 60° C. for 16 hr. The mixture is concentrated, taken into 1:1 EtOAc and $CH_2Cl_2$, filtered and purified by silica (0-100% EtOAc in $CH_2Cl_2$) to afford the title compound (22 mg, 78% yield). LCMS m/z=454.6 [M+H]$^+$, $t_R$=3.34 min. (compound same as Example 149)

Example 26

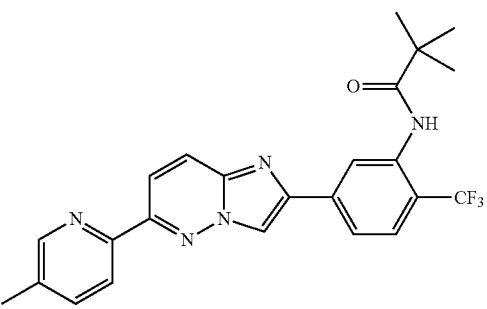 [SMILES: Cc1ccc(-c2ccc3nc(-c4ccc(C(F)(F)F)c(NC(=O)C(C)(C)C)c4)cn3n2)nc1]

2,2-dimethyl-N-[5-[6-(5-methyl-2-pyridyl)imidazo[2,1-f]pyridazin-2-yl]-2-(trifluoromethyl)phenyl]propanamide An 8 mL vial is charged with N-tert-butyl-5-(6-chloroimidazo[2,1-f]pyridazin-2-yl)-2-(trifluoromethyl)benzamide (0.025 g, 0.063 mmol), 5-methyl-2-pyridylzinc bromide (Sigma-Aldrich, 0.26 mL, 0.13 mmol, 0.5 M in THF), bis(triphenylphosphine)palladium(II) dichloride (0.0044 g, 0.0063 mmol) and THF (0.26 mL). The reaction vessel is purged with $N_2$ and the mixture stirred at 60° C. for 16 hr. The mixture is concentrated, taken up in 1:1 EtOAc and $CH_2Cl_2$, filtered and purified by silica (0-100% EtOAc in $CH_2Cl_2$) to afford the title compound (20 mg, 74% yield). LCMS m/z=454.6 [M+H]$^+$, $t_R$=3.32 min. (compound same as Example 150)

Example 27

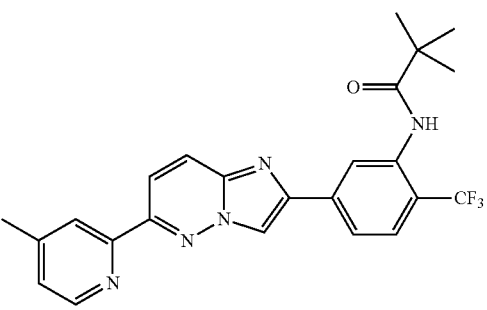 [SMILES: Cc1ccnc(-c2ccc3nc(-c4ccc(C(F)(F)F)c(NC(=O)C(C)(C)C)c4)cn3n2)c1]

2,2-dimethyl-N-[5-[6-(4-methyl-2-pyridyl)imidazo[2,1-f]pyridazin-2-yl]-2-(trifluoromethyl)phenyl]propanamide An 8 mL vial is charged with N-tert-butyl-5-(6-chloroimidazo[2,1-f]pyridazin-2-yl)-2-(trifluoromethyl)benzamide (0.025 g, 0.063 mmol), 4-methyl-2-pyridylzinc bromide (0.26 mL, 0.13 mmol, 0.5 M in THF), bis(triphenylphosphine)palladium(II) dichloride (0.0044 g, 0.0063 mmol) and THF (0.26 mL). The reaction vessel is purged with N₂ and the mixture stirred at 60° C. for 16 hr. The mixture is concentrated, taken up in 1:1 EtOAc and CH₂Cl₂, filtered and purified by silica (0-100% EtOAc in CH₂Cl₂) to afford the title compound (18 mg, 67% yield). LCMS m/z=454.6 [M+H]⁺, $t_R$=3.22 min. (compound same as Example 151)

Example 28

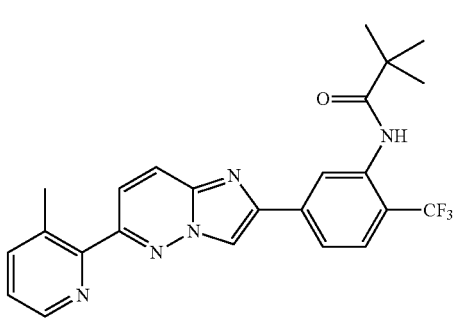 [SMILES: Cc1cccnc1-c1ccc2nc(-c3ccc(C(F)(F)F)c(NC(=O)C(C)(C)C)c3)cn2n1]

2,2-dimethyl-N-[5-[6-(3-methyl-2-pyridyl)imidazo[2,1-f]pyridazin-2-yl]-2-(trifluoromethyl)phenyl] propanamide An 8 mL vial is charged with N-tert-butyl-5-(6-chloroimidazo[2,1-f]pyridazin-2-yl)-2-(trifluoromethyl)benzamide (0.025 g, 0.063 mmol), 3-methyl-2-pyridylzinc bromide (0.26 mL, 0.13 mmol, 0.5 M in THF), bis(triphenylphosphine)palladium(II) dichloride (0.0044 g, 0.0063 mmol) and THF (0.26 mL). The reaction vessel is purged with N₂ and the mixture stirred at 60° C. for 16 hr. The mixture is concentrated, taken up in 1:1 EtOAc and CH₂Cl₂, filtered and purified by silica (0-100% EtOAc in CH₂Cl₂) to afford the title compound (19 mg, 70% yield). LCMS m/z=454.6 [M+H]⁺, $t_R$=3.06 min. (compound same as Example 152)

Example 29

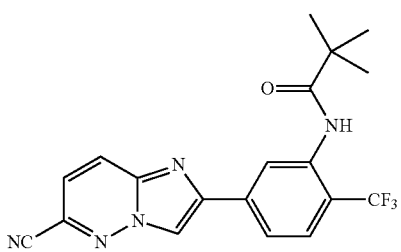 [SMILES: CC(C)(C)C(=O)Nc1cc(-c2cn3nc(C#N)ccc3n2)ccc1C(F)(F)F]

N-[5-(6-cyanoimidazo[2,1-f]pyridazin-2-yl)-2-(trifluoromethyl)phenyl]-2,2-dimethyl-propanamide An 8 mL vial is charged with N-[5-(6-chloroimidazo[2,1-f]pyridazin-2-yl)-2-(trifluoromethyl)phenyl]-2,2-dimethyl-propanamide (0.059 g, 0.15 mmol), copper cyanide (0.035 g, 0.3 mmol), and 4-methylmorpholine (0.43 mL). The mixture is stirred at 215° C. for 4 hr in the microwave, then cooled, diluted with Et₂O, sat. aqueous NaHCO₃ and the biphasic mixture is filtered. Organics are collected and aqueous layer is extracted twice more with Et₂O. Organics are combined, dried, concentrated, and purified by prep plate TLC (1:1 Hex:EtOAc) to give the title compound (15 mg, 26% yield). LCMS m/z=388.5 [M+H]⁺, $t_R$=2.56 min. (compound same as Example 173)

Example 30

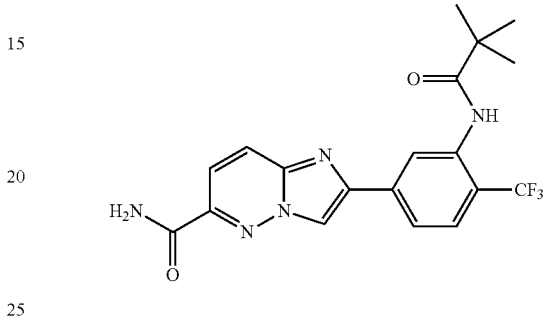

2-[3-(2,2-dimethylpropanoylamino)-4-(trifluoromethyl)phenyl]imidazo[2,1-f]pyridazine-6-carboxamide An 8 mL vial is charged with N-[5-(6-cyanoimidazo[2,1-f]pyridazin-2-yl)-2-(trifluoromethyl)phenyl]-2,2-dimethylpropanamide (0.019 g, 0.05 mmol), EtOH-DMSO (1.2 mL, 5:1), NaOH (0.1 mL, 1M in water), and H₂O₂ (0.1 mL, 30% in water). The mixture is stirred for 2 hr at room temp, diluted with water (4 mL), extracted EtOAc (2×) and CH₂Cl₂ (1 ×). Organics are dried, concentrated onto celite and purified on silica (0-100% EtOAc in CH₂Cl₂) to give the title compound (12 mg, 60% yield). LCMS m/z=406.5 [M+H]⁺, $t_R$=2.12 min. (compound same as Example 180)

Example 31

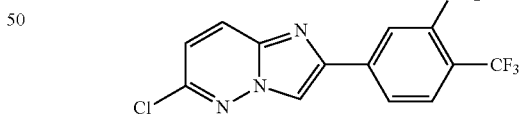

6-chloro-2-[3-nitro-4-(trifluoromethyl)phenyl]imidazo[1,2-a]pyridine

A solution of 2-amino-5-chloropyridine (0.064 g, 0.5 mmol) and 2-bromo-1-[3-nitro-4-(trifluoromethyl)phenyl]ethanone (0.156 g, 0.5 mmol) in acetonitrile (3 ml) is stirred at 100° C. for 18 hr. The mixture is concentrated and purified on silica (0 to 100% EtOAc in hexanes) to give the title compound (165 mg, 97% yield). LCMS m/z=342.3 [M+H]⁺, $t_R$=2.86 min.

Example 32

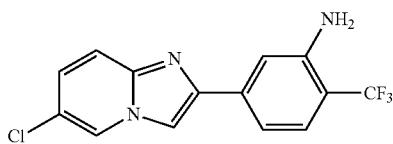 [SMILES: Nc1cc(-c2cn3cc(Cl)ccc3n2)ccc1C(F)(F)F]

6-chloro-2-[3-amino-4-(trifluoromethyl)phenyl]imidazo[1,2-a]pyridine

Iron (0.140 g) is added to a mixture of 6-chloro-2-[3-nitro-4-(trifluoromethyl)phenyl]imidazo[1,2-a]pyridine (0.171 g), HOAc (0.230 mL) and EtOH—H$_2$O (2 mL, 4:1). The mixture is stirred at 80° C. for 2 hours, then cooled, concentrated, taken into sat. NaHCO$_3$ aqueous solution, extracted with EtOAc and CH$_2$Cl$_2$. Organics are dried and concentrated to give the title compound (150 mg, 96% yield), which is used without further purification. LCMS m/z=312.4 [M+H]$^+$, $t_R$=1.96 min.

Example 33

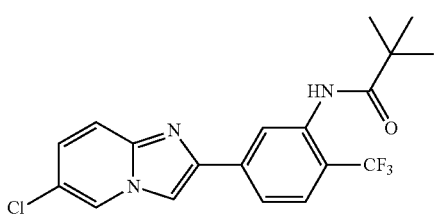 [SMILES: CC(C)(C)C(=O)Nc1cc(-c2cn3cc(Cl)ccc3n2)ccc1C(F)(F)F]

N-[5-(6-chloroimidazo[1,2-a]pyridin-2-yl)-2-(trifluoromethyl)phenyl]-2,2-dimethyl-propanamide A 20 mL vial is charged with 5-(6-chloroimidazo[1,2-a]pyridin-2-yl)-2-(trifluoromethyl)aniline (0.156 g, 0.5 mmol), acetonitrile (4.12 mL) and pyridine (0.081 mL). The mixture is added trimethylacetyl chloride (0.123 mL, 0.001 mol) and stirred for 20 min at 80° C. The solution is concentrated, taken into EtOAc (10 mL) and washed once with HCl (10 mL, 1M) and NaOH (10 mL, 1M). Organics are dried, concentrated purified on silica (0-100% EtOAc in Hexanes) to give the title compound (106 mg, 54% yield). LCMS m/z=396.4 [M+H]$^+$, $t_R$=2.54 min. (compound same as Example 81)

Example 34

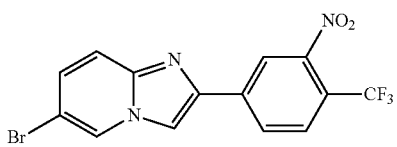

6-bromo-2-[3-nitro-4-(trifluoromethyl)phenyl]imidazo[1,2-a]pyridine

A stirred mixture of 2-amino-5-bromopyridine (0.259 g, 1.5 mmol) and 2-bromo-1-[3-nitro-4-(trifluoromethyl)phenyl]ethanone (0.468 g, 1.5 mmol) in acetonitrile (3 mL) is heated at 100° C. for 18 hr. The mixture is concentrated to give the title compound (618 mg), which is used without further purification. LCMS m/z=388.3 [M+H]$^+$, $t_R$=2.94 min.

Example 35

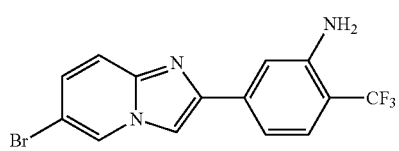 [SMILES: Nc1cc(-c2cn3cc(Br)ccc3n2)ccc1C(F)(F)F]

6-bromo-2-[3-amino-4-(trifluoromethyl)phenyl]imidazo[1,2-a]pyridine

Fe (0.447 g) is added to a mixture of 6-bromo-2-[3-nitro-4-(trifluoromethyl)phenyl]imidazo[1,2-a]pyridine (0.618 g), HOAc (0.733 mL), and EtOH—H$_2$O (10 mL, 4:1). The mixture is stirred at 80° C. for 2 hours, then concentrated, taken into sat. aqueous NaHCO$_3$ and extracted with EtOAc and CH$_2$Cl$_2$. Organics are dried and concentrated to give the title compound (463 mg), which is used without further purification. LCMS m/z=356.4 [M+H]$^+$, $t_R$=2.04 min.

Example 36

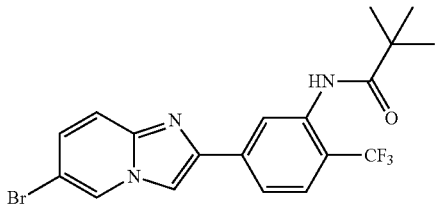

N-[5-(6-bromoimidazo[1,2-a]pyridin-2-yl)-2-(trifluoromethyl)phenyl]-2,2-dimethyl-propanamide A 20 mL vial is charged with 5-(6-bromoimidazo[1,2-a]pyridin-2-yl)-2-(trifluoromethyl)aniline (0.463 g, 0.0013 mol), acetonitrile (7 mL) and pyridine (0.210 mL). The mixture is added trimethylacetyl chloride (0.320 mL, 2.6 mmol) and stirred for 20 min at 80° C. The solution is concentrated, taken into EtOAc (10 mL) and washed once with HCl (10 mL, 1M) and NaOH (10 mL, 1M). Organics are dried, concentrated, and purified on silica (0-100% EtOAc in Hexanes) to give the title compound (212 mg, 37% yield). LCMS m/z=440.4 [M+H]+, $t_R$=2.67 min.

Example 37

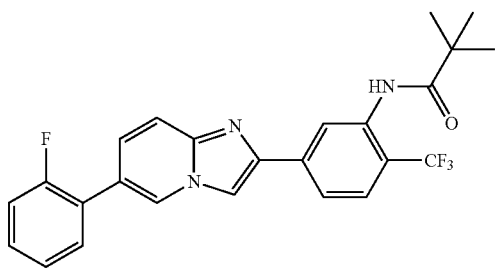 [SMILES: CC(C)(C)C(=O)Nc1cc(-c2cn3cc(-c4ccccc4F)ccc3n2)ccc1C(F)(F)F]

N-[5-[6-(2-fluorophenyl)imidazo[1,2-a]pyridin-2-yl]-2-(trifluoromethyl)phenyl]-2,2-dimethyl-propanamide An 8 mL vial is charged with N-[5-(6-bromoimidazo[1,2-a]pyridin-2-yl)-2-(trifluoromethyl)phenyl]-2,2-dimethyl-propanamide (0.044 g, 0.11 mol), (2-fluorophenyl)boronic acid (Combi-Blocks, 28 mg, 0.2 mmol), Na₂CO₃ (0.032 g, 0.3 mmol), bis(triphenylphosphine)palladium(II) dichloride (7 mg, 0.01 mmol) and isopropanol-water (1 mL, 3:1). The reaction mixture is stirred at 80° C. for 16 hr, then cooled, concentrated, taken into EtOAc and CH₂Cl₂ (1:1), filtered, concentrated onto celite and purified by silica gel chromatography (0-100% EtOAc in Hexanes) to give the title compound (25.4 mg, 55% yield). LCMS m/z=456.5 [M+H]+, $t_R$=2.69 min. (compound same as Example 83)

Example 38

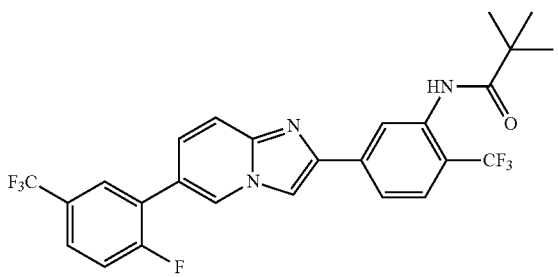 [SMILES: CC(C)(C)C(=O)Nc1cc(-c2cn3cc(-c4cc(C(F)(F)F)ccc4F)ccc3n2)ccc1C(F)(F)F]

N-[5-[6-[2-fluoro-5-(trifluoromethyl)phenyl]imidazo[1,2-a]pyridin-2-yl]-2-(trifluoromethyl)phenyl]-2,2-dimethyl-propanamide An 8 mL vial is charged with N-[5-(6-bromoimidazo[1,2-a]pyridin-2-yl)-2-(trifluoromethyl)phenyl]-2,2-dimethyl-propanamide (0.044 g, 0.11 mmol), 2-fluoro-5-(trifluoromethyl)phenyl]boronic acid (Combi-Blocks, 42 mg, 0.2 mmol), Na₂CO₃ (0.032 g, 0.3 mmol), bis(triphenylphosphine)palladium(II) dichloride (7 mg, 0.01 mmol) and isopropanol-water (1 mL, 3:1). The mixture is stirred at 80° C. for 16 hr, then cooled, concentrated, taken up in EtOAc and CH₂Cl₂ (1:1), filtered, concentrated onto celite and purified by silica gel chromatography (0-100% EtOAc in Hexanes) to give the title compound (29.9 mg, 57% yield). LCMS m/z=524.5 [M+H]+, $t_R$=3.09 min. (compound same as Example 84)

Example 39

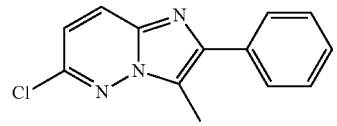 [SMILES: Cc1c(-c2ccccc2)nc2ccc(Cl)nn12]

6-chloro-3-methyl-2-phenylimidazo[1,2-b]pyridazine

A stirred solution of 6-chloropyridazin-3-amine (1.00 g, 7.71 mmol) and 2-bromo-1-phenylpropan-1-one (Sigma-Aldrich, 1.54 g, 7.71 mmol) in acetonitrile (50 mL) is heated at 80° C. for 16 hours. The mixture is concentrated to dryness and purified via chromatography (hexanes to EtOAc) to afford the title compound (1.52 g, 81%) as a tan solid: $R_f$ 0.52 (1:1 EtOAc:hexanes); LCMS (m/z)=244.2, 246.3 [M+H]+, $t_R$=2.61 min.

Example 40

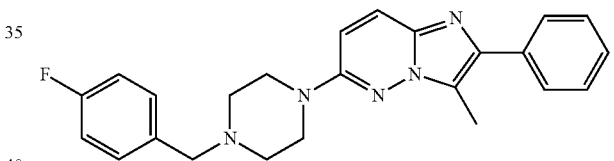

6-(4-(4-fluorobenzyl)piperazin-1-yl)-3-methyl-2-phenylimidazo[1,2-b]pyridazine

A solution of 6-chloro-3-methyl-2-phenylimidazo[1,2-b]pyridazine (1.00 g, 4.35 mmol) and 1-(4-fluorobenzyl)piperazine (Sigma-Aldrich, 1.54 g, 4.35 mmol) in acetonitrile (50 mL) containing triethylamine (13.0 mmol) is heated at 180° C. in the microwave for 5 hours. The reaction mixture is concentrated to dryness and then purified via chromatography (hexanes to EtOAc) to afford the title product (0.82 g, 81%) as an off-white solid: $R_f$ 0.30 (EtOAc); LCMS (m/z)= 402.4 [M+H]+, $t_R$=1.74 min. (compound same as Example 134)

Example 41

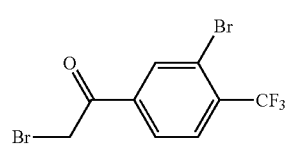 [SMILES: O=C(CBr)c1ccc(C(F)(F)F)c(Br)c1]

2-bromo-1-(3-bromo-4-(trifluoromethyl)phenyl) ethanone

To a stirred mixture of 3-amino-4-(trifluoromethyl)benzoic acid (Matrix Scientific, 2.05 g, 10 mmol) in aqueous HBr (48% in water, 20 mL) and H₂O (67 mL) at 0° C. is added NaNO₂ (0.828 g) in small portions over 15 min. After stirring the solution for 30 minutes the mixture is added dropwise to a solution of CuBr (2.5 g) in aqueous HBr (48% in water, 40 mL) and H₂O (100 mL). The mixture is stirred at 75° C. for 2 hours, then room temperature for 16 hours. The mixture is treated with 20% NaOH to raise the pH above 10 and then filtered through celite. The resulting solution is acidified with 6 M HCl to pH 1 and extracted with dichloromethane (3×100 mL). Organic layers are collected, dried over Na₂SO₄, filtered and concentrated to give 3-bromo-4-(trifluoromethyl)benzoic acid (2.30 g, 85.5% yield). LCMS m/z=269.1, 271.1 [M+H]⁺.

A mixture of the crude acid (2.0 g, 7.43 mmol) in thionyl chloride (25 mL) is refluxed for 16 hours. The mixture is concentrated under reduced pressure to give an yellow oil which is taken up in dichloromethane (50 mL) and trimethylsilyl diazomethane (18.5 mL, 2 M in Hexane) is added. The reaction is stirred at room temperature for 4 hours, cooled to 0° C. and HBr/HOAc (5.25 mL, 33% HBr in acetic acid) is added slowly (gas formation). After complete addition the mixture is stirred for 20 min at 0° C., then concentrated under reduced pressure to give the title compound (2.48 g, 96%) as an orange oil, which is used without further purification.

Example 42

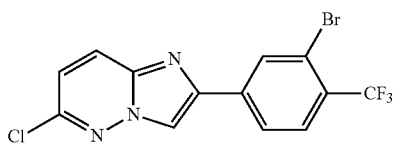 [SMILES: FC(F)(F)c1ccc(-c2cn3nc(Cl)ccc3n2)cc1Br]

2-(3-bromo-4-(trifluoromethyl)phenyl)-6-chloroimidazo[1,2-b]pyridazine

A stirred solution of 5-chloropyrazin-2-amine (0.928 g, 7.1 mmol) and 2-bromo-1-[3-bromo-4-(trifluoromethyl)phenyl]ethanone (2.48 g, 7.1 mmol) in acetonitrile (100 mL) is heated at 80° C. for 18 hr. The mixture is concentrated onto celite and purified by silica gel chromatography (0-100% EtOAc in Hexanes) to give the title compound (1.63 g, 61% yield). LCMS m/z=376.1, 378.1 [M+H]⁺; $t_R$=3.19 min. (compound same as Example 203)

Example 43

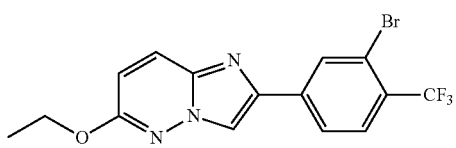 [SMILES: CCOc1ccc2nc(-c3ccc(C(F)(F)F)c(Br)c3)cn2n1]

2-(3-bromo-4-(trifluoromethyl)phenyl)-6-ethoxyimidazo[1,2-b]pyridazine

NaOEt (21% in EtOH, 2.97 mL) is added to a mixture of 2-[3-bromo-4-(trifluoromethyl)phenyl]-6-chloro-imidazo[2,1-f]pyridazine (1.5 g, 3.98 mmol) in THF (50 mL). The mixture is stirred for 4 hours at 50° C., then the THF solution is concentrated onto celite and purified by silica gel chromatography (0-100% EtOAc in Hexanes) to give the title compound (1.36 g, 88.8% yield). LCMS (m/z)=386.3, 388.3 [M+H]⁺, $t_R$=3.34 min. (compound same as Example 204)

Example 44

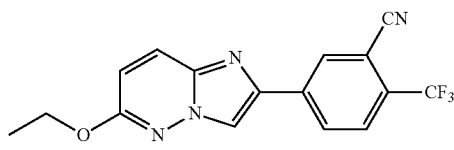 [SMILES: CCOc1ccc2nc(-c3ccc(C(F)(F)F)c(C#N)c3)cn2n1]

5-(6-ethoxyimidazo[2,1-f]pyridazin-2-yl)-2-(trifluoromethyl)benzonitrile

A mixture of 2-[3-bromo-4-(trifluoromethyl)phenyl]-6-ethoxy-imidazo[2,1-f]pyridazine (0.050 g, 0.129 mmol) and CuCN (0.058 g) in 4-methylmorpholine (2.0 mL) is heated in the microwave at 220° C. for 10 min. The mixture is diluted with MeOH (10 mL) and the solids are removed by filtration. The crude solution is concentrated to remove the MeOH. Water (50 mL) is added and the solid precipitate is collected. The crude product is purified by silica gel chromatography (0-100% EtOAc in Hexanes) to give the title compound (0.03 g, 71% yield). LCMS m/z=333.3 [M+H]⁺.

Example 45

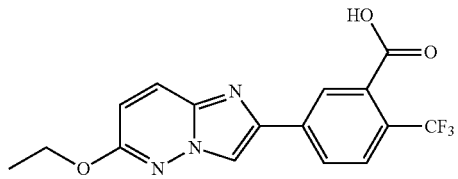 [SMILES: CCOc1ccc2nc(-c3ccc(C(F)(F)F)c(C(=O)O)c3)cn2n1]

5-(6-ethoxyimidazo[2,1-f]pyridazin-2-yl)-2-(trifluoromethyl)benzoic acid

A mixture of 5-(6-ethoxyimidazo[2,1-f]pyridazin-2-yl)-2-(trifluoromethyl)benzonitrile (0.030 g) and NaOH (2 mL, 10 N) is refluxed for 48 hours. The reaction mixture is cooled and extracted with Et₂O (2×2 mL). The pH is lowered to 1 and extracted with EtOAc (2×3 mL). The organics are collected, dried and concentrated to give the tile compound (0.03 g, 99% yield). LCMS m/z=352.3 [M+H]⁺.

Example 46

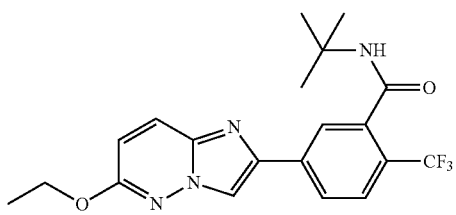 [SMILES: CCOc1ccc2nc(-c3ccc(C(F)(F)F)c(C(=O)NC(C)(C)C)c3)cn2n1]

N-tert-butyl-5-(6-ethoxyimidazo[2,1-f]pyridazin-2-yl)-2-(trifluoromethyl)benzamide An 8 mL vial is charged with acetonitrile (0.5 mL), 5-(6-ethoxyimidazo[2,1-f]pyridazin-2-yl)-2-(trifluoromethyl) benzoic acid (0.035 g, 0.0001 mol), tert-butylamine (0.016 mL), triethylamine (0.055 mL), and (benzotriazol-1-yloxy) tris(dimethylamino)phosphonium hexafluorophosphate (0.088 g). The mixture is stirred and heated at 80° C. for 16 hr, cooled, concentrated onto celite and purified by silica (0-100% EtOAc in Hexanes) to give the title compound (0.011 g, 28% yield). LCMS m/z=407.5 [M+H]$^+$, $t_R$=2.74 min. (compound same as Example 211)

Example 47

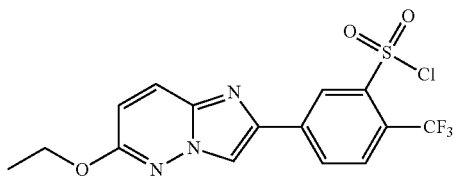 [SMILES: CCOc1ccc2nc(-c3ccc(C(F)(F)F)c(S(=O)(=O)Cl)c3)cn2n1]

5-(6-ethoxyimidazo[1,2-b]pyridazin-2-yl)-2-(trifluoromethyl)benzene-1-sulfonyl chloride To a stirred mixture of 5-(6-ethoxyimidazo[1,2-b]pyridazin-2-yl)-2-(trifluoromethyl)aniline (1.00 g, 3.10 mmol) in conc. HCl (6 mL) at −10° C. is added dropwise a solution of sodium nitrite (3.41 mmol) in water (3 mL) and the reaction mixture stirred for 30 minutes at −10° C. This mixture is then added to a solution of SO$_2$/AcOH (~0.2 g/mL, 50 mL) containing CuCl (1.55 mmol) at 0° C. in small portions. The reaction is allowed to warm to room temperature and stirred for an additional hour. The mixture is poured over into ice water (400 mL) and precipitate collected by filtration, washed with ice water (3×25 mL), dried under vacuum to afford 1.02 g (81%) of the title compound as a green solid. Product is used without further purification.

Example 48

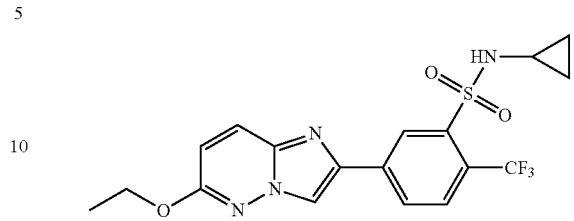

N-cyclopropyl-5-(6-ethoxyimidazo[1,2-b]pyridazin-2-yl)-2-(trifluoromethyl)benzenesulfonamide A solution of cyclopropanamine (0.025 mL, 0.369 mmol) in acetonitrile (1 mL) is added 5-(6-ethoxyimidazo[1,2-b] pyridazin-2-yl)-2-(trifluoromethyl)benzene-1-sulfonyl chloride (0.123 mmol). The mixture is stirred at 60° C. for 12 hours. The mixture is concentrated to dryness and then purified via chromatography using a gradient of hexanes to EtOAc to afford 0.035 g (67%) of the title compound as a white solid: LCMS (m/z)=427.4 [M+H]$^+$, $t_R$=2.76 min. (compound same as Example 212)

Example 49

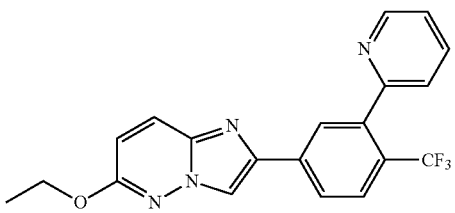 [SMILES: CCOc1ccc2nc(-c3ccc(C(F)(F)F)c(-c4ccccn4)c3)cn2n1]

6-ethoxy-2-(3-(pyridin-2-yl)-4-(trifluoromethyl)phenyl)imidazo[1,2-b]pyridazine

To a solution of 2-(3-bromo-4-(trifluoromethyl)phenyl)-6-ethoxyimidazo[1,2-b]pyridazine (0.025 g, 0.0647 mmol) in THF (0.647 mL) containing pyridin-2-ylzinc(II) bromide (0.323 mmol) is added Pd(dppf)Cl$_2$ (0.0194 mmol). The mixture is heated at 60° C. for 12 hours, then cooled, quenched with sat. aqueous NaHCO$_3$ (1 mL) and extracted with CH$_2$Cl$_2$ (3×3 mL). Organic layer is collected and concentrated to dryness. The crude product is purified via preparative TLC using CH$_2$Cl$_2$:EtOAc:methanol (1:1:0.1) to afford 0.0022 g (9%) of the title compound as a white solid: R$_f$ 0.35 (1:1 EtOAc:hexanes); LCMS (m/z)=385.4 [M+H]$^+$, $t_R$=2.69 min. (compound same as Example 218)

Example 50

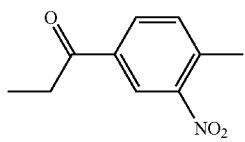

1-(4-methyl-3-nitrophenyl)propan-1-one

A solution of fuming nitric acid (100 mL) at 0° C. is added dropwise 1-p-tolylpropan-1-one (Sigma-Aldrich, 121 mmol) while maintaining the reaction temperature below 10° C. The reaction mixture is stirred at 0° C. for 1 hour then poured into excess ice water. The mixture is placed in a freezer overnight and precipitate collected by filtration, washed with ice water, and taken up in $CH_2Cl_2$. The organic solution is washed with sat. aqueous $NaHCO_3$ (100 mL), organic layer is collected, dried over $Na_2SO_4$, filtered and concentrated to dryness. The crude is purified via chromatography (hexanes to EtOAc) to afford the title compound (14.8 g, 63%) as a light yellow solid: $R_f$ 0.5 (1:4 EtOAc:hexanes).

Example 51

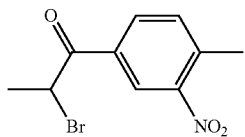

2-bromo-1-(4-methyl-3-nitrophenyl)propan-1-one

To a solution of 1-(4-methyl-3-nitrophenyl)propan-1-one (6.6 g, 34.1 mmol) in $CH_2Cl_2$ (200 mL) is added bromine (34.1 mmol) dropwise over 20 minutes. The reaction is stirred for 4 hours at room temp. and then washed with sat. aqueous $NaHCO_3$ (100 mL), organic layer is collected, dried over $Na_2SO_4$, filtered and concentrated to dryness to afford 9.0 g (97%) of the title compound as an orange oil: $R_f$ 0.53 (1:1 $CH_2Cl_2$:hexanes).

Example 52

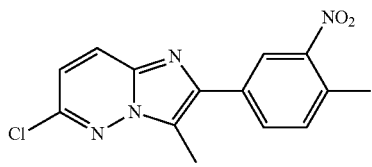 [SMILES: Cc1ccc(-c2nc3ccc(Cl)nn3c2C)cc1[N+](=O)[O-]]

6-chloro-3-methyl-2-(4-methyl-3-nitrophenyl)imidazo[1,2-b]pyridazine

A stirred solution of 6-chloropyridazin-3-amine (2.38 g, 18.3 mmol) and 2-bromo-1-(4-methyl-3-nitrophenyl)propan-1-one (5.0 g, 18.3 mmol) in acetonitrile (100 mL) is heated at 80° C. for 16 hours. The mixture is concentrated to dryness and then purified via silica chromatography (hexanes to EtOAc) to afford the title compound (3.2 g, 57%) as a light yellow solid: $R_f$ 0.30 ($CH_2Cl_2$); LCMS (m/z)=303.3, 305.2 $[M+H]^+$, $t_R$=2.84 min.

Example 53

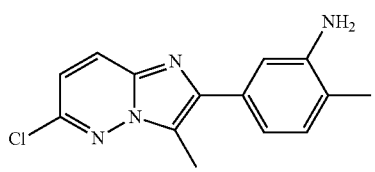 [SMILES: Cc1ccc(-c2nc3ccc(Cl)nn3c2C)cc1N]

5-(6-chloro-3-methylimidazo[1,2-b]pyridazin-2-yl)-2-methylaniline

To a mixture of 6-chloro-3-methyl-2-(4-methyl-3-nitrophenyl)imidazo[1,2-b]pyridazine (2.00 g, 6.60 mmol) in ethanol (100 mL) and water (25 mL) containing AcOH (39.6 mmol) is added iron (1.84 g, 33.0 mmol). The mixture is heated at 80° C. for 6 hours, then cooled, concentrated under reduced pressure and sat. aqueous $NaHCO_3$ (100 mL) is added. The mixture is extracted with EtOAc (3×50 mL). Organic layer is collected, dried over $Na_2SO_4$, filtered and concentrated to dryness. The crude is purified via chromatography (hexanes to EtOAc) to afford the title compound (1.45 g, 80%) as a yellow solid: $R_f$ 0.52 (EtOAc); LCMS (m/z)= 273.3, 275.3 $[M+H]^+$, $t_R$=1.79 min.

Example 54

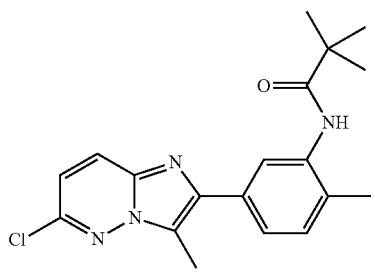 [SMILES: Cc1ccc(-c2nc3ccc(Cl)nn3c2C)cc1NC(=O)C(C)(C)C]

N-(5-(6-chloro-3-methylimidazo[1,2-b]pyridazin-2-yl)-2-methylphenyl)pivalamide

A solution of 5-(6-chloro-3-methylimidazo[1,2-b]pyridazin-2-yl)-2-methylaniline (1.40 g, 5.13 mmol) in acetonitrile (100 mL) and pyridine (15.3 mmol) is added trimethylacetylchloride (5.38 mmol). The mixture is stirred at room temperature for 4 hours. The reaction mixture is concentrated to dryness and then purified via chromatography using a gradient of hexanes to EtOAc to afford the title compound (1.25 g, 68%) as a

Example 55

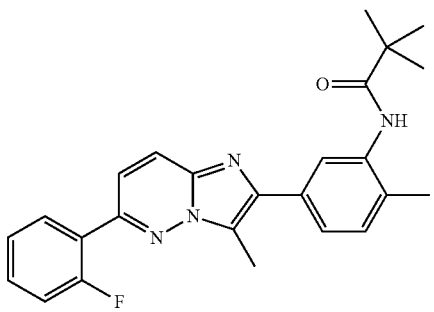 [SMILES: Cc1ccc(-c2nc3ccc(-c4ccccc4F)nn3c2C)cc1NC(=O)C(C)(C)C]

N-(5-(6-(2-fluorophenyl)-3-methylimidazo[1,2-b]pyridazin-2-yl)-2-methylphenyl)pivalamide To a mixture of N-(5-(6-chloro-3-methylimidazo[1,2-b]pyridazin-2-yl)-2-methylphenyl)pivalamide (0.100 g, 0.280 mmol), 4-fluorophenylboronic acid (0.420 mmol), Na$_2$CO$_3$ (0.840 mmol), 2-propanol (9 mL) and water (3 mL) that has been degassed with N$_2$ (5 minutes) is added PdCl$_2$(PPh$_3$)$_2$ (0.0280). The mixture is heated at 80° C. for 12 hours, diluted with sat. aqueous NaHCO$_3$ (50 mL) and extracted with EtOAc (3×25 mL). Organic layer is collected, dried over Na$_2$SO$_4$, filtered and concentrated to dryness. The crude product is purified via chromatography using a gradient of hexanes to EtOAc to afford the title compound (0.073 g, 62%) as a yellow solid: R$_f$ 0.29 (1:1 EtOAc:hexanes); LCMS (m/z)= 417.5 [M+H]$^+$, t$_R$=2.71 min. (compound same as Example 312)

Example 56

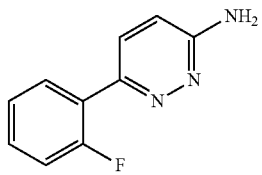 [SMILES: Nc1ccc(-c2ccccc2F)nn1]

6-(2-fluorophenyl)pyridazin-3-amine

To a mixture of 6-chloropyridazin-3-amine (3.00 g, 23.1 mmol), 4-fluorophenylboronic acid (34.7 mmol), Na$_2$CO$_3$ (69.3 mmol) in 2-propanol (150 mL) and water (50 mL) that has been degassed with N$_2$ (5 minutes) is added PdCl$_2$(PPh$_3$)$_2$(1.15 mmol). The mixture is heated at 80° C. for 12 hours, concentrated under reduced pressure, added sat. aqueous NaHCO$_3$ (100 mL) and extracted with EtOAc (3×100 mL). Organic layer is collected, dried over Na$_2$SO$_4$, filtered and concentrated to dryness. The crude product is purified via chromatography using a gradient of CH$_2$Cl$_2$ to 70% CH$_2$Cl$_2$:EtOAc:methanol (1:1:0.1) to afford the title compound (3.82 g, 87%) as a white solid: R$_f$ 0.37 (1:1:0.1 CH$_2$Cl$_2$:EtOAc:methanol); LCMS (m/z)=190.2 [M+H]$^+$, t$_R$=0.44 min.

Example 57

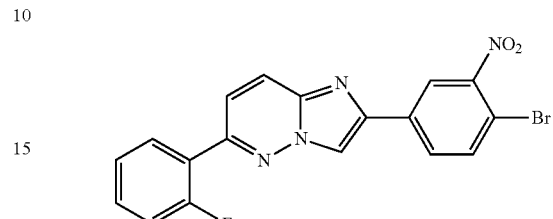

2-(4-bromo-3-nitrophenyl)-6-(2-fluorophenyl)imidazo[1,2-b]pyridazine

A stirred solution of 6-(2-fluorophenyl)pyridazin-3-amine (2.22 g, 11.7 mmol) and 2-bromo-1-(4-bromo-3-nitrophenyl)ethanone (3.78 g, 11.7 mmol) in acetonitrile (100 mL) is heated at 80° C. for 12 hours. The mixture is concentrated to dryness and then purified via chromatography using CH$_2$Cl$_2$ to afford the title compound (1.83 g, 37%) as a yellow solid: R$_f$ 0.46 (CH$_2$Cl$_2$); LCMS (m/z)=413.3, 415.3 [M+H]$^+$, t$_R$=3.19 min.

Example 58

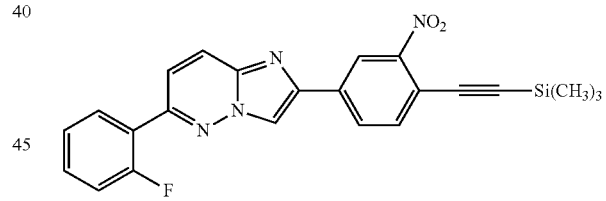

6-(2-fluorophenyl)-2-(3-nitro-4-((trimethylsilyl)ethynyl)phenyl)imidazo[1,2-b]pyridazine To a mixture of 2-(4-bromo-3-nitrophenyl)-6-(2-fluorophenyl)imidazo[1,2-b]pyridazine (0.500 g, 1.21 mmol), ethynyltrimethylsilane (2.42 mmol), PdCl$_2$(PPh$_3$)$_2$(0.0242 mmol) in THF (50 mL) containing triethylamine (6.05 mmol) is added CuI (0.0242 mmol). The mixture is degassed with N$_2$ (5 minutes) then heated at 60° C. for 12 hours. The mixture is filtered, followed by washing with EtOAC, filtrate collected, concentrated under reduced pressure and crude product is purified via chromatography using CH$_2$Cl$_2$ to afford the title compound (0.425 g, 81%) as a yellow solid: R$_f$ 0.56 (CH$_2$Cl$_2$); LCMS (m/z)=431.4 [M+H]$^+$, t$_R$=3.86 min.

Example 59

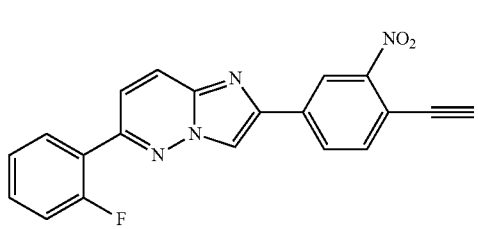 [SMILES: C#Cc1ccc(-c2cn3nc(-c4ccccc4F)ccc3n2)cc1[N+](=O)[O-]]

2-(4-ethynyl-3-nitrophenyl)-6-(2-fluorophenyl)imidazo[1,2-b]pyridazine

A stirred mixture of 6-(2-fluorophenyl)-2-(3-nitro-4-((trimethylsilyl)ethynyl)phenyl)imidazo[1,2-b]pyridazine (0.250 g, 0.58 mmol) in acetonitrile (100 mL) containing catalytic cesium carbonate (0.101 mmol) in water (0.031 mL) is heated at 60° C. for 4 hours. The mixture is concentrated to dryness then purified via chromatography using CH$_2$Cl$_2$ to afford the title product (0.170 g, 82%) as a yellow solid: R$_f$ 0.40 (CH$_2$Cl$_2$); LCMS (m/z)=359.4 [M+H]$^+$, t$_R$=3.02 min.

Example 60

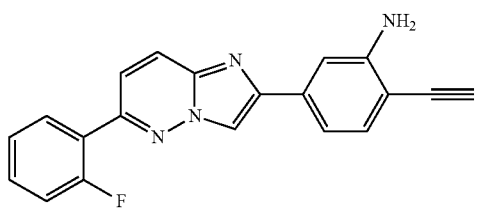 [SMILES: C#Cc1ccc(-c2cn3nc(-c4ccccc4F)ccc3n2)cc1N]

2-ethynyl-5-(6-(2-fluorophenyl)imidazo[1,2-b]pyridazin-2-yl)aniline

To a solution of 2-(4-ethynyl-3-nitrophenyl)-6-(2-fluorophenyl)imidazo[1,2-b]pyridazine (0.050 g, 0.139 mmol) in ethanol (3 mL) and water (1 mL) containing AcOH (0.834 mmol) is added iron (0.038 g, 0.695 mmol). The mixture is stirred and heated at 80° C. for 2 hours, then concentrated under reduced pressure and sat. aqueous NaHCO$_3$ (20 mL) is added. The mixture is extracted with EtOAc (3×20 mL). Organic layer is collected, dried over Na$_2$SO$_4$, filtered and concentrated to dryness. The crude product is purified via chromatography using a gradient of hexanes to EtOAc to afford the title compound (0.033 g, 73%) as a yellow solid: R$_f$ 0.30 (1:1 EtOAc:hexanes); LCMS (m/z)=329.4 [M+H]$^+$, t$_R$=2.65 min. (compound same as Example 320)

Example 61

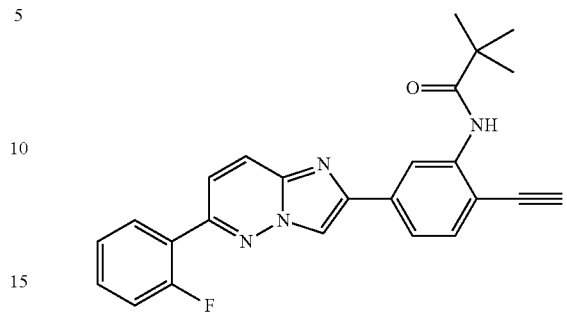

N-(2-ethynyl-5-(6-(2-fluorophenyl)imidazo[1,2-b]pyridazin-2-yl)phenyl)pivalamide A solution of 2-ethynyl-5-(6-(2-fluorophenyl)imidazo[1,2-b]pyridazin-2-yl)aniline (0.030 g, 0.0913 mmol) in acetonitrile (1 mL) containing pyridine (0.273 mmol) is added trimethylacetylchloride (0.0958 mmol). The mixture is stirred at room temperature for 4 hours, then concentrated to dryness and residue purified via silica chromatography (hexanes to EtOAc) to afford the title compound (0.029 g, 78%) as a yellow solid: R$_f$ 0.58 (1:1 EtOAc:hexanes); LCMS (m/z)= 413.5 [M+H]$^+$, t$_R$=3.19 min. (compound same as Example 321)

Example 62

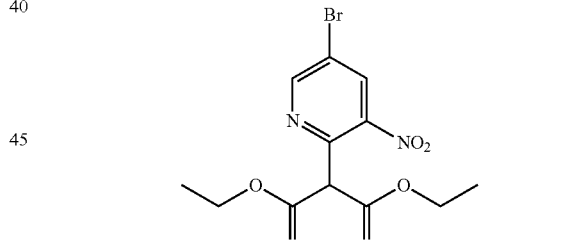

diethyl 2-(5-bromo-3-nitropyridin-2-yl)malonate

To a mixture of NaH (3.36 g, 60% mineral oil, 84.2 mmol) in DMF (60 mL) at 0° C. is added dropwise diethylmalonate (84.2 mmol). The mixture is allowed to warm to room temperature for 20 minutes and then cooled to 0° C. A solution of 5-bromo-2-chloro-3-nitropyridine (Combi-Blocks, 42.1 mmol) in DMF (20 mL) is slowly added and the reaction is allowed to warm to room temperature followed by heating at 40° C. for 3 hours. The reaction is quenched with AcOH in water (1M, 100 mL) and extracted with CH$_2$Cl$_2$ (3×200 mL). Organic layer is collected, dried over Na$_2$SO$_4$, filtered and concentrated to dryness. The crude product is purified via chromatography using CH$_2$Cl$_2$ to afford 12.8 g (84%) of the title compound as an oil: $R_f$ 0.65 ($CH_2Cl_2$); LCMS (m/z)= 361.3, 363.3 [M+H]$^+$, $t_R$=2.59 min.

Example 63

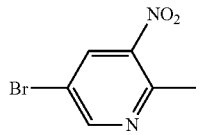

5-bromo-2-methyl-3-nitropyridine

A stirred mixture of diethyl 2-(5-bromo-3-nitropyridin-2-yl)malonate (12.5 g, 34.6 mmol) in HCl (7 N in water, 200 mL) is heated at reflux for 18 hours. The mixture is cooled to room temperature and extracted with $CH_2Cl_2$ (3×200 mL). Organic layer is collected, dried over $Na_2SO_4$, filtered and concentrated to dryness. The crude product is purified via chromatography using $CH_2Cl_2$ to afford the title compound (5.8 g, 84%) as a yellow solid: $R_f$ 0.67 ($CH_2Cl_2$); LCMS (m/z)=217.1, 219.2 [M+H]$^+$, $t_R$=2.01 min.

Example 64

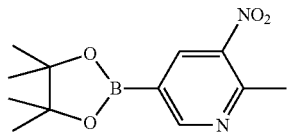

2-methyl-3-nitro-5-(4,4,5,5-tetramethyl-1,3,2-dioxaborolan-2-yl)pyridine

To a mixture of 5-bromo-2-methyl-3-nitropyridine (0.50 g, 0.230 mmol), bis-(pinacolato)diboron (2.30 mmol), potassium acetate (4.60 mmol) in 1,4-dioxane (5 mL) is added $Pd(dppf)_2Cl_2$ (0.0194 mmol). The mixture is heated in the microwave at 100° C. for 90 minutes, cooled, concentrated to dryness and crude product is purified via chromatography (hexanes to EtOAc) to afford 0.402 g (66%) of the title product as a yellow solid: LCMS (m/z)(boronic acid)=183.2 [M+H]$^+$, $t_R$=0.69 min.

Example 65

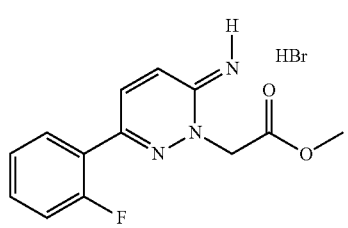 [SMILES: [H]/N=c1\ccc(-c2ccccc2F)nn1CC(=O)OC ; Br]

methyl 2-(3-(2-fluorophenyl)-6-iminopyridazin-1(6H)-yl)acetate hydrobromide

A stirred solution of 6-(2-fluorophenyl)pyridazin-3-amine (0.500 g, 2.64 mmol) and methyl 2-bromoacetate (2.90 mmol) in acetonitrile (15 mL) is heated at 80° C. for 4 hours. The mixture is cooled to 0° C. and precipitate collected by filtration, washed with cold acetonitrile (2×10 mL) to afford the title compound (0.693 g, 76%) as a white solid: LCMS (m/z)=262.3 [M+H]$^+$, $t_R$=0.47 min.

Example 66

2-chloro-6-(2-fluorophenyl)imidazo[1,2-b]pyridazine

To a solution of methyl 2-(3-(2-fluorophenyl)-6-iminopyridazin-1(6H)-yl)acetate hydrobromide (0.5 g, 1.46 mmol) in chlorobenzene (20 mL) is added $POCl_3$ (7.30 mmol). The reaction mixture is heated at 120° C. for 4 hours, cooled, concentrated under reduced pressure to dryness and sat. aqueous $NaHCO_3$ (25 mL) is added. The mixture is extracted with $CH_2Cl_2$ (3×20 mL). Organic layer is collected, dried over $Na_2SO_4$, filtered and concentrated to dryness. The crude product is purified via silica chromatography (hexanes to EtOAc) to afford the title compound (0.309 g, 85%) as a white solid: $R_f$ 0.39 (1:4 EtOAc:hexanes); LCMS (m/z)=248.2, 250.2 [M+H]$^+$, $t_R$=2.51 min.

Example 67

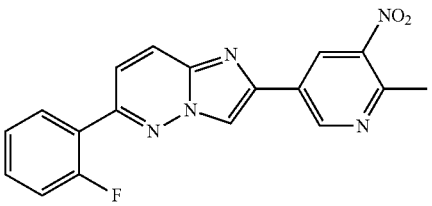 [SMILES: Cc1ncc(-c2cn3nc(-c4ccccc4F)ccc3n2)cc1[N+](=O)[O-]]

6-(2-fluorophenyl)-2-(6-methyl-5-nitropyridin-3-yl)imidazo[1,2-b]pyridazine

To a mixture of 2-chloro-6-(2-fluorophenyl)imidazo[1,2-b]pyridazine (0.100 g, 0.403 mmol), 2-methyl-3-nitro-5-(4,4,5,5-tetramethyl-1,3,2-dioxaborolan-2-yl)pyridine (0.605 mmol), $Na_2CO_3$ (2.01 mmol) in 2-propanol (3.75 mL) and water (1.25 mL) that has been degassed with $N_2$ (5 minutes) is added $PdCl_2(PPh_3)_2$(0.0403) mmol). The mixture is heated at 80° C. for 12 hours, then cooled, concentrated under reduced pressure, added sat. aqueous $NaHCO_3$ (20 mL) and extracted with EtOAc (3×20 mL). Organic layer is collected, dried over $Na_2SO_4$, filtered and concentrated to dryness. The crude product is purified via chromatography (hexanes to EtOAc) to afford the title compound (0.016 g, 11%) as a white solid: R_f 0.38 (1:1 EtOAc:hexanes); LCMS (m/z)=350.3 [M+H]+, t_R=2.71 min.

Example 68

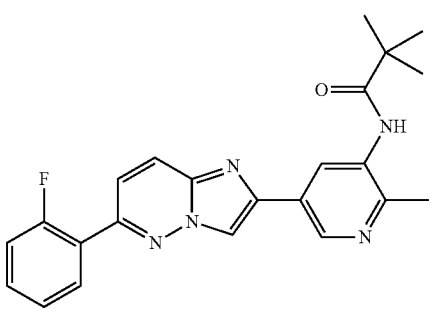 [SMILES: Cc1ncc(-c2cn3nc(-c4ccccc4F)ccc3n2)cc1NC(=O)C(C)(C)C]

N-(5-(6-(2-fluorophenyl)imidazo[1,2-b]pyridazin-2-yl)-2-methylpyridin-3-yl)pivalamide To a solution of 6-(2-fluorophenyl)-2-(6-methyl-5-nitropyridin-3-yl)imidazo[1,2-b]pyridazine (0.016 g, 0.0458 mmol) in ethanol (3 mL) and water (1 mL) containing AcOH (0.274 mmol) is added iron (0.013 g, 0.229 mmol). The mixture is heated at 80° C. for 2 hours. The mixture is concentrated under reduced pressure and sat. aqueous NaHCO_3 (10 mL) is added. The mixture is extracted with EtOAc (20 mL). Organic layer is collected and concentrated to dryness. Crude amine is taken up in acetonitrile (3 mL) containing pyridine (0.137 mmol). To this solution is added trimethylacetylchloride (0.0503 mmol). The mixture is stirred at room temperature for 4 hours, concentrated to dryness and then purified via silica chromatography using a gradient CH_2Cl_2 to CH_2Cl_2:EtOAc:methanol (1:1:0.1) to afford the title compound (0.008 g, 44%) as a light yellow solid: R_f 0.34 (1:1:0.1 CH_2Cl_2:EtOAc:methanol); LCMS (m/z)=404.4 [M+H]+, t_R=2.11 min. (compound same as Example 390)

Example 69

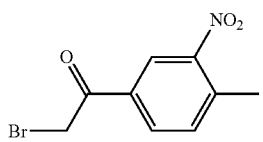

2-bromo-1-(4-methyl-3-nitro-phenyl)ethanone

A solution of 1-(4-methyl-3-nitro-phenyl)ethanone (Sigma-Aldrich, 25.08 g, 0.14 mol) in CH_2Cl_2 (269 mL) is cooled to 0° C. To this is added bromine (7.17 mL, 0.14 mol) at 0° C. with stirring. The reaction mixture is allowed to warm slowly to rt over a total of 90 minutes. Ice water (500 mL) is added, organics are collected and aqueous layer is extracted with CH_2Cl_2 (2×250 mL). The organic layers are combined, washed with water, dried with Na_2SO_4 and concentrated to give the title compound (36.1 g, 99% yield). LCMS m/z=258.3, 260.2 [M+H]+, t_R=2.39 min.

Example 70

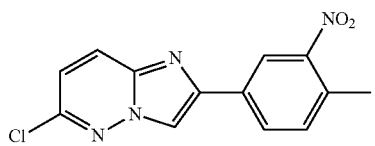 [SMILES: Cc1ccc(-c2cn3nc(Cl)ccc3n2)cc1[N+](=O)[O-]]

6-chloro-2-(4-methyl-3-nitro-phenyl)imidazo[2,1-f]pyridazine

A stirred solution of 6-chloropyridazin-3-amine (18.4 g, 0.14 mol) and 2-bromo-1-(4-methyl-3-nitro-phenyl)ethanone (36.13 g, 0.14 mol) in acetonitrile (219 mL) is heated at reflux for 18 hr. The mixture is diluted with water (500 mL), stirred at room temperature for 1 hour and solids are collected by filtration to give the title compound (35.65 g, 88% yield). LCMS m/z=289.4 [M+H]+, t_R=2.65 min.

Example 71

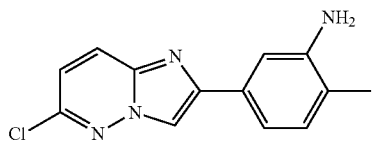 [SMILES: Cc1ccc(-c2cn3nc(Cl)ccc3n2)cc1N]

5-(6-chloroimidazo[2,1-f]pyridazin-2-yl)-2-methylaniline

Iron (1.34 g) is added to a mixture of 6-chloro-2-(4-methyl-3-nitro-phenyl)imidazo[2,1-f]pyridazine (1.15 g, 0.004 mol) and EtOH—AcOH (120 mL, 2:1). The mixture is stirred at 80° C. for 2 hours, cooled to room temperature, filtered through celite which is washed with EtOAc, and concentrated. The oily residue is dissolved in EtOAc (500 mL) and washed once with sat. NaHCO_3 (200 mL). Organic layer is dried and concentrated to give the title compound (0.85 g, 82%), which is used without further purification. LCMS m/z=259.4 [M+H]+, t_R=1.64 min.

Example 72

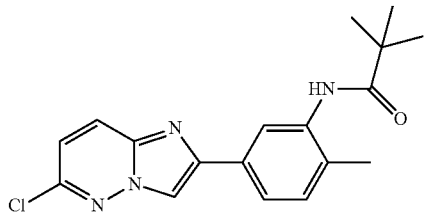 [SMILES: Cc1ccc(-c2cn3nc(Cl)ccc3n2)cc1NC(=O)C(C)(C)C]

N-[5-(6-chloroimidazo[2,1-f]pyridazin-2-yl)-2-methyl-phenyl]-2,2-dimethyl-propanamide A 40 mL vial is charged with 5-(6-chloroimidazo[2,1-f]pyridazin-2-yl)-2-methyl-aniline (0.85 g, 3.28 mmol), acetonitrile (14 mL) and pyridine (0.450 mL). The mixture is added trimethylacetyl chloride (0.628 mL, 0.0051 mol) and stirred for 20 min at 80° C. The mixture is concentrated, taken up in EtOAc (35 mL) and washed once with HCl (20 mL, 1M) and then NaOH (20 mL, 1M). Organic layer is dried, concentrated and purified on silica gel chromatography (0-100% EtOAc in Hexanes) to give the title compound (1.05 g, 94% yield). LCMS m/z=343.5 [M+H]$^+$, t$_R$=2.39 min. (compound same as Example 118)

Example 73

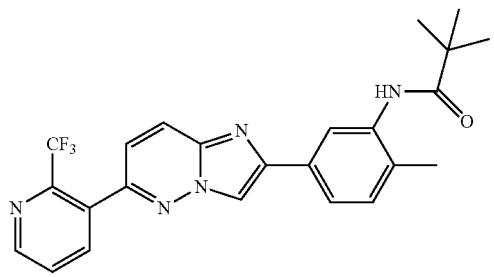 [SMILES: Cc1ccc(-c2cn3nc(-c4cccnc4C(F)(F)F)ccc3n2)cc1NC(=O)C(C)(C)C]

2,2-dimethyl-N-[2-methyl-5-[6-[2-(trifluoromethyl)-3-pyridyl]imidazo[2,1-f]pyridazin-2-yl]phenyl]propanamide An 8 mL vial is charged with N-[5-(6-chloroimidazo[2,1-f]pyridazin-2-yl)-2-methyl-phenyl]-2,2-dimethyl-propanamide (0.034 g, 0.0001 mol), [2-(trifluoromethyl)-3-pyridyl]boronic acid (Combi-Blocks, 0.038 g), bis(triphenylphosphine)palladium(II) dichloride (0.007 g), Na$_2$CO$_3$ (0.032 g), and isopropanol-water (1 mL, 3:1). The mixture is heated at 80° C. for 16 hr. The mixture is concentrated, taken up in EtOAc and CH$_2$Cl$_2$ (1:1), filtered, concentrated onto celite, and purified by silica gel chromatography (0-100% EtOAc in Hexanes) to give the title compound (0.015 g, 33% yield). LCMS m/z=454.6 [M+H]$^+$, t$_R$=2.52 min. (compound same as Example 284)

Example 74

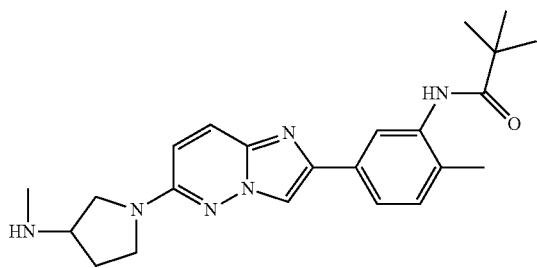 [SMILES: CNC1CCN(c2ccc3nc(-c4ccc(C)c(NC(=O)C(C)(C)C)c4)cn3n2)C1]

2,2-dimethyl-N-[2-methyl-5-[6-(3-methylaminopyrrolidin-1-yl)imidazo[2,1-f]pyridazin-2-yl]phenyl]propanamide An small microwave vial is charged butanol (0.183 mL), diisopropylethylamine (0.122 mL, 0.7 mmol), N-methylpyrrolidin-3-amine (0.050 g, 0.5 mmol), and N-[5-(6-chloroimidazo[2,1-f]pyridazin-2-yl)-2-methyl-phenyl]-2,2-dimethyl-propanamide (0.0397 g, 0.1 mmol). The vial is sealed and heated at 180° C. for 30 min in microwave. The mixture is concentrated, taken up in DMSO and purified on reverse phase preparative HPLC with gradient (15% B:85% A to 100% B, where solvent A=95% water, 5% acetonitrile and 0.1% TFA; solvent B=90% acetonitrile, 10% water and 0.1% TFA) to give the title compound (0.006 g, 15% yield). LCMS m/z=407.6 [M+H]$^+$, t$_R$=1.32 min. (compound same as Example 360)

Example 75

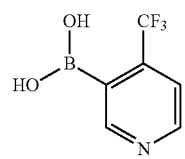 [SMILES: OB(O)c1cnccc1C(F)(F)F]

[4-(trifluoromethyl)-3-pyridyl]boronic acid n-Butyllithium (2.5 M in hexane, 2 mL) is added to a mixture of 3-bromo-4-(trifluoromethyl)pyridine (Matrix Scientific, 1 g, 0.022 mol) and triisopropylborate (1.25 mL) in anhydrous THF (9 mL) at −78° C. under nitrogen. The reaction mixture is stirred at −78° C. for 3.5 hr before warming gradually to room temperature. The reaction is quenched with water (9 mL). The organic solvent is removed under reduced pressure. The resulting aqueous phase is treated with NaOH (10 N) to obtain pH 10, washed with diethyl ether (1×8 mL), and aqueous phase is acidified to pH 5 using acetic acid. The solution is extracted with EtOAc (1×25 mL) and the organic layer is dried and evaporated to dryness to give the title compound (0.150 g, 15% yield). LCMS m/z=192.2 [M+H]$^+$, t$_R$=0.36 min.

Example 76

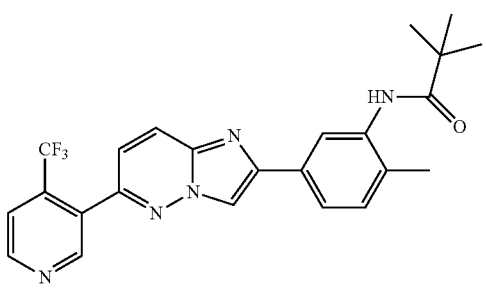 [SMILES: Cc1ccc(-c2cn3nc(-c4cnccc4C(F)(F)F)ccc3n2)cc1NC(=O)C(C)(C)C]

2,2-dimethyl-N-[2-methyl-5-[6-[4-(trifluoromethyl)-3-pyridyl]imidazo[2,1-f]pyridazin-2-yl]phenyl]propanamide An 8 mL vial is charged with N-[5-(6-chloroimidazo[2,1-f]pyridazin-2-yl)-2-methyl-phenyl]-2,2-dimethyl-propanamide (0.034 g, 0.1 mmol), [4-(trifluoromethyl)-3-pyridyl]boronic acid (0.038 g), bis(triphenylphosphine)palladium(II) dichloride (7 mg), Na$_2$CO$_3$ (0.032 g), and isopropanol-water (1 mL, 3:1). The mixture is heated at 80° C. for 16 hr, cooled, concentrated, taken up in 1:1 EtOAc and CH$_2$Cl$_2$, filtered, concentrated onto celite and purified by silica gel chromatography (10-100% EtOAc in Hexanes) to give the title compound (0.011 g, 25% yield). LCMS m/z=454.5 [M+H]$^+$, $t_R$=2.47 min. (compound same as Example 364)

Example 77

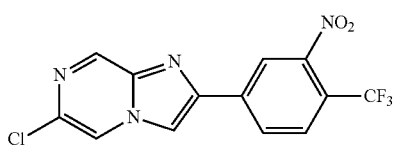

6-chloro-2-[3-nitro-4-(trifluoromethyl)phenyl]imidazo[1,2-a]pyrazine

A solution of 5-chloropyrazin-2-amine (0.336 g, 2.6 mmol) and 2-bromo-1-[3-nitro-4-(trifluoromethyl)phenyl]ethanone (0.811 g, 2.6 mmol) in acetonitrile (15 mL) is stirred at 100° C. for 18 hr. The mixture is concentrated to give the title compound (890 mg), which is used without further purification. LCMS m/z=343.3 [M+H]$^+$, $t_R$=2.65 min.

Example 78

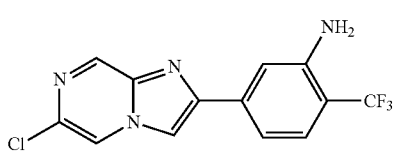

5-(6-chloroimidazo[1,2-a]pyrazin-2-yl)-2-(trifluoromethyl)aniline

Iron (0.726 g) is added to a mixture of 6-chloro-2-[3-nitro-4-(trifluoromethyl)phenyl]imidazo[1,2-a]pyrazine (0.891 g), HOAc (1.19 mL), and EtOH—H$_2$O (10 mL, 4:1). The mixture is stirred at 80° C. for 2 hours, cooled, concentrated and taken up into sat. aqueous NaHCO$_3$ and extracted with EtOAc and CH$_2$Cl$_2$. Organic layer is dried and concentrated to give the title compound (813 mg), which is used without further purification. LCMS m/z=313.4 [M+H]$^+$, $t_R$=2.29 min.

Example 79

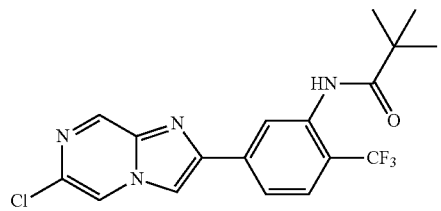

N-[5-(6-chloroimidazo[1,2-a]pyrazin-2-yl)-2-(trifluoromethyl)phenyl]-2,2-dimethyl-propanamide A 20 mL vial is charged with 5-(6-chloroimidazo[1,2-a]pyrazin-2-yl)-2-(trifluoromethyl)aniline (0.813 g, 2.6 mmol), acetonitrile (14 mL) and pyridine (0.420 mL). The mixture is added trimethylacetyl chloride (0.640 mL, 5.2 mmol) and stirred for 20 min at 80° C. The acetonitrile solution is concentrated onto celite and purified by silica gel chromatography (0-100% EtOAc in Hexanes) to give the title compound (256 mg, 25% yield). LCMS m/z=397.5 [M+H]$^+$, $t_R$=2.62 min. (compound same as Example 85)

Example 80

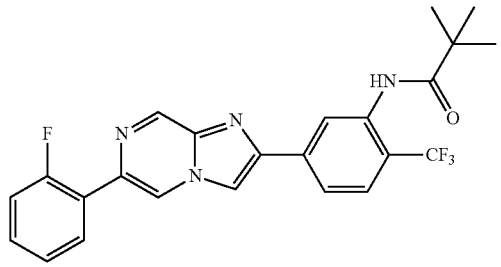 [SMILES: CC(C)(C)C(=O)Nc1cc(-c2cn3cc(-c4ccccc4F)ncc3n2)ccc1C(F)(F)F]

N-[5-[6-(2-fluorophenyl)imidazo[1,2-a]pyrazin-2-yl]-2-(trifluoromethyl)phenyl]-2,2-dimethyl-propanamide An 8 mL vial is charged with N-[5-(6-chloroimidazo[1,2-a]pyrazin-2-yl)-2-(trifluoromethyl)phenyl]-2,2-dimethyl-propanamide (0.0516 g, 0.13 mmol), 2-fluorophenylboronic acid (Combi-Blocks, 32 mg, 0.26 mmol), Na$_2$CO$_3$ (0.0413 g, 0.39 mmol), bis(triphenylphosphine)palladium(II) dichloride (0.009 g, 0.01 mmol), and isopropanol-water (1 mL, 3:1). The mixture is stirred at 70° C. for 16 hr. The reaction mixture is concentrated, taken up in EtOAc and CH$_2$Cl$_2$ (1:1) and purified by preparative plate TLC (1:1 Hexanes:EtoAc) to give the title compound (6 mg, 10% yield). LCMS m/z=457.5 [M+H]$^+$, $t_R$=3.06 min. (compound same as Example 86)

The following compounds are prepared essentially according to the procedures and examples set forth above, with modifications where necessary of the starting materials to provide the desired product.

| Example No. | Compound | LCMS (m/z) M + H |
|---|---|---|
| 81 | N-(5-(6-chloroimidazo[1,2-a]pyridin-2-yl)-2-(trifluoromethyl)phenyl)pivalamide | 396.4 |
| 82 | N-(5-(7-chloroimidazo[1,2-a]pyridin-2-yl)-2-(trifluoromethyl)phenyl)pivalamide | 396.4 |
| 83 | N-(5-(6-(2-fluorophenyl)imidazo[1,2-a]pyridin-2-yl)-2-(trifluoromethyl)phenyl)pivalamide | 456.4 |
| 84 | N-(5-(6-(2-fluoro-5-(trifluoromethyl)phenyl)imidazo[1,2-a]pyridin-2-yl)-2-(trifluoromethyl)phenyl)pivalamide | 524.4 |
| 85 | N-(5-(6-chloroimidazo[1,2-a]pyrazin-2-yl)-2-(trifluoromethyl)phenyl)pivalamide | 397.3 |
| 86 | N-(5-(6-(2-fluorophenyl)imidazo[1,2-a]pyrazin-2-yl)-2-(trifluoromethyl)phenyl)pivalamide | 457.4 |
| 87 | N-(5-(imidazo[1,2-a]pyrimidin-2-yl)-2-methoxyphenyl)furan-2-carboxamide | 335.4 |
| 88 | N-(3-(imidazo[1,2-a]pyrimidin-2-yl)phenyl)-2-phenoxyacetamide | 345.4 |
| 89 | N-(5-(imidazo[1,2-a]pyrimidin-2-yl)-2-methylphenyl)-3,3-dimethylbutanamide | 323.4 |
| 90 | 1-(3-(3-methylimidazo[1,2-a]pyrimidin-2-yl)phenyl)-3-phenylurea | 344.4 |
| 91 | 4-butoxy-N-(5-(imidazo[1,2-a]pyrimidin-2-yl)-2-methoxyphenyl)benzamide | 417.4 |
| 92 | N-(3-(3-methylimidazo[1,2-a]pyrimidin-2-yl)phenyl)cyclohexanecarboxamide | 335.4 |
| 94 | N-(5-(6-methoxyimidazo[1,2-b]pyridazin-2-yl)-2-methylphenyl)pivalamide | 339.4 |
| 95 | 2-chloro-N-(5-(6-methoxyimidazo[1,2-b]pyridazin-2-yl)-2-methylphenyl)-4-(methylsulfonyl)benzamide | 471.3 |
| 96 | 2-fluoro-N-(5-(6-methoxyimidazo[1,2-b]pyridazin-2-yl)-2-methylphenyl)benzamide | 377.4 |
| 97 | N-(5-(6-methoxyimidazo[1,2-b]pyridazin-2-yl)-2-methylphenyl)benzamide | 359.4 |
| 98 | 2-chloro-4-fluoro-N-(5-(6-methoxyimidazo[1,2-b]pyridazin-2-yl)-2-methylphenyl)benzamide | 411.3 |
| 99 | N-(5-(6-methoxyimidazo[1,2-b]pyridazin-2-yl)-2-methylphenyl)-2-(trifluoromethyl)benzamide | 427.4 |
| 100 | N-(5-(6-methoxyimidazo[1,2-b]pyridazin-2-yl)-2-methylphenyl)-3-(trifluoromethyl)benzamide | 427.3 |
| 101 | 2-(4-chlorophenyl)-N-(5-(6-methoxyimidazo[1,2-b]pyridazin-2-yl)-2-methylphenyl)acetamide | 407.3 |
| 102 | N-(4-fluorobenzyl)-5-(6-methoxyimidazo[1,2-b]pyridazin-2-yl)-2-methylaniline | 363.3 |
| 103 | N-(3,5-dimethoxybenzyl)-5-(6-methoxyimidazo[1,2-b]pyridazin-2-yl)-2-methylaniline | 405.4 |
| 104 | N,N-bis(3,5-dimethoxybenzyl)-5-(6-methoxyimidazo[1,2-b]pyridazin-2-yl)-2-methylaniline | 555.5 |
| 105 | N-(5-(imidazo[1,2-b]pyridazin-2-yl)-2-methylphenyl)pivalamide | 309.4 |
| 106 | N-(5-(6-methoxyimidazo[1,2-b]pyridazin-2-yl)-2,4-dimethylphenyl)pivalamide | 353.4 |
| 107 | N-(5-(imidazo[1,2-b]pyridazin-2-yl)-2,4-dimethylphenyl)pivalamide | 323.4 |
| 108 | N-(5-(imidazo[1,2-b]pyridazin-2-yl)-2-methylphenyl)-3,3-dimethylbutanamide | 323.4 |
| 109 | N-(5-(3-chloro-6-methoxyimidazo[1,2-b]pyridazin-2-yl)-2-methylphenyl)pivalamide | 373.3 |
| 110 | N-(2-chloro-5-(6-methoxyimidazo[1,2-b]pyridazin-2-yl)phenyl)pivalamide | 359.4 |
| 111 | N-(2-chloro-5-(6-methoxyimidazo[1,2-b]pyridazin-2-yl)phenyl)-3,3,3-trifluoropropanamide | 385.3 |
| 112 | N-(2-chloro-5-(6-methoxyimidazo[1,2-b]pyridazin-2-yl)phenyl)cyclopentanecarboxamide | 371.4 |
| 113 | N-(2-chloro-5-(imidazo[1,2-b]pyridazin-2-yl)phenyl)pivalamide | 329.4 |
| 114 | N-(5-(3-(4-fluorophenyl)-6-methoxyimidazo[1,2-b]pyridazin-2-yl)-2-methylphenyl)pivalamide | 433.5 |
| 115 | N-(4-chloro-3-(6-methoxyimidazo[1,2-b]pyridazin-2-yl)phenyl)pivalamide | 359.4 |
| 116 | N-(4-chloro-3-(6-methoxyimidazo[1,2-b]pyridazin-2-yl)phenyl)cyclopropanecarboxamide | 343.3 |
| 117 | N-(4-chloro-3-(6-methoxyimidazo[1,2-b]pyridazin-2-yl)phenyl)-3,3-dimethylbutanamide | 373.4 |
| 118 | N-(5-(6-chloroimidazo[1,2-b]pyridazin-2-yl)-2-methylphenyl)pivalamide | 343.4 |
| 119 | N-(2-chloro-5-(6-methoxyimidazo[1,2-b]pyridazin-2-yl)phenyl)-3,3,3-trifluoro-2,2-dimethylpropanamide | 413.3 |
| 120 | N-(2-chloro-5-(6-methoxyimidazo[1,2-b]pyridazin-2-yl)phenyl)-4,4,4-trifluoro-3-methylbutanamide | 413.3 |
| 121 | N-(5-(6-methoxy-3-methylimidazo[1,2-b]pyridazin-2-yl)-2-methylphenyl)pivalamide | 353.4 |
| 122 | N-(5-(6-chloroimidazo[1,2-b]pyridazin-2-yl)-2-methylphenyl)-3,3,3-trifluoro-2,2-dimethylpropanamide | 397.4 |
| 123 | N-(5-(6-(4-(4-fluorobenzyl)piperazin-1-yl)imidazo[1,2-b]pyridazin-2-yl)-2-methylphenyl)pivalamide | 501.5 |
| 124 | N-(5-(6-(butylthio)imidazo[1,2-b]pyridazin-2-yl)-2-methylphenyl)pivalamide | 397.5 |
| 125 | N-(5-(6-methoxyimidazo[1,2-b]pyridazin-2-yl)-2-(trifluoromethyl)phenyl)pivalamide | 393.4 |

-continued

| Example No. | Compound | |
|---|---|---|
| 126 | N-(5-(6-chloroimidazo[1,2-b]pyridazin-2-yl)-2-(trifluoromethyl)phenyl)pivalamide | 397.4 |
| 127 | N-(5-(6-cyclopropylimidazo[1,2-b]pyridazin-2-yl)-2-methylphenyl)pivalamide | 349.5 |
| 128 | N-(2-methyl-5-(6-morpholinoimidazo[1,2-b]pyridazin-2-yl)phenyl)pivalamide | 394.5 |
| 129 | N-(5-(6-(benzylthio)imidazo[1,2-b]pyridazin-2-yl)-2-methylphenyl)pivalamide | 431.4 |
| 130 | N-(5-(6-(butylsulfonyl)imidazo[1,2-b]pyridazin-2-yl)-2-methylphenyl)pivalamide | 429.4 |
| 131 | N-(4-chloro-5-(6-chloroimidazo[1,2-b]pyridazin-2-yl)-2-methylphenyl)pivalamide | 377.3 |
| 132 | N-(4-chloro-5-(6-methoxyimidazo[1,2-b]pyridazin-2-yl)-2-methylphenyl)pivalamide | 373.4 |
| 133 | N-(5-(6-cyclopentylimidazo[1,2-b]pyridazin-2-yl)-2-(trifluoromethyl)phenyl)pivalamide | 431.5 |
| 134 | 6-(4-(4-fluorobenzyl)piperazin-1-yl)-3-methyl-2-phenylimidazo[1,2-b]pyridazine | 402.5 |
| 135 | N-(5-(6-(methylthio)imidazo[1,2-b]pyridazin-2-yl)-2-(trifluoromethyl)phenyl)pivalamide | 409.4 |
| 136 | N-(5-(6-ethoxyimidazo[1,2-b]pyridazin-2-yl)-2-(trifluoromethyl)phenyl)pivalamide | 407.4 |
| 137 | N-(5-(6-(methylamino)imidazo[1,2-b]pyridazin-2-yl)-2-(trifluoromethyl)phenyl)pivalamide | 392.4 |
| 138 | N-(5-(6-(dimethylamino)imidazo[1,2-b]pyridazin-2-yl)-2-(trifluoromethyl)phenyl)pivalamide | 406.4 |
| 139 | N-(5-(6-cyclopropylimidazo[1,2-b]pyridazin-2-yl)-2-(trifluoromethyl)phenyl)pivalamide | 403.4 |
| 140 | N-(5-(6-isopropylimidazo[1,2-b]pyridazin-2-yl)-2-(trifluoromethyl)phenyl)pivalamide | 405.4 |
| 141 | N-(5-(6-(pyridin-2-yl)imidazo[1,2-b]pyridazin-2-yl)-2-(trifluoromethyl)phenyl)pivalamide | 440.3 |
| 142 | N-(5-(6-methylimidazo[1,2-b]pyridazin-2-yl)-2-(trifluoromethyl)phenyl)pivalamide | 377.4 |
| 143 | N-(5-(6-(4-fluorophenyl)imidazo[1,2-b]pyridazin-2-yl)-2-(trifluoromethyl)phenyl)pivalamide | 457.4 |
| 144 | 3-chloro-6-(4-(4-fluorobenzyl)piperazin-1-yl)-2-phenylimidazo[1,2-b]pyridazine | 422.4 |
| 145 | 3-methyl-2-phenyl-6-(piperazin-1-yl)imidazo[1,2-b]pyridazine | 294.4 |
| 146 | 3-bromo-6-(4-(4-fluorobenzyl)piperazin-1-yl)-2-(4-fluorophenyl)imidazo[1,2-b]pyridazine | 484.3 |
| 147 | N-(5-(6-(6-methoxypyridin-2-yl)imidazo[1,2-b]pyridazin-2-yl)-2-(trifluoromethyl)phenyl)pivalamide | 470.4 |
| 148 | N-(5-(6-(thiazol-2-yl)imidazo[1,2-b]pyridazin-2-yl)-2-(trifluoromethyl)phenyl)pivalamide | 446.4 |
| 149 | N-(5-(6-(6-methylpyridin-2-yl)imidazo[1,2-b]pyridazin-2-yl)-2-(trifluoromethyl)phenyl)pivalamide | 454.4 |
| 150 | N-(5-(6-(5-methylpyridin-2-yl)imidazo[1,2-b]pyridazin-2-yl)-2-(trifluoromethyl)phenyl)pivalamide | 454.4 |
| 151 | N-(5-(6-(4-methylpyridin-2-yl)imidazo[1,2-b]pyridazin-2-yl)-2-(trifluoromethyl)phenyl)pivalamide | 454.4 |
| 152 | N-(5-(6-(3-methylpyridin-2-yl)imidazo[1,2-b]pyridazin-2-yl)-2-(trifluoromethyl)phenyl)pivalamide | 454.4 |
| 153 | N-(5-(6-(pyridin-3-yl)imidazo[1,2-b]pyridazin-2-yl)-2-(trifluoromethyl)phenyl)pivalamide | 440.4 |
| 154 | (4-(3-methyl-2-phenylimidazo[1,2-b]pyridazin-6-yl)piperazin-1-yl)(phenyl)methanone | 398.4 |
| 155 | 1-(4-(3-methyl-2-phenylimidazo[1,2-b]pyridazin-6-yl)piperazin-1-yl)-2-phenylethanone | 412.5 |
| 156 | 1-(4-(3-methyl-2-phenylimidazo[1,2-b]pyridazin-6-yl)piperazin-1-yl)-3-phenylpropan-1-one | 426.5 |
| 157 | 3,3-dimethyl-1-(4-(3-methyl-2-phenylimidazo[1,2-b]pyridazin-6-yl)piperazin-1-yl)butan-1-one | 392.5 |
| 158 | tert-butyl 4-(3-methyl-2-phenylimidazo[1,2-b]pyridazin-6-yl)piperazine-1-carboxylate | 394.5 |
| 159 | N-cyclohexyl-4-(3-methyl-2-phenylimidazo[1,2-b]pyridazin-6-yl)piperazine-1-carboxamide | 419.5 |
| 160 | 3-methyl-2-phenyl-6-(4-(pyridin-2-ylmethyl)piperazin-1-yl)imidazo[1,2-b]pyridazine | 385.5 |
| 161 | 3-methyl-2-phenyl-6-(4-(pyridin-3-ylmethyl)piperazin-1-yl)imidazo[1,2-b]pyridazine | 385.5 |
| 162 | 3-methyl-2-phenyl-6-(4-(pyridin-4-ylmethyl)piperazin-1-yl)imidazo[1,2-b]pyridazine | 385.5 |
| 163 | 3-methyl-6-(4-(2-methylbenzyl)piperazin-1-yl)-2-phenylimidazo[1,2-b]pyridazine | 398.5 |
| 164 | 6-(4-(2,4-difluorobenzyl)piperazin-1-yl)-3-methyl-2-phenylimidazo[1,2-b]pyridazine | 420.4 |

-continued

| Example No. | Compound | |
|---|---|---|
| 165 | 3-methyl-2-phenyl-6-(4-(3-(trifluoromethyl)benzyl)piperazin-1-yl)imidazo[1,2-b]pyridazine | 452.5 |
| 166 | 3-methyl-2-phenyl-6-(4-(4-(trifluoromethoxy)benzyl)piperazin-1-yl)imidazo[1,2-b]pyridazine | 468.4 |
| 167 | 3-cyclopropyl-6-(4-(4-fluorobenzyl)piperazin-1-yl)-2-(4-fluorophenyl)imidazo[1,2-b]pyridazine | 446.5 |
| 168 | N-(1-benzylpiperidin-4-yl)-3-methyl-2-phenylimidazo[1,2-b]pyridazin-6-amine | 398.5 |
| 169 | N-(5-(6-(pyridin-4-yl)imidazo[1,2-b]pyridazin-2-yl)-2-(trifluoromethyl)phenyl)pivalamide | 440.4 |
| 170 | N-(5-(6-(6-methoxypyridin-3-yl)imidazo[1,2-b]pyridazin-2-yl)-2-(trifluoromethyl)phenyl)pivalamide | 470.4 |
| 171 | N-(5-(6-(2-fluorophenyl)imidazo[1,2-b]pyridazin-2-yl)-2-(trifluoromethyl)phenyl)pivalamide | 457.4 |
| 172 | N-(5-(6-(2-methoxyphenyl)imidazo[1,2-b]pyridazin-2-yl)-2-(trifluoromethyl)phenyl)pivalamide | 469.4 |
| 173 | N-(5-(6-cyanoimidazo[1,2-b]pyridazin-2-yl)-2-(trifluoromethyl)phenyl)pivalamide | 388.4 |
| 174 | N-(5-(6-(6-fluoropyridin-3-yl)imidazo[1,2-b]pyridazin-2-yl)-2-(trifluoromethyl)phenyl)pivalamide | 458.4 |
| 175 | N-(5-(6-(2-methoxypyridin-3-yl)imidazo[1,2-b]pyridazin-2-yl)-2-(trifluoromethyl)phenyl)pivalamide | 470.4 |
| 176 | N-(5-(6-(2-fluoropyridin-3-yl)imidazo[1,2-b]pyridazin-2-yl)-2-(trifluoromethyl)phenyl)pivalamide | 458.4 |
| 177 | N-(5-(6-(3-fluoropyridin-4-yl)imidazo[1,2-b]pyridazin-2-yl)-2-(trifluoromethyl)phenyl)pivalamide | 458.4 |
| 178 | tert-butyl 2-(2-(3-pivalamido-4-(trifluoromethyl)phenyl)imidazo[1,2-b]pyridazin-6-yl)-1H-pyrrole-1-carboxylate | 528.5 |
| 179 | N-(5-(6-(1H-pyrrol-2-yl)imidazo[1,2-b]pyridazin-2-yl)-2-(trifluoromethyl)phenyl)pivalamide | 428.4 |
| 180 | 2-(3-pivalamido-4-(trifluoromethyl)phenyl)imidazo[1,2-b]pyridazine-6-carboxamide | 406.4 |
| 181 | N-(5-(6-isopropoxyimidazo[1,2-b]pyridazin-2-yl)-2-(trifluoromethyl)phenyl)pivalamide | 421.4 |
| 182 | N-(5-(6-cyclobutoxyimidazo[1,2-b]pyridazin-2-yl)-2-(trifluoromethyl)phenyl)pivalamide | 433.4 |
| 183 | N-(5-(6-(2,4-difluorophenyl)imidazo[1,2-b]pyridazin-2-yl)-2-(trifluoromethyl)phenyl)pivalamide | 475.4 |
| 184 | N-(5-(6-(2,6-difluorophenyl)imidazo[1,2-b]pyridazin-2-yl)-2-(trifluoromethyl)phenyl)pivalamide | 475.4 |
| 185 | N-(5-(6-ethoxyimidazo[1,2-b]pyridazin-2-yl)-2-(trifluoromethyl)phenyl)isobutyramide | 393.4 |
| 186 | N-(5-(6-ethoxyimidazo[1,2-b]pyridazin-2-yl)-2-(trifluoromethyl)phenyl)cyclopropanecarboxamide | 391.4 |
| 187 | N-(5-(6-ethoxyimidazo[1,2-b]pyridazin-2-yl)-2-(trifluoromethyl)phenyl)-3,3-dimethylbutanamide | 421.3 |
| 188 | N-(5-(6-ethoxyimidazo[1,2-b]pyridazin-2-yl)-2-(trifluoromethyl)phenyl)-3,3,3-trifluoro-2,2-dimethylpropanamide | 461.4 |
| 189 | N-(5-(6-ethoxyimidazo[1,2-b]pyridazin-2-yl)-2-(trifluoromethyl)phenyl)cyclopentanecarboxamide | 419.4 |
| 190 | N-(5-(6-ethoxyimidazo[1,2-b]pyridazin-2-yl)-2-(trifluoromethyl)phenyl)cyclohexanecarboxamide | 433.4 |
| 191 | N-(5-(6-ethoxyimidazo[1,2-b]pyridazin-2-yl)-2-(trifluoromethyl)phenyl)benzamide | 427.4 |
| 192 | N-(5-(6-ethoxyimidazo[1,2-b]pyridazin-2-yl)-2-(trifluoromethyl)phenyl)-2-fluorobenzamide | 445.4 |
| 193 | N-(5-(6-ethoxyimidazo[1,2-b]pyridazin-2-yl)-2-(trifluoromethyl)phenyl)nicotinamide | 428.4 |
| 194 | N-(5-(6-ethoxyimidazo[1,2-b]pyridazin-2-yl)-2-(trifluoromethyl)phenyl)-2-phenylacetamide | 441.2 |
| 195 | N-(5-(6-(2-fluorophenoxy)imidazo[1,2-b]pyridazin-2-yl)-2-(trifluoromethyl)phenyl)pivalamide | 473.4 |
| 196 | N-(5-(6-(4-fluorophenoxy)imidazo[1,2-b]pyridazin-2-yl)-2-(trifluoromethyl)phenyl)pivalamide | 473.4 |
| 197 | N-(5-(6-(2-methoxyphenoxy)imidazo[1,2-b]pyridazin-2-yl)-2-(trifluoromethyl)phenyl)pivalamide | 485.4 |
| 198 | N-(5-(6-chloro-7,8-dimethylimidazo[1,2-b]pyridazin-2-yl)-2-(trifluoromethyl)phenyl)pivalamide | 425.4 |
| 199 | N-(5-(6-(2-fluoropyridin-3-yl)-7,8-dimethylimidazo[1,2-b]pyridazin-2-yl)-2-(trifluoromethyl)phenyl)pivalamide | 486.4 |
| 200 | N-(5-(6-(2-fluorophenyl)-7,8-dimethylimidazo[1,2-b]pyridazin-2-yl)-2-(trifluoromethyl)phenyl)pivalamide | 485.4 |
| 201 | N-(5-(6-ethoxy-7,8-dimethylimidazo[1,2-b]pyridazin-2-yl)-2-(trifluoromethyl)phenyl)pivalamide | 435.4 |
| 202 | N-(5-(7,8-dimethyl-6-(pyridin-2-yl)-imidazo[1,2-b]pyridazin-2-yl)-2-(trifluoromethyl)phenyl)pivalamide | 468.4 |

-continued

| Example No. | Compound | |
|---|---|---|
| 203 | 2-(3-bromo-4-(trifluoromethyl)phenyl)-6-chloroimidazo[1,2-b]pyridazine | 476.2 |
| 204 | 2-(3-bromo-4-(trifluoromethyl)phenyl)-6-ethoxyimidazo[1,2-b]pyridazine | 386.3 |
| 205 | N-(5-(6-(2-fluoro-4-methylphenyl)imidazo[1,2-b]pyridazin-2-yl)-2-(trifluoromethyl)phenyl)pivalamide | 471.4 |
| 206 | N-(5-(6-(2-fluoro-3-methoxyphenyl)imidazo[1,2-b]pyridazin-2-yl)-2-(trifluoromethyl)phenyl)pivalamide | 487.4 |
| 207 | N-(5-(6-(2-fluoro-5-(trifluoromethyl)phenyl)imidazo[1,2-b]pyridazin-2-yl)-2-(trifluoromethyl)phenyl)pivalamide | 525.4 |
| 208 | N-(5-(6-(2-chlorophenyl)imidazo[1,2-b]pyridazin-2-yl)-2-(trifluoromethyl)phenyl)pivalamide | 473.3 |
| 209 | N-(2-(trifluoromethyl)-5-(6-(2-(trifluoromethyl)phenyl)imidazo[1,2-b]pyridazin-2-yl)phenyl)pivalamide | 507.4 |
| 210 | N-(2-(trifluoromethyl)-5-(6-(4-(trifluoromethyl)phenyl)imidazo[1,2-b]pyridazin-2-yl)phenyl)pivalamide | 507.4 |
| 211 | N-(5-(6-ethoxyimidazo[1,2-b]pyridazin-2-yl)-2-(trifluoromethyl)phenyl)pivalamide | 407.4 |
| 212 | N-cyclopropyl-5-(6-ethoxyimidazo[1,2-b]pyridazin-2-yl)-2-(trifluoromethyl)benzenesulfonamide | 427.4 |
| 213 | 5-(6-ethoxyimidazo[1,2-b]pyridazin-2-yl)-N-(4-fluorobenzyl)-2-(trifluoromethyl)benzenesulfonamide | 495.4 |
| 214 | N-cyclohexyl-5-(6-ethoxyimidazo[1,2-b]pyridazin-2-yl)-2-(trifluoromethyl)benzenesulfonamide | 469.4 |
| 215 | N-benzyl-5-(6-ethoxyimidazo[1,2-b]pyridazin-2-yl)-2-(trifluoromethyl)benzenesulfonamide | 477.4 |
| 216 | N-tert-butyl-5-(6-ethoxyimidazo[1,2-b]pyridazin-2-yl)-2-(trifluoromethyl)benzenesulfonamide | 443.4 |
| 217 | 5-(6-ethoxyimidazo[1,2-b]pyridazin-2-yl)-N-methyl-2-(trifluoromethyl)benzenesulfonamide | 401.3 |
| 218 | 6-ethoxy-2-(3-(pyridin-2-yl)-4-(trifluoromethyl)phenyl)imidazo[1,2-b]pyridazine | 385.4 |
| 219 | N-(3-(6-(2-fluorophenyl)imidazo[1,2-b]pyridazin-2-yl)-2-methylphenyl)pivalamide | 403.4 |
| 220 | N-(5-(6-(2-fluorophenyl)imidazo[1,2-b]pyridazin-2-yl)-2-methylphenyl)pivalamide | 403.4 |
| 221 | N-(5-(6-(2-fluoro-5-(trifluoromethyl)phenyl)imidazo[1,2-b]pyridazin-2-yl)-2-methylphenyl)pivalamide | 471.4 |
| 222 | N-(5-(6-(3-fluorophenyl)imidazo[1,2-b]pyridazin-2-yl)-2-(trifluoromethyl)phenyl)pivalamide | 457.4 |
| 223 | N-(2-(trifluoromethyl)-5-(6-(3-(trifluoromethyl)phenyl)imidazo[1,2-b]pyridazin-2-yl)phenyl)pivalamide | 506.4 |
| 224 | N-(5-(6-(2,5-difluorophenyl)imidazo[1,2-b]pyridazin-2-yl)-2-(trifluoromethyl)phenyl)pivalamide | 475.4 |
| 225 | N-(2-cyano-5-(6-(2-(trifluoromethyl)phenyl)imidazo[1,2-b]pyridazin-2-yl)phenyl)pivalamide | 464.5 |
| 226 | N-(5-(6-(2-fluoro-5-methylphenyl)imidazo[1,2-b]pyridazin-2-yl)-2-(trifluoromethyl)phenyl)pivalamide | 471.4 |
| 227 | N-(5-(6-(5-chloro-2-fluorophenyl)imidazo[1,2-b]pyridazin-2-yl)-2-(trifluoromethyl)phenyl)pivalamide | 491.4 |
| 228 | N-(5-(6-(2-fluoro-5-methoxyphenyl)imidazo[1,2-b]pyridazin-2-yl)-2-(trifluoromethyl)phenyl)pivalamide | 487.4 |
| 229 | N-(5-(6-(3-methoxyphenyl)imidazo[1,2-b]pyridazin-2-yl)-2-(trifluoromethyl)phenyl)pivalamide | 469.4 |
| 230 | N-(5-(6-(thiophen-2-yl)imidazo[1,2-b]pyridazin-2-yl)-2-(trifluoromethyl)phenyl)pivalamide | 445.3 |
| 231 | N-(5-(6-benzylimidazo[1,2-b]pyridazin-2-yl)-2-(trifluoromethyl)phenyl)pivalamide | 453.4 |
| 232 | N-(5-(6-morpholinoimidazo[1,2-b]pyridazin-2-yl)-2-(trifluoromethyl)phenyl)pivalamide | 448.4 |
| 233 | N-(5-(6-(4-methylpiperidin-1-yl)imidazo[1,2-b]pyridazin-2-yl)-2-(trifluoromethyl)phenyl)pivalamide | 460.5 |
| 234 | N-(5-(6-(4-(methylsulfonyl)piperazin-1-yl)imidazo[1,2-b]pyridazin-2-yl)-2-(trifluoromethyl)phenyl)pivalamide | 525.4 |
| 235 | N-(5-(6-(4,4-difluoropiperidin-1-yl)imidazo[1,2-b]pyridazin-2-yl)-2-(trifluoromethyl)phenyl)pivalamide | 482.5 |
| 236 | N-(5-(6-(3,3-difluoropyrrolidin-1-yl)imidazo[1,2-b]pyridazin-2-yl)-2-(trifluoromethyl)phenyl)pivalamide | 468.4 |
| 237 | N-(5-(6-(4-hydroxypiperidin-1-yl)imidazo[1,2-b]pyridazin-2-yl)-2-(trifluoromethyl)phenyl)pivalamide | 462.5 |
| 238 | N-(5-(6-(4-chlorophenyl)imidazo[1,2-b]pyridazin-2-yl)-2-(trifluoromethyl)phenyl)pivalamide | 473.4 |
| 239 | N-(5-(6-p-tolylimidazo[1,2-b]pyridazin-2-yl)-2-(trifluoromethyl)phenyl)pivalamide | 453.4 |
| 240 | N-(5-(6-(2-(trifluoromethoxy)phenyl)imidazo[1,2-b]pyridazin-2-yl)-2-(trifluoromethyl)phenyl)pivalamide | 523.4 |
| 241 | N-(5-(6-o-tolylimidazo[1,2-b]pyridazin-2-yl)-2-(trifluoromethyl)phenyl)pivalamide | 453.4 |

-continued

| Example No. | Compound | |
|---|---|---|
| 242 | N-(5-(6-(3-hydroxyphenyl)imidazo[1,2-b]pyridazin-2-yl)-2-(trifluoromethyl)phenyl)pivalamide | 455.4 |
| 243 | N-(5-(6-(4-hydroxyphenyl)imidazo[1,2-b]pyridazin-2-yl)-2-(trifluoromethyl)phenyl)pivalamide | 455.4 |
| 244 | N-(5-(6-(4-methoxyphenyl)imidazo[1,2-b]pyridazin-2-yl)-2-(trifluoromethyl)phenyl)pivalamide | 469.4 |
| 245 | N-(5-(6-chloroimidazo[1,2-b]pyridazin-2-yl)-2-(trifluoromethoxy)phenyl)pivalamide | 413.3 |
| 246 | N-(5-(6-ethoxyimidazo[1,2-b]pyridazin-2-yl)-2-(trifluoromethoxy)phenyl)pivalamide | 423.4 |
| 247 | N-(5-(6-methoxyimidazo[1,2-b]pyridazin-2-yl)-2-(trifluoromethoxy)phenyl)pivalamide | 409.4 |
| 248 | N-(5-(6-(2-fluorophenyl)imidazo[1,2-b]pyridazin-2-yl)-2-(trifluoromethoxy)phenyl)pivalamide | 473.4 |
| 249 | N-(5-(6-butoxyimidazo[1,2-b]pyridazin-2-yl)-2-(trifluoromethoxy)phenyl)pivalamide | 451.4 |
| 250 | N-(5-(6-(2,6-dimethylmorpholino)imidazo[1,2-b]pyridazin-2-yl)-2-(trifluoromethyl)phenyl)pivalamide | 476.5 |
| 251 | N-(5-(6-(2-isopropoxyphenyl)imidazo[1,2-b]pyridazin-2-yl)-2-(trifluoromethyl)phenyl)pivalamide | 497.5 |
| 252 | N-(5-(6-(2-fluoro-5-isopropoxyphenyl)imidazo[1,2-b]pyridazin-2-yl)-2-(trifluoromethyl)phenyl)pivalamide | 515.5 |
| 253 | N-(5-(6-(2-fluoro-5-propoxyphenyl)imidazo[1,2-b]pyridazin-2-yl)-2-(trifluoromethyl)phenyl)pivalamide | 515.5 |
| 254 | N-(5-(6-(3-acetylphenyl)imidazo[1,2-b]pyridazin-2-yl)-2-(trifluoromethyl)phenyl)pivalamide | 481.4 |
| 255 | N-(5-(6-(2-acetamidophenyl)imidazo[1,2-b]pyridazin-2-yl)-2-(trifluoromethyl)phenyl)pivalamide | 496.4 |
| 256 | N-(5-(6-(3-(dimethylamino)phenyl)imidazo[1,2-b]pyridazin-2-yl)-2-(trifluoromethyl)phenyl)pivalamide | 482.5 |
| 257 | ethyl 2-(2-(3-pivalamido-4-(trifluoromethyl)phenyl)imidazo[1,2-b]pyridazin-6-yl)benzoate | 511.5 |
| 258 | N-(5-(6-(2-chlorophenyl)imidazo[1,2-b]pyridazin-2-yl)-2-methylphenyl)pivalamide | 419.4 |
| 259 | N-(2-methyl-5-(6-(2-(trifluoromethyl)phenyl)imidazo[1,2-b]pyridazin-2-yl)phenyl)pivalamide | 453.4 |
| 260 | N-(2-methyl-5-(6-(3-(trifluoromethyl)phenyl)imidazo[1,2-b]pyridazin-2-yl)phenyl)pivalamide | 453.4 |
| 261 | N-(5-(6-(2,5-difluorophenyl)imidazo[1,2-b]pyridazin-2-yl)-2-methylphenyl)pivalamide | 421.4 |
| 262 | N-(5-(6-(5-chloro-2-fluorophenyl)imidazo[1,2-b]pyridazin-2-yl)-2-methylphenyl)pivalamide | 437.4 |
| 263 | N-(2-methyl-5-(6-(2-(trifluoromethoxy)phenyl)imidazo[1,2-b]pyridazin-2-yl)phenyl)pivalamide | 469.3 |
| 264 | N-(5-(6-(3-hydroxyphenyl)imidazo[1,2-b]pyridazin-2-yl)-2-methylphenyl)pivalamide | 401.4 |
| 265 | N-(5-(6-(2-fluoropyridin-3-yl)imidazo[1,2-b]pyridazin-2-yl)-2-methylphenyl)pivalamide | 404.4 |
| 266 | N-(5-(6-(2,6-dimethylmorpholino)imidazo[1,2-b]pyridazin-2-yl)-2-(trifluoromethoxy)phenyl)pivalamide | 492.5 |
| 267 | N-(5-(6-morpholinoimidazo[1,2-b]pyridazin-2-yl)-2-(trifluoromethoxy)phenyl)pivalamide | 464.4 |
| 268 | N-(5-(6-(4-(methylsulfonyl)piperazin-1-yl)imidazo[1,2-b]pyridazin-2-yl)-2-(trifluoromethoxy)phenyl)pivalamide | 541.4 |
| 269 | N-(5-(6-(4-hydroxypiperidin-1-yl)imidazo[1,2-b]pyridazin-2-yl)-2-(trifluoromethoxy)phenyl)pivalamide | 478.5 |
| 270 | N-(5-(6-chloroimidazo[1,2-b]pyridazin-2-yl)-2-cyclopropylphenyl)pivalamide | 369.4 |
| 271 | N-(2-cyclopropyl-5-(6-(2-fluorophenyl)imidazo[1,2-b]pyridazin-2-yl)phenyl)pivalamide | 429.5 |
| 272 | N-(2-cyclopropyl-5-(6-ethoxyimidazo[1,2-b]pyridazin-2-yl)phenyl)pivalamide | 379.5 |
| 273 | N-(2-cyclopropyl-5-(6-(4-hydroxypiperidin-1-yl)imidazo[1,2-b]pyridazin-2-yl)phenyl)pivalamide | 434.5 |
| 274 | N-(5-(6-(5-cyano-2-fluorophenyl)imidazo[1,2-b]pyridazin-2-yl)-2-methylphenyl)pivalamide | 428.4 |
| 275 | N-(5-(6-(2-fluoro-5-(hydroxymethyl)phenyl)imidazo[1,2-b]pyridazin-2-yl)-2-methylphenyl)pivalamide | 433.5 |
| 276 | N-(5-(6-(2-hydroxyphenyl)imidazo[1,2-b]pyridazin-2-yl)-2-methylphenyl)pivalamide | 401.4 |
| 277 | N-(5-(6-(3,3-difluoropyrrolidin-1-yl)imidazo[1,2-b]pyridazin-2-yl)-2-methylphenyl)pivalamide | 414.5 |
| 278 | N-(2-methyl-5-(6-(2-methylpyridin-3-yl)imidazo[1,2-b]pyridazin-2-yl)phenyl)pivalamide | 400.5 |
| 279 | N-(5-(6-(5-chloro-2-fluoropyridin-3-yl)imidazo[1,2-b]pyridazin-2-yl)-2-methylphenyl)pivalamide | 438.4 |
| 280 | N-(5-(6-(2,6-difluoropyridin-3-yl)imidazo[1,2-b]pyridazin-2-yl)-2-methylphenyl)pivalamide | 422.4 |

-continued

| Example No. | Compound | |
|---|---|---|
| 281 | N-(5-(6-(5-fluoro-2-(trifluoromethyl)phenyl)imidazo[1,2-b]pyridazin-2-yl)-2-methylphenyl)pivalamide | 471.4 |
| 282 | N-(5-(6-(4,4-difluoropiperidin-1-yl)imidazo[1,2-b]pyridazin-2-yl)-2-methylphenyl)pivalamide | 428.5 |
| 283 | N-(5-(6-ethoxyimidazo[1,2-b]pyridazin-2-yl)-2-ethylphenyl)pivalamide | 367.5 |
| 284 | N-(2-methyl-5-(6-(2-(trifluoromethyl)pyridin-3-yl)imidazo[1,2-b]pyridazin-2-yl)phenyl)pivalamide | 454.4 |
| 285 | N-{5-[6-(1,1-dioxidothiomorpholin-4-yl)imidazo[1,2-b]pyridazin-2-yl]-2-methylphenyl}-2,2-dimethylpropanamide | 442.4 |
| 286 | N-(5-(6-(4-hydroxypiperidin-1-yl)imidazo[1,2-b]pyridazin-2-yl)-2-methylphenyl)pivalamide | 408.5 |
| 287 | N-{5-[6-(1,1-dioxidothiomorpholin-4-yl)imidazo[1,2-b]pyridazin-2-yl]-2-(trifluoromethyl)phenyl}-2,2-dimethylpropanamide | 496.4 |
| 288 | N-(5-(6-(piperidin-1-yl)imidazo[1,2-b]pyridazin-2-yl)-2-(trifluoromethyl)phenyl)pivalamide | 446.5 |
| 289 | N-(5-(6-(2-acetamidophenyl)imidazo[1,2-b]pyridazin-2-yl)-2-methylphenyl)pivalamide | 442.5 |
| 290 | N-(5-(6-(3-(dimethylamino)phenyl)imidazo[1,2-b]pyridazin-2-yl)-2-methylphenyl)pivalamide | 428.5 |
| 291 | N-(5-(6-(5-fluoro-2-(trifluoromethyl)phenyl)imidazo[1,2-b]pyridazin-2-yl)-2-(trifluoromethyl)phenyl)pivalamide | 425.4 |
| 292 | N-(2-(trifluoromethyl)-5-(6-(2-(trifluoromethyl)pyridin-3-yl)imidazo[1,2-b]pyridazin-2-yl)phenyl)pivalamide | 508.4 |
| 293 | N-(5-(6-(2-methylpyridin-3-yl)imidazo[1,2-b]pyridazin-2-yl)-2-(trifluoromethyl)phenyl)pivalamide | 454.4 |
| 294 | N-(5-(6-(2-methylpiperidin-1-yl)imidazo[1,2-b]pyridazin-2-yl)-2-(trifluoromethyl)phenyl)pivalamide | 460.5 |
| 295 | N-(2-ethyl-5-(6-(2-fluorophenyl)imidazo[1,2-b]pyridazin-2-yl)phenyl)pivalamide | 417.5 |
| 296 | N-(5-(6-(2-cyanophenyl)imidazo[1,2-b]pyridazin-2-yl)-2-ethylphenyl)pivalamide | 424.5 |
| 297 | tert-butyl 1-(2-(3-pivalamido-4-(trifluoromethyl)phenyl)imidazo[1,2-b]pyridazin-6-yl)pyrrolidin-3-ylcarbamate | 547.5 |
| 298 | N-(5-(6-((2-hydroxyethyl)(methyl)amino)imidazo[1,2-b]pyridazin-2-yl)-2-(trifluoromethyl)phenyl)pivalamide | 436.4 |
| 299 | N-(5-(6-((2-methoxyethyl)(methyl)amino)imidazo[1,2-b]pyridazin-2-yl)-2-(trifluoromethyl)phenyl)pivalamide | 450.5 |
| 300 | N-(5-(6-(2-(methylthio)ethylamino)imidazo[1,2-b]pyridazin-2-yl)-2-(trifluoromethyl)phenyl)pivalamide | 452.4 |
| 301 | N-(5-(6-(cyclopentylamino)imidazo[1,2-b]pyridazin-2-yl)-2-(trifluoromethyl)phenyl)pivalamide | 446.5 |
| 302 | N-(5-(6-(isobutylamino)imidazo[1,2-b]pyridazin-2-yl)-2-(trifluoromethyl)phenyl)pivalamide | 434.5 |
| 303 | N-(5-(6-(1-hydroxybutan-2-ylamino)imidazo[1,2-b]pyridazin-2-yl)-2-(trifluoromethyl)phenyl)pivalamide | 450.5 |
| 304 | N-(5-(6-(2-hydroxyethylamino)imidazo[1,2-b]pyridazin-2-yl)-2-(trifluoromethyl)phenyl)pivalamide | 422.4 |
| 305 | N-(5-(6-(1-methylpiperidin-4-yloxy)imidazo[1,2-b]pyridazin-2-yl)-2-(trifluoromethyl)phenyl)pivalamide | 476.5 |
| 306 | N-(5-(6-(2-morpholinoethoxy)imidazo[1,2-b]pyridazin-2-yl)-2-(trifluoromethyl)phenyl)pivalamide | 492.5 |
| 307 | N-(5-(6-(2-methylcyclohexyloxy)imidazo[1,2-b]pyridazin-2-yl)-2-(trifluoromethyl)phenyl)pivalamide | 475.5 |
| 308 | N-(5-(6-((1R,2S)-2-methylcyclohexyloxy)imidazo[1,2-b]pyridazin-2-yl)-2-(trifluoromethyl)phenyl)pivalamide | 475.5 |
| 309 | N-(5-(6-(2-(piperidin-1-yl)ethoxy)imidazo[1,2-b]pyridazin-2-yl)-2-(trifluoromethyl)phenyl)pivalamide | 490.5 |
| 310 | N-(5-(6-(tetrahydro-2H-pyran-4-yloxy)imidazo[1,2-b]pyridazin-2-yl)-2-(trifluoromethyl)phenyl)pivalamide | 463.4 |
| 311 | N-(5-(6-chloro-3-methylimidazo[1,2-b]pyridazin-2-yl)-2-methylphenyl)pivalamide | 357.4 |
| 312 | N-(5-(6-(2-fluorophenyl)-3-methylimidazo[1,2-b]pyridazin-2-yl)-2-methylphenyl)pivalamide | 417.5 |
| 313 | N-(5-(6-(4-hydroxypiperidin-1-yl)-3-methylimidazo[1,2-b]pyridazin-2-yl)-2-methylphenyl)pivalamide | 422.5 |
| 314 | N-(5-(6-(4-hydroxycyclohexylamino)imidazo[1,2-b]pyridazin-2-yl)-2-(trifluoromethyl)phenyl)pivalamide | 476.5 |
| 315 | N-(5-(6-(3,3-difluoroazetidin-1-yl)imidazo[1,2-b]pyridazin-2-yl)-2-(trifluoromethyl)phenyl)pivalamide | 454.4 |
| 316 | N-(5-(6-(4-methylpiperazin-1-yl)imidazo[1,2-b]pyridazin-2-yl)-2-(trifluoromethyl)phenyl)pivalamide | 461.5 |
| 317 | N-(5-(6-(4-ethylpiperazin-1-yl)imidazo[1,2-b]pyridazin-2-yl)-2-(trifluoromethyl)phenyl)pivalamide | 475.5 |
| 318 | N-(5-(6-(3-aminopyrrolidin-1-yl)imidazo[1,2-b]pyridazin-2-yl)-2-(trifluoromethyl)phenyl)pivalamide | 447.5 |

-continued

| Example No. | Compound | |
|---|---|---|
| 319 | N-(5-(6-(3-aminopyrrolidin-1-yl)imidazo[1,2-b]pyridazin-2-yl)-2-(trifluoromethyl)phenyl)pivalamide | 447.5 |
| 320 | 2-ethynyl-5-(6-(2-fluorophenyl)imidazo[1,2-b]pyridazin-2-yl)aniline | 329.4 |
| 321 | N-(2-ethynyl-5-(6-(2-fluorophenyl)imidazo[1,2-b]pyridazin-2-yl)phenyl)pivalamide | 413.4 |
| 322 | N-(2-methyl-5-(6-(6-(trifluoromethyl)pyridin-3-yl)imidazo[1,2-b]pyridazin-2-yl)phenyl)pivalamide | 454.4 |
| 323 | N-(5-(6-(3-(hydroxymethyl)phenyl)imidazo[1,2-b]pyridazin-2-yl)-2-(trifluoromethyl)phenyl)pivalamide | 469.4 |
| 324 | N-(5-(6-(2-isopropylphenyl)imidazo[1,2-b]pyridazin-2-yl)-2-(trifluoromethyl)phenyl)pivalamide | 481.5 |
| 325 | N-(5-(6-(3-(methylsulfonyl)phenyl)imidazo[1,2-b]pyridazin-2-yl)-2-(trifluoromethyl)phenyl)pivalamide | 517.4 |
| 326 | N-(5-(6-(3,5-dimethylisoxazol-4-yl)imidazo[1,2-b]pyridazin-2-yl)-2-(trifluoromethyl)phenyl)pivalamide | 458.4 |
| 327 | tert-butyl 4-(2-(3-pivalamido-4-(trifluoromethyl)phenyl)imidazo[1,2-b]pyridazin-6-yl)piperazine-1-carboxylate | 547.5 |
| 328 | N-(5-(6-(piperazin-1-yl)imidazo[1,2-b]pyridazin-2-yl)-2-(trifluoromethyl)phenyl)pivalamide | 447.5 |
| 329 | N-(5-(6-(2-methylpiperazin-1-yl)imidazo[1,2-b]pyridazin-2-yl)-2-(trifluoromethyl)phenyl)pivalamide | 461.5 |
| 330 | N-(5-(6-(piperidin-4-ylamino)imidazo[1,2-b]pyridazin-2-yl)-2-(trifluoromethyl)phenyl)pivalamide | 461.5 |
| 331 | tert-butyl 1-(2-(3-pivalamido-4-(trifluoromethyl)phenyl)imidazo[1,2-b]pyridazin-6-yl)piperidin-4-ylcarbamate | 561.5 |
| 332 | N-(5-(6-(4-aminopiperidin-1-yl)imidazo[1,2-b]pyridazin-2-yl)-2-(trifluoromethyl)phenyl)pivalamide | 461.5 |
| 333 | N-(5-(6-(2-hydroxycyclohexylamino)imidazo[1,2-b]pyridazin-2-yl)-2-(trifluoromethyl)phenyl)pivalamide | 476.5 |
| 334 | N-(5-(6-(2-chloropyridin-3-yl)imidazo[1,2-b]pyridazin-2-yl)-2-(trifluoromethyl)phenyl)pivalamide | 474.4 |
| 335 | N-(5-(6-(2-morpholinopyridin-3-yl)imidazo[1,2-b]pyridazin-2-yl)-2-(trifluoromethyl)phenyl)pivalamide | 525.5 |
| 336 | N-(5-(6-(3-hydroxypiperidin-1-yl)imidazo[1,2-b]pyridazin-2-yl)-2-(trifluoromethyl)phenyl)pivalamide | 462.5 |
| 337 | N-(5-(6-(3-hydroxypyrrolidin-1-yl)imidazo[1,2-b]pyridazin-2-yl)-2-(trifluoromethyl)phenyl)pivalamide | 448.4 |
| 338 | N-(2-ethyl-5-(6-(6-(trifluoromethyl)pyridin-3-yl)imidazo[1,2-b]pyridazin-2-yl)phenyl)pivalamide | 468.4 |
| 339 | N-(2-methyl-5-(3-methyl-6-(6-(trifluoromethyl)pyridin-3-yl)imidazo[1,2-b]pyridazin-2-yl)phenyl)pivalamide | 468.4 |
| 340 | (S)-N-(5-(6-(3-hydroxypyrrolidin-1-yl)imidazo[1,2-b]pyridazin-2-yl)-2-(trifluoromethyl)phenyl)pivalamide | 448.4 |
| 341 | (R)-N-(5-(6-(3-hydroxypyrrolidin-1-yl)imidazo[1,2-b]pyridazin-2-yl)-2-(trifluoromethyl)phenyl)pivalamide | 448.4 |
| 342 | N-(5-(6-(2-fluoro-4-methylpyridin-3-yl)imidazo[1,2-b]pyridazin-2-yl)-2-(trifluoromethyl)phenyl)pivalamide | 472.4 |
| 343 | N-(5-(6-(5-aminopyridin-3-yl)imidazo[1,2-b]pyridazin-2-yl)-2-(trifluoromethyl)phenyl)pivalamide | 455.4 |
| 344 | N-(5-(6-(2-aminopyridin-3-yl)imidazo[1,2-b]pyridazin-2-yl)-2-(trifluoromethyl)phenyl)pivalamide | 455.4 |
| 345 | N-(5-(6-(2-aminophenyl)imidazo[1,2-b]pyridazin-2-yl)-2-(trifluoromethyl)phenyl)pivalamide | 454.4 |
| 346 | (S)-N-(5-(6-(3-hydroxypyrrolidin-1-yl)imidazo[1,2-b]pyridazin-2-yl)-2-methylphenyl)pivalamide | 394.5 |
| 347 | (R)-N-(5-(6-(3-hydroxypyrrolidin-1-yl)imidazo[1,2-b]pyridazin-2-yl)-2-methylphenyl)pivalamide | 394.5 |
| 348 | N-(5-(6-(2-(hydroxymethyl)pyrrolidin-1-yl)imidazo[1,2-b]pyridazin-2-yl)-2-(trifluoromethyl)phenyl)pivalamide | 462.5 |
| 349 | N-(5-(6-(3-(methylamino)pyrrolidin-1-yl)imidazo[1,2-b]pyridazin-2-yl)-2-(trifluoromethyl)phenyl)pivalamide | 461.5 |
| 350 | N-(5-(6-(3-(dimethylamino)pyrrolidin-1-yl)imidazo[1,2-b]pyridazin-2-yl)-2-(trifluoromethyl)phenyl)pivalamide | 475.5 |
| 351 | N-(5-(6-(3-acetamidopyrrolidin-1-yl)imidazo[1,2-b]pyridazin-2-yl)-2-(trifluoromethyl)phenyl)pivalamide | 489.5 |
| 352 | N-(2-ethyl-5-(6-(2-(trifluoromethyl)pyridin-3-yl)imidazo[1,2-b]pyridazin-2-yl)phenyl)pivalamide | 468.4 |
| 353 | N-(2-methyl-5-(3-methyl-6-(2-(trifluoromethyl)pyridin-3-yl)imidazo[1,2-b]pyridazin-2-yl)phenyl)pivalamide | 468.4 |
| 354 | N-(5-(6-(3-(hydroxymethyl)piperidin-1-yl)imidazo[1,2-b]pyridazin-2-yl)-2-(trifluoromethyl)phenyl)pivalamide | 476.6 |
| 355 | N-(5-(6-thiomorpholinoimidazo[1,2-b]pyridazin-2-yl)-2-(trifluoromethyl)phenyl)pivalamide | 464.4 |
| 356 | N-(2-(trifluoromethyl)-5-(6-(3-(trifluoromethyl)piperidin-1-yl)imidazo[1,2-b]pyridazin-2-yl)phenyl)pivalamide | 514.5 |

-continued

| Example No. | Compound | |
|---|---|---|
| 357 | (R)-N-(5-(6-(3-hydroxypiperidin-1-yl)imidazo[1,2-b]pyridazin-2-yl)-2-(trifluoromethyl)phenyl)pivalamide | 462.5 |
| 358 | (S)-N-(5-(6-(3-hydroxypiperidin-1-yl)imidazo[1,2-b]pyridazin-2-yl)-2-(trifluoromethyl)phenyl)pivalamide | 462.5 |
| 359 | N-(5-(6-(bis(2-hydroxyethyl)amino)imidazo[1,2-b]pyridazin-2-yl)-2-(trifluoromethyl)phenyl)pivalamide | 466.5 |
| 360 | N-(2-methyl-5-(6-(3-(methylamino)pyrrolidin-1-yl)imidazo[1,2-b]pyridazin-2-yl)phenyl)pivalamide | 407.5 |
| 361 | N-(5-(6-(3-(dimethylamino)pyrrolidin-1-yl)imidazo[1,2-b]pyridazin-2-yl)-2-methylphenyl)pivalamide | 421.5 |
| 362 | N-(5-(6-(3-acetamidopyrrolidin-1-yl)imidazo[1,2-b]pyridazin-2-yl)-2-methylphenyl)pivalamide | 435.5 |
| 363 | N-(5-(6-(3-acetamidopyrrolidin-1-yl)-3-methylimidazo[1,2-b]pyridazin-2-yl)-2-methylphenyl)pivalamide | 449.5 |
| 364 | N-(2-methyl-5-(6-(4-(trifluoromethyl)pyridin-3-yl)imidazo[1,2-b]pyridazin-2-yl)phenyl)pivalamide | 454.4 |
| 365 | N-(5-(6-(2-fluoropyridin-4-yl)imidazo[1,2-b]pyridazin-2-yl)-2-methylphenyl)pivalamide | 404.4 |
| 366 | N-(5-(6-(5-chloropyridin-2-yl)imidazo[1,2-b]pyridazin-2-yl)-2-methylphenyl)pivalamide | 420.4 |
| 367 | N-(5-(6-(4-ethoxypiperidin-1-yl)imidazo[1,2-b]pyridazin-2-yl)-2-(trifluoromethyl)phenyl)pivalamide | 490.5 |
| 368 | N-(5-(6-(4-(2-methoxyethylamino)piperidin-1-yl)imidazo[1,2-b]pyridazin-2-yl)-2-(trifluoromethyl)phenyl)pivalamide | 519.5 |
| 369 | N-(5-(6-(4-morpholinopiperidin-1-yl)imidazo[1,2-b]pyridazin-2-yl)-2-(trifluoromethyl)phenyl)pivalamide | 531.5 |
| 370 | N-(5-(6-(4-(2,6-dimethylmorpholino)piperidin-1-yl)imidazo[1,2-b]pyridazin-2-yl)-2-(trifluoromethyl)phenyl)pivalamide | 559.5 |
| 371 | N-(5-(6-(1,4-dioxa-8-azaspiro[4.5]decan-8-yl)imidazo[1,2-b]pyridazin-2-yl)-2-(trifluoromethyl)phenyl)pivalamide | 504.5 |
| 372 | N-(5-(6-(pyrimidin-5-yl)imidazo[1,2-b]pyridazin-2-yl)-2-(trifluoromethyl)phenyl)pivalamide | 441.4 |
| 373 | N-(5-(6-(2-methoxypyrimidin-5-yl)imidazo[1,2-b]pyridazin-2-yl)-2-(trifluoromethyl)phenyl)pivalamide | 471.4 |
| 374 | N-(5-(6-(2-isopropoxyethoxy)imidazo[1,2-b]pyridazin-2-yl)-2-(trifluoromethyl)phenyl)pivalamide | 465.5 |
| 375 | N-(5-(6-(4-hydroxycyclohexyloxy)imidazo[1,2-b]pyridazin-2-yl)-2-(trifluoromethyl)phenyl)pivalamide | 476.5 |
| 376 | N-(5-(6-(2-hydroxypropoxy)imidazo[1,2-b]pyridazin-2-yl)-2-(trifluoromethyl)phenyl)pivalamide | 437.4 |
| 377 | N-(5-(6-(2-hydroxyethoxy)imidazo[1,2-b]pyridazin-2-yl)-2-(trifluoromethyl)phenyl)pivalamide | 423.4 |
| 378 | N-(5-(6-(2-(dimethylamino)pyrimidin-5-yl)imidazo[1,2-b]pyridazin-2-yl)-2-(trifluoromethyl)phenyl)pivalamide | 484.5 |
| 379 | N-(5-(6-(1-methyl-1H-pyrrol-2-yl)imidazo[1,2-b]pyridazin-2-yl)-2-(trifluoromethyl)phenyl)pivalamide | 442.4 |
| 380 | N-(5-(6-(bis(2-methoxyethyl)amino)imidazo[1,2-b]pyridazin-2-yl)-2-(trifluoromethyl)phenyl)pivalamide | 494.5 |
| 381 | N-(5-(6-(2-methylpyridin-4-yl)imidazo[1,2-b]pyridazin-2-yl)-2-(trifluoromethyl)phenyl)pivalamide | 454.4 |
| 382 | N-(5-(6-(3-methoxypyridin-4-yl)imidazo[1,2-b]pyridazin-2-yl)-2-(trifluoromethyl)phenyl)pivalamide | 470.4 |
| 383 | N-(5-(6-(4-methylpyridin-3-yl)imidazo[1,2-b]pyridazin-2-yl)-2-(trifluoromethyl)phenyl)pivalamide | 454.4 |
| 384 | N-(5-(6-(4-methoxypyridin-3-yl)imidazo[1,2-b]pyridazin-2-yl)-2-(trifluoromethyl)phenyl)pivalamide | 470.4 |
| 385 | N-(5-(6-(isoquinolin-4-yl)imidazo[1,2-b]pyridazin-2-yl)-2-(trifluoromethyl)phenyl)pivalamide | 490.4 |
| 386 | N-(5-(6-(4-chloropyridin-3-yl)imidazo[1,2-b]pyridazin-2-yl)-2-(trifluoromethyl)phenyl)pivalamide | 474.4 |
| 387 | N-(5-(6-methoxyimidazo[1,2-b]pyridazin-2-yl)-2-methylphenyl)pivalamide | 339.4 |
| 388 | N-(2-fluoro-5-(6-methoxyimidazo[1,2-b]pyridazin-2-yl)phenyl)furan-2-carboxamide | 353.4 |
| 389 | 2-cyclopentyl-N-(2-fluoro-5-(6-methoxyimidazo[1,2-b]pyridazin-2-yl)phenyl)acetamide | 369.4 |
| | | LCMS M + H |
| 390 | N-(5-(6-(2-fluorophenyl)imidazo[1,2-b]pyridazin-2-yl)-2-methylpyridin-3-yl)pivalamide | 404.4 |
| 391 | (R)-N-(2-methyl-5-(6-(3-(methylamino)pyrrolidin-1-yl)imidazo[1,2-b]pyridazin-2-yl)phenyl)pivalamide | 407.5 |
| 392 | (S)-N-(2-methyl-5-(6-(3-(methylamino)pyrrolidin-1-yl)imidazo[1,2-b]pyridazin-2-yl)phenyl)pivalamide | 407.5 |
| 393 | (R)-N-(5-(6-(3-(ethylamino)pyrrolidin-1-yl)imidazo[1,2-b]pyridazin-2-yl)-2-methylphenyl)pivalamide | 421.5 |

-continued

| Example No. | Compound | |
|---|---|---|
| 394 | (S)-N-(5-(6-(3-(ethylamino)pyrrolidin-1-yl)imidazo[1,2-b]pyridazin-2-yl)-2-methylphenyl)pivalamide | 421.5 |
| 395 | N-(5-(6-(3-fluoro-2-(trifluoromethyl)phenyl)imidazo[1,2-b]pyridazin-2-yl)-2-methylphenyl)pivalamide | 471.4 |
| 396 | N-(5-(6-(4-fluoro-2-(trifluoromethyl)phenyl)imidazo[1,2-b]pyridazin-2-yl)-2-methylphenyl)pivalamide | 471.4 |
| 397 | N-(5-(6-(2-fluoro-6-(trifluoromethyl)phenyl)imidazo[1,2-b]pyridazin-2-yl)-2-methylphenyl)pivalamide | 471.4 |
| 398 | N-(5-(6-(3-hydroxy-2-(trifluoromethyl)phenyl)imidazo[1,2-b]pyridazin-2-yl)-2-methylphenyl)pivalamide | 469.4 |
| 399 | N-(5-(6-(5-hydroxy-2-(trifluoromethyl)phenyl)imidazo[1,2-b]pyridazin-2-yl)-2-methylphenyl)pivalamide | 469.4 |
| 400 | N-(2-methyl-5-(6-(3-(trifluoromethyl)pyridin-2-yl)imidazo[1,2-b]pyridazin-2-yl)phenyl)pivalamide | 454.4 |
| 401 | N-(5-(6-(6'-chloro-2,3'-bipyridin-5-yl)imidazo[1,2-b]pyridazin-2-yl)-2-methylphenyl)pivalamide | 497.4 |
| 402 | N-(5-(6-(6-aminopyridin-3-yl)imidazo[1,2-b]pyridazin-2-yl)-2-methylphenyl)pivalamide | 401.5 |
| 403 | N-(5-(6-(5-methoxypyridin-3-yl)imidazo[1,2-b]pyridazin-2-yl)-2-methylphenyl)pivalamide | 416.5 |
| 404 | N-(5-(6-(6-hydroxypyridin-3-yl)imidazo[1,2-b]pyridazin-2-yl)-2-methylphenyl)pivalamide | 402.4 |
| 405 | N-(5-(6-(5-hydroxypyridin-3-yl)imidazo[1,2-b]pyridazin-2-yl)-2-methylphenyl)pivalamide | 402.4 |
| 406 | N-(5-(6-(2-hydroxypyridin-3-yl)imidazo[1,2-b]pyridazin-2-yl)-2-methylphenyl)pivalamide | 402.4 |
| 407 | N-(5-(6-(5-fluoropyridin-3-yl)imidazo[1,2-b]pyridazin-2-yl)-2-methylphenyl)pivalamide | 404.4 |
| 408 | N-(5-(6-(6-chloropyridin-3-yl)imidazo[1,2-b]pyridazin-2-yl)-2-methylphenyl)pivalamide | 420.4 |
| 409 | N-(5-(6-(4-hydroxy-2-(trifluoromethyl)phenyl)imidazo[1,2-b]pyridazin-2-yl)-2-methylphenyl)pivalamide | 469.4 |
| 410 | ethyl 2-(3-(2-(4-methyl-3-pivalamidophenyl)imidazo[1,2-b]pyridazin-6-yl)-2-(trifluoromethyl)phenoxy)acetate | 555.5 |
| 411 | ethyl 2-(4-(2-(4-methyl-3-pivalamidophenyl)imidazo[1,2-b]pyridazin-6-yl)-3-(trifluoromethyl)phenoxy)acetate | 555.5 |
| 412 | ethyl 6-(4-(2-(4-methyl-3-pivalamidophenyl)imidazo[1,2-b]pyridazin-6-yl)-3-(trifluoromethyl)phenoxy)hexanoate | 611.5 |
| 413 | ethyl 7-(4-(2-(4-methyl-3-pivalamidophenyl)imidazo[1,2-b]pyridazin-6-yl)-3-(trifluoromethyl)phenoxy)heptanoate | 525.5 |
| 414 | ethyl 6-(1-(2-(4-methyl-3-pivalamidophenyl)imidazo[1,2-b]pyridazin-6-yl)pyrrolidin-3-ylamino)hexanoate | 535.6 |
| 415 | ethyl 7-(1-(2-(4-methyl-3-pivalamidophenyl)imidazo[1,2-b]pyridazin-6-yl)pyrrolidin-3-ylamino)heptanoate | 549.6 |
| 416 | N-hydroxy-6-(4-(2-(4-methyl-3-pivalamidophenyl)imidazo[1,2-b]pyridazin-6-yl)-3-(trifluoromethyl)phenoxy)hexanamide | 598.5 |
| 417 | N-hydroxy-7-(4-(2-(4-methyl-3-pivalamidophenyl)imidazo[1,2-b]pyridazin-6-yl)-3-(trifluoromethyl)phenoxy)heptanamide | 612.5 |
| 418 | N-hydroxy-6-(1-(2-(4-methyl-3-pivalamidophenyl)imidazo[1,2-b]pyridazin-6-yl)pyrrolidin-3-ylamino)hexanamide | 522.6 |
| 419 | N-hydroxy-7-(1-(2-(4-methyl-3-pivalamidophenyl)imidazo[1,2-b]pyridazin-6-yl)pyrrolidin-3-ylamino)heptanamide | 536.6 |
| 420 | methyl 8-(2-methyl-5-(6-(2-(trifluoromethyl)pyridin-3-yl)imidazo[1,2-b]pyridazin-2-yl)phenylamino)-8-oxooctanoate | 540.5 |
| 421 | methyl 6-(2-methyl-5-(6-(2-(trifluoromethyl)pyridin-3-yl)imidazo[1,2-b]pyridazin-2-yl)phenylamino)-6-oxohexanoate | 512.4 |
| 422 | ethyl 6-(3-(2-(4-methyl-3-pivalamidophenyl)imidazo[1,2-b]pyridazin-6-yl)-2-(trifluoromethyl)phenoxy)hexanoate | 611.5 |
| 423 | ethyl 7-(3-(2-(4-methyl-3-pivalamidophenyl)imidazo[1,2-b]pyridazin-6-yl)-2-(trifluoromethyl)phenoxy)heptanoate | 625.5 |
| 424 | ethyl 6-(3-(2-(4-methyl-3-pivalamidophenyl)imidazo[1,2-b]pyridazin-6-yl)-4-(trifluoromethyl)phenoxy)hexanoate | 611.5 |
| 425 | ethyl 7-(3-(2-(4-methyl-3-pivalamidophenyl)imidazo[1,2-b]pyridazin-6-yl)-4-(trifluoromethyl)phenoxy)heptanoate | 625.5 |
| 426 | ethyl 4-(3-(2-(4-methyl-3-pivalamidophenyl)imidazo[1,2-b]pyridazin-6-yl)-2-(trifluoromethyl)phenoxy)butanoate | 583.5 |
| 427 | ethyl 5-(4-(2-(4-methyl-3-pivalamidophenyl)imidazo[1,2-b]pyridazin-6-yl)-3-(trifluoromethyl)phenoxy)pentanoate | 597.5 |
| 428 | ethyl 4-(4-(2-(4-methyl-3-pivalamidophenyl)imidazo[1,2-b]pyridazin-6-yl)-3-(trifluoromethyl)phenoxy)butanoate | 583.5 |
| 429 | $N^1$-hydroxy-$N^8$-(2-methyl-5-(6-(2-(trifluoromethyl)pyridin-3-yl)imidazo[1,2-b]pyridazin-2-yl)phenyl)octanediamide | 541.5 |
| 430 | 8-(2-methyl-5-(6-(2-(trifluoromethyl)pyridin-3-yl)imidazo[1,2-b]pyridazin-2-yl)phenylamino)-8-oxooctanoic acid | 526.5 |
| 431 | ethyl 4-(4-(2-(4-methyl-3-pivalamidophenyl)imidazo[1,2-b]pyridazin-6-yl)-6-(trifluoromethyl)pyridin-2-yloxy)butanoate | 584.5 |

-continued

| Example No. | Compound | |
|---|---|---|
| 432 | ethyl 4-(5-(2-(4-methyl-3-pivalamidophenyl)imidazo[1,2-b]pyridazin-6-yl)-6-(trifluoromethyl)pyridin-2-yloxy)butanoate | 584.5 |
| 433 | ethyl 5-(3-(2-(4-methyl-3-pivalamidophenyl)imidazo[1,2-b]pyridazin-6-yl)-4-(trifluoromethyl)phenoxy)pentanoate | 597.5 |
| 434 | ethyl 4-(3-(2-(4-methyl-3-pivalamidophenyl)imidazo[1,2-b]pyridazin-6-yl)-4-(trifluoromethyl)phenoxy)butanoate | 583.5 |
| 435 | ethyl 3-(2-methyl-5-(6-(2-(trifluoromethyl)pyridin-3-yl)imidazo[1,2-b]pyridazin-2-yl)phenylamino)-3-oxopropanoate | 484.4 |
| 436 | ethyl 4-(2-methyl-5-(6-(2-(trifluoromethyl)pyridin-3-yl)imidazo[1,2-b]pyridazin-2-yl)phenylamino)-4-oxobutanoate | 498.4 |
| 437 | N-hydroxy-4-(2-(4-methyl-3-pivalamidophenyl)imidazo[1,2-b]pyridazin-6-yl)-3-(trifluoromethyl)benzamide | 512.4 |
| 438 | N-hydroxy-6-(3-(2-(4-methyl-3-pivalamidophenyl)imidazo[1,2-b]pyridazin-6-yl)-2-(trifluoromethyl)phenoxy)hexanamide | 598.5 |
| 439 | N-(5-(6-(3-(2-(hydroxyamino)-2-oxoethoxy)-2-(trifluoromethyl)phenyl)imidazo[1,2-b]pyridazin-2-yl)-2-methylphenyl)pivalamide | 542.4 |
| 440 | $N^1$-hydroxy-$N^6$-(2-methyl-5-(6-(2-(trifluoromethyl)pyridin-3-yl)imidazo[1,2-b]pyridazin-2-yl)phenyl)adipamide | 513.4 |
| 441 | 2-(4-methyl-3-(6-(trifluoromethyl)pyridin-2-yl)phenyl)-6-(2-(trifluoromethyl)pyridin-3-yl)imidazo[1,2-b]pyridazine | 500.4 |
| 442 | N-(5-(6-cyclopentenylimidazo[1,2-b]pyridazin-2-yl)-2-methylphenyl)pivalamide | 375.5 |
| 443 | N-(5-(6-cyclohexenylimidazo[1,2-b]pyridazin-2-yl)-2-methylphenyl)pivalamide | 389.5 |
| 444 | N-(5-(6-(4,4-dimethylcyclohex-1-enyl)imidazo[1,2-b]pyridazin-2-yl)-2-methylphenyl)pivalamide | 417.5 |
| 445 | N-(2-methyl-5-(6-(thiazol-4-yl)imidazo[1,2-b]pyridazin-2-yl)phenyl)pivalamide | 392.4 |
| 446 | methyl 2-(2-(4-methyl-3-pivalamidophenyl)imidazo[1,2-b]pyridazin-6-yl)thiazole-4-carboxylate | 450.4 |
| 447 | N-(5-(6-(2-acetamidothiazol-5-yl)imidazo[1,2-b]pyridazin-2-yl)-2-methylphenyl)pivalamide | 449.4 |
| 448 | N-(2-methyl-5-(6-(2-morpholinothiazol-4-yl)imidazo[1,2-b]pyridazin-2-yl)phenyl)pivalamide | 477.5 |
| 449 | N-(5-(6-(benzo[c][1,2,5]oxadiazol-5-yl)imidazo[1,2-b]pyridazin-2-yl)-2-methylphenyl)pivalamide | 427.4 |
| 450 | N-(5-(6-(5-cyano-2-methylphenyl)imidazo[1,2-b]pyridazin-2-yl)-2-methylphenyl)pivalamide | 424.5 |
| 451 | N-(5-(6-(3-(N,N-dimethylsulfamoyl)phenyl)imidazo[1,2-b]pyridazin-2-yl)-2-methylphenyl)pivalamide | 492.5 |
| 452 | N-methyl-2-(2-(4-methyl-3-pivalamidophenyl)imidazo[1,2-b]pyridazin-6-yl)benzamide | 442.5 |
| 453 | N-methyl-3-(2-(4-methyl-3-pivalamidophenyl)imidazo[1,2-b]pyridazin-6-yl)benzamide | 442.5 |
| 454 | N-hydroxy-5-(4-(2-(4-methyl-3-pivalamidophenyl)imidazo[1,2-b]pyridazin-6-yl)-3-(trifluoromethyl)phenoxy)pentanamide | 584.5 |
| 455 | N-(5-(6-(4-(2-(hydroxyamino)-2-oxoethoxy)-2-(trifluoromethyl)phenyl)imidazo[1,2-b]pyridazin-2-yl)-2-methylphenyl)pivalamide | 542.4 |
| 456 | N-(2-methyl-5-(6-(4-(trifluoromethyl)pyridin-2-yl)imidazo[1,2-b]pyridazin-2-yl)phenyl)pivalamide | 454.4 |
| 457 | N-(2-methyl-5-(6-(5-(trifluoromethyl)pyridin-2-yl)imidazo[1,2-b]pyridazin-2-yl)phenyl)pivalamide | 454.4 |
| 458 | N-(2-methyl-5-(6-(6-(trifluoromethyl)pyridin-2-yl)imidazo[1,2-b]pyridazin-2-yl)phenyl)pivalamide | 454.4 |
| 459 | 6-(2-(4-methyl-3-pivalamidophenyl)imidazo[1,2-b]pyridazin-6-yl)nicotinic acid | 430.4 |
| 460 | N-(5-(6-(6-(hydroxymethyl)pyridin-2-yl)imidazo[1,2-b]pyridazin-2-yl)-2-methylphenyl)pivalamide | 416.5 |
| 461 | 4-methoxy-6-(2-(4-methyl-3-pivalamidophenyl)imidazo[1,2-b]pyridazin-6-yl)nicotinic acid | 460.4 |
| 463 | N-(5-(6-((2R,6S)-2,6-dimethylmorpholino)imidazo[1,2-b]pyridazin-2-yl)-2-(trifluoromethoxy)phenyl)pivalamide | 492.5 |
| 464 | N-(5-(6-((1R,2R)-2-methylcyclohexyloxy)imidazo[1,2-b]pyridazin-2-yl)-2-(trifluoromethyl)phenyl)pivalamide | 475.5 |
| 465 | N-(5-(6-((1R,4R)-4-hydroxycyclohexylamino)imidazo[1,2-b]pyridazin-2-yl)-2-(trifluoromethyl)phenyl)pivalamide | 476.5 |
| 466 | (R)-N-(5-(6-(2-methylpiperazin-1-yl)imidazo[1,2-b]pyridazin-2-yl)-2-(trifluoromethyl)phenyl)pivalamide | 461.5 |
| 467 | N-(5-(6-(3-hydroxypyrrolidin-1-yl)imidazo[1,2-b]pyridazin-2-yl)-2-(trifluoromethyl)phenyl)pivalamide | 448.4 |
| 468 | N-(5-(6-(3-hydroxypyrrolidin-1-yl)imidazo[1,2-b]pyridazin-2-yl)-2-methylphenyl)pivalamide | 394.5 |
| 469 | (R)-N-(5-(6-(2-(hydroxymethyl)pyrrolidin-1-yl)imidazo[1,2-b]pyridazin-2-yl)-2-(trifluoromethyl)phenyl)pivalamide | 462.5 |

| Example No. | Compound | |
|---|---|---|
| 470 | (R)-N-(5-(6-(3-(dimethylamino)pyrrolidin-1-yl)imidazo[1,2-b]pyridazin-2-yl)-2-(trifluoromethyl)phenyl)pivalamide | 475.5 |
| 471 | N-(5-(6-(3-hydroxypiperidin-1-yl)imidazo[1,2-b]pyridazin-2-yl)-2-(trifluoromethyl)phenyl)pivalamide | 462.5 |
| 472 | (R)-N-(5-(6-(3-(dimethylamino)pyrrolidin-1-yl)imidazo[1,2-b]pyridazin-2-yl)-2-methylphenyl)pivalamide | 421.5 |
| 473 | N-(2-methyl-5-(6-(3-(methylamino)pyrrolidin-1-yl)imidazo[1,2-b]pyridazin-2-yl)phenyl)pivalamide | 407.5 |
| 474 | N-(5-(6-(3-(ethylamino)pyrrolidin-1-yl)imidazo[1,2-b]pyridazin-2-yl)-2-methylphenyl)pivalamide | 421.5 |
| 475 | ethyl 2-(4-(2-(4-methyl-3-pivalamidophenyl)imidazo[1,2-b]pyridazin-6-yl)-6-(trifluoromethyl)pyridin-2-yloxy)acetate | 556.5 |
| 476 | ethyl 2-(5-(2-(4-methyl-3-pivalamidophenyl)imidazo[1,2-b]pyridazin-6-yl)-6-(trifluoromethyl)pyridin-2-yloxy)acetate | 556.5 |
| 477 | ethyl 2-(3-(2-(4-methyl-3-pivalamidophenyl)imidazo[1,2-b]pyridazin-6-yl)-4-(trifluoromethyl)phenoxy)acetate | 555.5 |
| 478 | N-(5-(6-(4-cyano-2-(trifluoromethyl)phenyl)imidazo[1,2-b]pyridazin-2-yl)-2-methylphenyl)pivalamide | 478.4 |
| 479 | 4-(2-(4-methyl-3-pivalamidophenyl)imidazo[1,2-b]pyridazin-6-yl)-3-(trifluoromethyl)benzoic acid | 497.4 |
| 480 | 2-methyl-5-(6-(2-(trifluoromethyl)pyridin-3-yl)imidazo[1,2-b]pyridazin-2-yl)benzonitrile | 380.4 |
| 481 | 2-methyl-5-(6-(2-(trifluoromethyl)pyridin-3-yl)imidazo[1,2-b]pyridazin-2-yl)benzoic acid | 399.4 |
| 482 | 2-methyl-5-(6-(2-(trifluoromethyl)pyridin-3-yl)imidazo[1,2-b]pyridazin-2-yl)benzamide | 398.4 |
| 483 | N-tert-butyl-2-methyl-5-(6-(2-(trifluoromethyl)pyridin-3-yl)imidazo[1,2-b]pyridazin-2-yl)benzamide | 454.4 |

Example 484

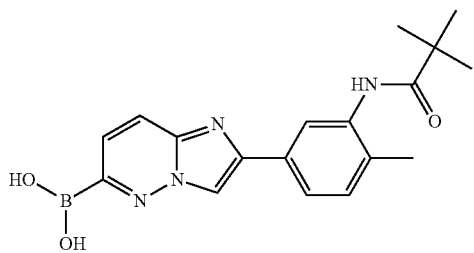 [SMILES: Cc1ccc(-c2cn3nc(B(O)O)ccc3n2)cc1NC(=O)C(C)(C)C]

2-(4-methyl-3-pivalamidophenyl)imidazo[1,2-b]pyridazin-6-ylboronic acid

A suspension of N-[5-(6-chloroimidazo[2,1-f]pyridazin-2-yl)-2-methyl-phenyl]-2,2-dimethyl-propanamide (15.43 g 0.045 mol), bis(pinacolato)diboron (17.14 g, 0.0675 mol), potassium acetate (8.833 g, 0.09 mol), [1,1'-bis(diphenylphosphino)ferrocene]dichloropalladium(II) (2.305 g, 3.15 mmol) in dioxane (153 mL) is heated at 90° C. for 16 hours. The reaction mixture is cooled, concentrated, added to an aqueous NaOH solution (150 mL, 3 M). The mixture is stirred for 1 hour then extracted with EtOAc (300 mL). Organic layers are washed with the NaOH solution (150 mL, 3 M). The aqueous portions are combined, washed twice with ether, and the aqueous pH is lowered to 5 with an aqueous HCl solution (6 M) to cause solid formation. This heterogeneous solution is cooled in the freezer for 2 hours, the solids are collected by filtration to give the desired product (8.56 g). The resulting aqueous solution is back extracted with EtOAc, combined with earlier organic portions and filtered through celite. The combined organic layer is dried, concentrated and taken up into an aqueous HCl solution (0.5 M). The solid product formed is collected by filtration and combined with the earlier batch, to afford a total 10.16 g of the desired title compound. LCMS (m/z)=353.5 [M+H]$^+$, $t_R$=2.04 min.

Example 485

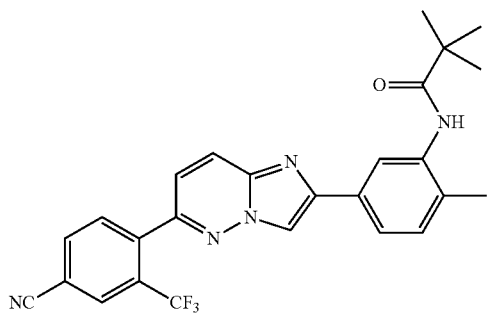 [SMILES: Cc1ccc(-c2cn3nc(-c4ccc(C#N)cc4C(F)(F)F)ccc3n2)cc1NC(=O)C(C)(C)C]

N-(5-(6-(4-cyano-2-(trifluoromethyl)phenyl)imidazo[1,2-b]pyridazin-2-yl)-2-methylphenyl)pivalamide A 200 mL flask is charged with 2-(4-methyl-3-pivalamidophenyl)imidazo[1,2-b]pyridazin-6-ylboronic acid (11.4 g, 0.0325 mol), 4-bromo-3-(trifluoromethyl)benzonitrile (10.16 g, 0.04 mol), $K_2CO_3$ (8.98 g, 0.065 mol), palladium acetate (0.510 g, 2.28 mmol), 2-dicyclohexylphosphino-2',6'-dimethoxy-1,1'-biphenyl (1.868 g, 4.55 mmol) and a solution of isopropanol-water (3:1, 80 mL). The mixture is degassed by bubbling $N_2$ through and heated at 90° C. for 5 hours. The mixture is then cooled and filtered through celite, concentrated and purified by silica gel chromatography (0-100% EtOAc in $CH_2Cl_2$). The desired fractions are combined and stirred for 24 hours with QuadraSil MP (a mercaptopropyl Example 486

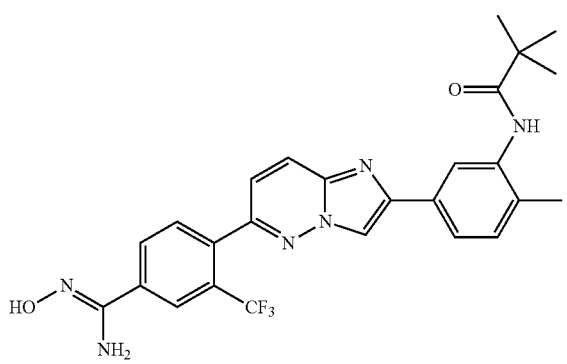 [SMILES: Cc1ccc(-c2cn3nc(-c4ccc(/C(N)=N/O)cc4C(F)(F)F)ccc3n2)cc1NC(=O)C(C)(C)C]

N-(5-(6-(4-(N'-hydroxycarbamimidoyl)-2-(trifluoromethyl)phenyl)imidazo[1,2-b]pyridazin-2-yl)-2-methylphenyl)pivalamide A 500-mL flask is charged with N-(5-(6-(4-cyano-2-(trifluoromethyl)phenyl)imidazo[1,2-b]pyridazin-2-yl)-2-methylphenyl)pivalamide (7.496 g, 0.0157 mol), hydroxylamine hydrochloride (6.55 g, 0.0942 mol), Et$_3$N (15.32 mL, 0.1099 mol), ethanol (82.5 mL) and the resulting mixture is stirred for 2 hours at 80° C. The mixture is concentrated onto celite and purified by silica gel chromatography (eluted by 0 to 100% of 10:1 EtOAc:MeOH in CH$_2$Cl$_2$). The isolated solid material (over 20 g) contains triethylamine and hydroxylamine salts, and the salts stay even after attempted recrystallization with isopropanol. This solid product is then added to a stirred mixture of saturated aqueous NaHCO$_3$ and EtOAc. Solid suspension is collected by filtration. The liquid portion is back extracted with EtOAc and the organic layers are combined, dried with Na$_2$SO$_4$, concentrated to afford additional solid product. The combined solid product is dried on a lyophilizer overnight, recrystallized from hot Isopropanol to afford the desired title product (6.56 g). LCMS (m/z)=511.6 [M+H]$^+$, t$_R$=2.49 min.

Example 487

N-(5-(6-(4-carbamimidoyl-2-(trifluoromethyl)phenyl)imidazo[1,2-b]pyridazin-2-yl)-2-methylphenyl)pivalamide A 20 mL vial is charged with N-(5-(6-(4-cyano-2-(trifluoromethyl)phenyl)imidazo[1,2-b]pyridazin-2-yl)-2-methylphenyl)pivalamide (0.052 g, 0.11 mmol) and a solution of HCl in MeOH (3 N, 3 mL) is added. The mixture is stirred at 65° C. for 60 hours. The reaction mixture is concentrated and taken up in a solution of NH$_3$ in MeOH (7 M, 1 mL) and stirred at 65° C. for an additional 18 hours. The mixture is concentrated, taken up into DMSO and purified on a Gilson preparative reverse phase HPLC to give the title compound (0.016 g, 29% yield). LCMS (m/z)=495.5 [M+H]$^+$, t$_R$=2.15 min.

Example 488

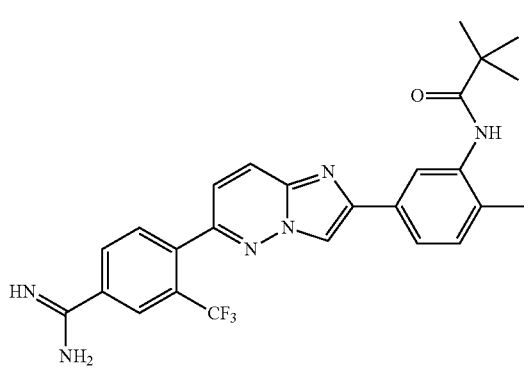 [SMILES: Cc1ccc(-c2cn3nc(-c4ccc(C(=N)N)cc4C(F)(F)F)ccc3n2)cc1NC(=O)C(C)(C)C]

N-(2-methyl-5-(6-(3,4,5-trimethoxybenzylamino)imidazo[1,2-b]pyridazin-2-yl)phenyl)pivalamide A 40-mL vial is charged with N-[5-(6-chloroimidazo[2,1-f]pyridazin-2-yl)-2-methyl-phenyl]-2,2-dimethyl-propanamide (1.0285 g, 3 mmol), tert-butyl xphos (0.255 g, 0.6 mmol), sodium tert-butoxide (0.577 g, 6 mmol), and bis(dibenzylideneacetone)palladium(0) (0.172 g, 0.3 mmol) and the vial is purged with N$_2$. Toluene (16 mL) and 3,4,5-trimethoxybenzylamine (1.54 mL, 9 mmol) is added and the mixture heated at 100° C. for 1 hr. The reaction mixture is filtered through celite, washed with 1:1:0.1 CH$_2$Cl$_2$:EtOAc:MeOH and concentrated onto celite, and purified by silica gel chromatography (0-100% 1:1:0.1 CH$_2$Cl$_2$:EtOAc:MeOH) to afford the title compound (0.604 g). LCMS (m/z)=504.6 [M+H]$^+$, t$_R$=2.31 min.

bound silica gel, 20 g) to scavenge the palladium, filtered and concentrated to give desired title compound (7.5 g). LCMS (m/z)=478.6 [M+H]$^+$, t$_R$=2.97 min.

Example 489

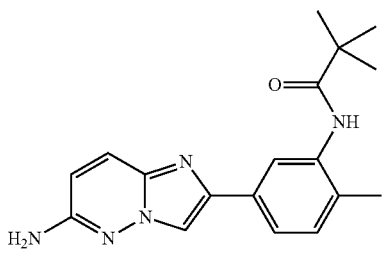 [SMILES: Cc1ccc(-c2cn3nc(N)ccc3n2)cc1NC(=O)C(C)(C)C]

N-[5-(6-aminoimidazo[2,1-f]pyridazin-2-yl)-2-methyl-phenyl]-2,2-dimethyl-propanamide A 40-mL vial is charged with N-(2-methyl-5-(6-(3,4,5-trimethoxybenzylamino)imidazo[1,2-b]pyridazin-2-yl)phenyl)pivalamide (0.604 g, 1.2 mmol) and TFA (5 mL) and the mixture is stirred at 50° C. for 16 hours. The reaction mixture is concentrated, taken up in CH₃CN and water is added. The mixture is concentrated to form solid from aqueous solution. The mixture is frozen and water is removed on a lyophilizer to afford the title compound (0.350 g). LCMS (m/z)=324.5 [M+H]⁺, $t_R$=1.96 min.

Example 490

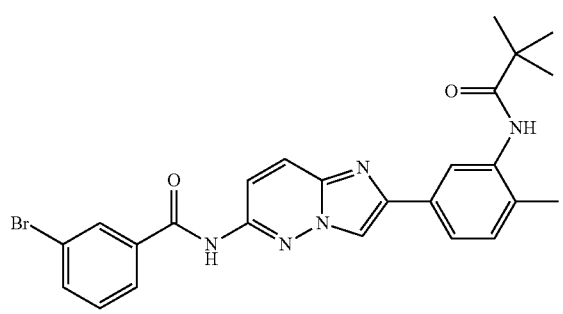 [SMILES: Cc1ccc(-c2cn3nc(NC(=O)c4cccc(Br)c4)ccc3n2)cc1NC(=O)C(C)(C)C]

3-bromo-N-[2-[3-(2,2-dimethylpropanoylamino)-4-methyl-phenyl]imidazo[2,1-f]pyridazin-6-yl]benzamide An 8-mL vial is charged with N-[5-(6-aminoimidazo[2,1-f]pyridazin-2-yl)-2-methyl-phenyl]-2,2-dimethyl-propanamide (0.097 g, 0.3 mmol), 3-bromobenzoyl chloride (0.059 mL, 0.45 mmol), pyridine (0.073 mL), and MeCN (1.0 mL). The mixture is stirred at room temperature for 16 hours, concentrated onto celite and purified by silica gel chromatography (0-100% 1:0.1 EtOAc:MeOH in CH₂Cl₂) to give the title compound (0.065 g). LCMS (m/z)=506.4 and 508.4 [M+H]⁺, $t_R$=2.96 min.

Example 491

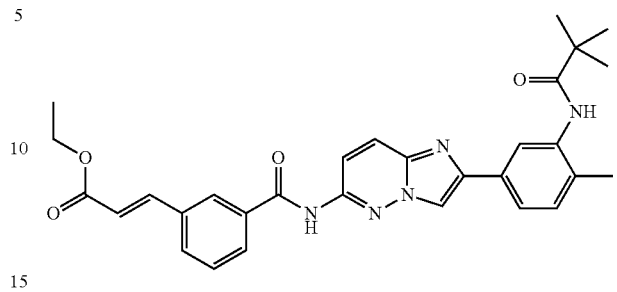

ethyl-3-[3-[[2-[3-(2,2-dimethylpropanoylamino)-4-methyl-phenyl]imidazo[2,1-f]pyridazin-6-yl]carbamoyl]phenyl]prop-2-enoate To a mixture of 3-bromo-N-[2-[3-(2,2-dimethylpropanoylamino)-4-methyl-phenyl]imidazo[2,1-f]pyridazin-6-yl] benzamide (0.126 g, 0.25 mmol), Ethyl acrylate (0.272 mL, 2.5 mmol), palladium(II) acetate (2.8 mg, 0.01 mmol), tri(o-tolyl)phosphine (0.0152 g, 0.05 mmol) in DMF (1.45 mL) is added DIPEA (0.174 mL, 1 mmol). The mixture is degassed with N₂ then sealed and heated at 110° C. for 18 hours. The reaction mixture is cooled, saturated aqueous NaHCO₃ (50 mL) added and extracted with EtOAc (×3). Organic layers are combined and washed with water, NaHCO₃, brine, then dried, concentrated and purified by silica gel chromatography (0-100% EtOAc in Hexanes) to give the title compound (0.040 g). LCMS (m/z)=526.6 [M+H]⁺, $t_R$=2.92 min.

Example 492

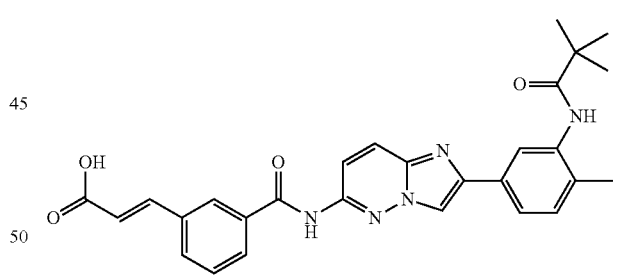

3-[3-[[2-[3-(2,2-dimethylpropanoylamino)-4-methyl-phenyl]imidazo[2,1-f]pyridazin-6-yl]carbamoyl]phenyl]prop-2-enoic acid A 20-mL vial is charged with ethyl-3-[3-[[2-[3-(2,2-dimethylpropanoylamino)-4-methyl-phenyl]imidazo[2,1-f]pyridazin-6-yl]carbamoyl]phenyl]prop-2-enoate (0.042 g, 0.08 mmol) and a solution of THF-MeOH (1 mL, 1:1). To this mixture is added aqueous NaOH (1 mL, 1 M), then stirred at 50° C. for 1 hour. The mixture is concentrated to remove the organics and extracted with EtOAc once. Aqueous HCl (1M) is added to lower the pH to 2 and the resulting solids are Example 493

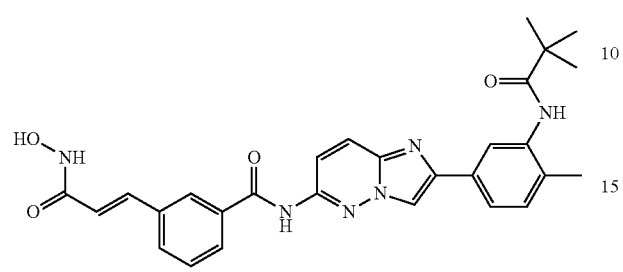

N-[2-[3-(2,2-dimethylpropanoylamino)-4-methyl-phenyl]imidazo[2,1-f]pyridazin-6-yl]-3-[3-(hydroxyamino)-3-oxo-prop-1-enyl]benzamide A 20-mL vial is charged with acetonitrile (0.4 mL), 3-[3-[[2-[3-(2,2-dimethylpropanoylamino)-4-methyl-phenyl]imidazo[2,1-f]pyridazin-6-yl]carbamoyl]phenyl]prop-2-enoic acid (0.025 g, 0.05 mmol), O-(tetrahydro-2H-pyran-2-yl)hydroxylamine (0.0088 g, 0.08 mmol), triethylamine (0.021 mL, 0.15 mmol) and (benzotriazol-1-yloxy)tris(dimethylamino)phosphonium hexafluorophosphate (0.033 g, 0.08 mmol). The mixture is stirred at room temperature for 2 hr, concentrated and taken up into saturated aqueous $Na_2CO_3$ (2 mL), extracted with EtOAc and $CH_2Cl_2$. Organic layers are combined, dried and concentrated to give crude N-[2-[3-(2,2-dimethylpropanoylamino)-4-methyl-phenyl]imidazo[2,1-f]pyridazin-6-yl]-3-[3-oxo-3-(tetrahydropyran-2-yloxyamino)prop-1-enyl]benzamide. This is taken up in a mixture of aqueous HCl (1 mL, 1M) and MeOH (1 mL), and is stirred at 50° C. for 1 hour. The mixture is concentrated, taken up in DMSO (1 mL) and purified on a Gilson preparative HPLC (reverse phase) to afford the title compound (0.015 g). LCMS (m/z)=513.5 [M+H]$^+$, $t_R$=2.31 min.

Example 494

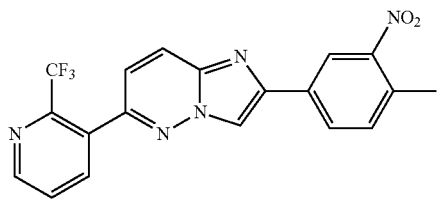 [SMILES: Cc1ccc(-c2cn3nc(-c4cccnc4C(F)(F)F)ccc3n2)cc1[N+](=O)[O-]]

2-(4-methyl-3-nitro-phenyl)-6-[2-(trifluoromethyl)-3-pyridyl]imidazo[2,1-f]pyridazine A 500 mL flask is charged with 6-chloro-2-(4-methyl-3-nitro-phenyl)imidazo[2,1-f]pyridazine (10.104 g, 0.035 mol), 3-(4,4,5,5-tetramethyl-1,3,2-dioxaborolan-2-yl)-2-(trifluoromethyl)pyridine (Journal of Organic Chemistry, 2011, 76, 1062) (13.38 g, 0.049 mol), KOAc (6.869 g, 0.07 mol), bis(dibenzylideneacetone)palladium(0) (2.01 g, 3.5 mmol), 2-dicyclohexylphosphino-2',4',6'-triisopropylbiphenyl (3.34 g, 0.007 mol), butanol (112 mL) and water (20 mL). The reaction mixture is heated at 90° C. for 4 hr. The reaction is filtered through celite and washed with EtOAc. The liquid layers are combined, concentrated onto celite and purified by silica gel chromatography (0-75% EtOAc in $CH_2Cl_2$) to give the title compound (7.98 g, 60% yield). LCMS (m/z)=400.4 [M+H]$^+$, $t_R$=2.76 min.

Example 495

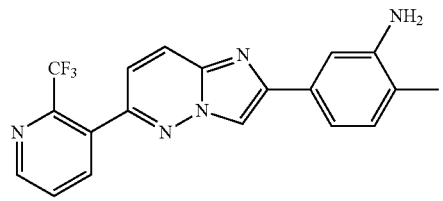

2-methyl-5-[6-[2-(trifluoromethyl)-3-pyridyl]imidazo[2,1-f]pyridazin-2-yl]aniline A mixture of 2-(4-methyl-3-nitro-phenyl)-6-[2-(trifluoromethyl)-3-pyridyl]imidazo[2,1-f]pyridazine (7.986 g, 0.02 mol) in EtOH—AcOH (48 mL, 1:1) is added slowly to a solution of iron powder (6.702 g, 0.12 mol) in EtOH—AcOH (60 mL, 2:1) at 60° C. The mixture is stirred at 70° C. for 60 min, cooled to room temperature, filtered through celite, washed with EtOAc and concentrated. The oily residue is dissolved in EtOAc (500 mL) and washed twice with saturated aqueous $NaHCO_3$ (200 mL). Organic layer is dried and concentrated to afford the title compound as a solid (7.3 g). LCMS (m/z)=370.5 [M+H]$^+$, $t_R$=1.85 min.

Example 496

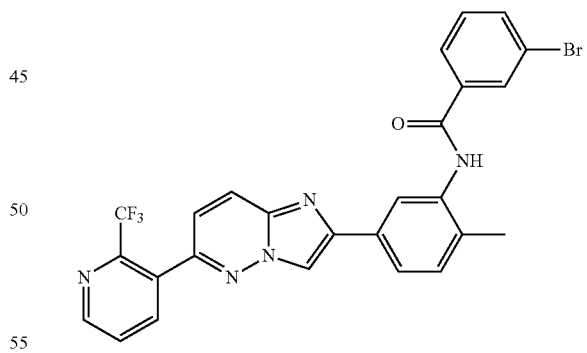

3-bromo-N-[2-methyl-5-[6-[2-(trifluoromethyl)-3-pyridyl]imidazo[2,1-f]pyridazin-2-yl]phenyl]benzamide A 20 mL vial is charged with 2-methyl-5-[6-[2-(trifluoromethyl)-3-pyridyl]imidazo[2,1-f]pyridazin-2-yl]aniline (0.444 g, 1.2 mmol), 3-bromobenzoyl chloride (0.378 mL, 1.8 mol), pyridine (0.292 mL, 3.6 mmol), MeCN (4 mL) and the mixture is stirred at room temperature for 18 hr. The reaction mixture is concentrated onto celite and purified by

Example 497

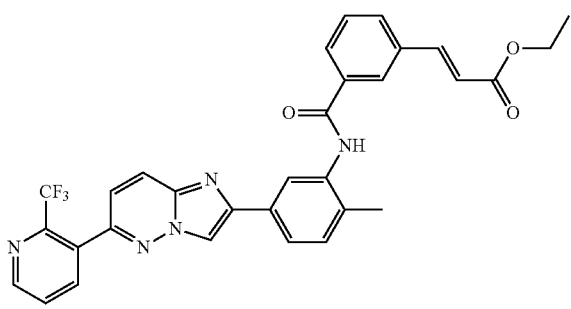 [SMILES: CCOC(=O)/C=C/c1cccc(C(=O)Nc2cc(-c3cn4nc(-c5cccnc5C(F)(F)F)ccc4n3)ccc2C)c1]

ethyl-3-[3-[[2-methyl-5-[6-[2-(trifluoromethyl)-3-pyridyl]imidazo[2,1-f]pyridazin-2-yl]phenyl]carbamoyl]phenyl]prop-2-enoate To a mixture of 3-bromo-N-[2-methyl-5-[6-[2-(trifluoromethyl)-3-pyridyl]imidazo[2,1-f]pyridazin-2-yl]phenyl]benzamide (0.442 g, 0.8 mmol), ethyl acrylate (0.872 mL, 8 mmol), palladium(II) acetate (9 mg, 0.04 mmol), tri(o-tolyl)phosphine (0.049 g, 0.16 mmol) in DMF (4.6 mL) and HMPA (0.4 mL) is added DIPEA (0.557 mL, 3.2 mmol). The mixture is degassed with $N_2$ then sealed and heated at 100° C. for 15 hours. The reaction is not complete, and is stirred at 100° C. for another 24 hours. The mixture is poured into saturated aqueous $NaHCO_3$ and extracted with EtOAc (2×). Organic layers are combined, dried and concentrated to give the title compound as a solid (485 mg), which is used without further purification. LCMS (m/z)=572.5 [M+H]+, $t_R$=3.14 min.

Example 498

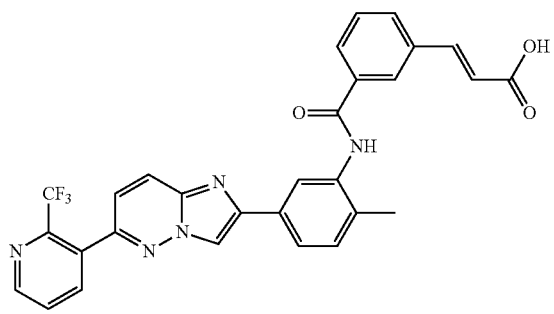 [SMILES: Cc1ccc(-c2cn3nc(-c4cccnc4C(F)(F)F)ccc3n2)cc1NC(=O)c1cccc(/C=C/C(=O)O)c1]

silica gel chromatography (0-100% EtOAc in $CH_2Cl_2$) to give the title compound (530 mg). LCMS (m/z)=552.3 and 554.3 [M+H]+, $t_R$=3.04 min.

3-[3-[[2-methyl-5-[6-[2-(trifluoromethyl)-3-pyridyl]imidazo[2,1-f]pyridazin-2-yl]phenyl]carbamoyl]phenyl]prop-2-enoic acid A 40-mL vial is charged with ethyl-3-[3-[[2-methyl-5-[6-[6-(trifluoromethyl)-2-pyridyl]imidazo[2,1-f]pyridazin-2-yl]phenyl]carbamoyl]phenyl]prop-2-enoate (0.486 g, 0.85 mmol), a mixture of THF-MeOH (3 mL, 1:1), and aqueous NaOH (2 mL, 1M). The mixture is stirred at 50° C. for 1 hour, cooled, concentrated and added water (2 mL). Aqueous HCl (1M) is added to lower the pH to 2 and the resulting solids are filtered to afford the title compound (435 mg). LCMS (m/z)= 544.5 [M+H]+, $t_R$=2.69 min.

Example 499

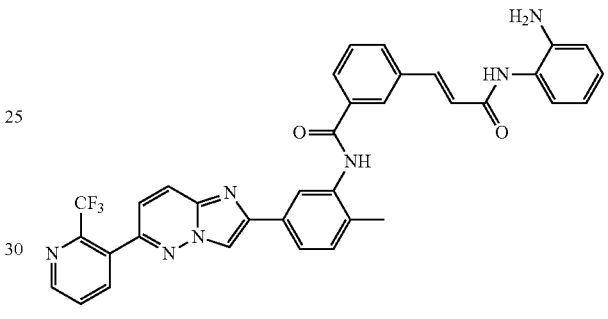

3-[3-[(2-aminophenyl)amino]-3-oxo-prop-1-enyl]-N-[2-methyl-5-[6-[2-(trifluoromethyl)-3-pyridyl]imidazo[2,1-f]pyridazin-2-yl]phenyl]benzamide A 4-mL vial is charged with acetonitrile (0.78 mL), 3-[3-[[2-methyl-5-[6-[6-(trifluoromethyl)-2-pyridyl]imidazo[2,1-f]pyridazin-2-yl]phenyl]carbamoyl]phenyl]prop-2-enoic acid (0.0544 g, 0.1 mmol), benzene-1,2-diamine (0.016 g, 0.15 mmol), triethylamine (0.042 mL, 0.3 mmol), and (benzotriazol-1-yloxy)tris(dimethylamino)phosphonium hexafluorophosphate (0.066 g, 0.15 mmol). The mixture is stirred at room temperature for 2 hr, concentrated, taken up in DMSO (1.5 mL) and purified on a Gilson preparative HPLC (reverse phase) to afford the title compound (18 mg). LCMS (m/z)=634.6 [M+H]+, $t_R$=2.77 min.

The following compounds are prepared essentially according to the procedures and examples set forth above, with modifications where necessary of the starting materials to provide the desired product.

| Example No. | Compound | LCMS (m/z) M + H |
|---|---|---|
| 500 | N-(2-methyl-5-(6-(3-methyl-1H-pyrazol-4-yl)imidazo[1,2-b]pyridazin-2-yl)phenyl)pivalamide | 389.5 |
| 501 | N-(5-(6-(3,5-dimethyl-1H-pyrazol-4-yl)imidazo[1,2-b]pyridazin-2-yl)-2-methylphenyl)pivalamide | 403.5 |
| 502 | N-(5-(6-(3,5-dimethylisoxazol-4-yl)imidazo[1,2-b]pyridazin-2-yl)-2-methylphenyl)pivalamide | 404.5 |

-continued

| Example No. | Compound | LCMS (m/z) M + H |
|---|---|---|
| 503 | N-(2-methyl-5-(6-(1,3,5-trimethyl-1H-pyrazol-4-yl)imidazo[1,2-b]pyridazin-2-yl)phenyl)pivalamide | 417.5 |
| 504 | N-(5-(6-(6-acetamido-2-methylpyridin-3-yl)imidazo[1,2-b]pyridazin-2-yl)-2-methylphenyl)pivalamide | 457.5 |
| 505 | N-(5-(6-(6-acetamidopyridin-3-yl)imidazo[1,2-b]pyridazin-2-yl)-2-methylphenyl)pivalamide | 443.5 |
| 506 | methyl 2-(2-methyl-5-(6-(2-(trifluoromethyl)pyridin-3-yl)imidazo[1,2-b]pyridazin-2-yl)phenyl)thiazole-4-carboxylate | 496.4 |
| 507 | 3,5-dimethyl-4-(2-methyl-5-(6-(2-(trifluoromethyl)pyridin-3-yl)imidazo[1,2-b]pyridazin-2-yl)phenyl)isoxazole | 450.4 |
| 508 | 4-(2-(4-methyl-3-pivalamidophenyl)imidazo[1,2-b]pyridazin-6-yl)-3-(trifluoromethyl)benzamide | 496.4 |
| 509 | methyl 7-(4-(2-(4-methyl-3-pivalamidophenyl)imidazo[1,2-b]pyridazin-6-yl)-3-(trifluoromethyl)benzamido)heptanoate | 638.5 |
| 510 | methyl 6-((4-(2-(4-methyl-3-pivalamidophenyl)imidazo[1,2-b]pyridazin-6-yl)-3-(trifluoromethyl)phenyl)amino)-6-oxohexanoate | 610.5 |
| 511 | N-(5-(6-(4-(N'-hydroxycarbamimidoyl)-2-(trifluoromethyl)phenyl)imidazo[1,2-b]pyridazin-2-yl)-2-methylphenyl)pivalamide | 511.5 |
| 512 | 4-(2-methyl-5-(6-(2-(trifluoromethyl)pyridin-3-yl)imidazo[1,2-b]pyridazin-2-yl)phenyl)thiazole | 438.3 |
| 513 | N-(5-(2-methyl-5-(6-(2-(trifluoromethyl)pyridin-3-yl)imidazo[1,2-b]pyridazin-2-yl)phenyl)thiazol-2-yl)acetamide | 495.4 |
| 514 | N-methyl-N-(2-methyl-5-(6-(2-(trifluoromethyl)pyridin-3-yl)imidazo[1,2-b]pyridazin-2-yl)phenyl)pivalamide | 468.4 |
| 515 | methyl 2-(N-(2-methyl-5-(6-(2-(trifluoromethyl)pyridin-3-yl)imidazo[1,2-b]pyridazin-2-yl)phenyl)pivalamido)acetate | 526.5 |
| 516 | methyl 7-(N-(2-methyl-5-(6-(2-(trifluoromethyl)pyridin-3-yl)imidazo[1,2-b]pyridazin-2-yl)phenyl)pivalamido)heptanoate | 596.5 |
| 517 | N-(5-(6-chloroimidazo[1,2-b]pyridazin-2-yl)-2-methylphenyl)-1-methylcyclopropanecarboxamide | 341.4 |
| 518 | 1-methyl-N-(2-methyl-5-(6-(2-(trifluoromethyl)pyridin-3-yl)imidazo[1,2-b]pyridazin-2-yl)phenyl)cyclopropanecarboxamide | 452.4 |
| 519 | N-(5-(6-(4-hydroxyphenyl)imidazo[1,2-b]pyridazin-2-yl)-2-methylphenyl)pivalamide | 401.4 |
| 520 | 4-(tert-butyl)-2-(2-methyl-5-(6-(2-(trifluoromethyl)pyridin-3-yl)imidazo[1,2-b]pyridazin-2-yl)phenyl)thiazole | 494.4 |
| 521 | 4-(2-(4-methyl-3-pivalamidophenyl)imidazo[1,2-b]pyridazin-6-yl)benzoic acid | 429.4 |
| 522 | N-(5-(6-(4-acetylphenyl)imidazo[1,2-b]pyridazin-2-yl)-2-methylphenyl)pivalamide | 427.5 |
| 523 | 3-fluoro-4-(2-(4-methyl-3-pivalamidophenyl)imidazo[1,2-b]pyridazin-6-yl)benzoic acid | 447.4 |
| 524 | N,N-dimethyl-4-(2-(4-methyl-3-pivalamidophenyl)imidazo[1,2-b]pyridazin-6-yl)benzamide | 456.5 |
| 525 | N-methyl-4-(2-(4-methyl-3-pivalamidophenyl)imidazo[1,2-b]pyridazin-6-yl)benzamide | 442.5 |
| 526 | 4-(2-(4-methyl-3-pivalamidophenyl)imidazo[1,2-b]pyridazin-6-yl)benzamide | 428.5 |
| 527 | N-(5-(6-(3-acetylphenyl)imidazo[1,2-b]pyridazin-2-yl)-2-methylphenyl)pivalamide | 427.6 |
| 528 | 3-(2-(4-methyl-3-pivalamidophenyl)imidazo[1,2-b]pyridazin-6-yl)benzoic acid | 429.4 |
| 529 | N-(5-(6-(5-acetyl-2-fluorophenyl)imidazo[1,2-b]pyridazin-2-yl)-2-methylphenyl)pivalamide | 445.5 |
| 530 | N1-hydroxy-N8-(4-(2-(4-methyl-3-pivalamidophenyl)imidazo[1,2-b]pyridazin-6-yl)-3-(trifluoromethyl)phenyl)octanediamide | 639.5 |
| 531 | N1-hydroxy-N6-(4-(2-(4-methyl-3-pivalamidophenyl)imidazo[1,2-b]pyridazin-6-yl)-3-(trifluoromethyl)phenyl)adipamide | 611.5 |
| 532 | methyl 8-((4-(2-(4-methyl-3-pivalamidophenyl)imidazo[1,2-b]pyridazin-6-yl)-3-(trifluoromethyl)phenyl)amino)-8-oxooctanoate | 638.5 |
| 533 | N-(5-(6-(4-(2-hydroxypropan-2-yl)-2-(trifluoromethyl)phenyl)imidazo[1,2-b]pyridazin-2-yl)-2-methylphenyl)pivalamide | 511.5 |
| 534 | N-(2-methyl-5-(6-(4-sulfamoylphenyl)imidazo[1,2-b]pyridazin-2-yl)phenyl)pivalamide | 464.4 |
| 535 | N-(2-methyl-5-(6-(4-sulfamoyl-2-(trifluoromethyl)phenyl)imidazo[1,2-b]pyridazin-2-yl)phenyl)pivalamide | 532.4 |
| 536 | N-(2-methyl-5-(6-(5-(trifluoromethyl)pyridin-3-yl)imidazo[1,2-b]pyridazin-2-yl)phenyl)pivalamide | 454.4 |
| 537 | 5-(2-(4-methyl-3-pivalamidophenyl)imidazo[1,2-b]pyridazin-6-yl)picolinamide | 429.5 |
| 538 | 6-(2-(4-methyl-3-pivalamidophenyl)imidazo[1,2-b]pyridazin-6-yl)nicotinamide | 429.5 |
| 539 | N-(5-(6-(4-(1,3,4-oxadiazol-2-yl)phenyl)imidazo[1,2-b]pyridazin-2-yl)-2-methylphenyl)pivalamide | 453.5 |

| Example No. | Compound | LCMS (m/z) M + H |
|---|---|---|
| 540 | 3-chloro-4-(2-(4-methyl-3-pivalamidophenyl)imidazo[1,2-b]pyridazin-6-yl)benzoic acid | 463.4 |
| 541 | 3-fluoro-4-(2-(4-methyl-3-pivalamidophenyl)imidazo[1,2-b]pyridazin-6-yl)benzamide | 446.4 |
| 542 | 1-(2-(4-methyl-3-pivalamidophenyl)imidazo[1,2-b]pyridazin-6-yl)piperidine-4-carboxamide | 435.5 |
| 543 | N-(5-(6-(4-carbamimidoyl-2-(trifluoromethyl)phenyl)imidazo[1,2-b]pyridazin-2-yl)-2-methylphenyl)pivalamide | 495.5 |
| 544 | N-(5-(6-(4-cyanopiperidin-1-yl)imidazo[1,2-b]pyridazin-2-yl)-2-methylphenyl)pivalamide | 417.5 |
| 545 | N-(5-(6-(4-cyano-2-fluorophenyl)imidazo[1,2-b]pyridazin-2-yl)-2-methylphenyl)pivalamide | 428.4 |
| 546 | N-(5-(6-(4-(N'-hydroxycarbamimidoyl)phenyl)imidazo[1,2-b]pyridazin-2-yl)-2-methylphenyl)pivalamide | 443.5 |
| 547 | N-(5-(6-(2-fluoro-4-hydroxyphenyl)imidazo[1,2-b]pyridazin-2-yl)-2-methylphenyl)pivalamide | 419.3 |
| 548 | N-(5-(6-(2-chloro-4-hydroxyphenyl)imidazo[1,2-b]pyridazin-2-yl)-2-methylphenyl)pivalamide | 435.4 |
| 549 | N-(2-methyl-5-(6-(4-(5-methyl-1,2,4-oxadiazol-3-yl)phenyl)imidazo[1,2-b]pyridazin-2-yl)phenyl)pivalamide | 467.2 |
| 550 | N-(5-(6-(4-aminophenyl)imidazo[1,2-b]pyridazin-2-yl)-2-methylphenyl)pivalamide | 400.5 |
| 551 | ethyl 3-(3-(2-(4-methyl-3-pivalamidophenyl)imidazo[1,2-b]pyridazin-6-yl)phenyl)acrylate | 483.5 |
| 552 | ethyl 3-(4-(2-(4-methyl-3-pivalamidophenyl)imidazo[1,2-b]pyridazin-6-yl)phenyl)acrylate | 483.5 |
| 553 | 8-((2-methyl-5-(6-(2-(trifluoromethyl)pyridin-3-yl)imidazo[1,2-b]pyridazin-2-yl)phenyl)amino)-8-oxooctanoic acid | 526.5 |
| 554 | 3-(3-(2-(4-methyl-3-pivalamidophenyl)imidazo[1,2-b]pyridazin-6-yl)phenyl)acrylic acid | 455.5 |
| 555 | 3-(4-(2-(4-methyl-3-pivalamidophenyl)imidazo[1,2-b]pyridazin-6-yl)phenyl)acrylic acid | 455.5 |
| 556 | methyl 8-((4-(2-(4-methyl-3-pivalamidophenyl)imidazo[1,2-b]pyridazin-6-yl)phenyl)amino)-8-oxooctanoate | 570.5 |
| 557 | N1-(2-methyl-5-(6-(2-(trifluoromethyl)pyridin-3-yl)imidazo[1,2-b]pyridazin-2-yl)phenyl)-N8-((tetrahydro-2H-pyran-2-yl)oxy)octanediamide | 625.5 |
| 558 | 3-(4-(2-(4-methyl-3-pivalamidophenyl)imidazo[1,2-b]pyridazin-6-yl)phenyl)-N-((tetrahydro-2H-pyran-2-yl)oxy)acrylamide | 554.5 |
| 559 | N-hydroxy-3-(3-(2-(4-methyl-3-pivalamidophenyl)imidazo[1,2-b]pyridazin-6-yl)phenyl)acrylamide | 470.5 |
| 560 | N-hydroxy-3-(4-(2-(4-methyl-3-pivalamidophenyl)imidazo[1,2-b]pyridazin-6-yl)phenyl)acrylamide | 470.5 |
| 561 | 8-((4-(2-(4-methyl-3-pivalamidophenyl)imidazo[1,2-b]pyridazin-6-yl)phenyl)amino)-8-oxooctanoic acid | 556.5 |
| 562 | N1-(4-(2-(4-methyl-3-pivalamidophenyl)imidazo[1,2-b]pyridazin-6-yl)phenyl)-N8-((tetrahydro-2H-pyran-2-yl)oxy)octanediamide | 655.6 |
| 563 | N1-hydroxy-N8-(4-(2-(4-methyl-3-pivalamidophenyl)imidazo[1,2-b]pyridazin-6-yl)phenyl)octanediamide | 571.6 |
| 564 | N-(5-(6-(2-chloro-4-cyanophenyl)imidazo[1,2-b]pyridazin-2-yl)-2-methylphenyl)pivalamide | 444.4 |
| 565 | N-(5-(6-(2-chloro-5-cyanophenyl)imidazo[1,2-b]pyridazin-2-yl)-2-methylphenyl)pivalamide | 444.4 |
| 566 | N-(5-(6-(4-(N'-hydroxycarbamimidoyl)piperidin-1-yl)imidazo[1,2-b]pyridazin-2-yl)-2-methylphenyl)pivalamide | 450.5 |
| 567 | N-(5-(6-(2-fluoro-4-(N'-hydroxycarbamimidoyl)phenyl)imidazo[1,2-b]pyridazin-2-yl)-2-methylphenyl)pivalamide | 461.5 |
| 568 | N-(5-(6-(2-chloro-4-(N'-hydroxycarbamimidoyl)phenyl)imidazo[1,2-b]pyridazin-2-yl)-2-methylphenyl)pivalamide | 477.4 |
| 569 | N-(5-(6-(2-chloro-5-(N'-hydroxycarbamimidoyl)phenyl)imidazo[1,2-b]pyridazin-2-yl)-2-methylphenyl)pivalamide | 477.4 |
| 570 | N-(5-(6-(4-carbamimidoylpiperazin-1-yl)imidazo[1,2-b]pyridazin-2-yl)-2-(trifluoromethyl)phenyl)pivalamide | 489.5 |
| 571 | N-(5-(6-(4-carbamimidoyl-2-methylpiperazin-1-yl)imidazo[1,2-b]pyridazin-2-yl)-2-(trifluoromethyl)phenyl)pivalamide | 503.5 |
| 572 | ethyl 3-(2-(4-methyl-3-pivalamidophenyl)imidazo[1,2-b]pyridazin-6-yl)acrylate | 407.5 |
| 573 | methyl 3-(4-chloro-3-(2-(4-methyl-3-pivalamidophenyl)imidazo[1,2-b]pyridazin-6-yl)phenyl)acrylate | 503.4 |
| 574 | N-(5-(6-(4-cyano-2-methylphenyl)imidazo[1,2-b]pyridazin-2-yl)-2-methylphenyl)pivalamide | 424.5 |
| 575 | N-(5-(6-(6-aminopyridin-2-yl)imidazo[1,2-b]pyridazin-2-yl)-2-methylphenyl)pivalamide | 401.5 |
| 576 | N-(5-(6-(4-(N'-hydroxycarbamimidoyl)-2-methylphenyl)imidazo[1,2-b]pyridazin-2-yl)-2-methylphenyl)pivalamide | 457.5 |

| Example No. | Compound | LCMS (m/z) M + H |
|---|---|---|
| 577 | N-(5-(6-(5-(N'-hydroxycarbamimidoyl)-2-methylphenyl)imidazo[1,2-b]pyridazin-2-yl)-2-methylphenyl)pivalamide | 457.5 |
| 578 | N-hydroxy-3-(2-(4-methyl-3-pivalamidophenyl)imidazo[1,2-b]pyridazin-6-yl)acrylamide | 394.4 |
| 579 | 3-(4-chloro-3-(2-(4-methyl-3-pivalamidophenyl)imidazo[1,2-b]pyridazin-6-yl)phenyl)-N-hydroxyacrylamide | 504.4 |
| 580 | N1-hydroxy-N8-(6-(2-(4-methyl-3-pivalamidophenyl)imidazo[1,2-b]pyridazin-6-yl)pyridin-2-yl)octanediamide | 572.5 |
| 581 | N-(5-(6-(2-cyanopyridin-3-yl)imidazo[1,2-b]pyridazin-2-yl)-2-methylphenyl)pivalamide | 411.4 |
| 582 | methyl 4-(2-(4-methyl-3-pivalamidophenyl)imidazo[1,2-b]pyridazin-6-yl)benzoate | 443.5 |
| 583 | methyl 3-(2-(4-methyl-3-pivalamidophenyl)imidazo[1,2-b]pyridazin-6-yl)benzoate | 443.5 |
| 584 | 4-(2-(4-methyl-3-pivalamidophenyl)imidazo[1,2-b]pyridazin-6-yl)-N-((tetrahydro-2H-pyran-2-yl)oxy)benzamide | 528.5 |
| 585 | 3-(2-(4-methyl-3-pivalamidophenyl)imidazo[1,2-b]pyridazin-6-yl)-N-((tetrahydro-2H-pyran-2-yl)oxy)benzamide | 528.5 |
| 586 | N-(5-(6-(4-(hydrazinyl(imino)methyl)-2-(trifluoromethyl)phenyl)imidazo[1,2-b]pyridazin-2-yl)-2-methylphenyl)pivalamide | 510.5 |
| 587 | N-(2-methyl-5-(6-((3,4,5-trimethoxybenzyl)amino)imidazo[1,2-b]pyridazin-2-yl)phenyl)pivalamide | 504.5 |
| 588 | N-hydroxy-4-(2-(4-methyl-3-pivalamidophenyl)imidazo[1,2-b]pyridazin-6-yl)benzamide | 444.5 |
| 589 | N-hydroxy-3-(2-(4-methyl-3-pivalamidophenyl)imidazo[1,2-b]pyridazin-6-yl)benzamide | 444.5 |
| 590 | N-(2-methyl-5-(6-(4-(5-oxo-2,5-dihydro-1H-1,2,4-triazol-3-yl)-2-(trifluoromethyl)phenyl)imidazo[1,2-b]pyridazin-2-yl)phenyl)pivalamide | 536.4 |
| 591 | N-(5-(6-aminoimidazo[1,2-b]pyridazin-2-yl)-2-methylphenyl)pivalamide | 324.4 |
| 592 | methyl 4-(((2-(4-methyl-3-pivalamidophenyl)imidazo[1,2-b]pyridazin-6-yl)amino)methyl)benzoate | 472.5 |
| 593 | N-(5-(6-((4-(hydroxymethyl)benzyl)amino)imidazo[1,2-b]pyridazin-2-yl)-2-methylphenyl)pivalamide | 444.5 |
| 594 | 3-bromo-N-(2-(4-methyl-3-pivalamidophenyl)imidazo[1,2-b]pyridazin-6-yl)benzamide | 506.4 |
| 595 | N-(5-(6-(3-bromophenylsulfonamido)imidazo[1,2-b]pyridazin-2-yl)-2-methylphenyl)pivalamide | 542.3 |
| 596 | N-(5-(6-(5-cyano-2-(trifluoromethyl)phenyl)imidazo[1,2-b]pyridazin-2-yl)-2-methylphenyl)pivalamide | 478.4 |
| 597 | N-(2-aminophenyl)-4-(2-(4-methyl-3-pivalamidophenyl)imidazo[1,2-b]pyridazin-6-yl)benzamide | 519.5 |
| 598 | N-(2-aminophenyl)-3-(2-(4-methyl-3-pivalamidophenyl)imidazo[1,2-b]pyridazin-6-yl)benzamide | 519.5 |
| 599 | N-(2-aminophenyl)-4-(((2-(4-methyl-3-pivalamidophenyl)imidazo[1,2-b]pyridazin-6-yl)amino)methyl)benzamide | 548.5 |
| 600 | 4-(((2-(4-methyl-3-pivalamidophenyl)imidazo[1,2-b]pyridazin-6-yl)amino)methyl)-N-((tetrahydro-2H-pyran-2-yl)oxy)benzamide | 557.5 |
| 601 | N-(5-(6-(5-(N'-hydroxycarbamimidoyl)-2-(trifluoromethyl)phenyl)imidazo[1,2-b]pyridazin-2-yl)-2-methylphenyl)pivalamide | 511.5 |
| 602 | ethyl 3-(3-((2-(4-methyl-3-pivalamidophenyl)imidazo[1,2-b]pyridazin-6-yl)carbamoyl)phenyl)acrylate | 526.5 |
| 603 | ethyl 3-(3-(N-(2-(4-methyl-3-pivalamidophenyl)imidazo[1,2-b]pyridazin-6-yl)sulfamoyl)phenyl)acrylate | 562.5 |
| 604 | N-hydroxy-4-(((2-(4-methyl-3-pivalamidophenyl)imidazo[1,2-b]pyridazin-6-yl)amino)methyl)benzamide | 473.5 |
| 605 | 3-(3-(hydroxyamino)-3-oxoprop-1-en-1-yl)-N-(2-(4-methyl-3-pivalamidophenyl)imidazo[1,2-b]pyridazin-6-yl)benzamide | 513.5 |
| 606 | N-hydroxy-3-(3-(N-(2-(4-methyl-3-pivalamidophenyl)imidazo[1,2-b]pyridazin-6-yl)sulfamoyl)phenyl)acrylamide | 549.4 |
| 607 | ethyl 3-(3-(N-(5-(6-chloroimidazo[1,2-b]pyridazin-2-yl)-2-methylphenyl)sulfamoyl)phenyl)acrylate | 497.4 |
| 608 | ethyl 3-(3-(N-(5-(6-(3-ethoxy-3-oxoprop-1-en-1-yl)imidazo[1,2-b]pyridazin-2-yl)-2-methylphenyl)sulfamoyl)phenyl)acrylate | 561.4 |
| 609 | ethyl 3-(3-((5-(6-chloroimidazo[1,2-b]pyridazin-2-yl)-2-methylphenyl)carbamoyl)phenyl)acrylate | 461.4 |
| 610 | ethyl 3-(2-(3-(3-ethoxy-3-oxoprop-1-en-1-yl)benzamido)-4-methylphenyl)imidazo[1,2-b]pyridazin-6-yl)acrylate | 525.6 |
| 611 | N-(2-(4-methyl-3-pivalamidophenyl)imidazo[1,2-b]pyridazin-6-yl)picolinamide | 429.5 |
| 612 | 3-chloro-N-(2-(4-methyl-3-pivalamidophenyl)imidazo[1,2-b]pyridazin-6-yl)picolinamide | 463.4 |
| 613 | 4-chloro-N-(2-(4-methyl-3-pivalamidophenyl)imidazo[1,2-b]pyridazin-6-yl)picolinamide | 463.4 |

-continued

| Example No. | Compound | LCMS (m/z) M + H |
|---|---|---|
| 614 | N-hydroxy-3-(3-(((2-(4-methyl-3-pivalamidophenyl)imidazo[1,2-b]pyridazin-6-yl)amino)methyl)phenyl)acrylamide | 499.5 |
| 615 | N-(5-(6-chloroimidazo[1,2-b]pyridazin-2-yl)-2-methylphenyl)-3-(3-(hydroxyamino)-3-oxoprop-1-en-1-yl)benzamide | 448.4 |
| 616 | 3-(3-(hydroxyamino)-3-oxoprop-1-en-1-yl)-N-(5-(6-methoxyimidazo[1,2-b]pyridazin-2-yl)-2-methylphenyl)benzamide | 444.4 |
| 617 | 3-(3-(N-(5-(6-chloroimidazo[1,2-b]pyridazin-2-yl)-2-methylphenyl)sulfamoyl)phenyl)-N-hydroxyacrylamide | 484.3 |
| 618 | N-hydroxy-3-(3-(N-(5-(6-methoxyimidazo[1,2-b]pyridazin-2-yl)-2-methylphenyl)sulfamoyl)phenyl)acrylamide | 480.4 |
| 619 | N-(5-(6-(2-chloro-3-fluorophenyl)imidazo[1,2-b]pyridazin-2-yl)-2-methylphenyl)pivalamide | 437.4 |
| 620 | N-(5-(6-chloroimidazo[1,2-b]pyridazin-2-yl)-2-methylphenyl)-2-cyano-2-methylpropanamide | 354.4 |
| 621 | 2-cyano-2-methyl-N-(2-methyl-5-(6-(2-(trifluoromethyl)pyridin-3-yl)imidazo[1,2-b]pyridazin-2-yl)phenyl)propanamide | 465.4 |
| 622 | 3-amino-2,2-dimethyl-N-(2-methyl-5-(6-(2-(trifluoromethyl)pyridin-3-yl)-2,3-dihydroimidazo[1,2-b]pyridazin-2-yl)phenyl)propanamide | 471.5 |
| 623 | 3-(3-((2-aminophenyl)amino)-3-oxoprop-1-en-1-yl)-N-(2-methyl-5-(6-(2-(trifluoromethyl)pyridin-3-yl)imidazo[1,2-b]pyridazin-2-yl)phenyl)benzamide | 634.5 |
| 624 | N-(2-aminophenyl)-3-(3-(N-(2-methyl-5-(6-(2-(trifluoromethyl)pyridin-3-yl)imidazo[1,2-b]pyridazin-2-yl)phenyl)sulfamoyl)phenyl)acrylamide | 670.4 |
| 625 | 3-(3-(hydroxyamino)-3-oxoprop-1-en-1-yl)-N-(2-methyl-5-(6-(2-(trifluoromethyl)pyridin-3-yl)imidazo[1,2-b]pyridazin-2-yl)phenyl)benzamide | 559.4 |
| 626 | N-hydroxy-3-(3-(N-(2-methyl-5-(6-(2-(trifluoromethyl)pyridin-3-yl)imidazo[1,2-b]pyridazin-2-yl)phenyl)sulfamoyl)phenyl)acrylamide | 595.4 |

Example 627

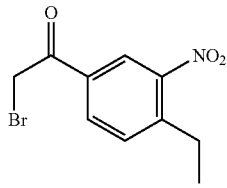

2-bromo-1-(4-ethyl-3-nitrophenyl)ethanone

A solution of 1-(4-methyl-3-nitro-phenyl)ethanone (AMGEN INC.; MEMORY PHARMACEUTICALS CORPORATION WO2007/103260 A1) (18.0 g, 0.093 mol) in CH$_2$Cl$_2$ (130 mL) is cooled to 0° C. To this is added bromine (5.3 mL, 0.0103 mol) at 0° C. with stirring. The reaction mixture is allowed to warm slowly to room temp and stirred for a total of 90 minutes. Ice water (500 mL) is added, organics collected and aqueous layer is extracted with CH$_2$Cl$_2$ (2×250 mL). The organic layers are combined, washed with water, dried with Na$_2$SO$_4$ and concentrated to give the title compound (25.0 g, 99% yield).

Example 628

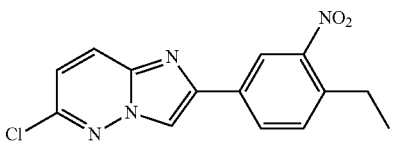 [SMILES: CCc1ccc(-c2cn3nc(Cl)ccc3n2)cc1[N+](=O)[O-]]

6-chloro-2-(4-ethyl-3-nitrophenyl)imidazo[1,2-b]pyridazine

A solution of 6-chloropyridazin-3-amine (4.76 g, 0.037 mol) and 2-bromo-1-(4-ethyl-3-nitrophenyl)ethanone (10.0 g, 0.037 mol) in acetonitrile (100 mL) is heated at reflux for 18 hr. The reaction mixture is diluted with water (500 mL), stirred at room temperature for 1 hour and solids are collected by filtration to give the title compound (6.9 g, 62% yield). LCMS m/z=303.3, 305.4 [M+H]$^+$, t$_R$=2.90 min.

Example 629

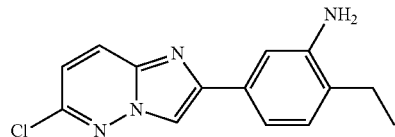

5-(6-chloroimidazo[1,2-b]pyridazin-2-yl)-2-ethylaniline

Iron powder (4.61 g, 0.0825 mol) is added to a mixture of 6-chloro-2-(4-ethyl-3-nitrophenyl)imidazo[1,2-b]pyridazine (5.0 g, 0.0165 mol) in EtOH—H$_2$O (150 mL, 4:1)containing AcOH (5.66 mL, 0.099 mol) at 80° C. The mixture is stirred at 80° C. for 4 hrs. The reaction mixture is cooled to room temp, filtered through celite, washed with EtOAc and concentrated. The oily residue is dissolved in EtOAc (200 mL) and washed twice with 100 mL Sat. NaHCO$_3$. Compound is concentrated onto celite and purified by silica gel chromatography (0-100% EtOAc in hexanes) to give the title compound (4.02 g, 89%). LCMS m/z=273.3, 275.3 [M+H]$^+$, t$_R$=1.93 min.

Example 630

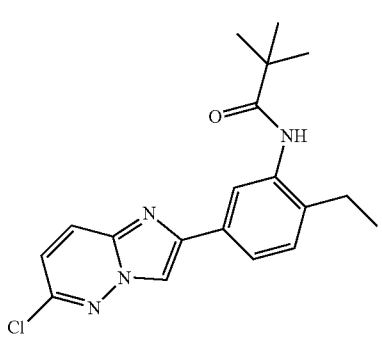 [SMILES: CCc1ccc(-c2cn3nc(Cl)ccc3n2)cc1NC(=O)C(C)(C)C]

N-(5-(6-chloroimidazo[1,2-b]pyridazin-2-yl)-2-ethylphenyl)pivalamide

A flask is charged with 5-(6-chloroimidazo[1,2-b]pyridazin-2-yl)-2-ethylaniline (4.00 g, 0.0146 mol), acetonitrile (120 mL) and pyridine (3.54 mL, 0.0438 mol). The mixture is stirred and trimethylacetyl chloride (1.98 mL, 0.0161 mol) is added and the mixture stirred for 16 hr at room temp. When the reaction is complete the mixture is diluted with water (500 mL) and stirred for 1 hour, and solid collected, washed with water (3×50 mL). Crude product is purified by silica gel chromatography (0-50% EtOAc in CH$_2$Cl$_2$) to give the title compound (4.8 g, 92%). LCMS m/z=357.5, 359.4 [M+H]$^+$, $t_R$=2.57 min.

Example 631

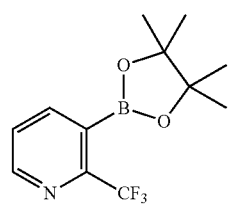 [SMILES: CC1(C)OB(c2cccnc2C(F)(F)F)OC1(C)C]

3-(4,4,5,5-tetramethyl-1,3,2-dioxaborolan-2-yl)-2-(trifluoromethyl)pyridine

A mixture of 3-bromo-2-(trifluoromethyl)pyridine (Oakwood Products, 11.3 g, 0.05 mol), bis(pinacolato)diboron (12.7 g, 0.05 mol), potassium acetate (9.8 g, 0.1 mol), [1,1'-bis(diphenylphosphino)ferrocene]dichloropalladium(II) (2.56 g, 0.0035 mol) is suspended in 1,4 dioxane (106 mL) in a round bottom flask. The flask is heated at reflux for 2 hours. The reaction is concentrated onto celite and purified by silica gel chromatography (0-100% EtOAc in Hexanes) to give the title compound (9.2 g, 67%). LCMS m/z=274.4 [M+H]$^+$, $t_R$=2.64 min.

Example 632

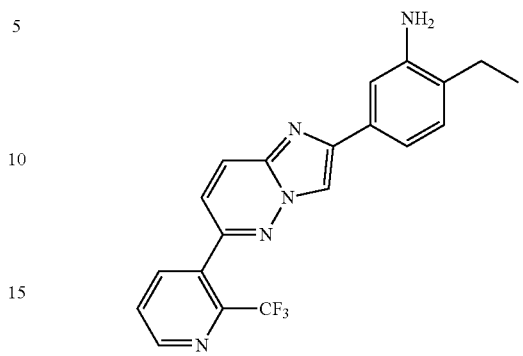

2-ethyl-5-(6-(2-(trifluoromethyl)pyridin-3-yl)imidazo[1,2-b]pyridazin-2-yl)aniline A 250 mL flask is charged with N-(5-(6-chloroimidazo[1,2-b]pyridazin-2-yl)-2-ethylphenyl)pivalamide (2.45 g, 0.00686 mol), 3-(4,4,5,5-tetramethyl-1,3,2-dioxaborolan-2-yl)-2-(trifluoromethyl)pyridine (2.34 g, 0.00857 mol), K$_2$CO$_3$ (2.37 g, 0.0171 mol), palladium(II)acetate (0.154 g, 0.686 mmol), 2-dicyclohexylphosphino-2',6'-dimethoxybiphenyl (0.563 g, 0.00137 mol), isopropanol:water (150 mL, 3:1). The mixture is stirred and heated at 60° C. for 6 hr. The mixture is concentrated to dryness, crude product taken up in EtOAc (100 mL), washed with water (50 mL), organic collected and concentrated onto celite and purified by silica gel chromatography (0-75% EtOAc in CH$_2$Cl$_2$). Intermediate is taken up in EtOH (100 mL) and conc. HCl (90 mL) is added. The reaction mixture is heated to reflux for 18 hrs. Reaction is concentrated, taken up in EtOAc (100 mL), washed with 100 mL Sat. NaHCO$_3$. Compound is concentrated onto celite and purified by silica gel chromatography (0-100% EtOAc in CH$_2$Cl$_2$) to give the title compound (1.98 g, 75% over two steps). LCMS m/z=384.4, 385.4 [M+H]$^+$, $t_R$=2.59 min.

Example 633

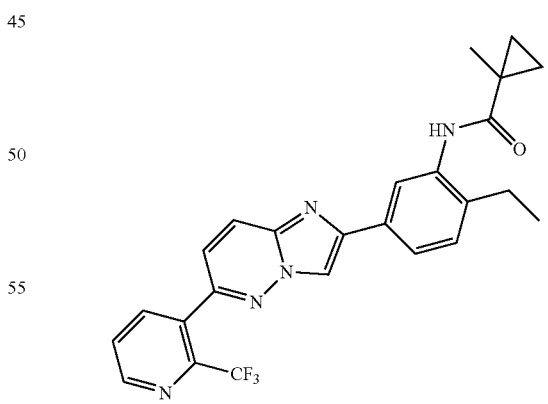

N-(2-ethyl-5-(6-(2-(trifluoromethyl)pyridin-3-yl)imidazo[1,2-b]pyridazin-2-yl)phenyl)-1-methyl-cyclopropanecarboxamide A flask is charged with 2-ethyl-5-(6-(2-(trifluoromethyl)pyridin-3-yl)imidazo[1,2-b]pyridazin-2-yl)aniline (0.500 g, 0.0013 mol), acetonitrile (5 mL) and pyridine (0.315 mL). The mixture is stirred and 1-methylcyclopropanecarbonyl chloride (0.169 g, 0.00143 mol) is added and the mixture stirred for 4 hrs at room temp. When the reaction is complete the mixture is concentrated onto silica gel and purified by silica gel chromatography (0-80% EtOAc in $CH_2Cl_2$) to give the title compound (0.400 g, 66%). LCMS m/z=466.5, 467.5 [M+H]$^+$, $t_R$=2.99 min. $^1$H-NMR (500 MHz, DMSO-d$_6$): δ 9.01 (s, 1H), 8.93 (d, J=4.9 Hz, 1H), 8.92 (s, 1H), 8.27 (m, 2H), 7.91 (m, 2H), 7.43 (d, J=9.3 Hz, 1H), 7.35 (d, J=7.8 Hz, 1H), 2.59 (q, J=7.6, 2H), 1.44 (s, 3H), 1.15 (t, J=7.6 Hz, 3H), 1.11 (dd, J=6.4, 3.4 Hz, 2H), 0.65 (dd, J=6.4, 3.4 Hz, 2H).

The following compounds are prepared essentially according to the procedures and examples set forth above, with modifications where necessary of the starting materials to provide the desired product.

| Example No. | Compound | LCMS (m/z) M + H |
|---|---|---|
| 634 | (R)—N-(5-(6-(3-(methylamino)pyrrolidin-1-yl)imidazo[1,2-b]pyridazin-2-yl)-2-(trifluoromethyl)phenyl)pivalamide | 461.5 |
| 635 | (R)—N-(5-(6-(3-(ethylamino)pyrrolidin-1-yl)imidazo[1,2-b]pyridazin-2-yl)-2-(trifluoromethyl)phenyl)pivalamide | 475.5 |
| 636 | N-(2-ethyl-5-(6-(2-(trifluoromethy)pyridin-3-y)imidazo[1,2-b]pyridazin-2-yl)phenyl)-1-methylcyclopropanecarboxamide | 466.5 |
| 637 | 2-amino-N,3-dimethyl-N-(1-(2-(4-methyl-3-pivalamidophenyl)imidazo[1,2-b]pyridazin-6-yl)pyrrolidin-3-yl)butanamide | 506.6 |
| 638 | 3,3,3-trifluoro-2,2-dimethyl-N-(2-methyl-5-(6-(2-(trifluoromethyl)pyridin-3-yl)imidazo[1,2-b]pyridazin-2-yl)phenyl)propanamide | 508.4 |
| 639 | N-(4-chloro-2-methyl-5-(6-(2-(trifluoromethyl)pyridin-3-yl)imidazo[1,2-b]pyridazin-2-yl)phenyl)pivalamide | 488.4 |
| 640 | (R)—N-(4-chloro-5-(6-(3-hydroxypyrrolidin-1-yl)imidazo[1,2-b]pyridazin-2-yl)-2-methylphenyl)pivalamide | 428.5 |
| 641 | N-(5-(3-chloro-6-(2-(trifluoromethyl)pyridin-3-yl)imidazo[1,2-b]pyridazin-2-yl)-2-methylphenyl)pivalamide | 488.4 |
| 642 | N-(2-chloro-5-(6-(2-(trifluoromethyl)pyridin-3-yl)imidazo[1,2-b]pyridazin-2-yl)phenyl)pivalamide | 474.4 |
| 643 | (R)—N-(2-chloro-5-(6-(3-hydroxypyrrolidin-1-yl)imidazo[1,2-b]pyridazin-2-yl)phenyl)pivalamide | 414.5 |
| 644 | N-(2-cyclopropyl-5-(6-(2-(trifluoromethyl)pyridin-3-yl)imidazo[1,2-b]pyridazin-2-yl)phenyl)pivalamide | 480.5 |
| 645 | N-(2-methyl-5-(6-(2-(trifluoromethyl)pyridin-3-yl)imidazo[1,2-b]pyridazin-2-yl)phenyl)pyrrolidine-2-carboxamide | 467.5 |
| 646 | 1-tert-butyl-3-(2-methyl-5-(6-(2-(trifluoromethyl)pyridin-3-yl)imidazo[1,2-b]pyridazin-2-yl)phenyl)urea | 469.5 |
| 647 | 1-methyl-N-(2-methyl-5-(6-(2-(trifluoromethyl)pyridin-3-yl)imidazo[1,2-b]pyridazin-2-yl)phenyl)pyrrolidine-2-carboxamide | 481.5 |
| 648 | 1-ethyl-N-(2-methyl-5-(6-(2-(trifluoromethyl)pyridin-3-yl)imidazo[1,2-b]pyridazin-2-yl)phenyl)pyrrolidine-2-carboxamide | 495.5 |
| 649 | N-(4-fluoro-2-methyl-5-(6-(2-(trifluoromethyl)pyridin-3-yl)imidazo[1,2-b]pyridazin-2-yl)phenyl)pivalamide | 472.5 |
| 650 | N-(2-chloro-4-fluoro-5-(6-(2-(trifluoromethyl)pyridin-3-yl)imidazo[1,2-b]pyridazin-2-yl)phenyl)pivalamide | 492.4 |
| 651 | 1-cyclopropyl-3-(2-methyl-5-(6-(2-(trifluoromethyl)pyridin-3-yl)imidazo[1,2-b]pyridazin-2-yl)phenyl)urea | 453.5 |
| 652 | N-(2,4-difluoro-5-(6-(2-(trifluoromethyl)pyridin-3-yl)imidazo[1,2-b]pyridazin-2-yl)phenyl)pivalamide | 476.4 |
| 653 | N-(2-chloro-5-(6-(2-(trifluoromethyl)pyridin-3-yl)imidazo[1,2-b]pyridazin-2-yl)phenyl)-1-methylcyclopropanecarboxamide | 472.4 |
| 654 | 1-(2-chloro-5-(6-(2-(trifluoromethyl)pyridin-3-yl)imidazo[1,2-b]pyridazin-2-yl)phenyl)-3-cyclopropylurea | 473.4 |
| 655 | 3-(2-chloro-5-(6-(2-(trifluoromethyl)pyridin-3-yl)imidazo[1,2-b]pyridazin-2-yl)phenyl)-1,1-diethylurea | 489.4 |
| 656 | N-(2-chloro-5-(6-(2-(trifluoromethyl)pyridin-3-yl)imidazo[1,2-b]pyridazin-2-yl)phenyl)pyrrolidine-1-carboxamide | 487.4 |
| 657 | ethyl 2-chloro-4-fluoro-5-(6-(2-(trifluoromethyl)pyridin-3-yl)imidazo[1,2-b]pyridazin-2-yl)phenylcarbamate | 480.4 |
| 658 | N-(2-fluoro-5-(6-(2-(trifluoromethyl)pyridin-3-yl)imidazo[1,2-b]pyridazin-2-yl)phenyl)pivalamide | 458.5 |
| 659 | N-(2-chloro-4-fluoro-5-(6-(2-(trifluoromethyl)pyridin-3-yl)imidazo[1,2-b]pyridazin-2-yl)phenyl)-2,2-dimethylbutanamide | 506.4 |
| 660 | N-(2-chloro-4-fluoro-5-(6-(2-(trifluoromethyl)pyridin-3-yl)imidazo[1,2-b]pyridazin-2-yl)phenyl)-3,3,3-trifluoro-2,2-dimethylpropanamide | 546.4 |
| 661 | N-(2-chloro-4-fluoro-5-(6-(2-(trifluoromethyl)pyridin-3-yl)imidazo[1,2-b]pyridazin-2-yl)phenyl)-4,4,4-trifluoro-3-methylbutanamide | 546.4 |
| 662 | N-(2-chloro-4-fluoro-5-(6-(2-(trifluoromethyl)pyridin-3-yl)imidazo[1,2-b]pyridazin-2-yl)phenyl)-2,2-dimethylpentanamide | 520.4 |
| 663 | N-(2-(2-(trifluoromethyl)pyridin-3-yl)-5-(6-(2-(trifluoromethyl)pyridin-3-yl)imidazo[1,2-b]pyridazin-2-yl)phenyl)pivalamide | 584.3 |
| 664 | N-(2-chloro-5-(6-(2-(trifluoromethyl)pyridin-3-yl)imidazo[1,2-b]pyridazin-2-yl)phenyl)-2,2-dimethylbutanamide | 488.4 |
| 665 | N-(2-chloro-5-(6-(2-(trifluoromethyl)pyridin-3-yl)imidazo[1,2-b]pyridazin-2-yl)phenyl)-3,3,3-trifluoro-2,2-dimethylpropanamide | 528.4 |
| 666 | N-(2-chloro-5-(6-(2-(trifluoromethyl)pyridin-3-yl)imidazo[1,2-b]pyridazin-2-yl)phenyl)-4,4,4-trifluoro-3-methylbutanamide | 528.4 |

| Example No. | Compound | LCMS (m/z) M + H |
|---|---|---|
| 667 | N-(2-chloro-5-(6-(2-(trifluoromethyl)pyridin-3-yl)imidazo[1,2-b]pyridazin-2-yl)phenyl)-2,2-dimethylpentanamide | 502.5 |
| 668 | isopropyl 2-chloro-5-(6-(2-(trifluoromethyl)pyridin-3-yl)imidazo[1,2-b]pyridazin-2-yl)phenylcarbamate | 476.4 |
| 669 | N-(2-chloro-5-(6-(2-(trifluoromethyl)pyridin-3-yl)imidazo[1,2-b]pyridazin-2-yl)phenyl)-3,3-difluoroazetidine-1-carboxamide | 509.4 |
| 670 | N-(2-chloro-5-(6-(2-(trifluoromethyl)pyridin-3-yl)imidazo[1,2-b]pyridazin-2-yl)phenyl)cyclohexanecarboxamide | 500.4 |
| 671 | N-(2-chloro-5-(6-(2-(trifluoromethyl)pyridin-3-yl)imidazo[1,2-b]pyridazin-2-yl)phenyl)cyclopentanecarboxamide | 486.4 |
| 672 | N-(2-chloro-5-(6-(2-(trifluoromethyl)pyridin-3-yl)imidazo[1,2-b]pyridazin-2-yl)phenyl)-3,3-dimethylbutanamide | 488.4 |
| 673 | ethyl 2-chloro-5-(6-(2-(trifluoromethyl)pyridin-3-yl)imidazo[1,2-b]pyridazin-2-yl)phenylcarbamate | 462.4 |
| 674 | N-(2-fluoro-5-(6-(2-(trifluoromethyl)pyridin-3-yl)imidazo[1,2-b]pyridazin-2-yl)phenyl)-1-methylcyclopropanecarboxamide | 456.4 |
| 675 | N-(2-chloro-5-(6-(2-(trifluoromethyl)pyridin-3-yl)imidazo[1,2-b]pyridazin-2-yl)phenyl)-3,3,3-trifluoropropanamide | 500.4 |
| 676 | N-(2-chloro-5-(6-(2-(trifluoromethyl)pyridin-3-yl)imidazo[1,2-b]pyridazin-2-yl)phenyl)cyclopropanecarboxamide | 458.4 |
| 677 | N-(2-fluoro-5-(6-(2-(trifluoromethyl)pyridin-3-yl)imidazo[1,2-b]pyridazin-2-yl)phenyl)cyclohexanecarboxamide | 484.5 |
| 678 | N-(2-fluoro-5-(6-(2-(trifluoromethyl)pyridin-3-yl)imidazo[1,2-b]pyridazin-2-yl)phenyl)cyclopentanecarboxamide | 470.5 |
| 679 | N-(2-fluoro-5-(6-(2-(trifluoromethyl)pyridin-3-yl)imidazo[1,2-b]pyridazin-2-yl)phenyl)-3,3-dimethylbutanamide | 472.5 |
| 680 | 3,3,3-trifluoro-N-(2-fluoro-5-(6-(2-(trifluoromethyl)pyridin-3-yl)imidazo[1,2-b]pyridazin-2-yl)phenyl)propanamide | 484.4 |
| 681 | N-(2-fluoro-5-(6-(2-(trifluoromethyl)pyridin-3-yl)imidazo[1,2-b]pyridazin-2-yl)phenyl)cyclopropanecarboxamide | 442.4 |
| 682 | ethyl 2-fluoro-5-(6-(2-(trifluoromethyl)pyridin-3-yl)imidazo[1,2-b]pyridazin-2-yl)phenylcarbamate | 446.4 |
| 683 | isopropyl 2-fluoro-5-(6-(2-(trifluoromethyl)pyridin-3-yl)imidazo[1,2-b]pyridazin-2-yl)phenylcarbamate | 460.4 |
| 684 | 3,3-difluoro-N-(2-fluoro-5-(6-(2-(trifluoromethyl)pyridin-3-yl)imidazo[1,2-b]pyridazin-2-yl)phenyl)azetidine-1-carboxamide | 493.4 |
| 685 | 1,1-diethyl-3-(2-fluoro-5-(6-(2-(trifluoromethyl)pyridin-3-yl)imidazo[1,2-b]pyridazin-2-yl)phenyl)urea | 473.5 |
| 686 | N-(2-fluoro-5-(6-(2-(trifluoromethyl)pyridin-3-yl)imidazo[1,2-b]pyridazin-2-yl)phenyl)pyrrolidine-1-carboxamide | 471.4 |
| 687 | N-(2-ethyl-5-(6-(2-(trifluoromethyl)pyridin-3-yl)imidazo[1,2-b]pyridazin-2-yl)phenyl)cyclohexanecarboxamide | 494.5 |
| 688 | N-(2-ethyl-5-(6-(2-(trifluoromethyl)pyridin-3-yl)imidazo[1,2-b]pyridazin-2-yl)phenyl)cyclopentanecarboxamide | 480.5 |
| 689 | N-(2-ethyl-5-(6-(2-(trifluoromethyl)pyridin-3-yl)imidazo[1,2-b]pyridazin-2-yl)phenyl)-2,2-dimethylbutanamide | 482.5 |
| 690 | N-(2-ethyl-5-(6-(2-(trifluoromethyl)pyridin-3-yl)imidazo[1,2-b]pyridazin-2-yl)phenyl)-3,3,3-trifluoro-2,2-dimethylpropanamide | 522.5 |
| 691 | N-(2-ethyl-5-(6-(2-(trifluoromethyl)pyridin-3-yl)imidazo[1,2-b]pyridazin-2-yl)phenyl)-3,3-dimethylbutanamide | 482.5 |
| 692 | N-(2-ethyl-5-(6-(2-(trifluoromethyl)pyridin-3-yl)imidazo[1,2-b]pyridazin-2-yl)phenyl)-3,3,3-trifluoropropanamide | 494.4 |
| 693 | 1,1-diethyl-3-(2-ethyl-5-(6-(2-(trifluoromethyl)pyridin-3-yl)imidazo[1,2-b]pyridazin-2-yl)phenyl)urea | 483.5 |
| 694 | N-(2-ethyl-5-(6-(2-(trifluoromethyl)pyridin-3-yl)imidazo[1,2-b]pyridazin-2-yl)phenyl)pyrrolidine-1-carboxamide | 481.5 |
| 695 | N-(2-ethyl-5-(6-(2-(trifluoromethyl)pyridin-3-yl)imidazo[1,2-b]pyridazin-2-yl)phenyl)-3,3-difluoroazetidine-1-carboxamide | 503.5 |
| 696 | N-(2-ethyl-5-(6-(2-(trifluoromethyl)pyridin-3-yl)imidazo[1,2-b]pyridazin-2-yl)phenyl)-3-methyloxetane-3-carboxamide | 482.5 |
| 697 | 2-chloro-5-(6-(2-(trifluoromethyl)pyridin-3-yl)imidazo[1,2-b]pyridazin-2-yl)benzenesulfonamide | 454.3 |
| 698 | 2-chloro-N-methyl-5-(6-(2-(trifluoromethyl)pyridin-3-yl)imidazo[1,2-b]pyridazin-2-yl)benzenesulfonamide | 468.3 |
| 699 | N-tert-butyl-2-chloro-5-(6-(2-(trifluoromethyl)pyridin-3-yl)imidazo[1,2-b]pyridazin-2-yl)benzenesulfonamide | 510.4 |
| 700 | 2-chloro-N,N-dimethyl-5-(6-(2-(trifluoromethyl)pyridin-3-yl)imidazo[1,2-b]pyridazin-2-yl)benzenesulfonamide | 482.4 |
| 701 | 2-chloro-N-ethyl-5-(6-(2-(trifluoromethyl)pyridin-3-yl)imidazo[1,2-b]pyridazin-2-yl)benzenesulfonamide | 482.4 |
| 702 | 2-chloro-N-cyclopropyl-5-(6-(2-(trifluoromethyl)pyridin-3-yl)imidazo[1,2-b]pyridazin-2-yl)benzenesulfonamide | 494.4 |
| 703 | 2-chloro-N,N-diethyl-5-(6-(2-(trifluoromethyl)pyridin-3-yl)imidazo[1,2-b]pyridazin-2-yl)benzenesulfonamide | 510.4 |

In Vitro Biological Evaluation

Example 704

Hedgehog conditioned media was obtained by transfecting 293H cells with the full length gene encoding human Sonic Hedgehog (hShh) inserted into the pCMV6 expression vector, which contains a neomycin selectable marker and expresses the protein of interest with a C-terminal FLAG affinity tag. After selection in G418 containing media, conditioned media from Hedgehog expressing clones were tested for the ability to activate the hedgehog-responsive GLi-luciferase reporter in the Shh Light II cell line obtained by license from John Hopkins University (Taipale J, et al. *Effects of oncogenic mutations in Smoothened and Patched can be reversed by cyclopamine. Nature* 406: 1005-1009, 2000).

C3H10T1/2 cells were transfected with a pCMV expression vector containing the full length gene sequence encoding the human Smoothened receptor. Pooled cells, designated 10T1/2/Smo#3, growing in G418 selection media responded to activation by 10-20% conditioned hShh media with an approximate 5-10 fold increase in alkaline phosphaste (ALP) activity over untransfected parent C3H10T1/2 cells as measured by the conversion of the free acid of 4-methylumbelliferyl phosphate to a fluorescent product.

A test compound library was screened against hShh and 500 nM SAG (a direct agonist of the Smoothened receptor) activated 10T1/2/Smo#3 cells and Shh Light II reporter cells for the ability to block Hedgehog pathway activation. Concurrently, cell viability was measured by utilizing Celltiter-Blue® (Promega, Madison Wis.) viability assay. Active compounds were defined as those that inhibited Hedgehog signaling by greater than 50% with no concurrent loss in cell viability.

Compound specificity for Smoothened binding was further verified by utilizing a competitive fluorescent binding assay against 5-10 nM Cyclopamine-BODIPY and a 293H cell line overexpressing human Smoothened. To further test for non-specific biological activity, compounds were screened in a TCF/LCF reporter assay of Wnt3a activation and in a CMV-driven Luciferase constitutive reporter assay.

Data for several exemplary compounds of the disclosure are listed below. Their inhibitory activity against Hedgehog pathway activation on 10T1/2/Smo#3 cells as measured by ALP activity and Shh Light II reporter cells as measured by luciferase activity is shown in Table 1 below. In Table 1, +++ stands for an IC50 value that is less than 0.3 μM, ++ between 0.3 and 3 μM, + between 3 and 30 μM.

TABLE 1

| Example No. | 10T1/2/Smo#3 ALP activity (hShh Activation) | Shh Light II luciferase activity (SAG activation) | Shh Light II luciferase activity (hShh activation) |
|---|---|---|---|
| 4 | ++ | ++ | + |
| 96 | ++ | ++ | ++ |
| 101 | + | + | ++ |
| 104 | + | + | + |
| 105 | ++ | + | ++ |
| 106 | ++ | ++ | ++ |
| 109 | + | + | ++ |
| 113 | ++ | + | ++ |
| 114 | + | + | + |
| 117 | + | + | + |
| 119 | + | + | + |
| 121 | ++ | + | ++ |
| 123 | ++ | ++ | ++ |
| 124 | ++ | ++ | ++ |
| 127 | +++ | ++ | ++ |
| 128 | ++ | + | + |
| 130 | ++ | +++ | ++ |
| 134 | +++ | ++ | ++ |
| 137 | ++ | ++ | ++ |
| 141 | + | +++ | +++ |
| 144 | + | + | + |
| 145 | + | + | + |
| 148 | ++ | ++ | ++ |
| 149 | ++ | ++ | ++ |
| 153 | ++ | ++ | +++ |
| 155 | ++ | +++ | ++ |
| 158 | + | ++ | + |
| 161 | ++ | ++ | ++ |
| 168 | ++ | ++ | ++ |
| 173 | + | + | + |
| 180 | + | + | + |
| 196 | ++ | + | ++ |
| 198 | ++ | + | ++ |
| 33 | ++ | ++ | ++ |
| 43 (same as 204) | + | + | + |
| 80 (same as 86) | +++ | ++ | +++ |
| 207 | +++ | +++ | +++ |
| 212 | + | + | + |
| 37 (same as 83) | ++ | ++ | ++ |
| 218 (same as 49) | ++ | + | ++ |
| 219 | ++ | + | ++ |
| 225 | +++ | + | +++ |
| 231 | ++ | + | ++ |
| 235 | +++ | ++ | +++ |
| 247 | +++ | +++ | +++ |
| 248 | +++ | ++ | ++ |
| 273 | ++ | + | + |
| 283 | ++ | + | ++ |
| 295 | +++ | ++ | +++ |
| 300 | ++ | +++ | ++ |
| 303 | ++ | ++ | ++ |
| 313 | ++ | ++ | ++ |
| 321 | ++ | ++ | +++ |
| 346 | +++ | +++ | +++ |
| 352 | +++ | +++ | +++ |
| 363 | ++ | ++ | ++ |
| 369 | ++ | ++ | ++ |
| 385 | ++ | ++ | ++ |
| 390 | ++ | ++ | +++ |
| 391 | +++ | ++ | +++ |
| 393 | +++ | ++ | +++ |
| 397 | +++ | +++ | +++ |
| 399 | +++ | +++ | +++ |
| 412 | ++ | ++ | +++ |
| 417 | + | ++ | ++ |
| 400 | +++ | +++ | +++ |
| 410 | ++ | ++ | +++ |
| 429 | ++ | ++ | + |
| 89 | + | + | + |
| 92 | + | + | + |
| 479 | +++ | +++ | +++ |
| 483 | +++ | ++ | +++ |
| 437 | +++ | +++ | +++ |
| 450 | +++ | +++ | +++ |
| 284 | +++ | +++ | +++ |
| 508 | +++ | ++ | +++ |
| 509 | +++ | ++ | +++ |
| 511 | +++ | +++ | +++ |
| 518 | +++ | +++ | +++ |
| 529 | +++ | ++ | +++ |
| 542 | +++ | ++ | +++ |
| 554 | ++ | + | +++ |
| 560 | ++ | + | +++ |
| 569 | +++ | ++ | +++ |
| 597 | +++ | +++ | +++ |

TABLE 1-continued

| Example No. | 10T1/2/Smo#3 ALP activity (hShh Activation) | Shh Light II luciferase activity (SAG activation) | Shh Light II luciferase activity (hShh activation) |
|---|---|---|---|
| 605 | +++ | +++ | +++ |
| 623 | +++ | ++ | +++ |
| 633 | +++ | +++ | +++ |
| 639 | +++ | +++ | +++ |
| 642 | +++ | +++ | +++ |
| 646 | +++ | ++ | +++ |
| 650 | +++ | +++ | +++ |
| 655 | +++ | +++ | +++ |
| 662 | +++ | +++ | +++ |
| 669 | +++ | +++ | +++ |

Additional data for compounds of the invention is shown below in Table 2. Their inhibitory activities against Hedgehog pathway activation are shown as $IC_{50}$ values in μM on 10T1/2/Smo#3 cells as measured by ALP activity, or on Shh Light II reporter cells as measured by luciferase activity (hShh activation).

TABLE 2

| Example No. | ALP | Shh |
|---|---|---|
| 81 | 2.433 | 1.072 |
| 82 | >10 | 6.06 |
| 83 | 1.347 | 1.006 |
| 84 | 2.488 | 1.579 |
| 85 | 1.319 | 4.387 |
| 86 | 0.547 | 0.53 |
| 93 | >10 | >10 |
| 94 | 1.515 | 0.614 |
| 95 | ND | 7.856 |
| 96 | 1.089 | 0.398 |
| 97 | 1.125 | 0.679 |
| 98 | 2.035 | 1.337 |
| 99 | 3.692 | >10 |
| 100 | 1.056 | 1.093 |
| 101 | 7.011 | 0.89 |
| 102 | 4.206 | 9.12 |
| 103 | 3.93 | >10 |
| 104 | >10 | >10 |
| 105 | 1.813 | 1.107 |
| 106 | 2.5 | 0.774 |
| 107 | 7.274 | 2.772 |
| 108 | 5.234 | 2.473 |
| 109 | 7.002 | 2.651 |
| 110 | 8.044 | >10 |
| 111 | 9.017 | >10 |
| 112 | 9.518 | >10 |
| 113 | 1.562 | 1 |
| 114 | >10 | 7.665 |
| 115 | 2.813 | 2.874 |
| 116 | >10 | 9.646 |
| 117 | 6.739 | 2.795 |
| 118 | 1.205 | 0.613 |
| 119 | 4.542 | 5.654 |
| 120 | 6.285 | >10 |
| 121 | 1.873 | 1.996 |
| 122 | 1.943 | 3.038 |
| 123 | 0.488 | 0.712 |
| 124 | 0.604 | 0.895 |
| 125 | 1.254 | 0.435 |
| 126 | 5.571 | 7.717 |
| 127 | 0.11 | 4.966 |
| 128 | 0.422 | >10 |
| 129 | 0.789 | 1.771 |
| 130 | 0.526 | 0.898 |
| 131 | 8.276 | 1.447 |
| 132 | >10 | 1.491 |
| 133 | 0.849 | 0.487 |
| 134 | 0.232 | 0.926 |
| 135 | 5.234 | 1.252 |
| 136 | 0.452 | 0.158 |
| 137 | 0.995 | 0.623 |
| 138 | 2.171 | 3.453 |
| 139 | 0.451 | 0.186 |
| 140 | 0.314 | 0.721 |
| 141 | 9.059 | 0.26 |
| 142 | 0.365 | 1.41 |
| 143 | 2.691 | 0.466 |
| 144 | 3.971 | >10 |
| 145 | 4.784 | 5.436 |
| 146 | 6.981 | >10 |
| 147 | >10 | 1.044 |
| 148 | 1.942 | 0.608 |
| 149 | 1.748 | 1.022 |
| 150 | 2.744 | 1.277 |
| 151 | 1.809 | 0.899 |
| 152 | 0.59 | 0.314 |
| 153 | 0.41 | 0.264 |
| 154 | 2.892 | 3.401 |
| 155 | 1.27 | 2.095 |
| 156 | 8.835 | 3.431 |
| 157 | >10 | 1.951 |
| 158 | 7.343 | 0.847 |
| 159 | 0.435 | 0.44 |
| 160 | 0.627 | 2.509 |
| 161 | 0.404 | 0.911 |
| 162 | 1.111 | 1.396 |
| 163 | 1.051 | 1.058 |
| 164 | 0.55 | 0.463 |
| 165 | >10 | 0.89 |
| 166 | 1.966 | 0.995 |
| 167 | >10 | 2.272 |
| 168 | 2.977 | 1.923 |
| 169 | 0.423 | 0.71 |
| 170 | 0.681 | 0.562 |
| 171 | 0.221 | 0.041 |
| 172 | 0.403 | 0.936 |
| 173 | 4.428 | 4.404 |
| 174 | 0.215 | 0.689 |
| 175 | 0.513 | 0.799 |
| 176 | 0.097 | 0.079 |
| 177 | 0.236 | 0.357 |
| 178 | 0.607 | 0.468 |
| 179 | 1.437 | 0.454 |
| 180 | 5.726 | 3.883 |
| 181 | 1.067 | 0.245 |
| 182 | 1.855 | 1.739 |
| 183 | 0.995 | 0.327 |
| 184 | 0.061 | 0.191 |
| 185 | 1.667 | 1.777 |
| 186 | 8.382 | >10 |
| 187 | >10 | >10 |
| 188 | 0.875 | 1.404 |
| 189 | 2.096 | 1.996 |
| 190 | 5.255 | >10 |
| 191 | 1.571 | 0.579 |
| 192 | 4.756 | 1.581 |
| 193 | 2.342 | 7.764 |
| 194 | >10 | 1.751 |
| 195 | 0.718 | 0.267 |
| 196 | 1.618 | 0.726 |
| 197 | 0.875 | 0.357 |
| 198 | 1.97 | 1.678 |
| 199 | 0.111 | 0.337 |
| 200 | 0.284 | 0.281 |
| 201 | 0.869 | 0.402 |
| 202 | 1.321 | 0.221 |
| 203 | 9.454 | >10 |
| 204 | 9.528 | >10 |
| 205 | 0.196 | 0.279 |
| 206 | 0.246 | 0.341 |
| 207 | 0.043 | 0.043 |
| 208 | 0.14 | 0.095 |
| 209 | 0.097 | 0.072 |
| 210 | 0.375 | 0.223 |
| 211 | 6.963 | 1.024 |
| 212 | 5.759 | >10 |
| 213 | 3.86 | >10 |
| 214 | 1.585 | >10 |

TABLE 2-continued

| Example No. | ALP | Shh |
| --- | --- | --- |
| 215 | 3.122 | >10 |
| 216 | 8.284 | 8.569 |
| 217 | 0.535 | 6.597 |
| 218 | 2.121 | 1.72 |
| 219 | 0.952 | 1.264 |
| 220 | 0.028 | 0.052 |
| 221 | 0.105 | 0.086 |
| 222 | 0.425 | 0.156 |
| 223 | 0.289 | 0.097 |
| 224 | 0.062 | 0.082 |
| 225 | 0.065 | 0.048 |
| 226 | ND | 1.482 |
| 227 | 0.141 | 0.065 |
| 228 | ND | 0.325 |
| 229 | ND | 0.313 |
| 230 | ND | 1.548 |
| 231 | ND | 0.905 |
| 232 | 0.414 | 0.428 |
| 233 | 0.339 | 0.329 |
| 234 | 0.23 | 0.547 |
| 235 | 0.271 | 0.318 |
| 236 | 0.1 | 0.289 |
| 237 | 0.211 | 0.245 |
| 238 | 0.23 | 0.625 |
| 239 | 0.335 | 0.523 |
| 240 | 0.07 | 0.326 |
| 241 | 0.096 | 0.208 |
| 242 | 0.446 | 0.402 |
| 243 | 0.295 | 0.306 |
| 244 | 1.632 | 0.308 |
| 245 | 2.974 | ND |
| 246 | 1.321 | ND |
| 247 | 1.863 | ND |
| 248 | 0.231 | ND |
| 249 | 0.889 | ND |
| 250 | 0.259 | ND |
| 251 | 0.518 | ND |
| 252 | 0.392 | 0.722 |
| 253 | 0.448 | 0.899 |
| 254 | 0.36 | ND |
| 255 | 0.49 | 0.563 |
| 256 | 0.446 | 1.139 |
| 257 | 0.497 | ND |
| 258 | 0.105 | 0.129 |
| 259 | 0.08 | 0.084 |
| 260 | 0.325 | 0.297 |
| 261 | 0.091 | 0.142 |
| 262 | 0.103 | 0.342 |
| 263 | 0.102 | 0.228 |
| 264 | 0.544 | 2.009 |
| 265 | 0.082 | 0.083 |
| 266 | 1.532 | ND |
| 267 | 2.076 | ND |
| 268 | 1.942 | ND |
| 269 | 1.008 | ND |
| 270 | 9.426 | ND |
| 271 | 0.246 | ND |
| 272 | 1.259 | ND |
| 273 | 0.442 | ND |
| 274 | 0.02 | 0.144 |
| 275 | ND | 1.8 |
| 276 | ND | 1.96 |
| 277 | ND | 0.35 |
| 278 | 0.228 | 0.162 |
| 279 | 0.129 | 0.282 |
| 280 | 0.236 | 0.475 |
| 281 | 0.038 | 0.072 |
| 282 | ND | 1.45 |
| 283 | 1.815 | 2.228 |
| 284 | 0.029 | 0.057 |
| 285 | 1.007 | 0.788 |
| 286 | 0.127 | 0.193 |
| 287 | 0.462 | 0.491 |
| 288 | 0.258 | 0.345 |
| 289 | 0.09 | 0.284 |
| 290 | 0.296 | 0.321 |
| 291 | 0.325 | 0.289 |
| 292 | 0.019 | 0.047 |
| 293 | 0.221 | 0.31 |
| 294 | 0.254 | 0.256 |
| 295 | 0.326 | 0.32 |
| 296 | 0.226 | 0.311 |
| 297 | 0.463 | 0.452 |
| 298 | 0.612 | 0.403 |
| 299 | 0.478 | 0.338 |
| 300 | 0.703 | 0.535 |
| 301 | 1.055 | 0.406 |
| 302 | 0.443 | 0.522 |
| 303 | 0.783 | 0.994 |
| 304 | 0.393 | 0.559 |
| 305 | 3.498 | 1.894 |
| 306 | 0.446 | 0.402 |
| 307 | 0.4 | 0.352 |
| 308 | 1.202 | 1.069 |
| 309 | 0.973 | 0.339 |
| 310 | 1.775 | 0.721 |
| 311 | 2.418 | 2.083 |
| 312 | 0.326 | 0.213 |
| 313 | 0.636 | 0.826 |
| 314 | ND | 0.346 |
| 315 | ND | 0.807 |
| 316 | ND | 0.937 |
| 317 | ND | 1.25 |
| 318 | ND | 0.203 |
| 319 | ND | 0.347 |
| 320 | ND | 9.259 |
| 321 | ND | 0.323 |
| 322 | ND | 0.917 |
| 323 | ND | 2.578 |
| 324 | ND | 1.46 |
| 325 | ND | 0.74 |
| 326 | ND | 0.217 |
| 327 | ND | 0.484 |
| 328 | ND | 3.542 |
| 329 | ND | 2.02 |
| 330 | ND | 0.676 |
| 331 | ND | 0.478 |
| 332 | ND | 0.698 |
| 333 | ND | 0.893 |
| 334 | 0.213 | 0.278 |
| 335 | ND | 1.611 |
| 336 | ND | 0.23 |
| 337 | 0.194 | 0.308 |
| 338 | ND | 0.398 |
| 339 | ND | 0.277 |
| 340 | 0.114 | 0.115 |
| 341 | 0.109 | 0.123 |
| 342 | ND | 0.409 |
| 343 | ND | 0.34 |
| 344 | ND | 8.739 |
| 345 | ND | 5.494 |
| 346 | 0.023 | 0.044 |
| 347 | 0.022 | 0.046 |
| 348 | ND | 0.339 |
| 349 | 0.009 | 0.045 |
| 350 | 0.028 | 0.065 |
| 351 | 0.021 | 0.038 |
| 352 | 0.014 | 0.011 |
| 353 | 0.056 | 0.074 |
| 354 | 0.554 | 0.332 |
| 355 | 0.24 | 0.142 |
| 356 | 0.514 | 0.309 |
| 357 | 0.445 | 0.151 |
| 358 | 0.387 | 0.225 |
| 359 | 1.905 | 1.847 |
| 360 | 0.032 | 0.026 |
| 361 | 0.11 | 0.084 |
| 362 | 0.155 | 0.104 |
| 363 | 1.244 | 0.612 |
| 364 | 0.001 | 0.003 |
| 365 | 0.36 | 0.124 |
| 366 | 1.098 | 0.227 |
| 367 | 0.343 | 0.312 |
| 368 | 0.321 | 0.118 |
| 369 | 0.363 | 0.713 |
| 370 | 0.333 | 0.321 |

TABLE 2-continued

| Example No. | ALP | Shh |
| --- | --- | --- |
| 371 | 0.296 | 0.138 |
| 372 | 0.633 | 0.827 |
| 373 | 0.533 | 0.929 |
| 374 | 1.279 | 0.634 |
| 375 | 0.372 | 0.316 |
| 376 | 0.874 | 0.616 |
| 377 | 0.704 | 0.657 |
| 378 | 0.963 | 1.535 |
| 379 | 1.859 | >10 |
| 380 | 0.383 | 0.273 |
| 381 | 0.58 | 1.253 |
| 382 | 0.536 | 1.218 |
| 383 | 0.141 | 0.193 |
| 384 | 0.227 | 0.689 |
| 385 | 1.384 | 0.778 |
| 386 | 1.714 | 3.087 |
| 390 | 0.469 | 0.27 |
| 391 | 0.123 | 0.057 |
| 392 | 0.093 | 0.077 |
| 393 | 0.034 | 0.031 |
| 394 | 0.189 | 0.041 |
| 395 | 0.087 | 0.015 |
| 396 | 0.082 | 0.031 |
| 397 | 0.315 | 0.073 |
| 398 | ND | 0.681 |
| 399 | 0.175 | 0.105 |
| 400 | 0.039 | 0.011 |
| 401 | 0.234 | 0.4 |
| 402 | ND | 1.558 |
| 403 | ND | 0.474 |
| 404 | ND | 0.873 |
| 405 | ND | 1.98 |
| 406 | ND | 2.061 |
| 407 | ND | 0.353 |
| 408 | ND | 0.34 |
| 409 | ND | 0.236 |
| 410 | 0.403 | 0.121 |
| 411 | 0.679 | 0.251 |
| 412 | 0.665 | 0.225 |
| 413 | 0.548 | 0.318 |
| 414 | ND | 0.947 |
| 415 | ND | 1.755 |
| 416 | ND | 0.253 |
| 417 | ND | 0.38 |
| 418 | ND | 1.388 |
| 419 | ND | 0.968 |
| 420 | ND | 1.373 |
| 421 | ND | 3.306 |
| 422 | 0.312 | 0.869 |
| 423 | 0.265 | 1.564 |
| 424 | 4.099 | 7.457 |
| 425 | 0.239 | 0.086 |
| 426 | 0.707 | 0.17 |
| 427 | 0.176 | 0.027 |
| 428 | 0.734 | 0.078 |
| 429 | 1.28 | 0.167 |
| 430 | ND | 5.426 |
| 431 | ND | 0.422 |
| 432 | 0.675 | 0.121 |
| 433 | 0.736 | 0.193 |
| 434 | ND | 0.353 |
| 435 | ND | 1.274 |
| 436 | ND | 0.975 |
| 437 | 0.15 | 0.071 |
| 438 | 2.599 | 1.164 |
| 439 | 0.746 | 0.365 |
| 440 | ND | 4.062 |
| 441 | ND | 2.557 |
| 442 | ND | 1.063 |
| 443 | ND | 1.875 |
| 444 | 0.604 | 1.24 |
| 445 | 0.578 | 0.794 |
| 446 | ND | 1.381 |
| 447 | ND | 0.293 |
| 448 | 0.643 | 1.275 |
| 449 | 0.281 | 0.311 |
| 450 | 0.337 | 0.322 |
| 451 | 1.005 | 0.96 |
| 452 | ND | 0.385 |
| 453 | 0.751 | 0.582 |
| 454 | ND | 2.047 |
| 455 | ND | 3.458 |
| 456 | ND | 0.365 |
| 457 | ND | 0.334 |
| 458 | ND | 0.421 |
| 459 | ND | 9.291 |
| 460 | ND | 1.12 |
| 461 | ND | 8.387 |
| 463 | 1.532 | ND |
| 464 | 0.4 | 0.352 |
| 465 | ND | 0.346 |
| 466 | ND | 2.02 |
| 467 | 0.114 | 0.115 |
| 468 | 0.023 | 0.044 |
| 469 | ND | 0.339 |
| 470 | 0.028 | 0.065 |
| 471 | 0.445 | 0.151 |
| 472 | 0.11 | 0.084 |
| 473 | 0.093 | 0.077 |
| 474 | 0.034 | 0.031 |
| 475 | ND | 2.614 |
| 476 | ND | 0.427 |
| 477 | 0.521 | 0.247 |
| 478 | 0.327 | 0.08 |
| 479 | 0.086 | 0.006 |
| 480 | ND | 5.192 |
| 481 | ND | >10 |
| 482 | ND | >10 |
| 483 | 0.114 | 0.072 |
| 500 | ND | 0.45 |
| 501 | ND | 1 |
| 502 | ND | 0.58 |
| 503 | ND | 0.33 |
| 504 | ND | 0.36 |
| 505 | ND | 0.99 |
| 506 | ND | 1.34 |
| 507 | ND | 2.5 |
| 508 | 0.11 | 0.092 |
| 509 | 0.213 | 0.158 |
| 510 | ND | 0.379 |
| 511 | 0.002 | 0.01 |
| 512 | 0.205 | 0.311 |
| 513 | ND | 0.376 |
| 514 | ND | 0.392 |
| 515 | ND | 0.911 |
| 516 | ND | 1.712 |
| 517 | ND | >10 |
| 518 | 0.071 | 0.016 |
| 519 | ND | 1.699 |
| 520 | ND | 0.492 |
| 521 | ND | >10 |
| 522 | ND | 1.295 |
| 523 | ND | 9.633 |
| 524 | ND | 0.479 |
| 525 | ND | 0.441 |
| 526 | ND | 0.783 |
| 527 | ND | 1.048 |
| 528 | ND | 5.847 |
| 529 | 0.116 | 0.197 |
| 530 | ND | 6.677 |
| 531 | 1.138 | 0.586 |
| 533 | 0.449 | 0.301 |
| 534 | ND | 1.448 |
| 535 | 0.139 | 0.056 |
| 536 | ND | 0.37 |
| 537 | ND | 0.734 |
| 538 | ND | 0.43 |
| 539 | ND | 0.35 |
| 540 | 0.891 | 0.447 |
| 541 | 0.181 | 0.255 |
| 542 | 0.088 | 0.094 |
| 543 | 0.007 | 0.004 |
| 544 | 0.462 | 0.224 |
| 545 | 0.443 | 0.082 |
| 546 | ND | 1.131 |
| 547 | ND | 0.793 |

TABLE 2-continued

| Example No. | ALP | Shh |
|---|---|---|
| 548 | ND | 0.763 |
| 549 | ND | 0.204 |
| 550 | ND | 0.418 |
| 551 | ND | 0.364 |
| 552 | ND | 0.356 |
| 553 | ND | 0.701 |
| 554 | 1.192 | 0.316 |
| 555 | ND | 0.346 |
| 556 | 0.737 | 0.395 |
| 557 | 1.076 | 0.14 |
| 558 | 1.059 | 0.391 |
| 559 | 0.604 | 0.322 |
| 560 | 0.481 | 0.402 |
| 561 | ND | 2.303 |
| 562 | 0.756 | 0.376 |
| 563 | ND | 0.622 |
| 564 | 0.06 | 0.02 |
| 565 | 0.061 | 0.009 |
| 566 | 0.371 | 0.285 |
| 567 | 0.298 | 0.219 |
| 568 | 0.099 | 0.1 |
| 569 | 0.086 | 0.032 |
| 570 | 0.73 | 0.24 |
| 571 | 0.554 | 0.129 |
| 572 | ND | 0.596 |
| 573 | 1.045 | 0.07 |
| 574 | ND | 0.364 |
| 575 | ND | 0.599 |
| 576 | ND | 0.155 |
| 577 | ND | 0.063 |
| 578 | ND | 9.275 |
| 579 | ND | 0.317 |
| 580 | ND | 1.319 |
| 581 | ND | 0.082 |
| 582 | ND | 1.136 |
| 583 | ND | 0.742 |
| 584 | ND | 1.905 |
| 585 | ND | 0.925 |
| 586 | ND | 0.087 |
| 587 | ND | 0.632 |
| 588 | ND | 1.046 |
| 589 | ND | 0.498 |
| 590 | ND | 0.456 |
| 591 | ND | 0.578 |
| 592 | ND | 0.443 |
| 593 | ND | 2.044 |
| 594 | 0.03 | 0.02 |
| 595 | ND | 0.348 |
| 596 | 0.094 | 0.018 |
| 597 | 0.285 | 0.039 |
| 598 | 0.424 | 0.059 |
| 599 | 0.248 | 0.048 |
| 600 | >10 | 0.13 |
| 601 | 0.04 | 0.066 |
| 602 | 0.314 | 0.155 |
| 603 | ND | 8.176 |
| 604 | ND | 0.157 |
| 605 | 0.062 | 0.03 |
| 606 | 0.484 | 0.066 |
| 607 | ND | 2.102 |
| 608 | ND | 2.045 |
| 609 | ND | >10 |
| 610 | ND | 0.465 |
| 611 | ND | 0.049 |
| 612 | ND | 0.078 |
| 613 | ND | 0.283 |
| 614 | ND | 4.368 |
| 615 | ND | 2.235 |
| 616 | ND | >10 |
| 617 | ND | 8.597 |
| 618 | ND | 9.085 |
| 619 | ND | 0.035 |
| 620 | ND | 3.198 |
| 621 | ND | 0.053 |
| 622 | ND | 0.534 |
| 623 | 0.145 | 0.198 |
| 624 | ND | 0.824 |
| 625 | ND | 0.813 |
| 626 | ND | 2.906 |
| 634 | 0.098 | 0.12 |
| 635 | 0.159 | 0.11 |
| 636 | 0.035 | 0.131 |
| 637 | 0.418 | 2.175 |
| 638 | 0.02 | 0.02 |
| 639 | 0.055 | 0.03 |
| 640 | 0.138 | 0.107 |
| 641 | 0.034 | 0.076 |
| 642 | 0.006 | 0.013 |
| 643 | 0.023 | 0.146 |
| 644 | 0.015 | 0.072 |
| 645 | 0.155 | 0.589 |
| 646 | 0.016 | 0.038 |
| 647 | 0.094 | 0.186 |
| 648 | 0.373 | 0.4 |
| 649 | 0.05 | 0.08 |
| 650 | 0.025 | 0.1 |
| 651 | 0.127 | 0.139 |
| 652 | 0.036 | 0.034 |
| 653 | 0.08 | 0.01 |
| 654 | 0.764 | 0.228 |
| 655 | 0.07 | 0.023 |
| 656 | 0.117 | 0.038 |
| 657 | 0.251 | 0.096 |
| 658 | 0.085 | 0.027 |
| 659 | 0.075 | 0.022 |
| 660 | 0.017 | 0.032 |
| 661 | 0.015 | 0.031 |
| 662 | 0.161 | 0.039 |
| 663 | 3.542 | 6.229 |
| 664 | 0.105 | 0.024 |
| 665 | 0.12 | 0.019 |
| 666 | 0.527 | 0.064 |
| 667 | 0.203 | 0.064 |
| 668 | 0.631 | 0.283 |
| 669 | 0.125 | 0.028 |
| 670 | 0.62 | 0.061 |
| 671 | 0.315 | 0.024 |
| 672 | 0.565 | 0.086 |
| 673 | 0.678 | 0.169 |
| 674 | 0.14 | 0.059 |
| 675 | 0.777 | 0.099 |
| 676 | 0.721 | 0.111 |
| 677 | 0.637 | 0.146 |
| 678 | 0.342 | 0.139 |
| 679 | 0.658 | 0.254 |
| 680 | 3.609 | 0.518 |
| 681 | 6.565 | 0.976 |
| 682 | 1.743 | 0.571 |
| 683 | 2.551 | 0.559 |
| 684 | 0.356 | 0.095 |
| 685 | 0.274 | 0.139 |
| 686 | 0.218 | 0.149 |
| 687 | 1.594 | 0.463 |
| 688 | 0.578 | 0.103 |
| 689 | 0.188 | 0.064 |
| 690 | 0.225 | 0.059 |
| 691 | 1.219 | 0.459 |
| 692 | 0.951 | 0.416 |
| 693 | 0.186 | 0.192 |
| 694 | 0.174 | 0.339 |
| 695 | 0.158 | 0.368 |
| 696 | 0.229 | 0.254 |
| 697 | >10 | >10 |
| 698 | >10 | 4.247 |
| 699 | >10 | 2.295 |
| 700 | >10 | 2.501 |
| 701 | >10 | 2.615 |
| 702 | >10 | 3.983 |
| 703 | >10 | 1.596 |

ND: not determined

In Vivo Biological Evaluation

Example 705

Mouse Skin Pharmacodynamic Model

Figure 2:
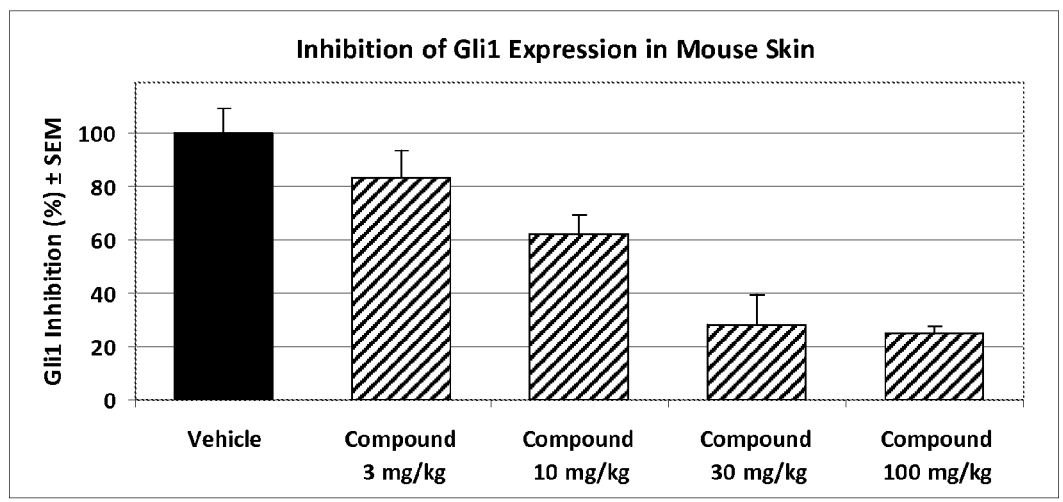
FIG. 2 is a graph showing the results of testing the compound of Example 284 as an inhibitor of expression of Gli1 as described in Example 705.

The activity of several compounds of the invention as inhibitors of expression of Gli1 is determined using the protocol outlined by Lucas et. al. (Bioorg Med Chem. Lett. 2010, 20(12), 3618-22) as follows. Female NOD-Scid mice aged 5-8 weeks are shaved on one side of the hind flank. Four days after shaving, mice are anesthetized and regrown hair is removed using hair removal wax strips. After 5 days, mice are dosed orally with compounds or vehicle. At 6 hours after dosing, animals are sacrificed and the waxed regions of skin are excised and stored in RNALater solution at 4° C. Skin samples are homogenized in Lysis buffer; RNA is purified. RNA is converted to cDNA using reverse transcriptase prior to quantitative, real time PCR analysis. Gli1 expression is normalized to GAPDH expression using the standard curve method. FIGS. 1 and 2 show that compounds of the invention inhibit against Hedgehog pathway activation, and thus are capable of depressing Gli1 expression

Example 706

PC3 Xenograft Model

Figure 3:
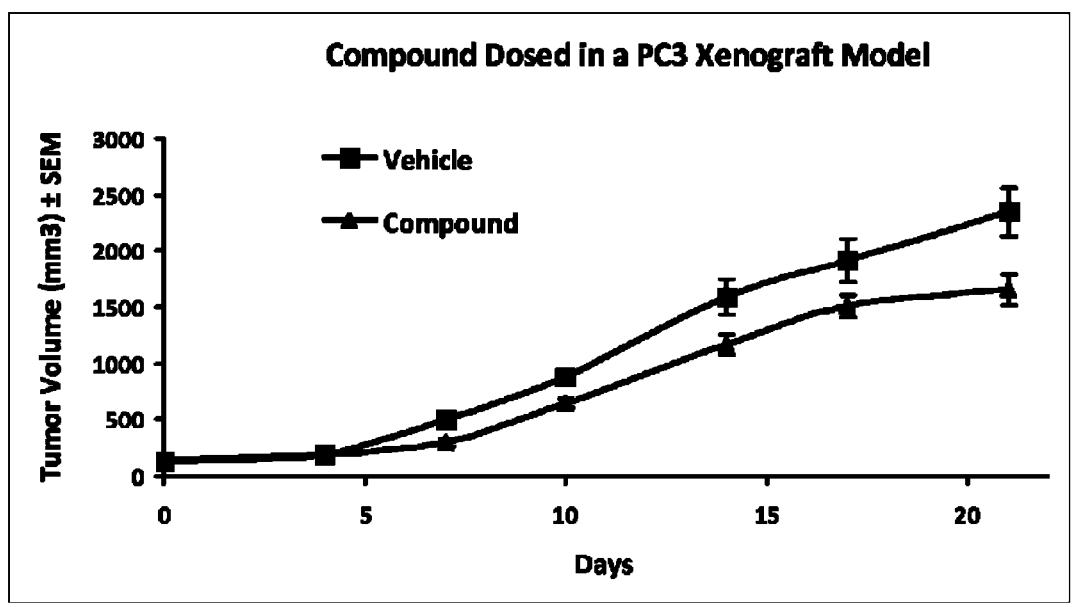
FIG. 3 is a graph showing the results of testing the compound of Example 284 as an inhibitor of tumor growth in a human prostate carcinoma PC-3 nude xenograft model as described in Example 706.

Tumor-growth inhibition activity of compounds of the invention is evaluated in a human prostate carcinoma PC-3 nude xenograft model. The compound is prepared in CMC containing 0.2% Tween 80. BALB/cA-nude mice are of five weeks of age. Aliquots of PC-3 tumor cell suspension are implanted in a group of mice, and days later the mice, now bearing tumors 60-150 cubic mm, are randomized among the control and treated groups (n=6). Compound is dosed PO at 50 mg/kg BID×21. Tumor volume is calculated according to the standard equation, V ½×a×b² where a and b indicate length and width respectively. Results are shown in FIG. 3 for the Compound of Example 284.

The disclosures of all articles and references mentioned in this application, including patents, are incorporated herein by reference in their entirety.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:

1. A compound according to formula:

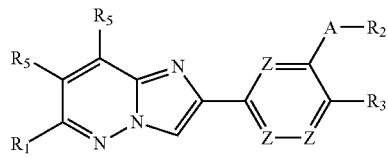

or a pharmaceutically acceptable salt thereof, wherein
$R_1$ is pyridyl optionally substituted at a substitutable position with one or more of $R_8$
wherein $R_8$ is halogen, —CN, —OH, —SH, —NO$_2$, —NH$_2$, —NH(C$_1$-C$_6$ alkyl), —N(C$_1$-C$_6$ alkyl)$_2$, —NH(C$_1$-C$_6$ alkyl)-OH, —NH(C$_1$-C$_6$ alkyl)-(C$_1$-C$_6$ alkoxy), —C$_1$-C$_6$ alkoxy-OH, —C$_1$-C$_6$ alkoxy-(C$_1$-C$_6$ alkoxy), C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, hydroxy(C$_1$-C$_6$ alkyl), (C$_1$-C$_6$ alkoxy)C$_1$-C$_6$ alkyl, amino(C$_1$-C$_6$ alkyl), —S(C$_1$-C$_6$ alkyl), —CO$_2$H, —CO$_2$(C$_1$-C$_6$ alkyl), —C(O)(C$_1$-C$_6$ alkyl), —SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl), —CON(H)OR$_{80}$ where R$_{80}$ is hydrogen or a hydroxy protecting group, —CONH$_2$, —CONH(C$_1$-C$_6$ alkyl), —CON(C$_1$-C$_6$ alkyl)$_2$, —NHCO(C$_1$-C$_6$ alkyl), —C(=NH)NH$_2$, —C(=NH)NH—NH$_2$, —C(=NOH)NH$_2$, or —NHCO$_2$(C$_1$-C$_6$ alkyl) wherein each alkyl, alkenyl, alkynyl, alkoxy is optionally substituted at a substitutable carbon with —CO$_2$(C$_1$-C$_6$)alkyl or —CON(H)OR$_{80}$;
$R_2$ is hydrogen, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_3$-C$_8$ cycloalkyl, aryl, heteroaryl, heterocyclyl, (C$_3$-C$_8$ cycloalkyl)C$_1$-C$_6$ alkyl, (aryl)C$_1$-C$_6$ alkyl, (heteroaryl) C$_1$-C$_6$ alkyl, (heterocyclyl)C$_1$-C$_6$ alkyl, (aryloxy)C$_1$-C$_6$ alkyl, or (heteroaryloxy)C$_1$-C$_6$ alkyl, wherein each alkyl, alkenyl, alkynyl, cycloalkyl, aryl, heteroaryl, or heterocyclyl group is optionally substituted at a substitutable position with one or more of $R_{10}$;
wherein $R_{10}$ is halogen, —CN, —OH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ alkoxy, C$_1$-C$_6$ haloalkoxy, hydroxy(C$_1$-C$_6$ alkyl), (C$_1$-C$_6$ alkoxy)C$_1$-C$_6$ alkyl, amino(C$_1$-C$_6$ alkyl), —CO$_2$H, —CO$_2$(C$_1$-C$_6$ alkyl), —SO$_2$(C$_1$-C$_6$ alkyl), —CONH$_2$, —CONH(C$_1$-C$_6$ alkyl), —CON(C$_1$-C$_6$ alkyl)$_2$, —CON(H)OR$_{80}$, —NHCO(C$_1$-C$_6$ alkyl), or —NHCO$_2$(C$_1$-C$_6$ alkyl), wherein each alkyl, alkenyl, alkynyl, alkoxy is optionally substituted at a substitutable carbon with one $R_{102}$,
where $R_{102}$ is —COR$_{104}$ where $R_{104}$ is —(C$_1$-C$_6$) alkoxy, —NHOR$_{80}$, or —NR$_7$R$_{110}$,
where $R_{110}$ is aryl or heteroaryl, each of which is optionally substituted with up to three of halogen, —CN, —OH, —SH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, hydroxy(C$_1$-C$_6$ alkyl), (C$_1$-C$_6$ alkoxy)C$_1$-C$_6$ alkyl, amino(C$_1$-C$_6$ alkyl), or —S(C$_1$-C$_6$ alkyl); and
$R_7$ is hydrogen or C$_1$-C$_8$ alkyl optionally with C$_1$-C$_4$ alkoxycarbonyl;

R$_3$ is hydrogen, halogen, —CN, —OH, —SH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_3$-C$_8$ cycloalkyl, aryl, heteroaryl, heterocyclyl, (aryl)C$_1$-C$_6$ alkyl, or (heteroaryl)C$_1$-C$_6$ alkyl;

A is N(R$_7$)C(O)—, —N(R$_7$)C(O)O—, —C(O)N(R$_7$)—, —N(R$_7$)C(O)N(R$_7$)—, OC(O)N(R$_7$)—, —S(O)$_2$N(R$_7$)—, —OS(O)$_2$N(R$_7$)—, —N(R$_7$)S(O)$_2$—, or —OS(O)$_2$O—;

R$_5$ represents hydrogen, halogen, —CN, —OH, —SH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, hydroxy(C$_1$-C$_6$ alkyl), (C$_1$-C$_6$ alkoxy)C$_1$-C$_6$ alkyl, amino(C$_1$-C$_6$ alkyl), C$_3$-C$_8$ cycloalkyl, aryl, heteroaryl, heterocyclyl, (aryl)C$_1$-C$_6$ alkyl, or (heteroaryl)C$_1$-C$_6$ alkyl wherein each alkyl, alkenyl, alkynyl, cycloalkyl, aryl, heteroaryl, or heterocyclyl group is optionally substituted at a substitutable position with one or more of R$_{10}$;

each Z is independently N or CR$_6$, provided only one Z is N; and each R$_6$ is independently hydrogen, halogen, —CN, —OH, —SH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, hydroxy(C$_1$-C$_6$ alkyl), (C$_1$-C$_6$ alkoxy)C$_1$-C$_6$ alkyl, amino(C$_1$-C$_6$ alkyl), C$_3$-C$_8$ cycloalkyl, aryl, heteroaryl, heterocyclyl, (aryl)C$_1$-C$_6$ alkyl, or (heteroaryl)C$_1$-C$_6$ alkyl wherein each alkyl, alkenyl, alkynyl, cycloalkyl, aryl, heteroaryl, or heterocyclyl group is optionally substituted at a substitutable position with one or more of R$_{10}$.

2. A compound according to claim 1, wherein each R$_5$ is independently hydrogen, halogen, —CN, —OH, —SH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_3$-C$_8$ cycloalkyl, aryl, heteroaryl, or heterocyclyl, wherein each alkyl, alkenyl, alkynyl, cycloalkyl, aryl, heteroaryl, or heterocyclyl group is optionally substituted at a substitutable position with one or more of R$_{10}$;

wherein R$_{10}$ is halogen, —CN, —OH, —NO$_2$, —NH$_2$, —NH(C$_1$-C$_6$ alkyl), —N(C$_1$-C$_6$ alkyl)$_2$, C$_1$-C$_6$ alkoxy, C$_1$-C$_6$ haloalkyl, C$_1$-C$_6$ alkoxy, C$_1$-C$_6$ haloalkoxy, —CO$_2$H, —CO$_2$(C$_1$-C$_6$ alkyl), —SO$_2$(C$_1$-C$_6$ alkyl), —CONH$_2$, —CONH(C$_1$-C$_6$ alkyl), —CON(C$_1$-C$_6$ alkyl)$_2$, —CON(H)OH, —NHCO(C$_1$-C$_6$ alkyl), or —NHCO$_2$(C$_1$-C$_6$ alkyl).

3. A compound according to claim 1, wherein each R$_5$ is independently hydrogen, C$_1$-C$_6$ alkyl, C$_3$-C$_8$ cycloalkyl, or aryl optionally substituted at a substitutable position with one or more of R$_{10}$.

4. A compound according to claim 3, wherein each R$_5$ is hydrogen, C$_1$-C$_6$ alkyl, C$_3$-C$_8$ cycloalkyl, or aryl optionally substituted at a substitutable position with one or more of halogen.

5. A compound according to claim 4, wherein each Z is CR$_6$.

6. A compound according to claim 5, wherein A is —N(R$_7$)C(O)—, —C(O)N(R$_7$)—, or —S(O)$_2$N(R$_7$)—.

7. A compound according to claim 6, wherein

R$_2$ is C$_1$-C$_6$ alkyl, C$_1$-C$_6$ haloalkyl, C$_3$-C$_8$ cycloalkyl, aryl, heteroaryl, (C$_3$-C$_8$ cycloalkyl)C$_1$-C$_6$ alkyl, (aryl)C$_1$-C$_6$ alkyl, or (aryloxy)C$_1$-C$_6$ alkyl, wherein each alkyl, cycloalkyl, or aryl group is optionally substituted at a substitutable position with one or more of R$_{10}$.

8. A compound according to claim 4, wherein -A-R$_2$ is —N(R$_7$)C(O)(C$_1$-C$_6$ alkyl).

9. A compound according to claim 1, which is 2,2-dimethyl-N-[5-[6-(6-methyl-2-pyridyl)imidazo[2,1-f]pyridazin-2-yl]-2-(trifluoromethyl)phenyl]propanamide;

2,2-dimethyl-N-[5-[6-(5-methyl-2-pyridyl)imidazo[2,1-f]pyridazin-2-yl]-2-(trifluoromethyl)phenyl]propanamide;

2,2-dimethyl-N-[5-[6-(4-methyl-2-pyridyl)imidazo[2,1-f]pyridazin-2-yl]-2-(trifluoromethyl)phenyl]propanamide;

2,2-dimethyl-N-[5-[6-(3-methyl-2-pyridyl)imidazo[2,1-f]pyridazin-2-yl]-2-(trifluoromethyl)phenyl]propanamide;

2,2-dimethyl-N-[2-methyl-5-[6-[2-(trifluoromethyl)-3-pyridyl]imidazo[2,1-f]pyridazin-2-yl]phenyl]propanamide;

2,2-dimethyl-N-[2-methyl-5-[6-[4-(trifluoromethyl)-3-pyridyl]imidazo[2,1-f]pyridazin-2-yl]phenyl]propanamide;

N-(5-(6-(pyridin-2-yl)imidazo[1,2-b]pyridazin-2-yl)-2-(trifluoromethyl)phenyl)pivalamide;

N-(5-(6-(6-methoxypyridin-2-yl)imidazo[1,2-b]pyridazin-2-yl)-2-(trifluoromethyl)phenyl)pivalamide;

N-(5-(6-(6-methylpyridin-2-yl)imidazo[1,2-b]pyridazin-2-yl)-2-(trifluoromethyl)phenyl)pivalamide;

N-(5-(6-(5-methylpyridin-2-yl)imidazo[1,2-b]pyridazin-2-yl)-2-(trifluoromethyl)phenyl)pivalamide;

N-(5-(6-(4-methylpyridin-2-yl)imidazo[1,2-b]pyridazin-2-yl)-2-(trifluoromethyl)phenyl)pivalamide;

N-(5-(6-(3-methylpyridin-2-yl)imidazo[1,2-b]pyridazin-2-yl)-2-(trifluoromethyl)phenyl)pivalamide;

N-(5-(6-(pyridin-3-yl)imidazo[1,2-b]pyridazin-2-yl)-2-(trifluoromethyl)phenyl)pivalamide;

N-(5-(6-(pyridin-4-yl)imidazo[1,2-b]pyridazin-2-yl)-2-(trifluoromethyl)phenyl)pivalamide;

N-(5-(6-(6-methoxypyridin-3-yl)imidazo[1,2-b]pyridazin-2-yl)-2-(trifluoromethyl)phenyl)pivalamide;

N-(5-(6-(6-fluoropyridin-3-yl)imidazo[1,2-b]pyridazin-2-yl)-2-(trifluoromethyl)phenyl)pivalamide;

N-(5-(6-(2-methoxypyridin-3-yl)imidazo[1,2-b]pyridazin-2-yl)-2-(trifluoromethyl)phenyl)pivalamide;

N-(5-(6-(2-fluoropyridin-3-yl)imidazo[1,2-b]pyridazin-2-yl)-2-(trifluoromethyl)phenyl)pivalamide;

N-(5-(6-(3-fluoropyridin-4-yl)imidazo[1,2-b]pyridazin-2-yl)-2-(trifluoromethyl)phenyl)pivalamide;

N-(5-(6-(2-fluoropyridin-3-yl)-7,8-dimethylimidazo[1,2-b]pyridazin-2-yl)-2-(trifluoromethyl)phenyl)pivalamide;

N-(5-(7,8-dimethyl-6-(pyridin-2-yl)imidazo[1,2-b]pyridazin-2-yl)-2-(trifluoromethyl)phenyl)pivalamide;

N-(5-(6-(2-fluoropyridin-3-yl)imidazo[1,2-b]pyridazin-2-yl)-2-methylphenyl)pivalamide;

N-(2-methyl-5-(6-(2-methylpyridin-3-yl)imidazo[1,2-b]pyridazin-2-yl)phenyl)pivalamide;

N-(5-(6-(5-chloro-2-fluoropyridin-3-yl)imidazo[1,2-b]pyridazin-2-yl)-2-methylphenyl)pivalamide;

N-(5-(6-(2,6-difluoropyridin-3-yl)imidazo[1,2-b]pyridazin-2-yl)-2-methylphenyl)pivalamide;

N-(2-methyl-5-(6-(2-(trifluoromethyl)pyridin-3-yl)imidazo[1,2-b]pyridazin-2-yl)phenyl)pivalamide;

N-(2-(trifluoromethyl)-5-(6-(2-(trifluoromethyl)pyridin-3-yl)imidazo[1,2-b]pyridazin-2-yl)phenyl)pivalamide;

N-(5-(6-(2-methylpyridin-3-yl)imidazo[1,2-b]pyridazin-2-yl)-2-(trifluoromethyl)phenyl)pivalamide;
N-(2-methyl-5-(6-(6-(trifluoromethyl)pyridin-3-yl)imidazo[1,2-b]pyridazin-2-yl)phenyl)pivalamide;
N-(5-(6-(2-chloropyridin-3-yl)imidazo[1,2-b]pyridazin-2-yl)-2-(trifluoromethyl)phenyl)pivalamide;
N-(5-(6-(2-morpholinopyridin-3-yl)imidazo[1,2-b]pyridazin-2-yl)-2-(trifluoromethyl)phenyl)pivalamide;
N-(2-ethyl-5-(6-(6-(trifluoromethyl)pyridin-3-yl)imidazo[1,2-b]pyridazin-2-yl)phenyl)pivalamide;
N-(2-methyl-5-(3-methyl-6-(6-(trifluoromethyl)pyridin-3-yl)imidazo[1,2-b]pyridazin-2-yl)phenyl)pivalamide;
N-(5-(6-(2-fluoro-4-methylpyridin-3-yl)imidazo[1,2-b]pyridazin-2-yl)-2-(trifluoromethyl)phenyl)pivalamide
N-(5-(6-(5-aminopyridin-3-yl)imidazo[1,2-b]pyridazin-2-yl)-2-(trifluoromethyl)phenyl)pivalamide;
N-(5-(6-(2-aminopyridin-3-yl)imidazo[1,2-b]pyridazin-2-yl)-2-(trifluoromethyl)phenyl)pivalamide;
N-(2-ethyl-5-(6-(2-(trifluoromethyl)pyridin-3-yl)imidazo[1,2-b]pyridazin-2-yl)phenyl)pivalamide;
N-(2-methyl-5-(3-methyl-6-(2-(trifluoromethyl)pyridin-3-yl)imidazo[1,2-b]pyridazin-2-yl)phenyl)pivalamide;
N-(2-methyl-5-(6-(4-(trifluoromethyl)pyridin-3-yl)imidazo[1,2-b]pyridazin-2-yl)phenyl)pivalamide;
N-(5-(6-(2-fluoropyridin-4-yl)imidazo[1,2-b]pyridazin-2-yl)-2-methylphenyl)pivalamide;
N-(5-(6-(5-chloropyridin-2-yl)imidazo[1,2-b]pyridazin-2-yl)-2-methylphenyl)pivalamide;
N-(5-(6-(2-methylpyridin-4-yl)imidazo[1,2-b]pyridazin-2-yl)-2-(trifluoromethyl)phenyl)pivalamide;
N-(5-(6-(3-methoxypyridin-4-yl)imidazo[1,2-b]pyridazin-2-yl)-2-(trifluoromethyl)phenyl)pivalamide;
N-(5-(6-(4-methylpyridin-3-yl)imidazo[1,2-b]pyridazin-2-yl)-2-(trifluoromethyl)phenyl)pivalamide;
N-(5-(6-(4-methoxypyridin-3-yl)imidazo[1,2-b]pyridazin-2-yl)-2-(trifluoromethyl)phenyl)pivalamide;
N-(5-(6-(4-chloropyridin-3-yl)imidazo[1,2-b]pyridazin-2-yl)-2-(trifluoromethyl)phenyl)pivalamide;
N-(2-methyl-5-(6-(3-(trifluoromethyl)pyridin-2-yl)imidazo[1,2-b]pyridazin-2-yl)phenyl)pivalamide;
N-(5-(6-(6'-chloro-2,3'-bipyridin-5-yl)imidazo[1,2-b]pyridazin-2-yl)-2-methylphenyl)pivalamide;
N-(5-(6-(6-aminopyridin-3-yl)imidazo[1,2-b]pyridazin-2-yl)-2-methylphenyl)pivalamide;
N-(5-(6-(5-methoxypyridin-3-yl)imidazo[1,2-b]pyridazin-2-yl)-2-methylphenyl)pivalamide;
N-(5-(6-(6-hydroxypyridin-3-yl)imidazo[1,2-b]pyridazin-2-yl)-2-methylphenyl)pivalamide;
N-(5-(6-(5-hydroxypyridin-3-yl)imidazo[1,2-b]pyridazin-2-yl)-2-methylphenyl)pivalamide;
N-(5-(6-(2-hydroxypyridin-3-yl)imidazo[1,2-b]pyridazin-2-yl)-2-methylphenyl)pivalamide;
N-(5-(6-(5-fluoropyridin-3-yl)imidazo[1,2-b]pyridazin-2-yl)-2-methylphenyl)pivalamide;
N-(5-(6-(6-chloropyridin-3-yl)imidazo[1,2-b]pyridazin-2-yl)-2-methylphenyl)pivalamide;
methyl 8-(2-methyl-5-(6-(2-(trifluoromethyl)pyridin-3-yl)imidazo[1,2-b]pyridazin-2-yl)phenylamino)-8-oxooctanoate;
methyl 6-(2-methyl-5-(6-(2-(trifluoromethyl)pyridin-3-yl)imidazo[1,2-b]pyridazin-2-yl)phenylamino)-6-oxohexanoate;
$N^1$-hydroxy-$N^8$-(2-methyl-5-(6-(2-(trifluoromethyl)pyridin-3-yl)imidazo[1,2-b]pyridazin-2-yl)phenyl)octanediamide;
8-(2-methyl-5-(6-(2-(trifluoromethyl)pyridin-3-yl)imidazo[1,2-b]pyridazin-2-yl)phenylamino)-8-oxooctanoic acid;
ethyl 4-(4-(2-(4-methyl-3-pivalamidophenyl)imidazo[1,2-b]pyridazin-6-yl)-6-(trifluoromethyl)pyridin-2-yloxy)butanoate;
ethyl 4-(5-(2-(4-methyl-3-pivalamidophenyl)imidazo[1,2-b]pyridazin-6-yl)-6-(trifluoromethyl)pyridin-2-yloxy)butanoate;
ethyl 3-(2-methyl-5-(6-(2-(trifluoromethyl)pyridin-3-yl)imidazo[1,2-b]pyridazin-2-yl)phenylamino)-3-oxopropanoate;
ethyl 4-(2-methyl-5-(6-(2-(trifluoromethyl)pyridin-3-yl)imidazo[1,2-b]pyridazin-2-yl)phenylamino)-4-oxobutanoate;
$N^1$-hydroxy-$N^6$-(2-methyl-5-(6-(2-(trifluoromethyl)pyridin-3-yl)imidazo[1,2-b]pyridazin-2-yl)phenyl)adipamide;
2-(4-methyl-3-(6-(trifluoromethyl)pyridin-3-yl)phenyl)-6-(2-(trifluoromethyl)pyridin-3-yl)imidazo[1,2-b]pyridazine;
N-(2-methyl-5-(6-(4-(trifluoromethyl)pyridin-2-yl)imidazo[1,2-b]pyridazin-2-yl)phenyl)pivalamide;
N-(2-methyl-5-(6-(5-(trifluoromethyl)pyridin-2-yl)imidazo[1,2-b]pyridazin-2-yl)phenyl)pivalamide;
N-(2-methyl-5-(6-(6-(trifluoromethyl)pyridin-2-yl)imidazo[1,2-b]pyridazin-2-yl)phenyl)pivalamide;
6-(2-(4-methyl-3-pivalamidophenyl)imidazo[1,2-b]pyridazin-6-yl)nicotinic acid;
N-(5-(6-(6-(hydroxymethyl)pyridin-2-yl)imidazo[1,2-b]pyridazin-2-yl)-2-methylphenyl)pivalamide;
4-methoxy-6-(2-(4-methyl-3-pivalamidophenyl)imidazo[1,2-b]pyridazin-6-yl)nicotinic acid;
ethyl 2-(5-(2-(4-methyl-3-pivalamidophenyl)imidazo[1,2-b]pyridazin-6-yl)-6-(trifluoromethyl)pyridin-2-yloxy)acetate;
N-tert-butyl-2-methyl-5-(6-(2-(trifluoromethyl)pyridin-3-yl)imidazo[1,2-b]pyridazin-2-yl)benzamide;
N-(5-(6-(6-acetamido-2-methylpyridin-3-yl)imidazo[1,2-b]pyridazin-2-yl)-2-methylphenyl)pivalamide;
N-(5-(6-(6-acetamidopyridin-3-yl)imidazo[1,2-b]pyridazin-2-yl)-2-methylphenyl)pivalamide;
N-methyl-N-(2-methyl-5-(6-(2-(trifluoromethyl)pyridin-3-yl)imidazo[1,2-b]pyridazin-2-yl)phenyl)pivalamide;
methyl 2-(N-(2-methyl-5-(6-(2-(trifluoromethyl)pyridin-3-yl)imidazo[1,2-b]pyridazin-2-yl)phenyl)pivalamido)acetate;
methyl 7-(N-(2-methyl-5-(6-(2-(trifluoromethyl)pyridin-3-yl)imidazo[1,2-b]pyridazin-2-yl)phenyl)pivalamido)heptanoate;
1-methyl-N-(2-methyl-5-(6-(2-(trifluoromethyl)pyridin-3-yl)imidazo[1,2-b]pyridazin-2-yl)phenyl)cyclopropanecarboxamide;
N-(2-methyl-5-(6-(5-(trifluoromethyl)pyridin-3-yl)imidazo[1,2-b]pyridazin-2-yl)phenyl)pivalamide;
6-(2-(4-methyl-3-pivalamidophenyl)imidazo[1,2-b]pyridazin-6-yl)nicotinamide;
8-((2-methyl-5-(6-(2-(trifluoromethyl)pyridin-3-yl)imidazo[1,2-b]pyridazin-2-yl)phenyl)amino)-8-oxooctanoic acid;
N1-(2-methyl-5-(6-(2-(trifluoromethyl)pyridin-3-yl)imidazo[1,2-b]pyridazin-2-yl)phenyl)-N8-((tetrahydro-2H-pyran-2-yl)oxy)octanediamide;
N-(5-(6-(6-aminopyridin-2-yl)imidazo[1,2-b]pyridazin-2-yl)-2-methylphenyl)pivalamide;

N1-hydroxy-N8-(6-(2-(4-methyl-3-pivalamidophenyl)imidazo[1,2-b]pyridazin-6-yl)pyridin-2-yl)octanediamide;
N-(5-(6-(2-cyanopyridin-3-yl)imidazo[1,2-b]pyridazin-2-yl)-2-methylphenyl)pivalamide;
2-cyano-2-methyl-N-(2-methyl-5-(6-(2-(trifluoromethyl)pyridin-3-yl)imidazo[1,2-b]pyridazin-2-yl)phenyl)propanamide;
3-amino-2,2-dimethyl-N-(2-methyl-5-(6-(2-(trifluoromethyl)pyridin-3-yl)-2,3-dihydroimidazo[1,2-b]pyridazin-2-yl)phenyl)propanamide;
3-(3-((2-aminophenyl)amino)-3-oxoprop-1-en-1-yl)-N-(2-methyl-5-(6-(2-(trifluoromethyl)pyridin-3-yl)imidazo[1,2-b]pyridazin-2-yl)phenyl)benzamide;
N-(2-aminophenyl)-3-(3-(N-(2-methyl-5-(6-(2-(trifluoromethyl)pyridin-3-yl)imidazo[1,2-b]pyridazin-2-yl)phenyl)sulfamoyl)phenyl)acrylamide;
3-(3-(hydroxyamino)-3-oxoprop-1-en-1-yl)-N-(2-methyl-5-(6-(2-(trifluoromethyl)pyridin-3-yl)imidazo[1,2-b]pyridazin-2-yl)phenyl)benzamide;
N-hydroxy-3-(3-(N-(2-methyl-5-(6-(2-(trifluoromethyl)pyridin-3-yl)imidazo[1,2-b]pyridazin-2-yl)phenyl)sulfamoyl)phenyl)acrylamide;
N-(2-ethyl-5-(6-(2-(trifluoromethyl)pyridin-3-yl)imidazo[1,2-b]pyridazin-2-yl)phenyl)-1-methylcyclopropanecarboxamide;
3,3,3-trifluoro-2,2-dimethyl-N-(2-methyl-5-(6-(2-(trifluoromethyl)pyridin-3-yl)imidazo[1,2-b]pyridazin-2-yl)phenyl)propanamide;
N-(4-chloro-2-methyl-5-(6-(2-(trifluoromethyl)pyridin-3-yl)imidazo[1,2-b]pyridazin-2-yl)phenyl)pivalamide;
N-(5-(3-chloro-6-(2-(trifluoromethyl)pyridin-3-yl)imidazo[1,2-b]pyridazin-2-yl)-2-methylphenyl)pivalamide;
N-(2-chloro-5-(6-(2-(trifluoromethyl)pyridin-3-yl)imidazo[1,2-b]pyridazin-2-yl)phenyl)pivalamide;
N-(2-cyclopropyl-5-(6-(2-(trifluoromethyl)pyridin-3-yl)imidazo[1,2-b]pyridazin-2-yl)phenyl)pivalamide;
N-(2-methyl-5-(6-(2-(trifluoromethyl)pyridin-3-yl)imidazo[1,2-b]pyridazin-2-yl)phenyl)pyrrolidine-2-carboxamide;
1-tert-butyl-3-(2-methyl-5-(6-(2-(trifluoromethyl)pyridin-3-yl)imidazo[1,2-b]pyridazin-2-yl)phenyl)urea;
1-methyl-N-(2-methyl-5-(6-(2-(trifluoromethyl)pyridin-3-yl)imidazo[1,2-b]pyridazin-2-yl)phenyl)pyrrolidine-2-carboxamide;
1-ethyl-N-(2-methyl-5-(6-(2-(trifluoromethyl)pyridin-3-yl)imidazo[1,2-b]pyridazin-2-yl)phenyl)pyrrolidine-2-carboxamide;
N-(4-fluoro-2-methyl-5-(6-(2-(trifluoromethyl)pyridin-3-yl)imidazo[1,2-b]pyridazin-2-yl)phenyl)pivalamide;
N-(2-chloro-4-fluoro-5-(6-(2-(trifluoromethyl)pyridin-3-yl)imidazo[1,2-b]pyridazin-2-yl)phenyl)pivalamide;
1-cyclopropyl-3-(2-methyl-5-(6-(2-(trifluoromethyl)pyridin-3-yl)imidazo[1,2-b]pyridazin-2-yl)phenyl)urea;
N-(2,4-difluoro-5-(6-(2-(trifluoromethyl)pyridin-3-yl)imidazo[1,2-b]pyridazin-2-yl)phenyl)pivalamide;
N-(2-chloro-5-(6-(2-(trifluoromethyl)pyridin-3-yl)imidazo[1,2-b]pyridazin-2-yl)phenyl)-1-methylcyclopropanecarboxamide;
1-(2-chloro-5-(6-(2-(trifluoromethyl)pyridin-3-yl)imidazo[1,2-b]pyridazin-2-yl)phenyl)-3-cyclopropylurea;
3-(2-chloro-5-(6-(2-(trifluoromethyl)pyridin-3-yl)imidazo[1,2-b]pyridazin-2-yl)phenyl)-1,1-diethylurea;
N-(2-chloro-5-(6-(2-(trifluoromethyl)pyridin-3-yl)imidazo[1,2-b]pyridazin-2-yl)phenyl)pyrrolidine-1-carboxamide;
ethyl 2-chloro-4-fluoro-5-(6-(2-(trifluoromethyl)pyridin-3-yl)imidazo[1,2-b]pyridazin-2-yl)phenylcarbamate;
N-(2-fluoro-5-(6-(2-(trifluoromethyl)pyridin-3-yl)imidazo[1,2-b]pyridazin-2-yl)phenyl)pivalamide;
N-(2-chloro-4-fluoro-5-(6-(2-(trifluoromethyl)pyridin-3-yl)imidazo[1,2-b]pyridazin-2-yl)phenyl)-2,2-dimethylbutanamide;
N-(2-chloro-4-fluoro-5-(6-(2-(trifluoromethyl)pyridin-3-yl)imidazo[1,2-b]pyridazin-2-yl)phenyl)-3,3,3-trifluoro-2,2-dimethylpropanamide;
N-(2-chloro-4-fluoro-5-(6-(2-(trifluoromethyl)pyridin-3-yl)imidazo[1,2-b]pyridazin-2-yl)phenyl)-4,4,4-trifluoro-3-methylbutanamide;
N-(2-chloro-4-fluoro-5-(6-(2-(trifluoromethyl)pyridin-3-yl)imidazo[1,2-b]pyridazin-2-yl)phenyl)-2,2-dimethylpentanamide;
N-(2-(2-(trifluoromethyl)pyridin-3-yl)-5-(6-(2-(trifluoromethyl)pyridin-3-yl)imidazo[1,2-b]pyridazin-2-yl)phenyl)pivalamide;
N-(2-chloro-5-(6-(2-(trifluoromethyl)pyridin-3-yl)imidazo[1,2-b]pyridazin-2-yl)phenyl)-2,2-dimethylbutanamide;
N-(2-chloro-5-(6-(2-(trifluoromethyl)pyridin-3-yl)imidazo[1,2-b]pyridazin-2-yl)phenyl)-3,3,3-trifluoro-2,2-dimethylpropanamide;
N-(2-chloro-5-(6-(2-(trifluoromethyl)pyridin-3-yl)imidazo[1,2-b]pyridazin-2-yl)phenyl)-4,4,4-trifluoro-3-methylbutanamide;
N-(2-chloro-5-(6-(2-(trifluoromethyl)pyridin-3-yl)imidazo[1,2-b]pyridazin-2-yl)phenyl)-2,2-dimethylpentanamide;
isopropyl 2-chloro-5-(6-(2-(trifluoromethyl)pyridin-3-yl)imidazo[1,2-b]pyridazin-2-yl)phenylcarbamate;
N-(2-chloro-5-(6-(2-(trifluoromethyl)pyridin-3-yl)imidazo[1,2-b]pyridazin-2-yl)phenyl)-3,3-difluoroazetidine-1-carboxamide;
N-(2-chloro-5-(6-(2-(trifluoromethyl)pyridin-3-yl)imidazo[1,2-b]pyridazin-2-yl)phenyl)cyclohexanecarboxamide;
N-(2-chloro-5-(6-(2-(trifluoromethyl)pyridin-3-yl)imidazo[1,2-b]pyridazin-2-yl)phenyl)cyclopentanecarboxamide;
N-(2-chloro-5-(6-(2-(trifluoromethyl)pyridin-3-yl)imidazo[1,2-b]pyridazin-2-yl)phenyl)-3,3-dimethylbutanamide;
ethyl 2-chloro-5-(6-(2-(trifluoromethyl)pyridin-3-yl)imidazo[1,2-b]pyridazin-2-yl)phenylcarbamate;
N-(2-fluoro-5-(6-(2-(trifluoromethyl)pyridin-3-yl)imidazo[1,2-b]pyridazin-2-yl)phenyl)-1-methylcyclopropanecarboxamide;
N-(2-chloro-5-(6-(2-(trifluoromethyl)pyridin-3-yl)imidazo[1,2-b]pyridazin-2-yl)phenyl)-3,3,3-trifluoropropanamide;
N-(2-chloro-5-(6-(2-(trifluoromethyl)pyridin-3-yl)imidazo[1,2-b]pyridazin-2-yl)phenyl)cyclopropanecarboxamide;
N-(2-fluoro-5-(6-(2-(trifluoromethyl)pyridin-3-yl)imidazo[1,2-b]pyridazin-2-yl)phenyl)cyclohexanecarboxamide;
N-(2-fluoro-5-(6-(2-(trifluoromethyl)pyridin-3-yl)imidazo[1,2-b]pyridazin-2-yl)phenyl)cyclopentanecarboxamide;
N-(2-fluoro-5-(6-(2-(trifluoromethyl)pyridin-3-yl)imidazo[1,2-b]pyridazin-2-yl)phenyl)-3,3-dimethylbutanamide;

3,3,3-trifluoro-N-(2-fluoro-5-(6-(2-(trifluoromethyl)pyridin-3-yl)imidazo[1,2-b]pyridazin-2-yl)phenyl)propanamide;

N-(2-fluoro-5-(6-(2-(trifluoromethyl)pyridin-3-yl)imidazo[1,2-b]pyridazin-2-yl)phenyl)cyclopropanecarboxamide;

ethyl 2-fluoro-5-(6-(2-(trifluoromethyl)pyridin-3-yl)imidazo[1,2-b]pyridazin-2-yl)phenylcarbamate;

isopropyl 2-fluoro-5-(6-(2-(trifluoromethyl)pyridin-3-yl)imidazo[1,2-b]pyridazin-2-yl)phenylcarbamate;

3,3-difluoro-N-(2-fluoro-5-(6-(2-(trifluoromethyl)pyridin-3-yl)imidazo[1,2-b]pyridazin-2-yl)phenyl)azetidine-1-carboxamide;

1,1-diethyl-3-(2-fluoro-5-(6-(2-(trifluoromethyl)pyridin-3-yl)imidazo[1,2-b]pyridazin-2-yl)phenyl)urea;

N-(2-fluoro-5-(6-(2-(trifluoromethyl)pyridin-3-yl)imidazo[1,2-b]pyridazin-2-yl)phenyl)pyrrolidine-1-carboxamide;

N-(2-ethyl-5-(6-(2-(trifluoromethyl)pyridin-3-yl)imidazo[1,2-b]pyridazin-2-yl)phenyl)cyclohexanecarboxamide;

N-(2-ethyl-5-(6-(2-(trifluoromethyl)pyridin-3-yl)imidazo[1,2-b]pyridazin-2-yl)phenyl)cyclopentanecarboxamide;

N-(2-ethyl-5-(6-(2-(trifluoromethyl)pyridin-3-yl)imidazo[1,2-b]pyridazin-2-yl)phenyl)-2,2-dimethylbutanamide;

N-(2-ethyl-5-(6-(2-(trifluoromethyl)pyridin-3-yl)imidazo[1,2-b]pyridazin-2-yl)phenyl)-3,3,3-trifluoro-2,2-dimethylpropanamide;

N-(2-ethyl-5-(6-(2-(trifluoromethyl)pyridin-3-yl)imidazo[1,2-b]pyridazin-2-yl)phenyl)-3,3-dimethylbutanamide;

N-(2-ethyl-5-(6-(2-(trifluoromethyl)pyridin-3-yl)imidazo[1,2-b]pyridazin-2-yl)phenyl)-3,3,3-trifluoropropanamide;

1,1-diethyl-3-(2-ethyl-5-(6-(2-(trifluoromethyl)pyridin-3-yl)imidazo[1,2-b]pyridazin-2-yl)phenyl)urea;

N-(2-ethyl-5-(6-(2-(trifluoromethyl)pyridin-3-yl)imidazo[1,2-b]pyridazin-2-yl)phenyl)pyrrolidine-1-carboxamide;

N-(2-ethyl-5-(6-(2-(trifluoromethyl)pyridin-3-yl)imidazo[1,2-b]pyridazin-2-yl)phenyl)-3,3-difluoroazetidine-1-carboxamide;

N-(2-ethyl-5-(6-(2-(trifluoromethyl)pyridin-3-yl)imidazo[1,2-b]pyridazin-2-yl)phenyl)-3-methyloxetane-3-carboxamide;

2-chloro-5-(6-(2-(trifluoromethyl)pyridin-3-yl)imidazo[1,2-b]pyridazin-2-yl)benzenesulfonamide;

2-chloro-N-methyl-5-(6-(2-(trifluoromethyl)pyridin-3-yl)imidazo[1,2-b]pyridazin-2-yl)benzenesulfonamide;

N-tert-butyl-2-chloro-5-(6-(2-(trifluoromethyl)pyridin-3-yl)imidazo[1,2-b]pyridazin-2-yl)benzenesulfonamide;

2-chloro-N,N-dimethyl-5-(6-(2-(trifluoromethyl)pyridin-3-yl)imidazo[1,2-b]pyridazin-2-yl)benzenesulfonamide;

2-chloro-N-ethyl-5-(6-(2-(trifluoromethyl)pyridin-3-yl)imidazo[1,2-b]pyridazin-2-yl)benzenesulfonamide;

2-chloro-N-cyclopropyl-5-(6-(2-(trifluoromethyl)pyridin-3-yl)imidazo[1,2-b]pyridazin-2-yl)benzenesulfonamide;

2-chloro-N,N-diethyl-5-(6-(2-(trifluoromethyl)pyridin-3-yl)imidazo[1,2-b]pyridazin-2-yl)benzenesulfonamide;

or a pharmaceutically acceptable salt of any of the above compounds.

10. A compound according to claim 1, wherein each $R_5$ is hydrogen.

11. A compound according to claim 10, wherein each Z is $CR_6$.

12. A compound according to claim 11, wherein each $R_6$ is independently hydrogen, halogen, or $C_1$-$C_6$ alkyl.

13. A compound according to claim 12, wherein each $R_6$ is hydrogen.

14. A compound according to claim 13, wherein
$R_3$ is hydrogen, halogen, —CN, $C_1$-$C_6$ alkyl, $C_1$-$C_6$ haloalkyl, $C_1$-$C_6$ alkoxy, $C_1$-$C_6$ haloalkoxy, or $C_3$-$C_8$ cycloalkyl.

15. A compound according to claim 14, wherein A is —N($R_7$)C(O)—.

16. A compound according to claim 15, wherein
$R_2$ is hydrogen, $C_1$-$C_6$ alkyl, $C_1$-$C_6$ haloalkyl, $C_3$-$C_8$ cycloalkyl, aryl, heteroaryl, ($C_3$-$C_8$ cycloalkyl)$C_1$-$C_6$ alkyl, (aryl)$C_1$-$C_6$ alkyl, (heteroaryl)$C_1$-$C_6$ alkyl, (aryloxy)$C_1$-$C_6$ alkyl, or (heteroaryloxy)$C_1$-$C_6$ alkyl, wherein each alkyl, cycloalkyl, aryl, or heteroaryl group is optionally substituted at a substitutable position with one or more of $R_{10}$.

17. A compound according to claim 16, wherein $R_2$ is $C_1$-$C_6$ alkyl or
$C_1$-$C_6$ haloalkyl.

18. A compound according to claim 17, wherein $R_2$ is $C_1$-$C_6$ alkyl.

19. A compound according to claim 16, wherein $R_2$ is $C_3$-$C_8$ cycloalkyl which is optionally substituted at a substitutable position with one or more of $R_{10}$.

20. A compound according to claim 1 which is
1-methyl-N-(2-methyl-5-(6-(2-(trifluoromethyl)pyridin-3-yl)imidazo[1,2-b]pyridazin-2-yl)phenyl)cyclopropanecarboxamide;

N-(2-ethyl-5-(6-(2-(trifluoromethyl)pyridin-3-yl)imidazo[1,2-b]pyridazin-2-yl)phenyl)-1-methylcyclopropanecarboxamide;

N-(2-chloro-5-(6-(2-(trifluoromethyl)pyridin-3-yl)imidazo[1,2-b]pyridazin-2-yl)phenyl)-1-methylcyclopropanecarboxamide;

N-(2-fluoro-5-(6-(2-(trifluoromethyl)pyridin-3-yl)imidazo[1,2-b]pyridazin-2-yl)phenyl)-1-methylcyclopropanecarboxamide;

N-(2-chloro-5-(6-(2-(trifluoromethyl)pyridin-3-yl)imidazo[1,2-b]pyridazin-2-yl)phenyl)cyclopropanecarboxamide;

N-(2-fluoro-5-(6-(2-(trifluoromethyl)pyridin-3-yl)imidazo[1,2-b]pyridazin-2-yl)phenyl)cyclopropanecarboxamide; or a pharmaceutically acceptable salt of any of the above compounds.

21. A compound according to claim 1 which is
N-(2-chloro-5-(6-(2-(trifluoromethyl)pyridin-3-yl)imidazo[1,2-b]pyridazin-2-yl)phenyl)cyclopentanecarboxamide;

N-(2-fluoro-5-(6-(2-(trifluoromethyl)pyridin-3-yl)imidazo[1,2-b]pyridazin-2-yl)phenyl)cyclopentanecarboxamide;

N-(2-ethyl-5-(6-(2-(trifluoromethyl)pyridin-3-yl)imidazo[1,2-b]pyridazin-2-yl)phenyl)cyclopentanecarboxamide; or a pharmaceutically acceptable salt of any of the above compounds.

22. A compound according to claim 1 which is
N-(2-chloro-5-(6-(2-(trifluoromethyl)pyridin-3-yl)imidazo[1,2-b]pyridazin-2-yl)phenyl)cyclohexanecarboxamide;

N-(2-fluoro-5-(6-(2-(trifluoromethyl)pyridin-3-yl)imidazo[1,2-b]pyridazin-2-yl)phenyl)cyclohexanecarboxamide;

N-(2-ethyl-5-(6-(2-(trifluoromethyl)pyridin-3-yl)imidazo[1,2-b]pyridazin-2-yl)phenyl)cyclohexanecarboxamide;

a pharmaceutically acceptable salt of any of the above compounds.

23. A pharmaceutical composition comprising a compound according to claim 1 and a pharmaceutically acceptable carrier, solvent, adjuvant or diluent.

* * * * *